(12) United States Patent
Bailey et al.

(10) Patent No.: US 8,367,395 B2
(45) Date of Patent: Feb. 5, 2013

(54) PRODUCTION OF STEROLS IN OLEAGINOUS YEAST AND FUNGI

(75) Inventors: Richard B. Bailey, South Natick, MA (US); Joshua Trueheart, Concord, MA (US); Kevin T. Madden, Arlington, MA (US)

(73) Assignee: DSM IP Assets B.V., Heerlen (NL)

( * ) Notice: Subject to any disclaimer, the term of this patent is extended or adjusted under 35 U.S.C. 154(b) by 123 days.

(21) Appl. No.: 12/443,350

(22) PCT Filed: Sep. 28, 2007

(86) PCT No.: PCT/US2007/021091
§ 371 (c)(1),
(2), (4) Date: May 28, 2009

(87) PCT Pub. No.: WO2008/130372
PCT Pub. Date: Oct. 30, 2008

(65) Prior Publication Data
US 2010/0305341 A1 Dec. 2, 2010

Related U.S. Application Data

(60) Provisional application No. 60/848,582, filed on Sep. 28, 2006.

(51) Int. Cl.
*C12N 9/00* (2006.01)
*C12N 9/10* (2006.01)
*C12N 1/00* (2006.01)
*C12N 15/00* (2006.01)
*C07H 21/04* (2006.01)

(52) U.S. Cl. .................. 435/254.11; 435/183; 435/193; 435/320.1; 536/23.2

(58) Field of Classification Search .................. None
See application file for complete search history.

(56) References Cited

U.S. PATENT DOCUMENTS

2006/0088903 A1 4/2006 Lang et al.
2009/0324800 A1 12/2009 Bailey et al.

FOREIGN PATENT DOCUMENTS

EP 0 486 290 B1 5/1992

OTHER PUBLICATIONS

Merkulov et al. Yeast. Feb. 2000;16(3):197-206.*
Chica et al. Curr Opin Biotechnol. Aug. 2005;16(4):378-84.*
Sen et al. Appl Biochem Biotechnol. Dec. 2007;143(3):212-23.*
Veen et al. FEMS Yeast Res. Oct. 2003;4(1):87-95.*
Madzak et al. J Biotechnol. Apr. 8, 2004;109(1-2):63-81.*
Athenstaedt et al., "Lipid particle composition of the yeast *Yarrowia lipolytica* depends on the carbon source", Proteomica, 6:1450-1459 (2006).
Merkulov et al., "Cloning and characterization of the *Yarrowia lipolytica* squalene synthase (SQS1) gene and functional complementation of the *Saccharomyces cerevisiae* erg9 mutation", Yeast, 16:197-206 (2000).
International Search Report for PCT/US2007/021091, mailed Jan. 13, 2009.
International Preliminary Report on Patentability for PCT/US2007, 021091, mailed Mar. 31, 2009.

* cited by examiner

*Primary Examiner* — Christian Fronda
(74) *Attorney, Agent, or Firm* — Choate, Hall & Stewart, LLP

(57) ABSTRACT

The present invention provides methods for production of one or more sterol compounds. Further provided are methods and systems for producing engineered oleaginous yeast or fungi that are capable of production of one or more sterol compounds, and compositions which utilize the produced sterol compound(s).

9 Claims, 37 Drawing Sheets

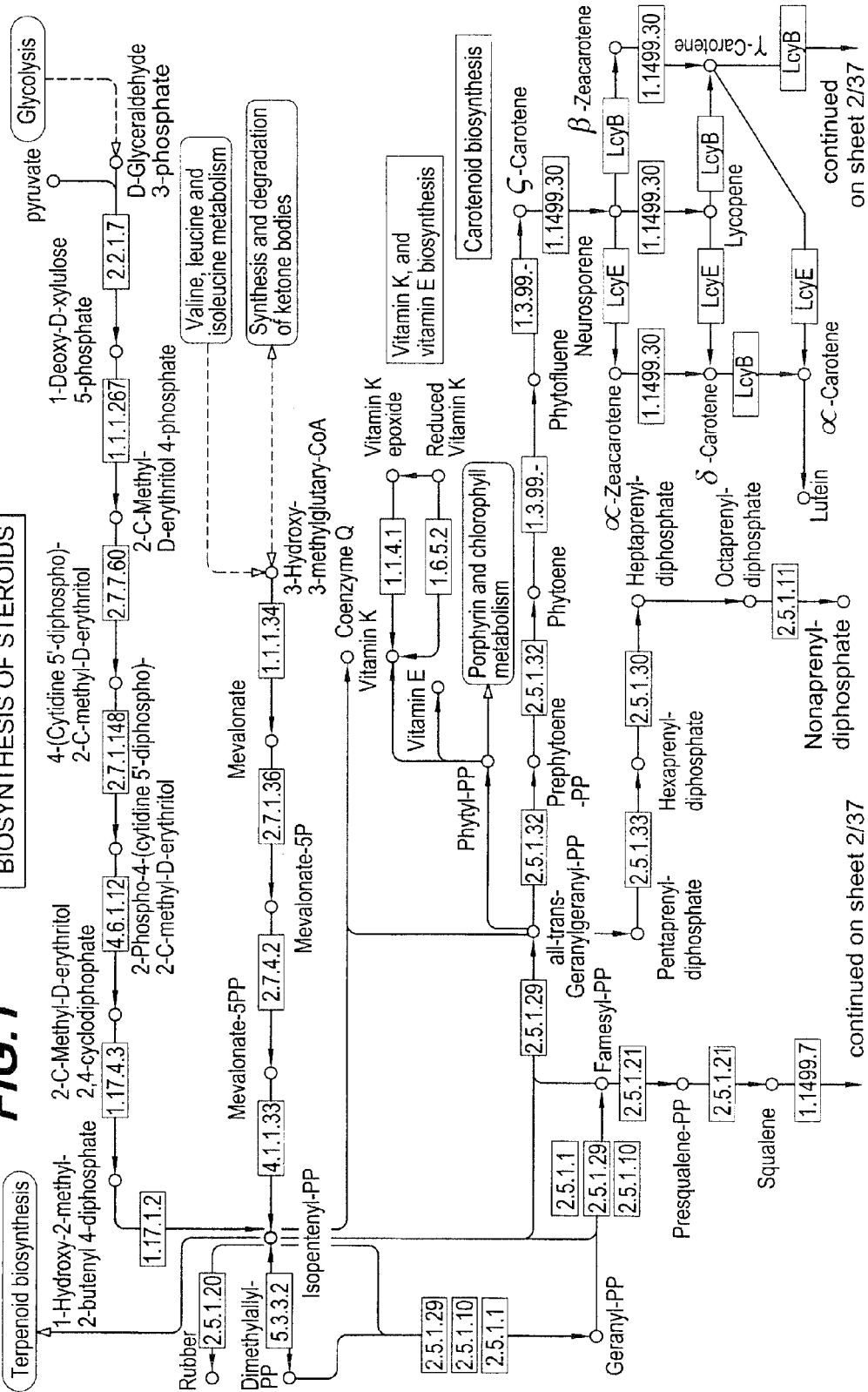
FIG. 1 BIOSYNTHESIS OF STEROIDS

FIG. 7A

*Alignment of representative fungal HMG-CoA reductase polypeptides.*

| FIG.7A |
|--------|
| FIG.7B |
| ⋮ |
| FIG.7I |

FIG. 7

```
                             1                                                        50
A. nidulans HMG       (1)   -MASVLRRKFGTE--GGSDAEPSWLKRQVFGCIQSISRRAACHPIHTIV
G. zeae HMG           (1)   -MASILPKKFRGETAPAEKTTPSWASKRLTPIAQEISRLACSHPIHTIV
N. crassa HMG         (1)   MIASSLHPSKFRGEQPATQAATPSWINKKVPPFQKISKITSSNPIHTIV
S. cerevisea HMG2     (1)   ----------------------MSLPLKTIVHLVKPEACTARFSARYPIHIV
S. cerevisea HMG1     (1)   -------------------MPPLFKGLKQMAKPIAYVSRFSAKPPIHIE
Y. lipolytica HMG     (1)   ---------------------------MLQAAIGKIVGFAVNRPIHIVV
          Consensus   (1)           MAS LL RE  E       A PSW  K LT PIQ ISRFAA HPIHTIV
                             51                                                       100
A. nidulans HMG      (48)   MIALLASTTYVGLLEGSLEDSFRNSNNVAGHVDVDSLLLGNRSLRLGEGT
G. zeae HMG          (50)   IAVMLASTSYVGLLQESFFSTDLP---TVGKADWSLVEGSRVLRAGPET
N. crassa HMG        (51)   IVALLASSSYIGLLQNSLFNVTR----SVRKAEWESLQAGSRMLRAGANT
S. cerevisea HMG2    (32)   MAVLLSAARYLSVTQSYLNEWKLDSN------QYSTYLSIKPDELFEKCTH
S. cerevisea HMG1    (32)   FSLIISAFAYLSVIQYYFNGMQLDSNS-----VFETAPNKDSNTLFQECSH
Y. lipolytica HMG    (23)   LTSIVASTAYLALLDIAIPGEEG-------TQPISYYHFAKSYDNPAD
          Consensus  (51)   LVALLASTAYLGLLQ  SLF W L SN           D TSL  GSR LR G   T
```

```
                         101                                                        150
A. nidulans HMG   (98)   SWKWQVEDSLNQDDQKVGNPELKREVDQHLALTLMFPDSISKS-ASTAP
G. zeae HMG       (97)   AWNWKAIEQDSIQ----------HAGADADHLALLTLMFPDIHSAESSSTAP
N. crassa HMG     (97)   EWNWQNHDPEAP-----------------VPANANHLALTLMFPDIAES--GPVVA
S. cereviseae HMG2 (77)  YKRSPVSDTWKLLS-----SKEFADIYTPFHYLSTISFSKDNSTLP
S. cereviseae HMG1 (78)  YLVRDSSLDGWVSIT----AHEASELPAPHHYLLNLNFSPNETDSIP
Y. lipolytica HMG (65)   ---WIHUAEADTIP----------SDAYRLAFAQIRVSDVQGGEIAPTIP
Consensus        (101)       WRW  ID   I       AADA HLAL TLVFPDTQS E ASTIP
                         151                                                        200
A. nidulans HMG  (147)   AADAIFVPANASAQLL PHTPNLESFESHDSSLVFTLPFDQVFQLRAVQE
G. zeae HMG      (139)   RSSHVFVPQNLSTTPLPSTKNSFTAYSQDSILAYSLFYAEG-----
N. crassa HMG    (135)   QTNTVPLPSNLSTPLPSTAISFT-MSQDSALAFSLFYSDAPEFLANAQE
S. cereviseae HMG2 (121) SLDDVIYSVDHTRYLLSEEPKLPTELVSENGTKWRLRNNSN----
S. cereviseae HMG1 (122) ELANTVFEKDNLKYLLQEDLSVSKEISSTDGTKWRLRSDRK----
Y. lipolytica HMG (100)  CAVAVSDLDHRIVMDYKQWAPWTASNEQIASENHIWKHSFK----D-
Consensus        (151)   A   VPVP N  SI LLP T  IFT YSQDSSL FSLPYS
                         201                                                        250
A. nidulans HMG  (197)   LPDPTLEDDEGEQKR---WIMRATRGPVSGPNGTHSSWLSDAWSSFVDLL
G. zeae HMG      (180)   -----------------PDVVQWANNAWTEFLDLL
N. crassa HMG    (184)   IPNAVSSQETIETERGHEKKMWIMKAARVQTRSSTVKWVQNAWVEFLDLL
S. cereviseae HMG2 (162) ---------------------------FILDLINIYRNMVKQFSNKT
S. cereviseae HMG1 (163) ---------------------------SLFDVKTLAYSLFDVFSENN
Y. lipolytica HMG (142)  ---------------------------HVAFSWIKWFRWAYLRLSTLL
Consensus        (201)       DIV W  NAW   FSDLI
```

FIG.7B

```
                      251                                                  300
A. nidulans HMG (244) KHAETIDIIMTLGYLAMYLSFASLEFSMKQLGSKFWIATTVLFSGMFAF
G. zeae HMG     (198) KNAETLDIVIMFLGYTAMHLTFVSLELSMRKIGSKFWLGICTLFSSVFAF
N. crassa HMG   (234) RNAETIDILIMALGYISMHLTFVSLELSMRRMGSNFWIATSVIFSSIFAF
S. cereviseae HMG2 (182) SEFDQFDLEIELAAYLQFYTLCCLFNDMRKLGSKFWLSEFSALSNSACAL
S. cereviseae HMG1 (183) TQADPFDVLIMVIAYLMMFYTIFGLFNDMRKTGSNFWLSASTVVNSASSL
Y. lipolytica HMG (163) QGADNFDIAVVALQYLAMHYTFFSLFRSKRKVGSHEWLIASMALVSSFFAF
Consensus       (251) KNADTFDIIM LGYLAMHYTF SLF SMRKLGSKFWLATS LFSSIFAF
                      301                                                  350
A. nidulans HMG (294) LFGLLVTTKFG-VPLNLLLSEGLPEIMTTIGEKPTLTRAVLSASIDK
G. zeae HMG     (248) LFGLLVTTKLG-VPISVILLSEGLPEHMLTIGEKNMLIRAVMSHALEH
N. crassa HMG   (284) LFGLLVTTKLG-VEMNMVLLSEGLPELWVTIGFEKNIMTRAVLSHALQH
S. cereviseae HMG2 (232) YLSLYTTHSLLKKPASLSLVIGLPFTVVIISEKHKVRLAAFSLQKFHRI
S. cereviseae HMG1 (233) FLALYTQCLLGKEVSALTLFEGLPFLWVVGEKHKIKIAQYALEKFERV
Y. lipolytica HMG (213) LLAVVASSLG-YRPSMIITMSEGLPEHIVAIEFDRKVNLASEVITSKSSQ
Consensus       (301) LLGLLVTTKLG VPISMLLSEGLPFLVVTIGFEKKIVLTRAVLS AID
                      351                                                  400
A. nidulans HMG (343) KRQGS------ATSTPSSIQDSIQTAIREQGEFITRDYCIEISLLIA
G. zeae HMG     (297) RRQIQNSKSGKGSPERSMQNVIQYAVQSAIKEKGEFIMRDYAIEIVILAL
N. crassa HMG   (333) RRPTE--KSGKPSKQADSAHSIQSAIQLAIKEKGEDIVKDYAIEAGIIML
S. cereviseae HMG2 (282) S--------IDKKITVSNIIYEAMFQEGAYIIRDYLFYISSFIQ
S. cereviseae HMG1 (283) G--------LSKRIITDEIVFESVSEEGGRLIQDILCIEAFIQ
Y. lipolytica HMG (262) --------LARMVQVITKIASKALFEVSLEVALEL
Consensus       (351)  S   SIQ AIQ AIKE GFEIIRDYAIEISLLIA

FIG.7C
```

```
                      551                                              600
A. nidulans HMG  (524) DPFKVAENGLDATYVSAKSQKLETLVTVVPPIKVKLEYPSVHYAKLGES-
G. zeae HMG      (488) DPFKVASNGLDATLAPAKSNNRPTLVTVLTPIKYELEYPSIHYALGSAIN
N. crassa HMG    (527) DPFKVASNGLDIILEAARADGRETTVTVLTPIRYELEYPSTHYDLPQKS-
S. cereviseae HMG2 (439) S---TIYSLPNFINYKDIGNLSNQVIISVLPKQMYTPLKKYHQIEDSVL-
S. cereviseae HMG1 (440) K---ERVSLPDEITSNASENEKEQAIVSVTPLLMYKPIKSYQRIEDMVL-
Y. lipolytica HMG (416) TPITLSPELLHATPASVP----VVTFVPSVVEHSQLIQLEDALTE-
Consensus        (551) DPFKVA NLLDAI AAAKSN RETLVTVVTPIKYELEYPSIHY E  S 601                                              650
A. nidulans HMG  (573) ----QSIEEYTDQLLDAVGGHVLNGVLKSIEDPVISKWITAVLTISIVL
G. zeae HMG      (538) GNNAEYTDAFHHHFQGYGVGGRMVGGILKSIEDPVLSKWIVTALALSVAL
N. crassa HMG    (576) -----AEVEGGDYANLGGYGGRMVGSILKSLEDPTLSKWIVVALATSVAL
S. cereviseae HMG2 (485) ------------------LEDSVSNAIRDQFISKIIFFAFAVSISI-
S. cereviseae HMG1 (486) ------------------LERNVSVAIRDFVSKLVLSALVCSAVH-
Y. lipolytica HMG (460) ------------------FIAACSKIIGDPVISKYIFCLMVSTAL
Consensus        (601)                    G GG MLGSVSKSIEDPVISKWIVALALSIAL 651                                              700
A. nidulans HMG  (619) NGYLFNAARWSIKEQAAPAPKEP----------------------
G. zeae HMG      (588) NGYLFNAVARWGIKDPNVPEHNIDRNELARAQQFNDTGSATLPLGEYMPF
N. crassa HMG    (621) NGYLFNAARWGIKDPNVPDHPINPKELDEAQKENDTASATLPLGEYMKPL
S. cereviseae HMG2 (514) NVYLLNAAKIHTGYMNFQPCSNKIDCLVVQQKSATIEFSETRSMPLASGL
S. cereviseae HMG1 (515) NVYLLNAARIHTSYTADQLVKTEVTKKSFTAPVQKASTPVLTNKTVISGS
Y. lipolytica HMG (488) NVYIFGATREVVRTQSVKVVEKHMPIVIE------K----------
Consensus        (651) NVYLFNAARW IKDPNV       EV EL   Q    N    SA L   I   T
```

FIG.7D

```
                        551                                                                600
A. nidulans HMG  (524) DPFKVAENGLDATYVSAKSCKLETLVTVVEPIKVKLEYPSVHYAKLGES-
G. zeae HMG      (488) DPFKVASNGLDATLAPAKSNNRPTLVTVLTPIKYELEYPSIHYALGSAIN
N. crassa HMG    (527) DPFKVASNGLDIILEARADGRETTVTVLTPIRYELEYPSTHYDLPQKS-
S. cereviseae HMG2 (439) S---TIYSIPNFINYKDIGNLSNQVIISVLPKQMYTPLKKYHQIEDSVL
S. cereviseae HMG1 (440) K---ERVSLPDEIISNASENFKEQAIVSVTPLLMYKPIKSYQRIEDMVL-
Y. lipolytica HMG (416) TPITLSPELLHAIPASVP------VWVTFVPSWVEHSQLIEQLEDALTE-
Consensus        (551) DPFKVA NLLDAI AAAKSN RETLVVTPIKYELEYPSIHY E  S 601                                                                650
A. nidulans HMG  (573) -----QSIEEYTDQLLDAVGGHVLNGVLKSIEDPVISKWITAVLTISIVL
G. zeae HMG      (538) GNNAEYTDAFHHHFQGYGVGGRMVGGILKSLEDPVLSKWIVIALAISVAL
N. crassa HMG    (576) AEVEGGDYANLGGYGVGGRMVGSILKSILKSLEDPTLSKWIVALAISVAL
S. cereviseae HMG2 (485) --------L-----------IFDSVSNAIRDQFTISKIFFFAFAVSISI
S. cereviseae HMG1 (486) --------L-----------LLRNVSVAIRDFVSKLVLSALVCSAVL
Y. lipolytica HMG (460) ----------------------FIAACSKIIGDPVISKYIFLCLMVSTAL
Consensus        (601)                    L     G GG MLGSVSKSIEDPVISKWIVIALALSIAL
                                                                                           700
A. nidulans HMG  (619) NGYLFNAARWSIKEFQAAPAPKEP-------------------------
G. zeae HMG      (588) NGYLFNVARWGIKDPNVPEHNIDRMELARAQQFNDTGSATLPLGEYMPFT
N. crassa HMG    (621) NGYLFNAARWGIKDPNVPDHPINPKELDEAQKENDTASATLPLGEYMKPT
S. cereviseae HMG2 (514) NVYLLNAAKIHTGYMNFQPCSNKTDDLVVQQKSATIEFSETRSMPLASGL
S. cereviseae HMG1 (515) NVYLLNAARIHTSYTADQLVKTEVTKKSFTAPVQKASTPVLTNKTVTSGS
Y. lipolytica HMG (488) NVYLFGATREVRTQSVKVVEKHMPIMIE--K------------------
Consensus        (651) NVYLFNAARW IKDPNV         EV EL    Q  N    SA L    I  T
```

*FIG.7E*

```
                        701                                                  750
A. nidulans HMG  (643) ------------------------AKPKVYPKTDLNAGPKRSMEECEAMLKA
    G. zeae HMG  (638) FMR--TEPSTPAIFDEAEGLQMTKARSDKLPNRIPNEE-----LEKLIAE
  N. crassa HMG  (671) APSSPVAPITESSTDENDAQAKENRAVTLAAQRATTIRSQGELDKMIAE
 S. cerevisea HMG2 (564) E----TPVTAKDIISEEIQNN----ECVYALSSQDEFIRPLSNLVELJEK
 S. cereviseae HMG1 (565) K-----VKSISAQSSSSGESSSEEDDSRUIESLDKKIRPLELEALLSS
 Y. lipolytica HMG (518) --------RSEREEDTSSELSIELTVGKQPKVTETRSLDDLEATMKA
      Consensus   (701)                         TPA TDDE S  S      V  KI    IRSLEELEALLAA 751                                                  800
A. nidulans HMG  (671) KKAAYLSDELLHRSLSGKLEGYALLKSLENEELMSRVDAFLRAVKLRRA
    G. zeae HMG  (681) KRVKEMSDEEIVSLSMRCKIPGVYALLKTLG-   DETRAVKIRRS
  N. crassa HMG  (721) KRTHELNDEEJVHLSLKGKIPGVALEKTLK-    DETRAVKVRRS
 S. cerevisea HMG2 (607) EQLKNMNNTEVSNLVNGKLPLYSLEKKLE-     DTLRAVILVRRK
 S. cereviseae HMG1 (611) GNTKQLKNKEVARLVLHGKLPLYALEKKLG-    DTTRAVAVRRK
 Y. lipolytica HMG (558) GKTKLLEDHEVVKLSLEGKLPLYALFKOLG-    DNLRAVGIRRS
      Consensus   (751) KKTK L DEEVV LSL GKLPLYALEKTLG       DFTRAVKIRRS 801                                                  850
A. nidulans HMG  (721) VVSRTPATSAVTSSIETSKLHYEDYNYALVHGACCENVIGILPLPLGVAG
    G. zeae HMG  (722) LIARNRATSDITHSLERSKLPEKYNWERVFCACCENVIGYMPLPVGVAG
  N. crassa HMG  (762) IISRTKATEELTNILRSKLEYQNVNWAQVHGACCENVIGYMPIPVGVAG
 S. cerevisea HMG2 (648) ALIST----L-AESPILVSEKLPFRNYDYDRVEGACCENVIGYMPLPVGVAG
 S. cereviseae HMG1 (652) ALLSI----L-AEAPVLASCKLFYKNYDYDRVEGACCENVIGYMPLPVGVAG
 Y. lipolytica HMG (599) IISQ----Q-SNTKTLFTSKLYLHYDYDRVFGACCENVIGYMPLPVGVAG
      Consensus   (801) IISR  ATSALT SLESSKLPYKNYNYDRVFGACCENVIGYMPLPVGVAG
```

*FIG.7F*

```
                                 851                                                              900
A. nidulans HMG    (771) PLVTDGQSYFIPMATTEGVLVASASRGAKAINAGGAVIVLTGDGMTRGE
      G. zeae HMG  (772) RLVTDGQSYFIPMATTEGVLVASASRGCKAINAGGAVTVLTADGMTRGE
    N. crassa HMG  (812) PLVTDGQSEFVPMATTEGVLVASTSRGCKAINSGGAVTVLTADGMTRGE
 S. cereviseae HMG2(694) PLITDGTSYHIPMATTEGCLVASAMPGCKAINAGGATTVLTKDGMTRGE
 S. cereviseae HMG1(698) PLVTDGTSYHIPMATTEGCLVASAMRGCKAINAGGATTVLTKDGMIRGE
   Y. lipolytica HMG(645) PMNTDGKNYHIPMATTEGCLVASTMRGCKAINAGGVTVLTLDGMTRGE
        Consensus  (851) PLVIDGQSYHIPMATTEGVLVASASRGCKAINAGGAVTVLTADGMTRGP
                                 901                                                              950
A. nidulans HMG    (821) CVGFIPTLARAAAAKVWLDSEEGKSVMTAAFNSTSRFARLQHIKTALAGTY
      G. zeae HMG  (822) CVAFETLERAGAPAKLWIDSEAGSDIMKKAFNSTSRFARLQSMKTALAGTN
    N. crassa HMG  (862) CVQEETIERAGAPAKLWLDSEKGOSIMKKAFNSTSRFARLETMKTAMAGTN
 S. cereviseae HMG2(744) VVRFPTLIRSGACKIWLDSEEGQNSIKKAFNSTSRFARLQHTQTCLAGDL
 S. cereviseae HMG1(748) VVRFPTLKRSGACKIWLDSEEGQNALKKAFNSTSRFARLQHTQTCLAGDL
   Y. lipolytica HMG(695) CVSEPSIKRAGAAKIWLDESEGLKSMRKAFNSTSRFARLQSLHSTLAGNL
        Consensus  (901) CV FPTL RAGAAKIWLDSEEGQ SMKKAFNSTSRFARLQHIKTALAGTL
                                 951                                                              1000
A. nidulans HMG    (871) LYIRFKTTTGDAMGMNMISKGVEKAIHVMATECGEDDMATISMVSGNFCTD
      G. zeae HMG  (872) LYIRFKTTTGDAMGMNIISKGVEHALSVMSNEAGEDDMQIVSVSGNYCTD
    N. crassa HMG  (912) LYURFKITTTGDAMGMNIISKGVEHALSVMYNEG-FEDMNIVSLSGNYCTD
 S. cereviseae HMG2(794) LFMRFRTTTGDAMGMNMISKGVEYSIKQMVEEYGMEDMEVVSVSGNYCTD
 S. cereviseae HMG1(798) LFMRFRTTTGDAMGMNMISKGVEYSIKQMVEEYGMEDMEVMSVSGNYCTD
   Y. lipolytica HMG(745) LFIRFRTTTGDAMGMNMISKGVEHSLAVMKEYGFPLMDIVSVSGNYCTD
        Consensus  (951) LFIRFKTTTGDAMGMNMISKGVEHALSVMV EYGFEDMEIVSVSGNYCTD
```

```
                        1151                                                      1200
A. nidulans HMG  (1071) AAVLAGELSLCSALAAGHLVRAHMAHNRSAAPTRSATPVSAAVGATRGLS
G. zeae HMG      (1072) ASVLAGELSLCSALAAGHLVRAHMQHNRSAAPSRSTTPAPMTPVRSFDTK
N. crassa HMG    (1111) AAVLAGELSLCSALAAGHLVKAHMAHNRSAPPTRTSTPAPAAAAGLTMTS
S. cerevisea HMG2 (994) CAVLAGELSLCSALAAGHLVQSHMTHNRKTNKANELP----QPSNKGPPC
S. cereviseae HMG1 (998) CAVLAGELSLCAALAAGHLVQSHMTHNRKPAEPTKPNNLDATDINRLKDG
Y. lipolytica HMG (945) SGVLAAELSLCSALAAGHLVQSIMTHNFSQAPTPAKQSQADLQRLQNCSN
Consensus        (1151) AAVLAGELSLCSALAAGHLVQAHMTHNRSAAPTRS TP  A         T 1201                                                      1250
A. nidulans HMG  (1121) MTSSR---------------------------------------------
G. zeae HMG      (1122) VRCQPNNKDIRNILLTQHPSKPTITYSKRVIKSTIHLNPLLBALEDNSVQ
N. crassa HMG    (1161) S---N---PNAAAVERSRR-------------------------------
S. cerevisea HMG2 (1040) KTSALL--------------------------------------------
S. cereviseae HMG1 (1048) SVICIKS-------------------------------------------
Y. lipolytica HMG (995) ICIRS---------------------------------------------
Consensus        (1201) I S 1251                              1289
A. nidulans HMG  (1126) -----------------------------
G. zeae HMG      (1172) TRDVQLGDQVSTRGTLDAVGGPQGGVAAGGVARRVVGS
N. crassa HMG    (1174) -----------------------------
S. cerevisea HMG2 (1046) -----------------------------
S. cereviseae HMG1 (1055) -----------------------------
Y. lipolytica HMG (1000) -----------------------------
Consensus        (1251)
```

FIG. 71

FIG. 8A  Y. Lipolytica Genes

| Genbank protein GI number | Genbank protein Accession Number | polypeptide | Y.lipolytica gene | Oligo 1 | Oligo 2 |
|---|---|---|---|---|---|
| 50557288 | XP_506052 | HMG-CoA synthase | YALI0F30481g | MO4890-5'ctctagacacaaaaatgtcgcaacccccagaacgt | MO4981-5'cacgcgtctactgctgatctgtact |
| 50546973 | XP_500956 | Mevalonate Kinase | YALI0B16038g | MO4982-5'cgctagcccacaaaaatgactacatcatttcggcg c | MO4983-5'cacgcgtctaatgggtccagggaccga |
| 50552418 | XP_503619 | Phosphomevalonate kinase | YALI0E06193g | MO4984-5'ctctagacacaaaaatgaccactattcggtcccg | MO4985-5'cggcgcgccctacttgaacccctctcga |
| 50555265 | XP_505041 | Mevalonate Pyrophosphate Decarboxylase | YALI0F05632g | MO4986-5'ctctagacacaaaaatgatccaccaggcctccacc a | MO4987-5'cacgcgtctactgctgtttcagag |
| 50555131 | XP_504974 | IPP Isomerase | YALI0F04015g | MO4988-5'ctctagacacaaaaatgacgacgtctacagcga | MO4989-5'cacgcgtctacttgatccaccgccgaa |
| 50552378 | XP_503599 | FPP synthase | YALI0E05753 | MO4990-5'ctctagacacaaaaatgtccaaggcgaaattcgaa | MO4991-5'cacgcgtctacttctgtcgcttgtaaa |
| 50553402 | XP_504112 | Malic Enzyme | YALI0E18634g | MO4992-5'ctctagacacaaaaatgttacgactacgaaccat | MO4993-5'cacgcgtctagtcgtaacccgcacat |

FIG. 8B    Y. Lipolytica Genes

| | | | | | |
|---|---|---|---|---|---|
| 50552824 | XP_503822 | AMP Deaminase | YALI0E11495g | MO4996-5'cgctagcccacaaaaatgccgcagcaagcaatgga | MO4997-5'cacgcgttaaccatgcagccgctcaa |
| 50550873 | XP_502909 | Malate Dehydrogenase Homolog | YALI0D16753g | MO5000-5'ctctagacacaaaaatgttccgaacccgagttac | MO5001-5'cacgcgtttaagggttctgcttgacaa |
| 50550839 | XP_502892 | Isocitrate Dehydrogenase | YALI0D16247g | MO5004-5'ctctagacacaaaaatgacacaaacgcacaatct | MO5005-5'cacgcgtttacatcttgtacgcagggt |
| 50545147 | XP_500111 | Fructose 1,6 bisphosphatase | YALI0A15972g | MO5008-5'ctctagacacaaaaatggaagccaacccgaagt | MO5009-5'cacgcgttcatttcagaaggtacttct |
| 50552796 | XP_503808 | Acetoacetyl CoA thiolase | YALI0E11099g | MO4852-5'ctctagacacaaaaatgcgactcactctgccc | MO4853-5'cacgcgtctactgacagaagagagaccttc |
| 50554757 | XP_504787 | ATP citrate lyase subunit 1 | YALI0E34793g | MO4741-5'ttctagacccaaaaatgtctgccaacgagaacatct c | MO4743-5'aacgcgtctatgatcgagtcttggccttg |
| 50551515 | XP_503231 | ATP citrate lyase subunit 2 | YALI0D24431g | MO4760-5'ttctagacacaaaaatgtcagcgaaatccattcacg a | MO4861-5'cacgcgttaaactccgagaggagtgg |
| 50553046 | XP_503933 | Malate Dehydrogenase | YALI0E14190g | MO4994-5'ctctagacacaaaagtggttaaagctgtcgttgc | MO4995-5'cacgcgtttacttggcaggaggagggt |

FIG.8C

Y. Lipolytica Genes

| | | | | |
|---|---|---|---|---|
| 50553728 | XP_504275 | Glucose 6 Phosphate Dehydrogenase | YALI0E22649g | MO4998-<br>5'ctctagacacaaaaatgactggcaccttaccaa | MO4999-<br>5'cacgcgttcacgagagcccttggtga |
| 50546937 | XP_500938 | 6-phosphogluconate dehydrogenase | YALI0B15598g | MO5002-<br>5'ctctagacacaaaaatgactgacacttcaaacat | MO5003-<br>5'cacgcgtttaagcatcgtaagtggaag |
| 50550013 | XP_502479 | Isocitrate dehydrogenase | YALI0D06303g | MO5006-<br>5'ctctagacacaaaaatgctcaaccttagaaccgc | MO5007-<br>5'cacgcgtcacttgagtcgcttgataa |

FIG.9A
Schematic diagram of certain plasmids used herein
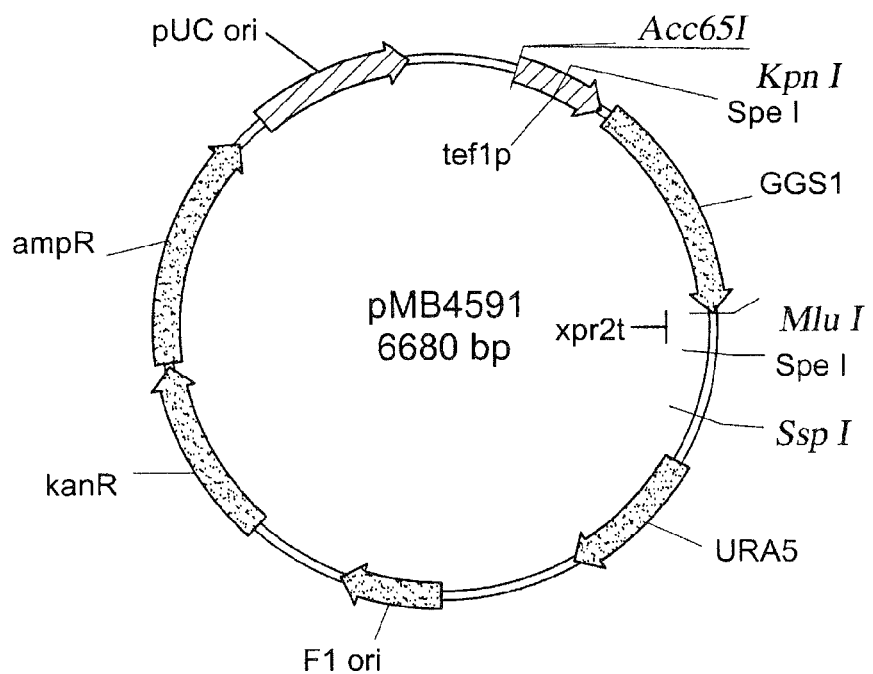
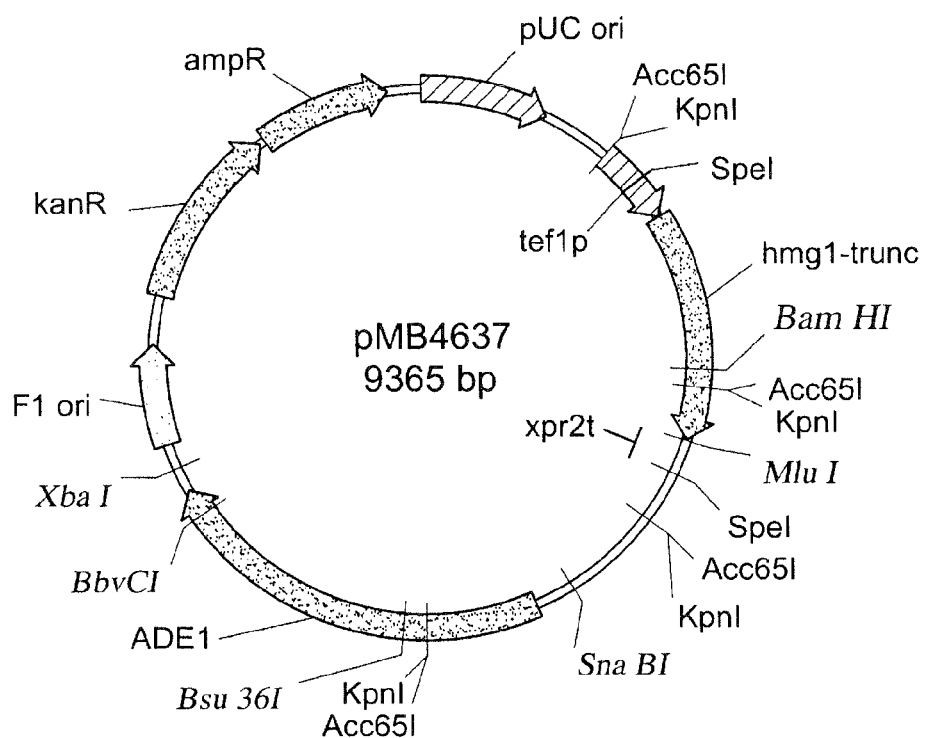

FIG.9B
Schematic diagram of certain plasmids used herein
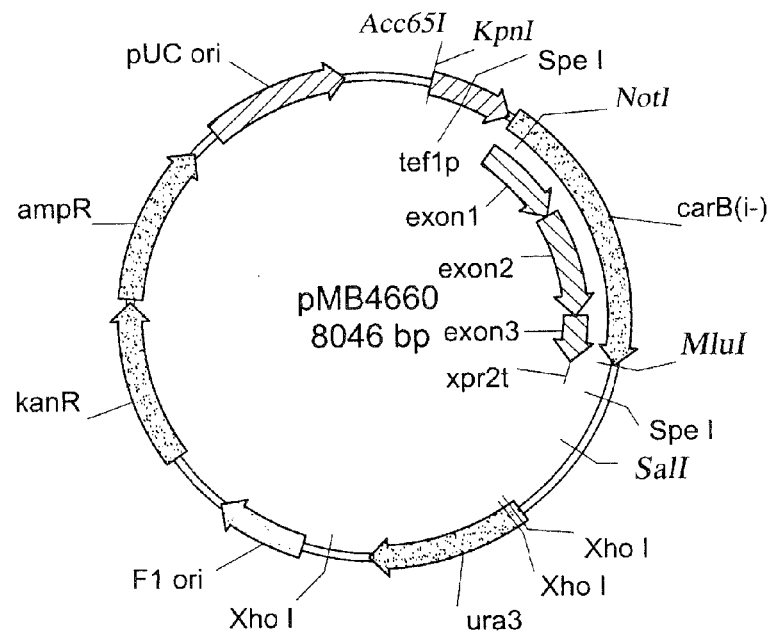
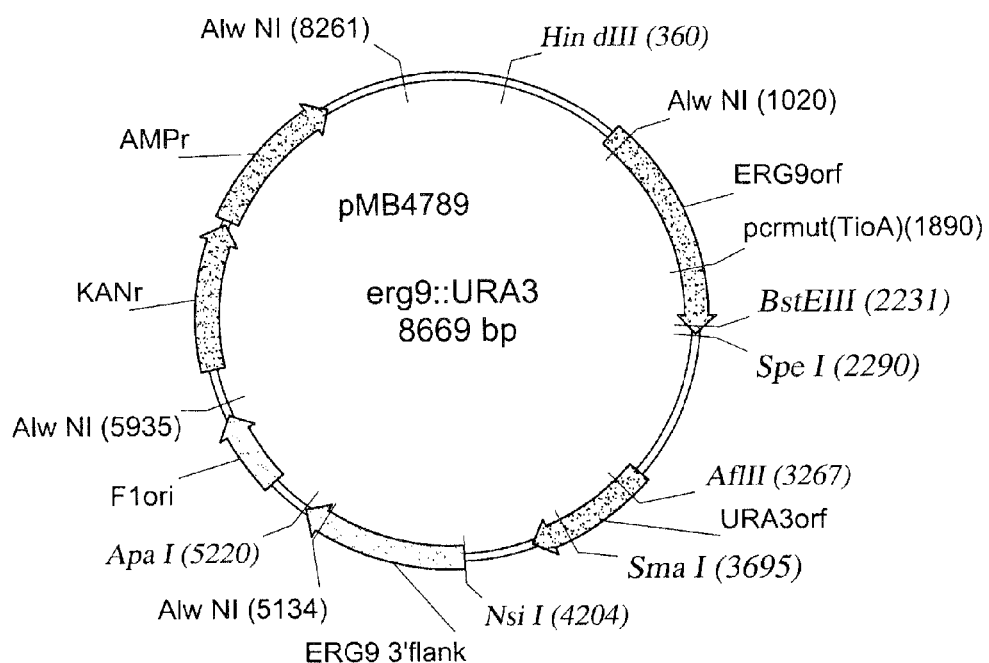

FIG.9C
Schematic diagram of certain plasmids used herein
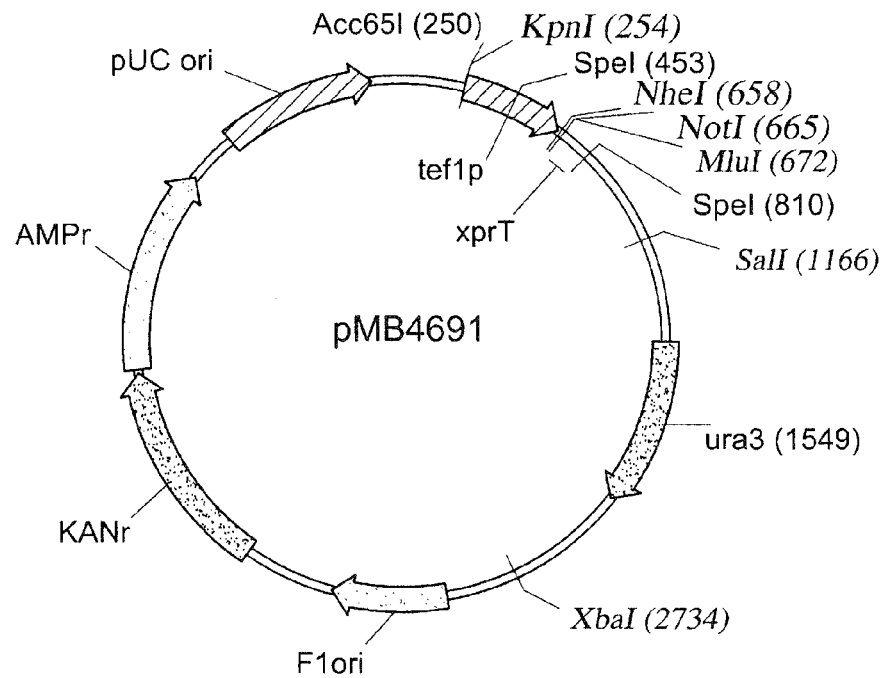
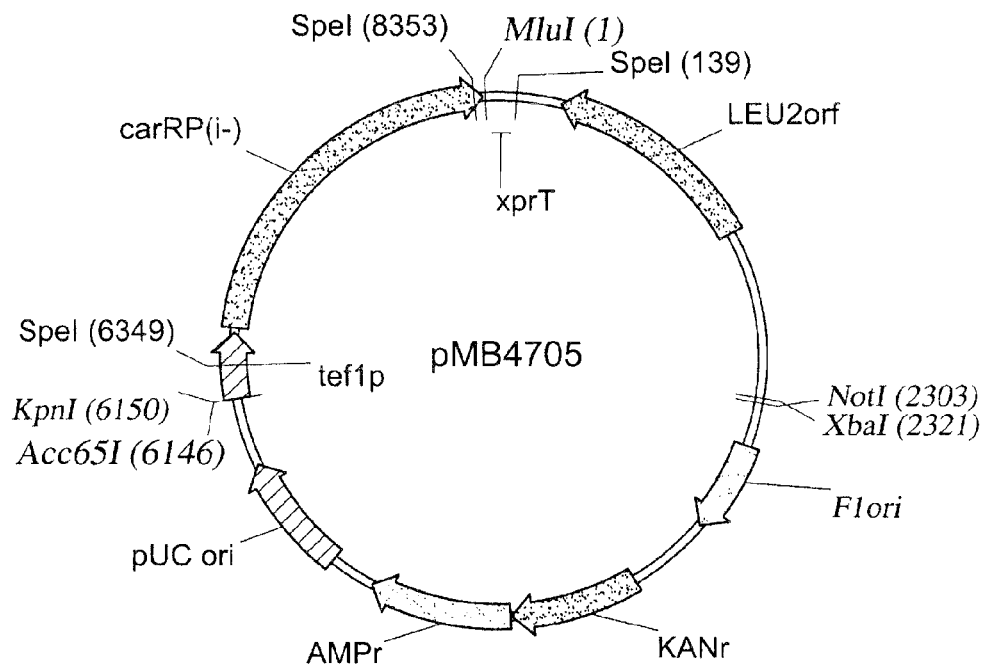

FIG. 10A

Vitamin D

Vitamin D is a steroid hormone that functions to regulate specific gene expression following interaction with its intracellular receptor. The biologically active form of the hormone is 1,25-dihydroxy vitamin $D_3$ (1,25-$(OH)_2D_3$, also termed calcitriol). Calcitriol functions primarily to regulate calcium and phosphorous homeostasis.

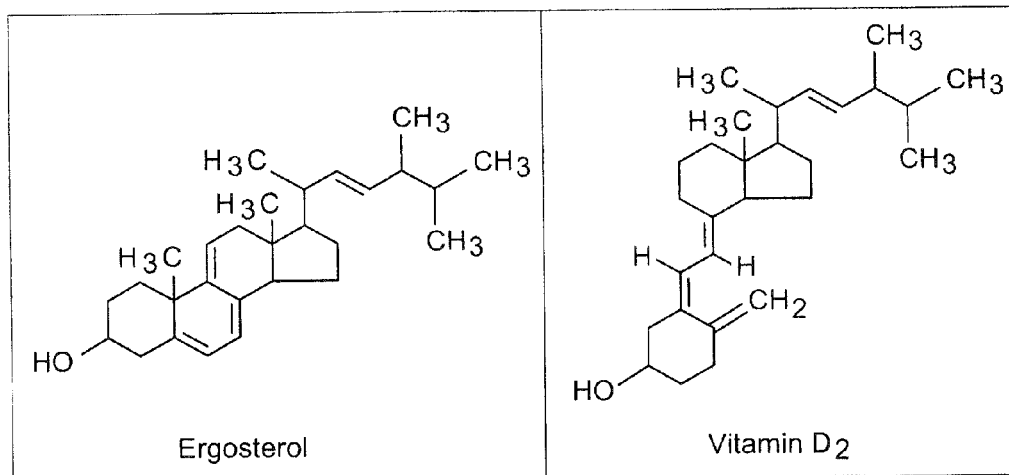

Ergosterol | Vitamin $D_2$

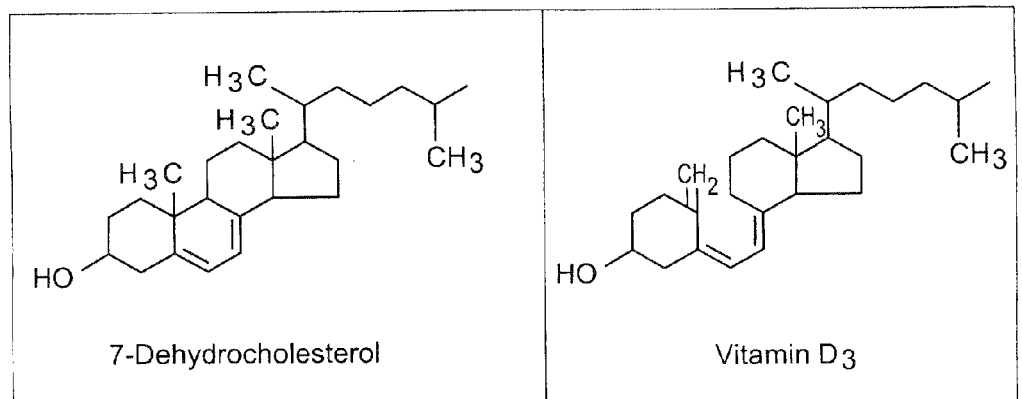

7-Dehydrocholesterol | Vitamin $D_3$

Active calitriol is derived from ergosterol (produced in plants) and from 7-dehydrocholesterol (produced in the skin). Ergocalciferol (vitamin $D_2$) is formed by uv irradiation of ergosterol. In the skin 7-dehydrocholesterol is converted to cholecalciferol (vitamin $D_3$) following uv irradiation.
Vitamin $D_2$ and $D_3$ are processed to $D_2$-calcitriol and $D_3$-calcitriol, respectively, by the same enzymatic pathways in the body. Cholecalciferol (or egrocalciferol) are absorbed from the intestine and transported to the liver bound to a specific vitamin D-binding protein. In the liver cholecalciferol is hydroxylated at the 25 position by a specific $D_3$-25-

FIG. 10B hydroxylase generating 25-hydroxy-$D_3$ [25-(OH)$D_3$] which is the major circulating form of vitamin D. Conversion of 25-(OH)$D_3$ to its biologically active form, calcitriol, occurs through the activity of a specific $D_3$-1-hydroxylase present in the proximal convoluted tubules of the kidneys, and in bone and placenta. 25-(OH)$D_3$ can also be hydroxylated at the 24 position by a specific $D_3$-24-hydroxylase in the kidneys, intestine, placenta and cartilage.

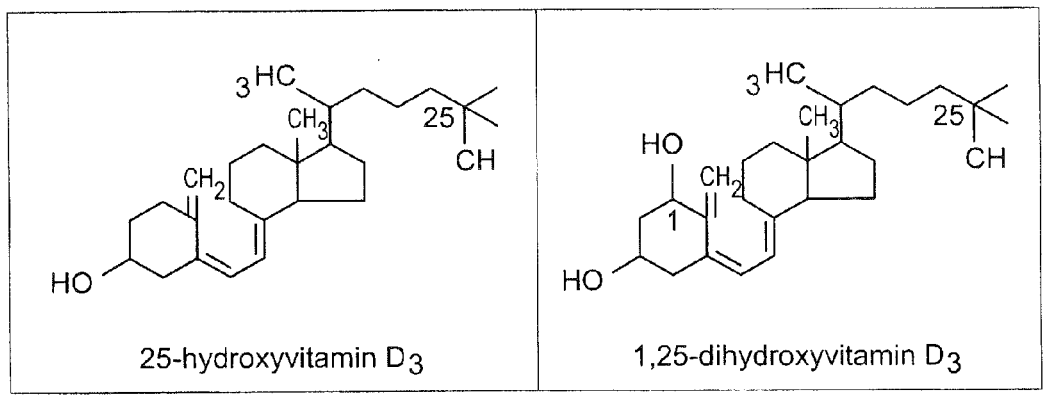

25-hydroxyvitamin $D_3$    1,25-dihydroxyvitamin $D_3$

Calcitriol functions in concert with parathyroid hormone (PTH) and calcitonin to regulate serum calcium and phosphorous levels. PTH is released in response to low serum calcium and induces the production of calcitriol. In contrast, reduced levels of PTH stimulate synthesis of the inactive 24,25-(OD)$_2D_3$. In the intestinal epithelium, calcitriol functions as a steroid hormone in inducing the expression of calbindin$D_{28K}$, a protein involved in intestinal calcium absorption. The increased absorption of calcium ions requires concomitant absorption of a negatively charged counter ion to maintain electrical neutrality. The predominant counter ion is Pi. When plasma calcium levels fall the major sites of action of calcitriol and PTH are bone where they stimulate bone resorption and the kidneys where they inhibit calcium excretion by stimulating reabsorption by the distal tubules. the role of calcitonin in calcium homeostasis is to decrease elevated serum calcium levels by inhibiting bone resorption.

Clinical Significance of Vitamin D Deficiency

As a result of the addition of vitamin D to milk, deficiencies in this vitamin are rare in this country. The main symptom of vitamin D deficiency in children is rickets and in adults is osteomalacia. Rickets is characterized improper mineralization during the development of the bones resulting in soft bones. Osteomalacia is characterized by demineralization of previously formed bone leading to increased softness and susceptibility to fracture.

FIG.11A
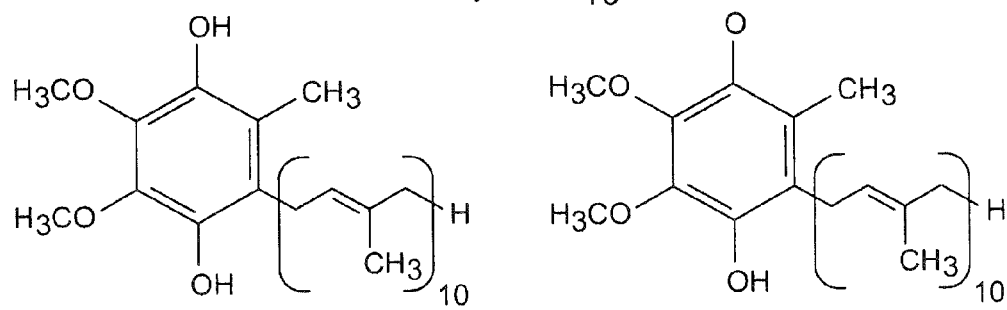
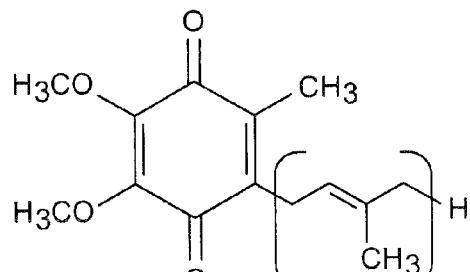

FIG.11B
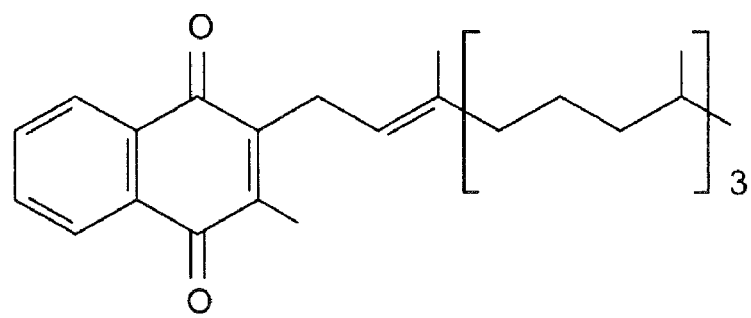
PHYLLOQUINONE
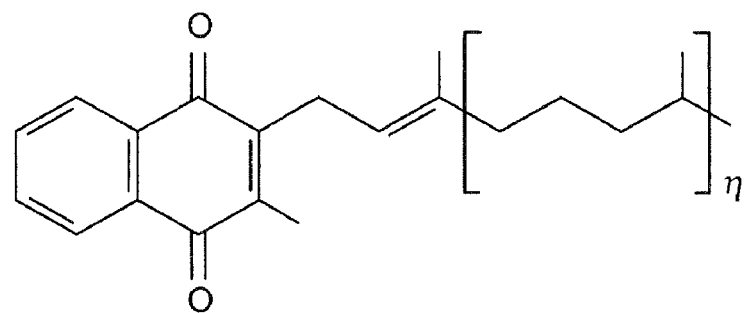
MENAQUINONES
VITAMIN K

FIG.11C
Vitamin E - Structures and Chemistry
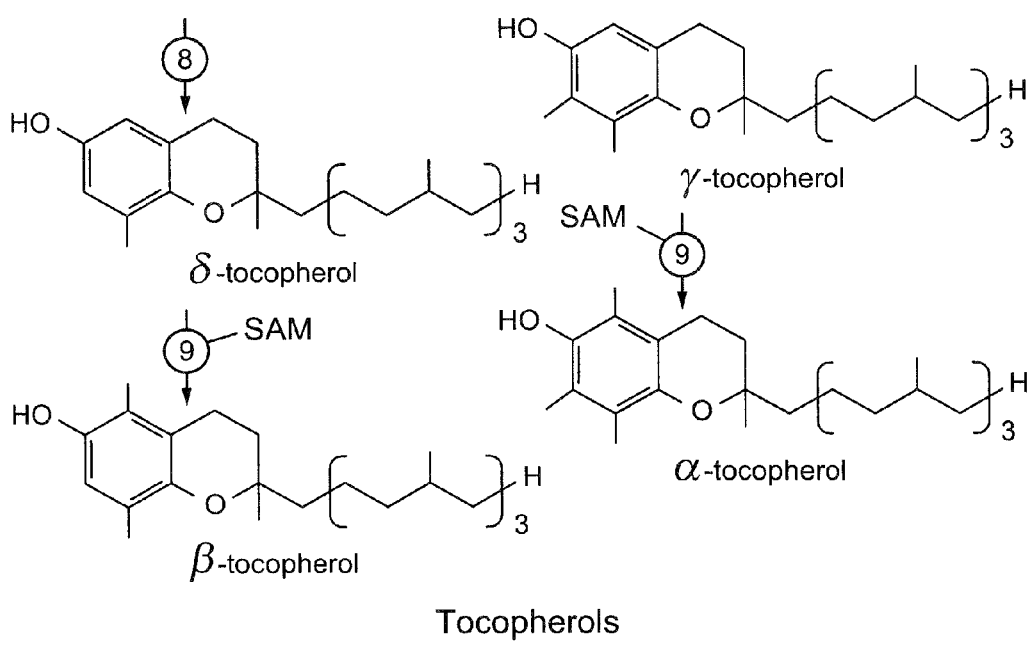
Tocopherols
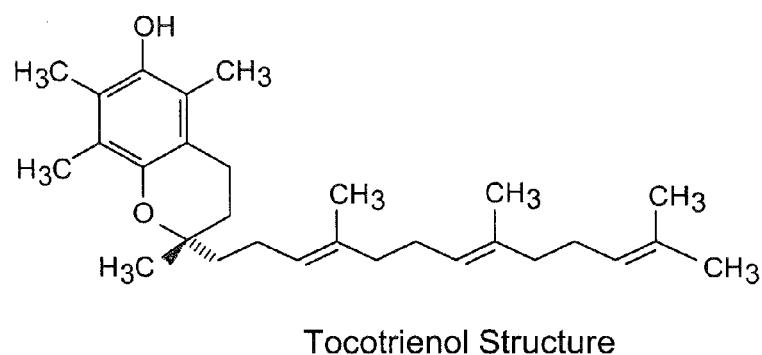
Tocotrienol Structure

PRODUCTION OF STEROLS IN OLEAGINOUS YEAST AND FUNGI

CROSS REFERENCE TO RELATED APPLICATIONS

This application is a national phase application under 35 U.S.C. §371 of PCT International Application No. PCT/US2007/021091, filed Sep. 28, 2007, which is copending with, shares at least one common inventor with, and claims priority to U.S. provisional patent application No. 60/848,582, filed Sep. 28, 2006, the contents of which are hereby incorporated by reference in their entirety.

BACKGROUND OF THE INVENTION

Sterol compounds play a variety of important roles in biological and industrial systems. For example, certain sterol compounds are provitamins or vitamins and/or lubricants or moisturizers; sterol compounds are also key synthetic intermediates for saponins and steroid hormones. Given the rapidly growing market for nutritional supplements and other products containing sterol compounds, there remains a need for improved systems for enabling cost effective production, isolation, and/or formulation of sterol compounds.

SUMMARY OF THE INVENTION

The present invention provides improved systems for the biological production of certain sterol compounds. In particular, the present invention provides improved systems for the biological production of sterol compounds such as squalene, lanosterol, zymosterol, ergosterol, 7-dehydrocholesterol (provitamin D3) and/or related compounds (e.g., metabolite derivatives, and particularly vitamin D compound(s)).

In one aspect, the invention encompasses the discovery that it is desirable to produce certain sterols, and particularly to produce squalene, lanosterol, zymosterol, ergosterol, 7-dehydrocholesterol (provitamin D3) and/or vitamin D compounds in oleaginous organisms. In some embodiments, the present invention thus provides biological systems able to accumulate sterols in lipid bodies. In some embodiments, the biological systems may produce higher levels of sterol compounds when such compounds are sequestered in lipid bodies. Regardless of whether absolute levels are higher; however, compounds that are accumulated within lipid bodies in oleaginous organisms are readily isolatable through isolation of the lipid bodies.

The present invention therefore provides oleaginous fungi (including, for example, yeast or other unicellular fungi) that produce certain sterols, and in particular that produce squalene, lanosterol, zymosterol, ergosterol, 7-dehydrocholesterol (provitamin D3) and/or one or more vitamin D compounds. The present invention also provides methods of constructing such yeast and fungi, methods of using such yeast and fungi to produce the sterol compounds. The present invention further provides methods of preparing certain sterol compounds, and particularly of preparing squalene, lanosterol, zymosterol, ergosterol, 7-dehydrocholesterol (provitamin D3) and/or one or more vitamin D compounds, as well as compositions containing them, such as food or feed additives, nutritional supplements, machine oil products (e.g., lubricants), or compositions for nutraceutical, pharmaceutical and/or cosmetic applications. In particular, the present invention provides systems and methods for generating yeast and fungi containing one or more oleaginic and/or sterologenic modifications that increase the oleaginicity and/or alter their sterol-producing capabilities as compared with otherwise identical organisms that lack the modification(s).

In some embodiments, the present invention provides a recombinant fungus. In certain embodiments, the recombinant fungus is oleaginous in that it can accumulate lipid to at least about 20% of its dry cell weight; and the recombinant fungus produces at least one sterol compound, and can accumulate the produced sterol compound to at least about 1% of its dry cell weight; wherein the recombinant fungus comprises at least one modification as compared with a parental fungus, which parental fungus both is not oleaginous and does not accumulate the sterol compound to at least about 1% of its dry cell weight, the at least one modification being selected from the group consisting of sterologenic modifications, oleaginic modifications, and combinations thereof, and wherein the at least one modification alters oleaginicity of the recombinant fungus, confers to the recombinant fungus oleaginy, confers to the recombinant fungus the ability to produce the at least one sterol compound to a level at least about 1% of its dry cell weight, or confers to the recombinant fungus the ability to produce at least one sterol compound which the parental fungus does not produce.

In other embodiments, the recombinant fungus is oleaginous in that it can accumulate lipid to at least about 20% of its dry cell weight; and the recombinant fungus produces at least one sterol compound selected from the group consisting of: squalene, lanosterol, zymosterol, ergosterol, 7-dehydrocholesterol (provitamin D3), and combinations thereof, and can accumulate the produced sterol compound to at least about 1% of its dry cell weight; wherein the recombinant fungus comprises at least one modification as compared with a parental fungus, the at least one modification being selected from the group consisting of sterologenic modifications, oleaginic modifications, and combinations thereof, and wherein the at least one modification alters oleaginicity of the recombinant fungus, confers to the recombinant fungus oleaginy, confers to the recombinant fungus the ability to produce the at least one sterol compound to a level at least about 1% of its dry cell weight, or confers to the recombinant fungus the ability to produce at least one sterol compound which the parental fungus does not naturally produce.

In certain embodiments, the recombinant fungus is oleaginous in that it can accumulate lipid to at least about 20% of its dry cell weight; and the recombinant fungus produces at least one sterol compound, and can accumulate the produced sterol compound to at least about 1% of its dry cell weight; wherein the recombinant fungus is a member of a genus selected from the group consisting of: *Aspergillus, Blakeslea, Bottytis, Candida, Cercospora, Cryptococcus, Cunninghamella, Fusarium (Gibberella), Kluyveromyces, Lipomyces, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phaffia),* and *Yarrowia*; or is a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujikuroi (Gibberella zeae), Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa,*

*Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous (Phaffia rhodozyma)*, and *Yarrowia lipolytica*; wherein the recombinant fungus comprises at least one modification as compared with a parental fungus, the at least one modification being selected from the group consisting of sterologenic modifications, oleaginic modifications, and combinations thereof, and wherein the at least one modification alters oleaginicity of the recombinant fungus, confers to the recombinant fungus oleaginy, confers to the recombinant fungus the ability to produce the at least one sterol compound to a level at least about 1% of its dry cell weight, or confers to the recombinant fungus the ability to produce at least one sterol compound which the parental fungus does not naturally produce.

In some embodiments, the recombinant fungus is oleaginous in that it can accumulate lipid to at least about 20% of its dry cell weight; and the recombinant fungus produces at least one sterol compound selected from the group consisting of: squalene, lanosterol, zymosterol, ergosterol, 7-dehydrocholesterol (provitamin D3), and combinations thereof, and can accumulate the produced sterol compound to at least about 1% of its dry cell weight; wherein the recombinant fungus is a member of a genus selected from the group, consisting of: *Aspergillus, Blakeslea, Botrytis, Candida, Cercospora, Cryptococcus, Cunninghamella, Fusarium (Gibberella), Kluyveromyces, Lipomyces, Mortierella, Mucor, Neurospora, Penicillium, Phycomyces, Pichia (Hansenula), Puccinia, Pythium, Rhodosporidium, Rhodotorula, Saccharomyces, Sclerotium, Trichoderma, Trichosporon, Xanthophyllomyces (Phaffia)*, and *Yarrowia*; or is of a species selected from the group consisting of: *Aspergillus terreus, Aspergillus nidulans, Aspergillus niger, Blakeslea trispora, Botrytis cinerea, Candida japonica, Candida pulcherrima, Candida revkaufi, Candida tropicalis, Candida utilis, Cercospora nicotianae, Cryptococcus curvatus, Cunninghamella echinulata, Cunninghamella elegans, Fusarium fujilcuroi (Gibberella zeae), Kluyveromyces lactis, Lipomyces starkeyi, Lipomyces lipoferus, Mortierella alpina, Mortierella ramanniana, Mortierella isabellina, Mortierella vinacea, Mucor circinelloides, Neurospora crassa, Phycomyces blakesleanus, Pichia pastoris, Puccinia distincta, Pythium irregulare, Rhodosporidium toruloides, Rhodotorula glutinis, Rhodotorula graminis, Rhodotorula mucilaginosa, Rhodotorula pinicola, Rhodotorula gracilis, Saccharomyces cerevisiae, Sclerotium rolfsii, Trichoderma reesei, Trichosporon cutaneum, Trichosporon pullans, Xanthophyllomyces dendrorhous (Phaffia rhodozyma)*, and *Yarrowia lipolytica*; wherein the recombinant fungus comprises at least one modification as compared with a parental fungus, the at least one modification being selected from the group consisting of sterologenic modifications, oleaginic modifications, and combinations thereof, and wherein the at least one modification alters oleaginicity of the recombinant fungus, confers to the recombinant fungus oleaginy, confers to the recombinant fungus the ability to produce the at least one sterol compound to a level at least about 1% of its dry cell weight, or confers to the recombinant fungus the ability to produce at least one sterol compound which the parental fungus does not naturally produce.

In some embodiments, a recombinant fungus accumulates at least one sterol compound to a level selected from the group consisting of: above about 1%, above about 2%, above about 3%, above about 5%, and above about 10% of the fungus' dry cell weight.

The present invention provides a strain of *Yarrowia lipolytica* comprising one or more modifications selected from the group consisting of an oleaginic modification, a sterologenic modification, and combinations thereof, such that the strain accumulates from 1% to 15% of its dry cell weight as at least one sterol compound.

The present invention provides an engineered *Y. lipolytica* strain that produces squalene or 7-dehydrocholesterol (provitamin D3), the strain containing one or more sterologenic modifications selected from the group consisting of: decreased expression or activity of a *Y. lipolytica* GGPP synthase polypeptide; increased expression or activity of a truncated HMG CoA reductase polypeptide; increased expression or activity of an FPP synthase polypeptide; increased expression or activity of an IPP isomerase polypeptide; increased expression or activity of an HMG-CoA synthase polypeptide; increased expression or activity of a mevalonate kinase polypeptide; increased expression or activity of a phosphomevalonate kinase polypeptide; increased expression or activity of a mevalonate pyrophosphate decarboxylate polypeptide; increased expression or activity of a cytosolic malic enzyme polypeptide; increased expression or activity of a malate dehydrogenase polypeptide; increased expression or activity of an AMP deaminase polypeptide; increased expression or activity of a glucose 6 phosphate dehydrogenase polypeptide; increased expression or activity of a malate dehydrogenase homolog2 polypeptide; increased expression or activity of a GND1-6-phosphogluconate dehydrogenase polypeptide; increased expression or activity of a isocitrate dehydrogenase polypeptide; increased expression or activity of a IDH2-isocitrate dehydrogenase polypeptide; increased expression or activity of a fructose 1,6 bisphosphatase polypeptide; increased expression or activity of a Erg10-acetoacetyl CoA thiolase polypeptide; increased expression or activity of a squalene synthase polypeptide; and combinations thereof.

The present invention provides an engineered *Y. lipolytica* strain containing a truncated HMG CoA reductase polypeptide. The present invention provides an engineered *Y. lipolytica* strain having increased expression or activity of a squalene synthase gene.

The present invention provides a method of producing a sterol compound, the method comprising steps of: cultivating the fungus of any one of the preceding claims under conditions that allow production of the sterol compound; and isolating the produced sterol compound.

In some embodiments, a recombinant fungus accumulates lipid in the form of cytoplasmic oil bodies.

The present invention provides a composition comprising: lipid bodies; at least one sterol compound; and intact fungal cells.

The present invention provides a composition comprising: an oil suspension comprising: lipid bodies; at least one sterol compound; and intact fungal cells; a binder or filler.

The present invention provides a composition comprising: an oil suspension comprising: lipid bodies; at least one sterol compound; and intact fungal cells; and one or more other agents selected from the group consisting of chelating agents, pigments, salts, surfactants, moisturizers, viscosity modifiers, thickeners, emollients, fragrances, preservatives, and combinations thereof.

The present invention provides an isolated sterol compound composition, prepared by a method comprising steps of: cultivating a fungus under conditions that allow production of a sterol compound; and isolating the produced sterol compound.

The present invention provides a sterol compound composition comprising a *Y. lipolytica* cell containing at least 1% sterol compounds by weight.

The present invention provides a sterol compound composition comprising *Y. lipolytica* lipid bodies; and at least one sterol compound, wherein the at least one sterol compound is present at a level that is at least 1% by weight of the lipid bodies.

The present invention provides a feedstuff comprising a sterol compound in lipid bodies.

Additional aspects of the present invention will be apparent to those of ordinary skill in the art from the present description, including the appended claims.

BRIEF DESCRIPTION OF THE DRAWING

FIGS. 7A-I show an alignment of certain representative fungal HMG-CoA reductase polypeptides. As can be seen, these polypeptides show very high identity across the catalytic region, and also have complex membrane spanning domains. In some embodiments of the invention, these membrane-spanning domains are disrupted or are removed, so that, for example, a hyperactive version of the polypeptide may be produced.

FIGS. 8A-C depicts Genbank and sequence information for various *Y. lipolytica* genes.

FIGS. 9A-M present schematic diagrams of certain plasmids used herein.

FIGS. 10A-B depict various vitamin D compounds.

FIGS. 11A-C depicts various quinone-derived compounds including ubiquinone/Coenzyme Q10 in its various oxidated forms (Panel A); vitamin K (Panel B); and vitamin E (Panel C).

DEFINITIONS

Figure 1:
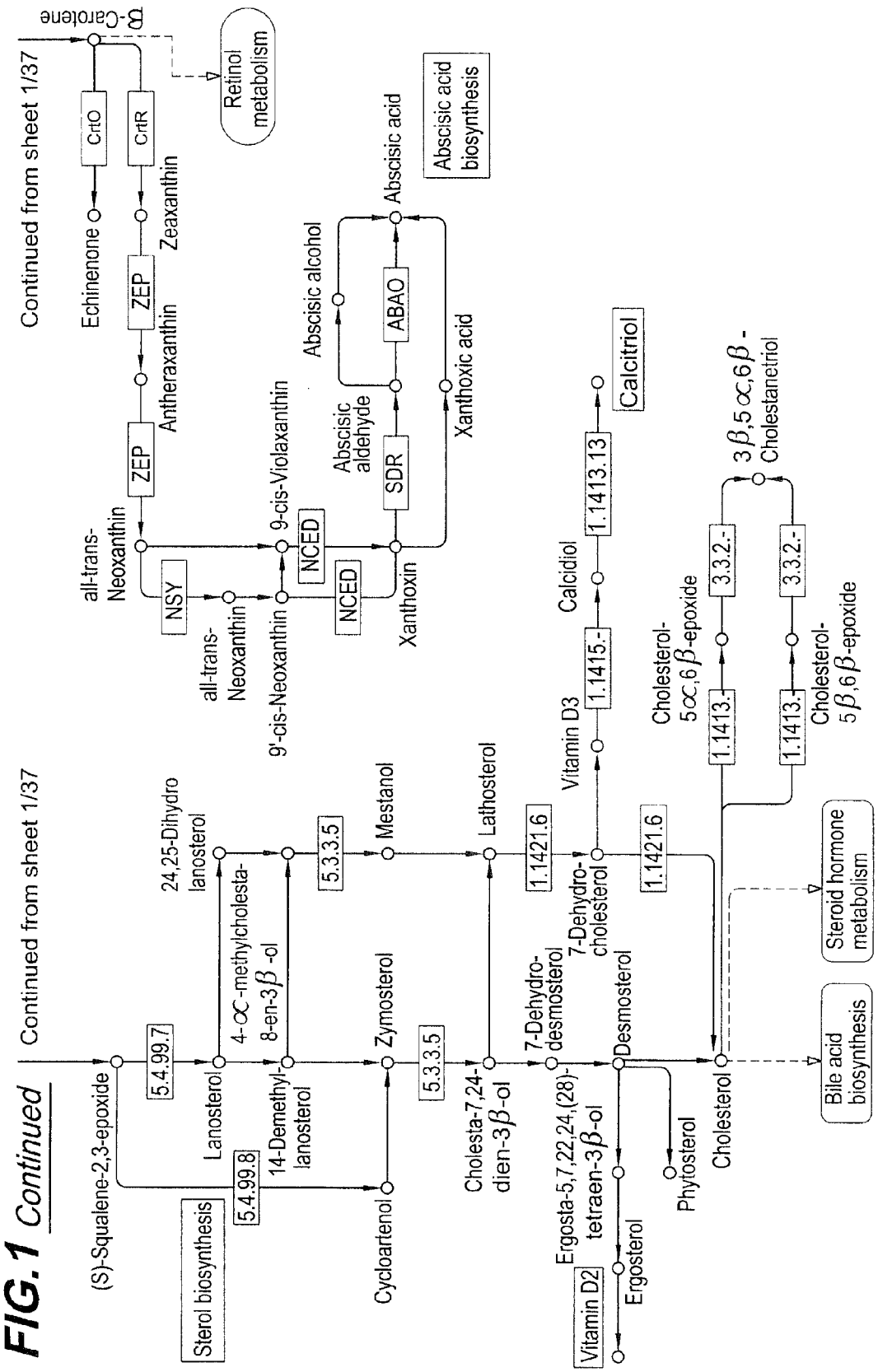
FIG. 1 depicts various biological pathways involved in steroid biosynthesis, including the sterol biosynthesis pathway that branches off at farnesyl pyrophosphate and includes squalene, lanosterol, zymosterol, ergosterol, 7-dehydrocholesterol (provitamin D3) as well as various vitamin D compounds. The enzymes involved in these pathways are depicted either as abbreviations of their names or by their EC numbers.

Aromatic amino acid biosynthesis polypeptide: The term "aromatic amino acid biosynthesis polypeptide" refers to any polypeptide that is involved in the synthesis of aromatic amino acids in yeast and/or bacteria through chorismate and the shikimate pathway. For example, as discussed herein, anthranilate synthase, enzymes of the shikimate pathway, chorismate mutase, chorismate synthase, DAHP synthase, and transketolase are all aromatic amino acid biosynthesis polypeptides. Each of these polypeptides is also a ubiquinone biosynthesis polypeptide or a ubiquinone biosynthesis competitor for purposes of the present invention, as production of chorismate is a precursor in the synthesis of para-hydroxybenzoate for the biosynthesis of ubiquinone. Representative examples of some of these enzymes are provided in Tables 32-37.

Aromatic amino acid pathway: The "aromatic amino acid pathway" is understood in the art to refer to a metabolic pathway that produces or utilizes shikimate pathway enzymes and chorismate in the production of phenylalanine, tryptophan or tyrosine. As discussed herein, two different pathways can produce the ubiquinoid precursor para-hydroxybenzoate the first, the "shikimate pathway" is utilized in prokaryotes and induces conversion of chorismate to para-hydroxybenzoate through the action of chorismate pyruvate lyase; the second is utilized in mammalian systems and induces induction of para-hydroxybenzoate by derivation of tyrosine or phenylalanine. The term "aromatic amino acid pathway" encompasses both of these pathways. Lower eukaryotes such as yeast can utilize either method for production of para-hydroxybenzoate.

Biosynthesis polypeptide: The term "biosynthesis polypeptide" as used herein (typically in reference to a particular compound or class of compounds), refers to polypeptides involved in the production of the compound or class of compounds. In some embodiments of the invention, biosynthesis polypeptides are synthetic enzymes that catalyze particular steps in a synthesis pathway that ultimately produces a relevant compound. In some embodiments, the term "biosynthesis polypeptide" may also encompass polypeptides that do not themselves catalyze synthetic reactions, but that regulate expression and/or activity of other polypeptides that do so.

$C_{5-9}$ quinone biosynthesis polypeptide: The term "$C_{5-9}$ quinone biosynthesis polypeptide" refers to any polypeptide that is involved in the synthesis of a $C_{5-9}$ quinone, for example a polyprenyldiphosphate synthase polypeptide. To mention but a few, these include, for example, pentaprenyl, hexaprenyl, heptaprenyl, octaprenyl, and/or solanesyl (nonaprenyl) diphosphate synthase polypeptides (i.e., polypeptides that perform the chemical reactions performed by the pentaprenyl, hexaprenyl, heptaprenyl, octaprenyl, and solanesyl (nonaprenyl) polypeptides, respectively, listed in Tables 57-61 (see also Okada et al., *Biochim. Biophys. Acta* 1302:

217, 1996; Okada et al., *J. Bacteriol.* 179:5992, 1997). As will be appreciated by those of ordinary skill in the art, in some embodiments of the invention, $C_{5-9}$ quinone biosynthesis polypeptides include polypeptides that affect the expression and/or activity of one or more other $C_{5-9}$ quinone biosynthesis polypeptides.

Carotenogenic modification: The term "carotenogenic modification", as used herein, refers to a modification of a host organism that adjusts production of one or more carotenoids, as described herein. For example, a carotenogenic modification may increase the production level of one or more carotenoids, and/or may alter relative production levels of different carotenoids. In principle, an inventive carotenogenic modification may be any chemical, physiological, genetic, or other modification that appropriately alters production of one or more carotenoids in a host organism produced by that organism as compared with the level produced in an otherwise identical organism not subject to the same modification. In most embodiments, however, the carotenogenic modification will comprise a genetic modification, typically resulting in increased production of one or more selected carotenoids. In some embodiments, the carotenogenic modification comprises at least one chemical, physiological, genetic, or other modification; in other embodiments, the carotenogenic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)). In some embodiments, the selected carotenoid is one or more of astaxanthin, β-carotene, canthaxanthin, lutein, lycopene, phytoene, zeaxanthin, and/or modifications of zeaxanthin or astaxanthin (e.g., glucoside, or other ester of zeaxanthin or astaxanthin). In some embodiments, the selected carotenoid is one or more xanthophylls, and/or a modification thereof (e.g., glucoside, esterified xanthophylls). In certain embodiments, the selected xanthophyll is selected from the group consisting of astaxanthin, lutein, zeaxanthin, lycopene, and modifications thereof. In some embodiments, the selected carotenoid is one or more of astaxanthin, β-carotene, canthaxanthin, lutein, lycopene, and zeaxanthin and/or modifications of zeaxanthin or astaxanthin. In some embodiments, the carotenoid is β-carotene. In some embodiments, the selected carotenoid is astaxanthin. In some embodiments, the selected carotenoid is other than β-carotene.

Carotenogenic polypeptide: The term "carotenogenic polypeptide", as used herein, refers to any polypeptide that is involved in the process of producing carotenoids in a cell, and may include polypeptides that are involved in processes other than carotenoid production but whose activities affect the extent or level of production of one or more carotenoids, for example by scavenging a substrate or reactant utilized by a carotenoid polypeptide that is directly involved in carotenoid production. Carotenogenic polypeptides include carotenoid biosynthesis polypeptides, as defined herein.

Carotenoid: The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{200}$. $C_{30}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{30}$ carotenoids may be formally derived from the acyclic $C_{30}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature; carotenoids include but are not limited to: antheraxanthin, adonirubin, adonixanthin, astaxanthin, canthaxanthin, capsorubrin, β-cryptoxanthin, α-carotene, β-carotene, β,ψ-carotene, δ-carotene, ε-carotene, echinenone, 3-hydroxyechinenone, 3'-hydroxyechinenone, γ-carotene, ψ-carotene, 4-keto-γ-carotene, ζ-carotene, α-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

Carotenoid biosynthesis polypeptide: The term "carotenoid biosynthesis polypeptide" refers to any polypeptide that is involved in the synthesis of one or more carotenoids. To mention but a few, these carotenoid biosynthesis polypeptides include, for example, polypeptides of phytoene synthase, phytoene dehydrogenase (or desaturase), lycopene cyclase, carotenoid ketolase, carotenoid hydroxylase, astaxanthin synthase, carotenoid epsilon hydroxylase, lycopene cyclase (beta and epsilon subunits), carotenoid glucosyltransferase, and acyl CoA:diacyglycerol acyltransferase. In some instances, a single gene may encode a protein with multiple carotenoid biosynthesis polypeptide activities. Representative examples of carotenoid biosynthesis polypeptide sequences are presented in Tables 17a-21 and 38-41. As will be appreciated by those of ordinary skill in the art, in some embodiments of the invention, carotenoid biosynthesis polypeptides include polypeptides that affect the expression and/or activity of one or more other carotenoid biosynthesis polypeptides.

Effective amount. The term "effective amount" is used herein to describe concentrations or amounts of compounds and/or compositions that, when administered to a subject, achieve a desired therapeutic or physiological effect.

FPP biosynthesis polypeptides: The term "FPP biosynthesis polypeptide" refers to any polypeptide that is involved in the synthesis of farnesyl pyrophosphate. As discussed herein, farnesyl pyrophosphate represents the branchpoint between the sterol biosynthesis pathway and the carotenoid and other biosynthesis pathways. One specific example of an FPP biosynthesis polypeptide is FPP synthase. Representative examples of FPP synthase polypeptide sequences are presented in Table 14. As will be appreciated by those of ordinary skill in the art, in some embodiments of the invention, FPP biosynthesis polypeptides include polypeptides that affect the expression and/or activity of one or more other FPP biosynthesis polypeptides.

Gene: The term "gene", as used herein, generally refers to a nucleic acid encoding a polypeptide, optionally including certain regulatory elements that may affect expression of one or more gene products (i.e., RNA or protein).

Heterologous: The term "heterologous", as used herein to refer to genes or polypeptides, refers to a gene or polypeptide that does not naturally occur in the organism in which it is being expressed. It will be understood that, in general, when a heterologous gene or polypeptide is selected for introduction into and/or expression by a host cell, the particular source organism from which the heterologous gene or polypeptide may be selected is not essential to the practice of the present invention. Relevant considerations may include, for example, how closely related the potential source and host organisms are in evolution, or how related the source organism is with other source organisms from which sequences of other relevant polypeptides have been selected. Where a plurality of different heterologous polypeptides are to be introduced into and/or expressed by a host cell, different polypeptides may be from different source organisms, or from the same source organism. To give but one example, in some cases, individual polypeptides may represent individual subunits of a complex protein activity and/or may be required to work in concert with other polypeptides in order to achieve the goals of the present invention. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell. For example, when the host cell is a *Yarrowia* strain (e.g., *Yarrowia lipolytica*), it will often be desirable to alter the gene sequence encoding a given polypeptide such that it conforms more closely with the codon preferences of such a *Yarrowia* strain. In certain embodiments, a gene sequence encoding a given polypeptide is altered to conform more closely with the codon preference of a species related to the host cell. For example, when the host cell is a *Yarrowia* strain (e.g., *Yarrowia lipolytica*), it will often be desirable to alter the gene sequence encoding a given polypeptide such that it conforms more closely with the codon preferences of a related fungal strain. Such embodiments are advantageous when the gene sequence encoding a given polypeptide is difficult to optimize to conform to the codon preference of the host cell due to experimental (e.g., cloning) and/or other reasons. In certain embodiments, the gene sequence encoding a given polypeptide is optimized even when such a gene sequence is derived from the host cell itself (and thus is not heterologous). For example, a gene sequence encoding a polypeptide of interest may not be codon optimized for expression in a given host cell even though such a gene sequence is isolated from the host cell strain. In such embodiments, the gene sequence may be further optimized to account for codon preferences of the host cell. Those of ordinary skill in the art will be aware of host cell codon preferences and will be able to employ inventive methods and compositions disclosed herein to optimize expression of a given polypeptide in the host cell.

Host cell: As used herein, the "host cell" is a fungal cell or yeast cell that is manipulated according to the present invention to accumulate lipid and/or to express one or more sterol compounds as described herein. A "modified host cell", as used herein, is any host cell which has been modified, engineered, or manipulated in accordance with the present invention as compared with a parental cell. In some embodiments, the modified host cell has at least one sterologenic and/or at least one oleagenic modification. In some embodiments, the modified host cell containing at least one oleaginic modification and/or one sterologenic modification further has at least one carotenogenic modification and/or at least one quinonogenic modification. In some embodiments, the parental cell is a naturally occurring parental cell.

Isolated: The term "isolated", as used herein, means that the isolated entity has been separated from at least one component with which it was previously associated. When most other components have been removed, the isolated entity is "purified" or "concentrated". Isolation and/or purification and/or concentration may be performed using any techniques known in the art including, for example, fractionation, extraction, precipitation, or other separation.

Isoprenoid biosynthesis polypeptide: The term "isoprenoid biosynthesis polypeptide" refers to any polypeptide that is involved in the synthesis of isoprenoids. For example, as discussed herein, acetoacetyl-CoA thiolase, HMG-CoA synthase, HMG-CoA reductase, mevalonate kinase, phosphomevalonate kinase, mevalonate pyrophosphate decarboxylase, and IPP isomerase are all involved in the mevalonate pathway for isoprenoid biosynthesis. Each of these proteins is also an isoprenoid biosynthesis polypeptide for purposes of the present invention, and sequences of representative examples of these enzymes are provided in Tables 7-13. As will be appreciated by those of ordinary skill in the art, in some embodiments of the invention, isoprenoid biosynthesis polypeptides include polypeptides that affect the expression and/or activity of one or more other isoprenoid biosynthesis polypeptides (e.g., of one or more enzymes that participate(s) in isoprenoid synthesis). Thus, for instance, transcription factors that regulate expression of isoprenoid biosynthesis enzymes can be isoprenoid biosynthesis polypeptides for purposes of the present invention.

Isoprenoid pathway: The term "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway". The term "isoprenoid pathway" is sufficiently general to encompass both of these types of pathway. Biosynthesis of isoprenoids from IPP occurs by polymerization of several five-carbon isoprene subunits. Isoprenoid metabolites derived from IPP are of varying size and chemical structure, including both cyclic and acyclic molecules. Isoprenoid metabolites include, but are not limited to, monoterpenes, sesquiterpenes, diterpenes, sterols, and polyprenols such as carotenoids.

Oleaginic modification: The term "oleaginic modification", as used herein, refers to a modification of a host organism that adjusts the desirable oleaginy of that host organism, as described herein. In some cases, the host organism will already be oleaginous in that it will have the ability to accumulate lipid to at least about 20% of its dry cell weight. It may nonetheless be desirable to apply an oleaginic modification to such an organism, in accordance with the present invention, for example to increase (or, in some cases, possibly to decrease) its total lipid accumulation, or to adjust the types or amounts of one or more particular lipids it accumulates (e.g., to increase relative accumulation of triacylglycerol). In other cases, the host organism, may be non-oleaginous (though may contain some enzymatic and/or regulatory components used in other organisms to accumulate lipid), and may require oleaginic modification in order to become oleaginous in accordance with the present invention. The present invention also contemplates application of oleaginic modification to non-oleaginous host strains such that their oleaginicity is increased even though, even after being modified, they may not be oleaginous as defined herein. In principle, the oleaginic modification may be any chemical, physiological, genetic, or other modification that appropriately alters oleaginy of a host organism as compared with an otherwise identical organism not subjected to the oleaginic modification. In most embodiments, however, the oleaginic modification will comprise a genetic modification, typically resulting in increased production and/or activity of one or more oleaginic polypeptides. In some embodiments, the oleaginic modification comprises at least one chemical, physiological, genetic, or other modification; in other embodiments, the oleaginic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Oleaginic polypeptide: The term "oleaginic polypeptide", as used herein, refers to any polypeptide that is involved in the process of lipid accumulation in a cell and may include polypeptides that are involved in processes other than lipid biosynthesis but whose activities affect the extent or level of accumulation of one or more lipids, for example by scavenging a substrate or reactant utilized by an oleaginic polypeptide that is directly involved in lipid accumulation. For example, as discussed herein, acetyl-CoA carboxylase, pyruvate decarboxylase, isocitrate dehydrogenase, ATP-citrate lyase, malic enzyme, malate dehydrogenase, and AMP deaminase, among other proteins, are all involved in lipid accumulation in cells. In general, reducing the activity of pyruvate decarboxylase or isocitrate dehydrogenase, and/or increasing the activity of acetyl CoA carboxylase, ATP-citrate lyase, malic enzyme, malate dehydrogenase, and/or AMP deaminase is expected to promote oleaginy. Each of these proteins is an oleaginic peptide for the purposes of the present invention, and sequences of representative examples of these enzymes are provided in Tables 1-6, and 65. Other peptides that can be involved in regenerating NADPH may include, for example, 6-phosphogluconate dehydrogenase (gnd); Fructose 1,6 bisphosphatase (fbp); Glucose 6 phosphate dehydrogenase (g6pd); NADH kinase (EC 2.7.1.86); and/or transhydrogenase (EC 1.6.1.1 and 1.6.1.2). Alternative or additional strategies to promote oleaginy may include one or more of the following: (1) increased or heterologous expression of one or more of acyl-CoA:diacylglycerol acyltransferase (e.g., DGA1; YALI0E32769g); phospholipid:diacylglycerol acyltransferase (e.g., LRO1; YALI0E16797g); and acyl-CoA:cholesterol acyltransferase (e.g., ARE genes such as ARE1, ARE2, YALI0F06578g), which are involved in triglyceride synthesis (Kalscheuer et al. *Appl Environ Microbiol* p. 7119-7125, 2004; Oelkers et al. *J Biol Chem* 277:8877-8881, 2002; and Sorger et al. *J Biol Chem* 279:31190-31196, 2004), (2) decreased expression of triglyceride lipases (e.g., TGL3 and/or TGL4; YALI0D17534g and/or YALI0F10010g (Kurat et al. *J Biol Chem* 281:491-500, 2006); and (3) decreased expression of one or more acyl-coenzyme A oxidase activities, for example encoded by POX genes (e.g. POX1, POX2, POX3, POX4, POX5; YALI0C23859g, YALI0D24750g, YALI0E06567g, YALI0E27654g, YALI0E32835g, YALI0F10857g; see, for example, Mlickova et al. *Appl Environ Microbiol* 70: 3918-3924, 2004; Binns et al. *J Cell Biol* 173:719, 2006). Each of these proteins is an oleaginic peptide for the purposes of the present invention, and sequences of representative examples of these enzymes are provided in Tables 66-81.

Oleaginous: The term "oleaginous", as used herein, refers to ability of an organism to accumulate lipid to at least about 20% of its dry cell weight. In certain embodiments of the invention, oleaginous yeast or fungi accumulate lipid to at least about 25% of their dry cell weight. In other embodiments, inventive oleaginous yeast or fungi accumulate lipid within the range of about 20-45% (e.g. 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%) of their dry cell weight. In some embodiments, oleaginous organisms may accumulate lipid to as much as about 70% of their dry cell weight. In some embodiments of the invention, oleaginous organisms may accumulate a large fraction of total lipid accumulation in the form of triacylglycerol. In certain embodiments, the majority of the accumulated lipid is in the form of triacylglycerol. Alternatively or additionally, the lipid may accumulate in the form of intracellular lipid bodies, or oil bodies. In certain embodiments, the present invention utilizes yeast or fungi that are naturally oleaginous. In some aspects, naturally oleaginous organisms are manipulated (e.g., genetically, chemically, or otherwise) so as to father increase the level of accumulated lipid in the organism. In other embodiments, yeast or fungi that are not naturally oleaginous are manipulated (e.g., genetically, chemically, or otherwise) to accumulate lipid as described herein. For example, for the purposes of the present invention, *Saccharomyces cerevisiae*, *Xanthophyllomyces dendrorhous* (*Phaffia rhodozyma*), and *Candida utilis* are not naturally oleaginous fungi.

PHB polypeptide or PHB biosynthesis polypeptide: The terms "PHB polypeptide" or "PHB biosynthesis polypeptide" as used herein refers to a polypeptide that is involved in the synthesis of para-hydroxybenzoate from chorismate. In prokaryotes and lower eukaryotes, synthesis of para-hydroxybenzoate occurs by the action of chorismate pyruvate lyase. Biosynthesis of para-hydroxybenzoate from tyrosine or phenylalanine occurs through a five-step process in mammalian cells. Lower eukaryotes such as yeast can utilize either method for production of para-hydroxybenzoate. For example, enzymes of the shikimate pathway, chorismate synthase, DAHP synthase, and transketolase are all PHB biosynthesis polypeptides. Each of these polypeptides is also a ubiquinone biosynthesis polypeptide or a ubiquinone biosynthesis competitor polypeptide for purposes of the present invention. Exemplary PHB polypeptides are provided in Tables 33 and 35-37.

Figure 7H:
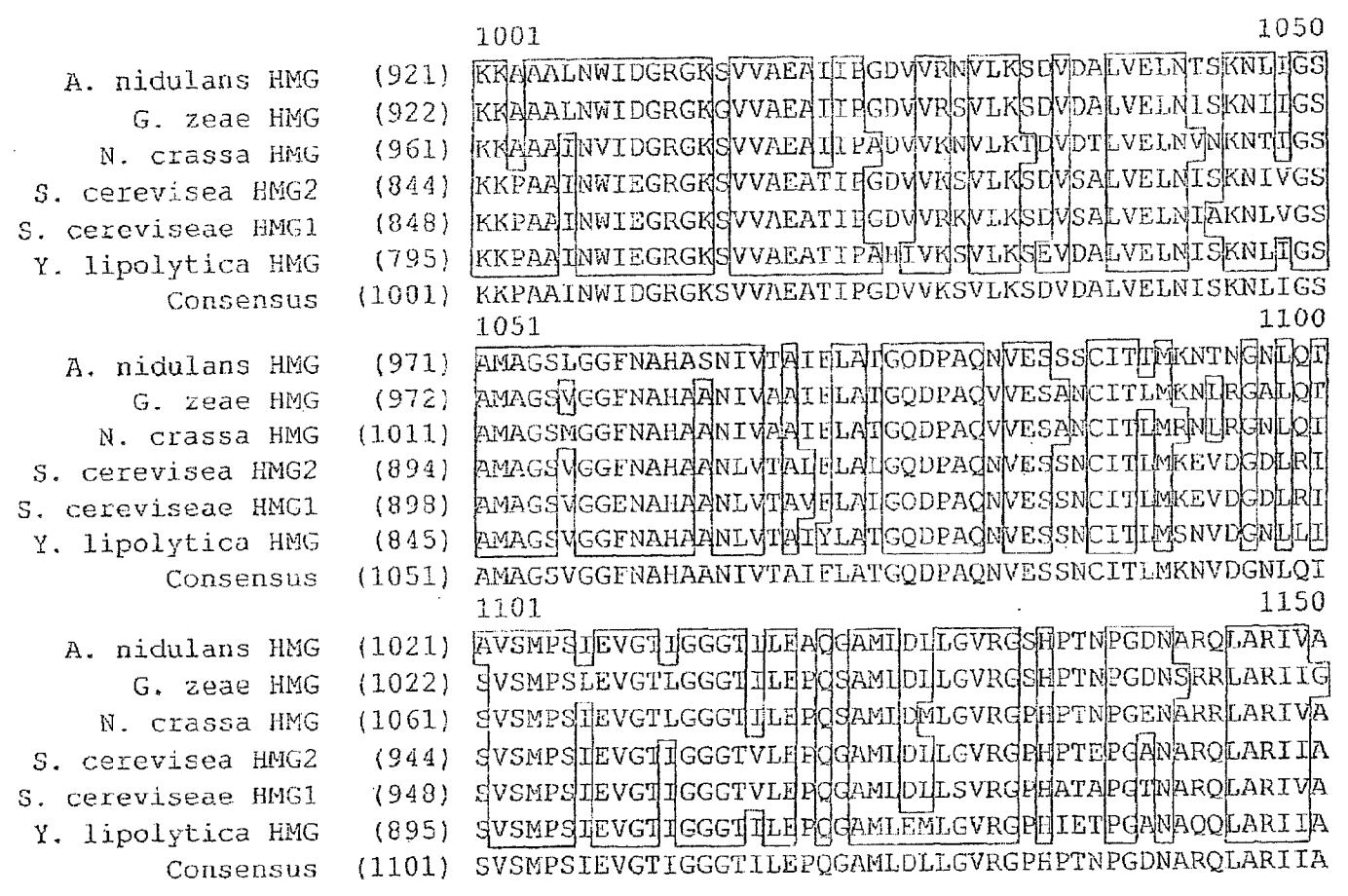

Polypeptide: The term "polypeptide", as used herein, generally has its art-recognized meaning of a polymer of at least three amino acids. However, the term is also used to refer to specific functional classes of polypeptides, such as, for example, biosynthesis polypeptides, $C_{5-9}$ quinone biosynthesis polypeptides, carotenogenic polypeptides, carotenoid biosynthesis polypeptides, FPP biosynthesis polypeptides, isoprenoid biosynthesis polypeptides, oleaginic polypeptides, sterol biosynthesis polypeptides, sterologenic polypeptides, ubiquinogenic polypeptides, ubiquinone biosynthesis polypeptides, Vitamin D biosynthesis polypeptides, Vitamin E biosynthesis polypeptides, Vitamin K biosynthesis polypeptides, etc. For each such class, the present specification provides several examples of known sequences of such polypeptides. Those of ordinary skill in the art will appreciate, however, that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreoever, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions (e.g., isocitrate dehydrogenase polypeptides often share a conserved AMP-binding motif; HMG-CoA reductase polypeptides typically include a highly conserved catalytic domain [see, for example, FIG. 7]; acetyl coA carboxylase typically has a carboxyl transferase domain; see, for example, Downing et al., *Chem. Abs.* 93:484, 1980; Gil et al., *Cell* 41:249, 1985; Jitrapakdee et al., *Curr Protein Pept Sci.* 4:217, 2003; U.S. Pat. No. 5,349,126, each of which is incorporated herein by reference in its entirety), usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides presented in the Tables herein.

Quinone biosynthesis polypeptide: A "quinone biosynthesis polypeptide", as that term is used herein, refers to any polypeptide involved in the synthesis of one or more quinone derived compounds, as described herein. In particular, quinone biosynthesis polypeptides include ubiquinone biosynthesis polypeptides, $C_{5-9}$ quinone biosynthesis polypeptides, vitamin K biosynthesis polypeptides, and vitamin E biosynthesis polypeptides.

Quinone derived compounds: The term "quinone derived compounds" is used herein to refer to certain compounds that either contain a quinone moiety or are derived from a precursor that contains a quinone moiety. In particular, quinone derived compounds according to the present invention are ubiquinones, $C_{5-9}$ quinone compounds, vitamin E compounds, and/or vitamin K compounds. Structures of representative quinone derived compounds are presented in FIG. 11.

Quinonogenic modification: The term "quinonogenic modification, as used herein, refers to refers to a modification of a host organism that adjusts production of one or more quinone derived compounds (e.g., ubiquinone, vitamin K compounds, vitamin E compounds, etc.), as described herein. For example, a quinonogenic modification may increase the production level of a particular quinone derived compound, or of a variety of different quinone derived compounds. In some embodiments of the invention, production of a particular quinone derived compound may be increased while production of other quinone derived compounds is decreased. In some embodiments of the invention, production of a plurality of different quinone derived compounds is increased. In principle, an inventive quinonogenic modification may be any chemical, physiological, genetic, or other modification that appropriately alters production of one or more quinone derived compounds in a host organism produced by that organism as compared with the level produced in an otherwise identical organism not subject to the same modification. In most embodiments, however, the quinonogenic modification will comprise a genetic modification, typically resulting in increased production of one or more quinone derived compounds (e.g., ubiquinone, vitamin K compounds, vitamin E compounds). In some embodiments, the quinonogenic modification comprises at least one chemical, physiological, genetic, or other modification; in other embodiments, the quinonogenic modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Quinonogenic polypeptide: The term "quinonogenic polypeptide", as used herein, refers to any polypeptide whose activity in a cell increases production of one or more quinone derived compounds (e.g., ubiquinone, vitamin K compounds, vitamin E compounds) in that cell. The term encompasses both polypeptides that are directly involved in quinone derived compound synthesis and those whose expression or activity affects the extent or level of production of one or more quinone derived compounds, for example by scavenging a substrate or reactant utilized by a quinone biosynthetic polypeptide that is directly involved in quinone derived compound production. Quinonologenic polypeptides include isoprenoid biosynthesis polypeptides, ubiquinone biosynthesis polypeptides, $C_{5-9}$ quinone biosynthesis polypeptides, vitamin E biosynthesis polypeptides, and vitamin K biosynthesis polypeptides. Quinonogenic polypeptides may also include ubiquinogenic polypeptides, etc. The term also encompasses polypeptides that may affect the extent to which one or more quinone derived compounds is accumulated in lipid bodies.

Small Molecule: In general, a small molecule is understood in the art to be an organic molecule that is less than about 5 kilodaltons (Kd) in size. In some embodiments, the small molecule is less than about 3 Kd, 2 Kd, or 1 Kd. In some embodiments, the small molecule is less than about 800 daltons (D), 600 D, 500 D, 400 D, 300 D, 200 D, or 100 D. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Source organism: The term "source organism", as used herein, refers to the organism in which a particular polypeptide sequence can be found in nature. Thus, for example, if one or more heterologous polypeptides is/are being expressed in a host organism, the organism in which the polypeptides are expressed in nature (and/or from which their genes were originally cloned) is referred to as the "source organism".

Where multiple heterologous polypeptides are being expressed in a host organism, one or more source organism(s) may be utilized for independent selection of each of the heterologous polypeptide(s). It will be appreciated that any and all organisms that naturally contain relevant polypeptide sequences may be used as source organisms in accordance with the present invention. Representative source organisms include, for example, animal, mammalian, insect, plant, fungal, yeast, algal, bacterial, archaebacterial, cyanobacterial, and protozoal source organisms.

Subject. The term "subject" is used throughout the present specification to describe an animal, in most instances a human, to whom inventive compositions are administered.

Sterol biosynthesis competitor: The term "sterol biosynthesis competitor", as used herein, refers to an agent whose presence or activity in a cell either (1) reduces the level of isopentenyl pyrophosphate (IPP) and/or farnesyl pyrophosphate (FPP) available to enter the sterol biosynthesis pathway; or (2) reduces the level or activity of one or more sterol biosysthesis polypeptides; or both. The term "sterol biosynthesis competitor" encompasses both polypeptide and non-polypeptide (e.g., small molecule) inhibitor agents. Particular examples of sterol biosynthesis competitor agents act on isoprenoid intermediates prior to IPP or FPP, such that less IPP or FPP is generated (see, for example, FIG. 1). Other examples include agents that act downstream of IPP and/or FPP and increase their partitioning into other metabolic pathways (e.g., toward carotenoid biosynthesis, ubiquinone biosynthesis, vitamin E biosyntheses, vitamin K biosynthesis, etc). Thus, sterol biosynthesis competitor agents include, but are not limited to, geranylgeranyl pyrophosphate (GGPP) synthase polypeptides, carotenogenic polypeptides, ubiquinogenic polypeptides, vitamin E biosynthesis polypeptides, vitamin K biosynthesis polypeptides, $C_{5-9}$ quinone biosynthesis polypeptides, etc. Furthermore, those of ordinary skill in the art will appreciate that certain competitor agents that do not act as inhibitors of sterol biosynthesis generally can nonetheless act as inhibitors of biosynthesis of a particular sterol compound. For instance, agents that inhibit conversion of squalene to squalene-2,3-epoxide may well increase production of one sterol compound (squalene) while inhibiting production of one or more other sterol compounds (e.g., vitamin D compound(s)). Similarly, agents that increase metabolism of lanosterol to 14-demethyl lanosterol and/or decrease metabolism of lanosterol to 2, 25 dihydrolanosterol may act as competitor agents with regard to vitamin $D_3$ biosynthesis specifically but not with regard to sterol compounds generally. Those of ordinary skill in the art, considering the known metabolic pathways relating to sterol production and/or metabolism (see, for example, FIG. 1 and other Figures and references herein) will readily appreciate a variety of other particular sterol biosynthesis competitors, including sterol biosynthesis polypeptides. Representative examples of sterol biosynthesis polypeptide sequences are presented in Tables 83-96. As will be appreciated by those of ordinary skill in the art, in some embodiments of the invention, sterol biosynthesis polypeptides include polypeptides that affect the expression and/or activity of one or more other sterol biosynthesis polypeptides.

Figure 4:
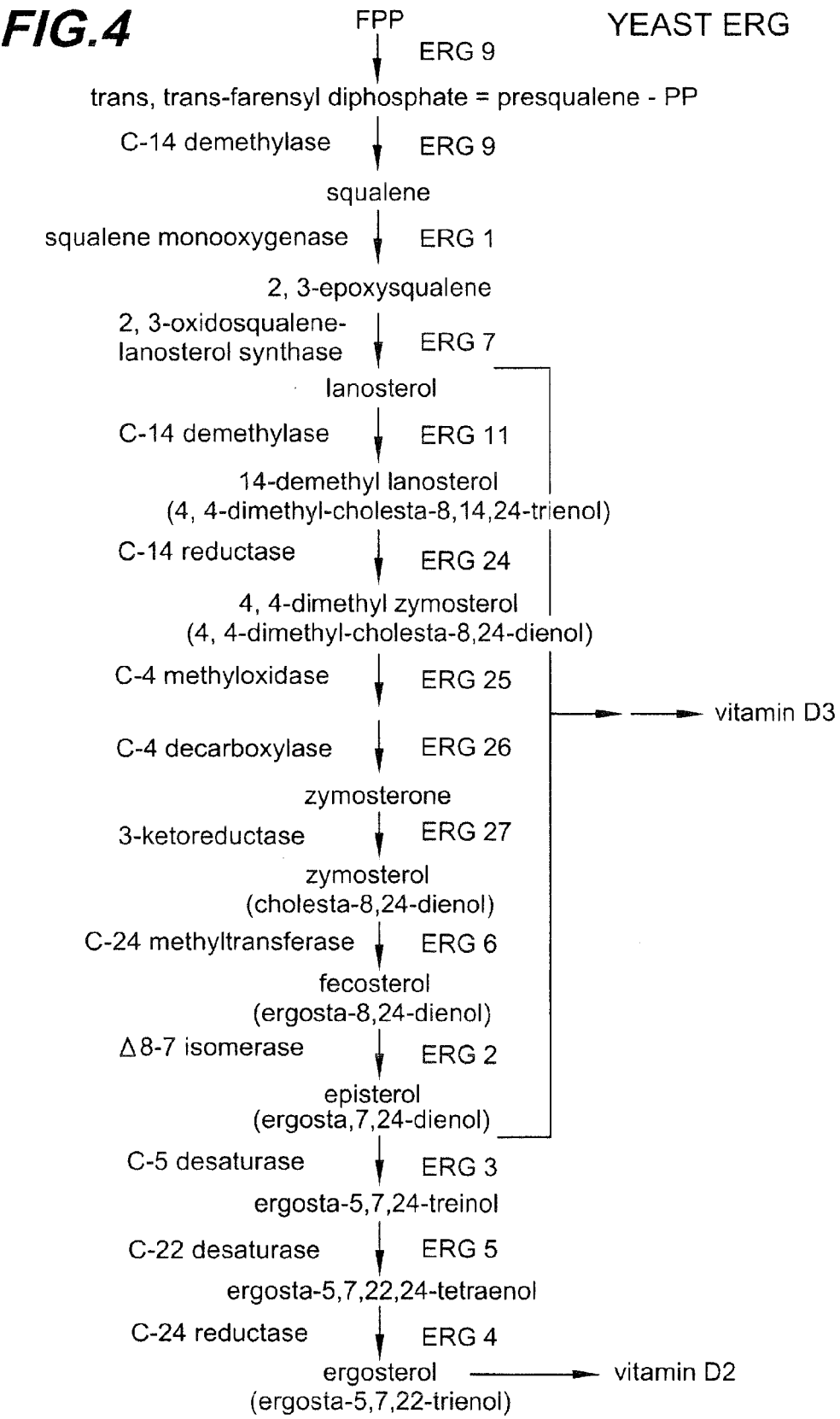
FIG. 4 depicts a sterol biosynthesis pathway that converts IPP (e.g., produced via the mevalonate or the non-mevalonate pathway depicted in FIG. 3) into various sterol compounds including, for example squalene, lanosterol, zymosterol, ergosterol, 7-dehydrocholesterol (provitamin D3), etc.

Sterol biosynthesis polypeptide: The term "sterol biosynthesis polypeptide", as used herein, refers to any polypeptide that is involved in the synthesis of one or more sterol compounds. Thus, sterol biosynthesis polypeptides can include isoprenoid biosynthesis polypeptides to the extent that they are involved in production of isopentyl pyrophosphate. Moreover, the term refers to any polypeptide that acts downstream of farnesyl pyrophosphate and is involved in the production of one or more sterol compounds. For example, sterol biosynthesis polypeptides include squalene synthase, which catalyses conversion of farnesyl pyrophosphate to presqualene pyrophosphate, and further catalyzes conversion of presqualene pyrophosphate to squalene (i.e., enzyme 2.5.1.21 in FIG. 1). In some embodiments of the invention, sterol biosynthesis polypeptides further include one or more polypeptides involved in metabolizing squalene into a vitamin D compound. Thus, sterol biosynthesis polypeptides can include one or more of the 1.14.99.7, 5.4.99.7, 5.4.99.8, 5.3.3.5, 1.14.21.6, 1.14.15.-, 1.14.13.13 enzyme polypeptides depicted in FIG. 1, as well as other enzyme polypeptides involved in the illustrated pathways. Furthermore, sterol biosynthesis polypeptides can include one or more of the enzyme polypeptides depicted in FIG. 4, including, for example, C-14 demethylase (ERG9), squalene monooxygenase (ERG1), 2,3-oxidosqualene-lanosterol synthase (ERG7), C-1 demethylase (ERG11), C-14 reductase (ERG24), C-4 methyloxidase (ERG25), C-4 decarboxylase (ERG26), 3-ketoreductase (ERG27), C-24 methyltransferase (ERG6), Δ8-7 isomerase (ERG2), C-5 desaturase (ERG3), C-22 desaturase (ERG5) and/or C-24 reductase (ERG4) polypeptides, and/or other polypeptides involved in producing one or more vitamin D compounds (e.g., vitamin D2, vitamin D3, or a precursor thereof). As will be appreciated by those of ordinary skill in the art, in some embodiments of the invention, sterol biosynthesis polypeptides include polypeptides that affect the expression and/or activity of one or more other sterol biosynthesis polypeptides. Thus, for instance, transcription factors that regulate expression of sterol biosynthesis enzymes can be sterol biosynthesis polypeptides for purposes of the present invention. To give but a couple of examples, the *S. cerevisiae* Upc2 and YLR228c genes, and the *Y. lipolytica* YALI0B00660g gene encode transcription factors that are sterol biosynthesis polypeptides according to certain embodiments of the present invention. For instance, the semidominant upc2-1 point mutation (G888D) exhibits increased sterol levels (Crowley et al., *J. Bacterial* 180:4177-4183, 1998). Corresponding YLR228c mutants have been made and tested (Shianna et al., *J Bacterial* 183:830, 2001); such mutants may be useful in accordance with the present invention, as may be YALI0B00660g derivatives with corresponding upc2-1 mutation(s). Representative examples of certain sterol biosynthesis polypeptide sequences are presented in Tables 16 and 83-95.

Sterol compound: The term "sterol compound", as used herein, refers in general to squalene or any metabolite that is derived from squalene, either through a biochemical reaction within a host cell, through whole-cell or enzymatic biocatalytic treatment of a distinct sterol compound, or through chemical or physical treatments (e.g. ultraviolet irradiation). In particular, the term encompasses squalene, lanosterol, zymosterol, ergosterol, 7-dehydrocholesterol (provitamin D3) and/or vitamin D compounds.

Sterologenic modification: The term "sterologenic modification", as used herein, refers to a modification of a host organism that adjusts production of one or more sterol compounds (e.g., squalene, lanosterol, zymosterol, ergosterol, 7-dehydrocholesterol (provitamin D3), vitamin D compound(s), etc.), as described herein. For example, a sterologenic modification may increase the production level of a particular sterol compound, or of a variety of different sterol compounds. In some embodiments of the invention, production of a particular sterol compound may be increased while production of other sterol compounds is decreased. In some embodiments of the invention, production of a plurality of different sterol compounds is increased. In principle, an inventive sterologenic modification may be any chemical, physiological, genetic, or other modification that appropriately alters production of one or more sterol compounds in a host organism produced by that organism as compared with the level produced in an otherwise identical organism not subject to the same modification. In most embodiments, however, the sterologenic modification will comprise a genetic modification, typically resulting in increased production of one or more sterol compounds (e.g., squalene, lanosterol, zymosterol, ergosterol, 7-dehydrocholesterol (provitamin D3) or vitamin D compound(s)). In some embodiments, the sterologenic modification comprises at least one chemical, physiological, genetic, or other modification; in other embodiments, the sterologenic modification comprises more than one chemical, physiological, genetic, or other modification. In certain aspects where more than one modification is utilized, such modifications can comprise any combination of chemical, physiological, genetic, or other modification (e.g., one or more genetic modification and chemical and/or physiological modification(s)).

Sterologenic polypeptide: The term "sterologenic polypeptide", as used herein, refers to any polypeptide whose activity in a cell increases production of one or more sterol compounds (e.g., squalene, lanosterol, zymosterol, ergosterol, 7-dehydrocholesterol (provitamin D3), vitamin D compound(s), etc.) in that cell. The term encompasses both polypeptides that are directly involved in sterol compound synthesis and those whose expression or activity affects the extent or level of production of one or more sterol compounds, for example by scavenging a substrate or reactant utilized by a sterol biosynthetic polypeptide that is directly involved in sterol compound production. Sterologenic polypeptides include isoprenoid biosynthesis polypeptides and sterol biosynthesis polypeptides, and the term also encompasses polypeptides that may affect the extent to which sterol compounds are accumulated in lipid bodies.

Ubiquinogenic modification: The term "ubiquinogenic modification", as used herein, refers to a modification of a host organism that adjusts production of ubiquinone (e.g., CoQ10), as described herein. For example, a ubiquinogenic modification may increase the production level of ubiquinone (e.g., CoQ10), and/or may alter relative levels of ubiquinone and/or ubiquinol. In principle, an inventive ubiquinogenic modification may be any chemical, physiological, genetic, or other modification that appropriately alters production of ubiquinone (e.g., CoQ10) in a host organism produced by that organism as compared with the level produced in an otherwise identical organism not subject to the same modification. In most embodiments, however, the ubiquinogenic modification will comprise a genetic modification, typically resulting in increased production of ubiquinone (CoQ10).

Ubiquinogenic polypeptide: The term "ubiquinogenic polypeptide," as used herein, refers to any polypeptide that is involved in the process of producing ubiquinone (e.g., CoQ10, CoQ9, CoQ8, CoQ7, CoQ6, CoQ5) in a cell, and may include polypeptides that are involved in processes other than ubiquinone production but whose expression or activity affects the extent or level of production of ubiquinone and/or ubiquinol. Ubiquinogenic polypeptides include ubiquinone biosynthesis polypeptides and $C_{5-9}$ quinone biosynthesis polypeptides Ubiquinone: The term "ubiquinone" is understood in the art to refer to a structural class of quinone derivatives with or without isoprenoid side chains. Ubiquinones are described in the Merck Index, 11th Edition, Merck & Co., Inc. Rahway, N.Y., USA, Abstr. 9751 (1989), which is incorporated herein by reference. A dual nomenclature exists for these compounds and is based upon the length of the terpenoid side chain. Those which contain an isoprene side chain are also referred to by the term coenzymes Q. A benzoquinone of this family is therefore properly referred to as either "Coenzyme Qn," where n is an integer from one to twelve and designates the number of isoprenoid units in the side chain, or alternatively, "ubiquinone (x)" where x designates the total number of carbon atoms in the side chain and is a multiple of five. Typically, n is an integer ranging from 0 to 12, in particular from 1 to 12, and more particularly 5, 6, 7, 8, 9, or 10. For example, the most common ubiquinone in animals has a ten isoprenoid side chain and is referred to as either Coenzyme Q10 or ubiquinone (50). In other organisms (e.g. fungi, bacteria), ubiquinones, for example $C_5$ (CoQ5), $C_6$ (CoQ6), $C_7$ (CoQ7), $C_8$ (CoQ8), or $C_9$ (CoQ9) (collectively $C_{5-9}$) quinones are more prevalent than Coenzyme Q10 (CoQ10). As mentioned, the ubiquinone may also lack an isoprene side chain, and may be selected from alkylubiquinones in which the alkyl group may contain from 1 to 20 and preferably from 1 to 12 carbon atoms, such as, for example, decylubiquinones such as 6-decylubiquinone or 2,3-dimethoxy-5-decyl-1,4-ubiquinone, derivatives thereof, and mixtures thereof. Ubiquinones may exist in reduced (ubiquinol), oxidized or superoxidized states. For example, the oxidation states of ubiquinone/Coenzyme Q10 are depicted in FIG. 11.

Ubiquinone biosynthesis polypeptide: The term "ubiquinone biosynthesis polypeptide" refers to any polypeptide that is involved in the synthesis of ubiquinone. To mention but a few, these ubiquinone biosynthesis polypeptides include, for example, polypeptides of prenyldiphosphate synthase, PUB-polyprenyltransferase, and O-methyltransferase, as well as $C_{5-9}$ quinone biosynthesis polypeptides. As will be appreciated by those of ordinary skill in the art, in some embodiments of the invention, ubiquinone biosynthesis polypeptides include polypeptides that affect the expression and/or activity of one or more other ubiquinone biosynthesis polypeptides. Representative examples of certain ubiquinone biosynthesis polypeptide sequences are presented in Tables 23, 23b, 23c, 24-31.

Vitamin D compound: The term "vitamin D compound", as used herein, refers to a group of steroid compounds including vitamin $D_3$ (cholecalciferol), vitamin $D_2$ (ergocalciferol), their provitamins, and certain metabolites. Vitamins $D_3$ and $D_2$ can be produced from their respective provitamins (e.g., 7-dehydrocholesterol and ergosterol) by ultraviolet irradiation (e.g., by the action of sunlight). The most biologically active form of vitamin D is 1,25-dihydroxy vitamin $D_3$, which is also known as calcitriol. Calcitriol is produced by hydroxylation of vitamin $D_3$ at the 25 position, followed by hydroxylation to generate calcitriol. FIGS. 10A-B present the structures of vitamins $D_3$, $D_2$, and other vitamin D compounds.

Vitamin D biosynthesis polypeptide: The term "vitamin D biosynthesis polypeptide" refers to any polypeptide that is involved in the synthesis of one or more vitamin D compounds. To mention but a few, these include, for example, the 1.14.99.7, 5.4.99.7, 5.4.99.8, 5.3.3.5, and/or 1.14.21.6, polypeptides depicted in FIG. 1. They further can include the hydroxylases that convert vitamin $D_3$ to calcitriol (e.g., the 1.14.15.- and 1.14.13.13 polypeptides depicted in FIG. 1). As will be appreciated by those of ordinary skill in the art, in some embodiments of the invention, vitamin D biosynthesis polypeptides include polypeptides that affect the expression and/or activity of one or more other vitamin D biosynthesis polypeptides. Particular examples of certain vitamin D biosynthesis polypeptides are presented in Tables 84-96.

Vitamin E biosynthesis polypeptide: The term "vitamin E biosynthesis polypeptide" refers to any polypeptide that is involved in the synthesis of vitamin E. To mention but a few, these include, for example, tyrA, pds1(hppd), VTE1, HPT1 (VTE2), VTE3, VTE4, and/or GGH polypeptides (i.e., polypeptides that perform the chemical reactions performed by tyrA, pds1(hppd), VTE1, HPT1(VTE2), VTE3, VTE4, and/or GGH, respectively). As will be appreciated by those of ordinary skill in the art, in some embodiments of the invention, vitamin E biosynthesis polypeptides include polypeptides that affect the expression and/or activity of one or more other vitamin E biosynthesis polypeptides. Particular examples of certain vitamin E biosynthesis polypeptides are presented in Tables 50-56.

Vitamin K biosynthesis polypeptide: The term "vitamin K biosynthesis polypeptide" refers to any polypeptide that is involved in the synthesis of vitamin K. To mention but a few, these include, for example, MenF, MenD, MenC, MenE, MenB, MenA, UbiE, and/or MenG polypeptides (i.e., polypeptides that perform the chemical reactions performed by MenF, MenD, MenC, MenE, MenB, MenA, UbiE, and/or MenG, respectively). As will be appreciated by those of ordinary skill in the art, in some embodiments of the invention, vitamin K biosynthesis polypeptides include polypeptides that affect the expression and/or activity of one or more other carotenoid biosynthesis polypeptides. Particular examples of certain vitamin K biosynthesis polypeptides are presented in Tables 42-49.

DETAILED DESCRIPTION OF CERTAIN PREFERRED EMBODIMENTS OF THE INVENTION

The present invention embraces the reasoning that certain sterol compounds can effectively be produced in oleaginous yeast and fungi. According to the present invention, strains that both (i) accumulate lipid, often in the form of cytoplasmic oil bodies; and (ii) produce sterol compounds at a level at least about 1%, of their dry cell weight, are generated through manipulation of host cells (i.e., strains, including, e.g., naturally-occurring strains and strains which have been previously modified).

In certain embodiments, strains can accumulate lipid typically to at least about 20% of their dry cell weight. In some embodiments, strains accumulate lipid to a level higher than at least about 20% of their dry cell weight (e.g., to a level at least about 15%, 16%, 17%, 18%, 19%, 20%, 21%, 22%, 23%, 24%, 25%, 30%, 35%, 40%, 45%, 50%, 55%, 60%, 65%, 70%, 75%, or even 80%) in some embodiments, strains accumulate lipid to a level below at least about 20% but above the level at which it is accumulated in the unmodified (i.e., parental) strain. In some such embodiments, modified strains accumulate lipid to a level about 5%, 6%, 7%, 8%, 9%, 10%, 11%, 12%, 13%, 14%, 15%, 16%, 17%, 18%, 19% of their dry cell weight.

In some embodiments sterol(s) can be produced in the strains to at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 35%, at least about 40%, at least about 45%, at least about 50%, or more of fungus' dry cell weight. Thus, the provided manipulated strains can then be used to produce one or more sterol compounds (e.g., squalene, lanosterol, zymosterol, ergosterol, 7-dehydrocholesterol (provitamin D3), one or more vitamin D compounds, etc). In some embodiments, the sterol compound(s) that partition(s) into the lipid bodies can readily be isolated. In some embodiments, the sterol compound is squalene, lanosterol, zymosterol, ergosterol, 7-dehydrocholesterol (provitamin D3); in some embodiments it is a vitamin D compound. In some embodiments, it is vitamin D3 or a provitamin thereof; in some embodiments, it is 7-dehydrocholesterol.

In some embodiments, it will be desirable to balance oleaginy and sterol production in cells such that, as soon as a minimum desirable level of oleaginy is achieved, substantially all further carbon is diverted into a sterologenic production pathway. In some embodiments of the invention, this strategy involves engineering cells to be oleaginous; in other embodiments, it involves engineering cells to accumulate a higher level of lipid, particularly cytoplasmic lipid, than they would do in the absence of such engineering even though the engineered cells may not become "oleaginous" as defined herein. In other embodiments, the extent to which an oleaginous host cell accumulates lipid is actually reduced so that remaining carbon can be utilized in sterol production.

To give but one example of adjustments that could be made to achieve a desired balance between oleaginy and sterol production, we note that, while increasing acetyl CoA carboxylase expression (and/or activity) promotes oleaginy, decreasing its expression and/or activity may promote sterol production. Those of ordinary skill in the art will appreciate that the expression and/or activity of acetyl CoA carboxylase, or of other polypeptides, may be adjusted up or down as desired according to the characteristics of a particular host cell of interest.

We note that engineered cells and processes of using them as described herein may provide one or more advantages as compared with unmodified (i.e., parental) cells. Such advantages may include, but are not limited to: increased yield (e.g., sterol compound content expressed as either % dry cell weight (mg/mg) or parts per million), titer (g sterol compound/L), specific productivity (mg sterol compound $g^{-1}$ biomass $hour^{-1}$), and/or volumetric productivity (g sterol compound $liter^{-1}$ $hour^{-1}$)) of the desired sterol compound (and/or intermediates thereof), and/or decreased formation of undesirable side products (for example, undesirable intermediates).

Thus, for example, the specific productivity for one or more desired sterol compound or total sterol compound content may be at or about 0.1, at or about 0.11, at or about 0.12, at or about 0.13, at or about 0.14, at or about 0.15, at or about 0.16, at or about 0.17, at or about 0.18, at or about 0.19, at or about 0.2, at or about 0.21, at or about 0.22, at or about 0.23, at or about 0.24, at or about 0.25, at or about 0.26, at or about 0.27, at or about 0.28, at or about 0.29, at or about 0.3, at or about 0.31, at or about 0.32, at or about 0.33, at or about 0.34, at or about 0.35, at or about 0.36, at or about 0.37, at or about 0.38, at or about 0.39, at or about 0.4, at or about 0.41, at or about 0.42, at or about 0.43, at or about 0.44, at or about 0.45, at or about 0.46, at or about 0.47, at or about 0.48, at or about 0.49, at or about 0.5, at or about 0.51, at or about 0.52, at or about 0.53, at or about 0.54, at or about 0.55, at or about 0.56, at or about 0.57, at or about 0.58, at or about 0.59, at or about 0.6, at or about 0.61, at or about 0.62, at or about 0.63, at or about 0.64, at or about 0.65, at or about 0.66, at or about 0.67, at or about 0.68, at or about 0.69, at or about 0.7, at or about 0.71, at or about 0.72, at or about 0.73, at or about 0.74, at or about 0.75, at or about 0.76, at or about 0.77, at or about 0.78, at or about 0.79, at or about 0.8, at or about 0.81, at or about 0.82, at or about 0.83, at or about 0.84, at or about 0.85, at or about 0.86, at or about 0.87, at or about 0.88, at or about 0.89, at or about 0.9, at or about 0.91, at or about 0.92, at or about 0.93, at or about 0.94, at or about 0.95, at or about 0.96, at or about 0.97, at or about 0.98, at or about 0.99, at or about 1, 1.05, at or about 1.1, at or about 1.15, at or about 1.2, at or about 1.25, at or about 1.3, at or about 1.35, at or about 1.4, at or about 1.45, at or about 1.5, at or about 1.55, at or about 1.6, at or about 1.65, at or about 1.7, at or about 1.75, at or about 1.8, at or about 1.85, at or about 1.9, at or about 1.95, at or about 2 mg hour$^{-1}$ or more.

Thus, for example, the volumetric productivity for one or more desired sterol compound (e.g. squalene, vitamin D compound) or total sterol compound content may be at or about 0.01, at or about 0.011, at or about 0.012, at or about 0.013, at or about 0.014, at or about 0.015, at or about 0.016, at or about 0.017, at or about 0.018, at or about 0.019, at or about 0.02, at or about 0.021, at or about 0.022, at or about 0.023, at or about 0.024, at or about 0.025, at or about 0.026, at or about 0.027, at or about 0.028, at or about 0.029, at or about 0.03, at or about 0.031, at or about 0.032, at or about 0.033, at or about 0.034, at or about 0.035, at or about 0.036, at or about 0.037, at or about 0.038, at or about 0.039, at or about 0.04, at or about 0.041, at or about 0.042, at or about 0.043, at or about 0.044, at or about 0.045, at or about 0.046, at or about 0.047, at or about 0.048, at or about 0.049, at or about 0.05, at or about 0.051, at or about 0.052, at or about 0.053, at or about 0.054, at or about 0.055, at or about 0.056, at or about 0.057, at or about 0.058, at or about 0.059, at or about 0.06, at or about 0.061, at or about 0.062, at or about 0.063, at or about 0.064, at or about 0.065, at or about 0.066, at or about 0.067, at or about 0.068, at or about 0.069, at or about 0.07, at or about 0.071, at or about 0.072, at or about 0.073, at or about 0.074, at or about 0.075, at or about 0.076, at or about 0.077, at or about 0.078, at or about 0.079, at or about 0.08, at or about 0.081, at or about 0.082, at or about 0.083, at or about 0.084, at or about 0.085, at or about 0.086, at or about 0.087, at or about 0.088, at or about 0.089, at or about 0.09, at or about 0.091, at or about 0.092, at or about 0.093, at or about 0.094, at or about 0.095, at or about 0.096, at or about 0.097, at or about 0.098, at or about 0.099, at or about 0.1, 0.105, at or about 0.110, at or about 0.115, at or about 0.120, at or about 0.125, at or about 0.130, at or about 0.135, at or about 0.14, at or about 0.145, at or about 0.15, at or about 0.155, at or about 0.16, at or about 0.165, at or about 0.17, at or about 0.175, at or about 0.18, at or about 0.185, at or about 0.19, at or about 0.195, at or about 0.20 grams liter$^{-1}$ hour$^{-1}$ or more.

Host Cells

Those of ordinary skill in the art will readily appreciate that a variety of yeast and fungal strains exist that are naturally oleaginous, and all yeast and fungal strains that have been analyzed have been shown to produce one or more sterol compounds, at least under certain culturing conditions. Most yeast and fungal strains accumulate ergosterol, a sterol compound. In general, yeast and fungal strains accumulate ergosterol as the predominant sterol compound. Most yeast and fungal strains accumulate ergosterol to several percent of the dry cell weight, whereas other sterol compounds such as squalene, lanosterol, zymosterol, episterol, and fecosterol accumulate to approximately 1% dry cell weight or less. Specific yeast strains have been modified to produce approximately 10% dry cell weight or more of the sterol compounds squalene and ergosterol (see, for example, EB00486290B1 and UA20060088903A1). Yeast and fungal strains do not typically accumulate significant quantities of sterol compounds of interest such as one or more vitamin D compounds such as 7-dehydrocholesterol or calcitriol. Any oleaginous strain may be utilized as a host strain according to the present invention, and may be engineered or otherwise manipulated to generate inventive oleaginous, sterol-producing strains. Alternatively, strains that naturally are not oleaginous may be employed. Furthermore, even when a particular strain has a natural capacity for oleaginy and for sterol production, its natural capabilities may be adjusted as described herein for optimal production of one or more particular desired sterol compounds.

In certain embodiments, engineering or manipulation of a strain results in modification of a type of lipid and/or sterol compound produced. For example, a strain may be naturally oleaginous and/or may naturally produce one or more sterol compound(s). However, engineering or modification of the strain may be employed so as to change the type or amount of lipid that is accumulated and/or to adjust sterol compound production. In some embodiments, squalene production will be optimized; in some embodiments, production of one or more vitamin D compounds will be optimized; in some embodiments, production of 7-dehydrocholesterol will be optimized; in some embodiments, production of calcitriol will be optimized; in some embodiments, production of lanosterol will be optimized; in some embodiments, production of zymosterol will be optimized; in some embodiments, production of ergosterol will be optimized.

When selecting a particular yeast or fungal strain for use in accordance with the present invention, it will generally be desirable to select one whose cultivation characteristics are amenable to commercial scale production. For example, it will generally (though not necessarily always) be desirable to avoid filamentous organisms, or organisms with particularly unusual or stringent requirements for growth conditions. In some embodiments of the invention, it will be desirable to utilize edible organisms as host cells, as they may optionally be formulated directly into pharmaceutical compositions, food or feed additives, or into nutritional supplements, as desired. Some embodiments of the invention utilize host cells that are genetically tractable, amenable to molecular genetics (e.g., can be efficiently transformed, especially with established or available vectors; optionally can incorporate and/or integrate multiple genes, for example sequentially; and/or have known genetic sequence; etc), devoid of complex growth requirements (e.g., a necessity for light), mesophilic (e.g., prefer growth temperatures within the range of about 20-32° C.) (e.g. 20, 21, 22, 23, 24, 25, 26, 27, 28, 29, 30, 31, 32° C.), able to assimilate a variety of carbon and nitrogen sources and/or capable of growing to high cell density. Alternatively or additionally, various embodiments of the invention utilize host cells that grow as single cells rather than, for example, as mycelia.

In general, when it is desirable to utilize a naturally oleaginous organism in accordance with the present invention, any modifiable and cultivatable oleaginous organism may be employed. In certain embodiments of the invention, yeast or fungi of genera including, but not limited to, *Blakeslea, Candida, Cryptococcus, Cunninghamella, Lipomyces, Mortierella, Mucor, Phycomyces, Pythium, Rhodosporidium, Rhodotorula, Thraustochytrium, Trichosporon*, and *Yarrowia* are employed. In certain particular embodiments, organisms of species that include, but are not limited to, *Blakeslea trispora, Candida pulcherrima, C. revkaufi, C. tropicalis, Cryptococcus curvatus, Cunninghamella echinulata, C. elegans, C. japonica, Lipomyces starkeyi, L. lipoferus, Mortierella alpina, M. isabellina, M. ramanniana, M. vinacea, Mucor circinelloides, Phycomyces blakesleanus, Pythium* irregulare, Rhodosporidium toruloides, Rhodotorula glutinis, R. gracilis, R. graminis, R. mucilaginosa, R. pinicola, Thraustochytrium sp, Trichosporon pullans, T. cutaneum, and Yarrowia lipolytica are used.

All of these naturally oleaginous strains produce one or more sterol compounds. In most cases, only low levels (less than about 1% dry cell weight) of sterol compound(s) other than ergosterol are produced by naturally-occurring sterologenic, oleaginous yeast or fungi.

The present invention may utilize any naturally oleaginous, sterol-compound-producing organism as a host cell. In general, the present invention may be utilized to increase carbon flow into the isoprenoid pathway in naturally sterol-producing organisms, and/or to shift production from one sterol compound (e.g., squalene, lanosterol, zymosterol, ergosterol, 7-dehydrocholesterol (provitamin D3) or a vitamin D compound) to another (e.g., a vitamin D compound or squalene, lanosterol, zymosterol, ergosterol, 7-dehydrocholesterol (provitamin D3), respectively). Introduction of one or more sterologenic modifications (e.g., increased expression of one or more endogenous or heterologous sterologenic polypeptides), in accordance with the present invention, can achieve these goals.

In certain embodiments of the invention, the utilized oleaginous, sterol-producing organism is a yeast or fungus, for example of a genus such as, but not limited to, *Yarrowia*; in some embodiments, the organism is of a species such as *Yarrowia lipolytica*.

When it is desirable to utilize strains that are naturally non-oleaginous as host cells in accordance with the present invention, genera of non-oleaginous yeast or fungi include, but are not limited to, *Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderma,* and *Xanthophyllomyces (Phaffia)*; in some embodiments, the organism is of a species including, but not limited to, *Aspergillus nidulans, A. niger, A. terreus, Botrytis cinerea, C. utilis, Cercospora nicotianae, Fusarium fujikuroi (Gibberella zeae), Kluyveromyces lactis, K lactis, Neurospora crassa, Pichia pastoris, Puccinia distincta, Saccharomyces cerevisiae, Schizosaccharomyces pombe, Sclerotium rolfsii, Trichoderma reesei,* and *Xanthophyllomyces dendrorhous (Phaffia rhodozyma)*.

It will be appreciated that the term "non-oleaginous", as used herein, encompasses both strains that naturally have some ability to accumulate lipid, especially cytoplasmically, but do not do so to a level sufficient to qualify as "oleaginous" as defined herein, as well as strains that do not naturally have any ability to accumulate extra lipid, e.g., extra-membranous lipid. It will further be appreciated that, in some embodiments of the invention, it will be sufficient to increase the natural level of oleaginy of a particular host cell, even if the modified cell does not qualify as oleaginous as defined herein. In some embodiments, the cell will be modified to accumulate at least about 19%, 18%, 17%, 16%, 15%, 14%, 13%, 12%, 11%, 10%, 9%, 8%, 7%, 6%, or 5% of dry cell weight as lipid, so long as the accumulation level is more than that observed in the unmodified parental cell.

As with the naturally oleaginous organisms, all of the naturally non-oleaginous fungi naturally produce one or more sterol compounds. Genera of naturally non-oleaginous fungi that may desirably be used as host cells in accordance with the present invention include, but are not limited to, *Aspergillus, Kluyveromyces, Penicillium, Saccharomyces, Xanthophyllomyces,* and *Pichia*; species include, but are not limited to, *Aspergillus niger, Candida utilis, Xanthophyllomyces dendrorhous (Phaffia rhodozyma)* and *Saccharomyces cerevisiae*.

In some embodiments of the invention, it may be desirable to utilize a host cell that is modified as compared with a naturally-occurring host cell so that its natural ability to produce one or more particular sterol compounds and/or to generate lipid bodies of a particular character, is modified. Thus, the engineering contemplated by the present invention may include, for instance, disrupting an endogenous pathway for production of a particular sterol compound and/or lipid in favor of an engineered pathway for production of the same or a different sterol compound and/or lipid. To give but one specific example, *S. cerevisiae*, like many yeasts, naturally express ERG5 and ERG6 polypeptides, and naturally produce certain sterol compounds. ERG5 and ERG6 polypeptides are involved in synthesis of vitamin $D_2$ intermediates and therefore are involved in a biosynthetic pathway that competes with the vitamin $D_3$ pathway. It is known that modified *S. cerevisiae* strains lacking either one of these polypeptides are viable. The absence (or reduction in activity) of one or both of ERG5 and ERG6 in *S. cerevisiae* or in other host cells (e.g., *Yarrowia lipolytica, C. utilis, Phaffia rhodozyma*) would be expected to reduce diversion of vitamin D intermediates to production of vitamin $D_2$, and thereby to increase production of certain sterol compounds related to vitamin $D_3$ (e.g., 7-dehydrocholesterol). In some embodiments of the invention, therefore, it may be desirable to utilize host cells that naturally produce vitamin D compounds but whose vitamin $D_2$ biosynthetic pathway has been disrupted or inhibited. In some embodiments of the invention, it may be desirable to utilize host cells that naturally produce vitamin D compounds but whose vitamin $D_3$ biosynthetic pathway has been disrupted or inhibited, optionally in addition to disruption or inhibition of a vitamin $D_2$ biosynthetic pathway. Such host cells might be particularly useful, for example, for production of squalene.

Those of ordinary skill in the art will appreciate that the selection of a particular host cell for use in accordance with the present invention will also affect, for example, the selection of expression sequences utilized with any heterologous polypeptide to be introduced into the cell, codon bias that can optionally be engineered into any nucleic acid to be expressed in the cell and will also influence various aspects of culture conditions, etc. Much is known about the different gene regulatory requirements, and cultivation requirements, of different host cells to be utilized in accordance with the present invention. (see, for example, with respect to *Yarrowia*, Barth et al. *FEMS Microbiol Rev.* 19:219, 1997; Madzak et al. *J Biotechnol.* 109:63, 2004; see, for example, with respect to *Xanthophyllomyces*, Verdoes et al. *Appl Environ Microbiol* 69: 3728-38, 2003; Visser et al. FEMS Yeast Res 4: 221-31, 2003; Martinez et al. Antonie Van Leeuwenhoek. 73(2):147-53, 1998; Kim et al. *Appl Environ Microbiol.* 64(5):1947-9, 1998; Wery et al. Gene. 184(1):89-97, 1997; see, for example, with respect to *Saccharomyces*, Guthrie and Fink *Methods in Enzymology* 194:1-933, 1991).

As discussed above, any of a variety of organisms may be employed as host cells in accordance with the present invention. In certain embodiments of the invention, host cells will be *Y. lipolytica* cells. Advantages of *Y. lipolytica* include, for example, tractable genetics and molecular biology, availability of genomic sequence (see, for example, Sherman et al. *Nucleic Acids Res.* 32 (Database issue):D315-8, 2004), suitability to various cost-effective growth conditions, ability to grow to high cell density. In addition, *Y. lipolytica* is naturally oleaginous, such that fewer manipulations may be required when using *Y. lipolytica* as opposed to other candidate host cell, to generate an oleaginous, strain that produces a particular sterol compound of interest. Furthermore, there is already extensive commercial experience with *Y. lipolytica*.

*Saccharomyces cerevisiae* is also a useful host cell in accordance with the present invention, particularly due to its experimental tractability and the extensive experience that researchers have accumulated with the organism. Although cultivation of *Saccharomyces* under high carbon conditions may result in increased ethanol production, this can generally be managed by process and/or genetic alterations.

The edible fungus, *Candida utilis* is also a useful host cell in accordance with the present invention. Molecular biology tools and techniques are available in *C. utilis* (for example, see Iwakiri et al. (2006) *Yeast* 23:23-34, Iwakiri et al. (2005) *Yeast* 2005 22:1079-87, Iwakiri et al. (2005) *Yeast* 22:1049-60, Rodriquez et al. (1998) *Yeast* 14:1399-406, Rodriquez et al. (1998) *FEMS Microbiol Lett.* 165:335-40, and Kondo et al. (1995) *J Bacteriol.* 177:7171-7).

To give but a few specific examples of useful expression sequences, promoters including, but not limited to the Leu2 promoter and variants thereof (see, for example, see U.S. Pat. No. 5,786,212); the EF1alpha protein and ribosomal protein S7gene promoters (see, for example, PCT Application WO 97/44470); the Gpm (see US 2005/0014270), Xpr2 (see U.S. Pat. No. 4,937,189), Tef1, Gpd1 (see, for example, US 2005/0014270A1), Cam1 (YALI0C24420g), YALI0D16467g, Tef4 (YALI0B12562g), Yef3 (YALI0E13277g), Pox2, Yat1 (see, for example US 2005/0130280; PCT Application WO 06/052754), Fba1 (see, for example WO 05/049805), and/or Gpat (see WO 06/031937) promoters; the sequences represented by SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NO: 12, subsequences thereof, and hybrid and tandem derivatives thereof (e.g., as disclosed in US 2004/0146975); the sequences represented by SEQ ID NO: 1, 2, or 3 including fragments (e.g. by 462-1016 and by 197-1016 of SEQ ID NO: 1; by 5-523 of SEQ ID NO:3) and complements thereof (e.g., as disclosed in U.S. Pat. No. 5,952,195); CYP52A2A (see, for example, US 2002/0034788); promoter sequences from fungal (e.g., *C. tropicalis*) catalase, citrate synthase, 3-ketoacyl-CoA thiolase A, citrate synthase, O-acetylhornserine sulphydrylase, protease, carnitine O-acetyltransferase, hydratase-dehydrogenase, epimerase genes; promoter sequences from Pox4 genes (see, for example, US 2004/0265980); and/or promoter sequences from Met2, Met3, Met6, Met25 and YALI0D12903g genes. Any such promoters can be used in conjunction with endogenous genes and/or heterologous genes for modification of expression patterns of endogenous polypeptides and/or heterologous polypeptides.

Alternatively or additionally, regulatory sequences useful in accordance with the present invention may include one or more Xpr2 promoter fragments, for example as described in U.S. Pat. No. 6,083,717 (e.g. SEQ ID NOS: 1-4 also including sequences with 80% or more identity to these SEQ ID NOs) in one or more copies either in single or in tandem. Similarly, exemplary terminator sequences include, but are not limited to, *Y. lipolytica* Xpr2 (see U.S. Pat. No. 4,937,189) and Pox2 (YALI0F10857g) terminator sequences as well as the terminator sequences disclosed in example 7 herein.

In some embodiments of this invention, it may be desirable to fused sequences encoding specific targeting signals to bacterial source genes. For example, in certain embodiments mitochondrial signal sequences are useful in conjunction with, e.g., bacterial polypeptides for effective targeting of polypeptides for proper functioning. Mitochondrial signal sequences are known in the art, and include, but are not limited to example, mitochondrial signal sequences provided in Table 22. In other embodiments, it may be desirable to utilize genes from other source organisms such as animals, plants, alga, or microalgae, fungi, yeast, insect, protozoa, and mammals.

Engineering Oleaginy

All living organisms synthesize lipids for use in their membranes and various other structures. However, most organisms do not accumulate in excess of about 10% of their dry cell weight as total lipid, and most of this lipid generally resides within cellular membranes.

Significant biochemical work has been done to define the metabolic enzymes necessary to confer oleaginy on microorganisms (primarily for the purpose of engineering single cell oils as commercial sources of arachidonic acid and docosahexaenoic acid; see for example Ratledge *Biochimie* 86:807, 2004, the entire contents of which are incorporated herein by reference). Although this biochemical work is compelling, there only have been a limited number of reports of de novo oleaginy being established through genetic engineering with the genes encoding the key metabolic enzymes. It should be noted that oleaginous organisms typically accumulate lipid only when grown under conditions of carbon excess and nitrogen limitation. The present invention further establishes that the limitation of other nutrients (e.g. phosphate or magnesium) can also induce lipid accumulation. The present invention establishes, for example, that limitation of nutrients such as phosphate and/or magnesium can induce lipid accumulation, much as is observed under conditions of nitrogen limitation. Under these conditions, the organism readily depletes the limiting nutrient but continues to assimilate the carbon source. The "excess" carbon is channeled into lipid biosynthesis so that lipids (usually triacylglycerols) accumulate in the cytosol, typically in the form of bodies.

In general, it is thought that, in order to be oleaginous, an organism must produce both acetyl-CoA and NADPH in the cytosol, which can then be utilized by the fatty acid synthase machinery to generate lipids. In at least some oleaginous organisms, acetyl-CoA is generated in the cytosol through the action of ATP-citrate lyase, which catalyzes the reaction:

$$\text{citrate} + \text{CoA} + \text{ATP} \rightarrow \text{acetyl-CoA} + \text{oxaloacetate} + \text{ADP} + P_i. \quad (1)$$

Of course, in order for ATP-citrate lyase to generate appropriate levels of acetyl-CoA in the cytosol, it must first have an available pool of its substrate citric acid. Citric acid is generated in the mitochondria of all eukaryotic cells through the tricarboxylic acid (TCA) cycle, and can be moved into the cytosol (in exchange for malate) by citrate/malate translocase.

In most oleaginous organisms, and in some non-oleaginous organisms, the enzyme isocitrate dehydrogenase, which operates as part of the TCA cycle in the mitochondria, is strongly AMP-dependent. Thus, when AMP is depleted from the mitochondria, this enzyme is inactivated. When isocitrate dehydrogenase is inactive, isocitrate accumulates in the mitochondria. This accumulated isocitrate is then equilibrated with citric acid, presumably through the action of aconitase. Therefore, under conditions of low AMP, citrate accumulates in the mitochondria. As noted above, mitochondrial citrate is readily transported into the cytosol.

Figure 2:
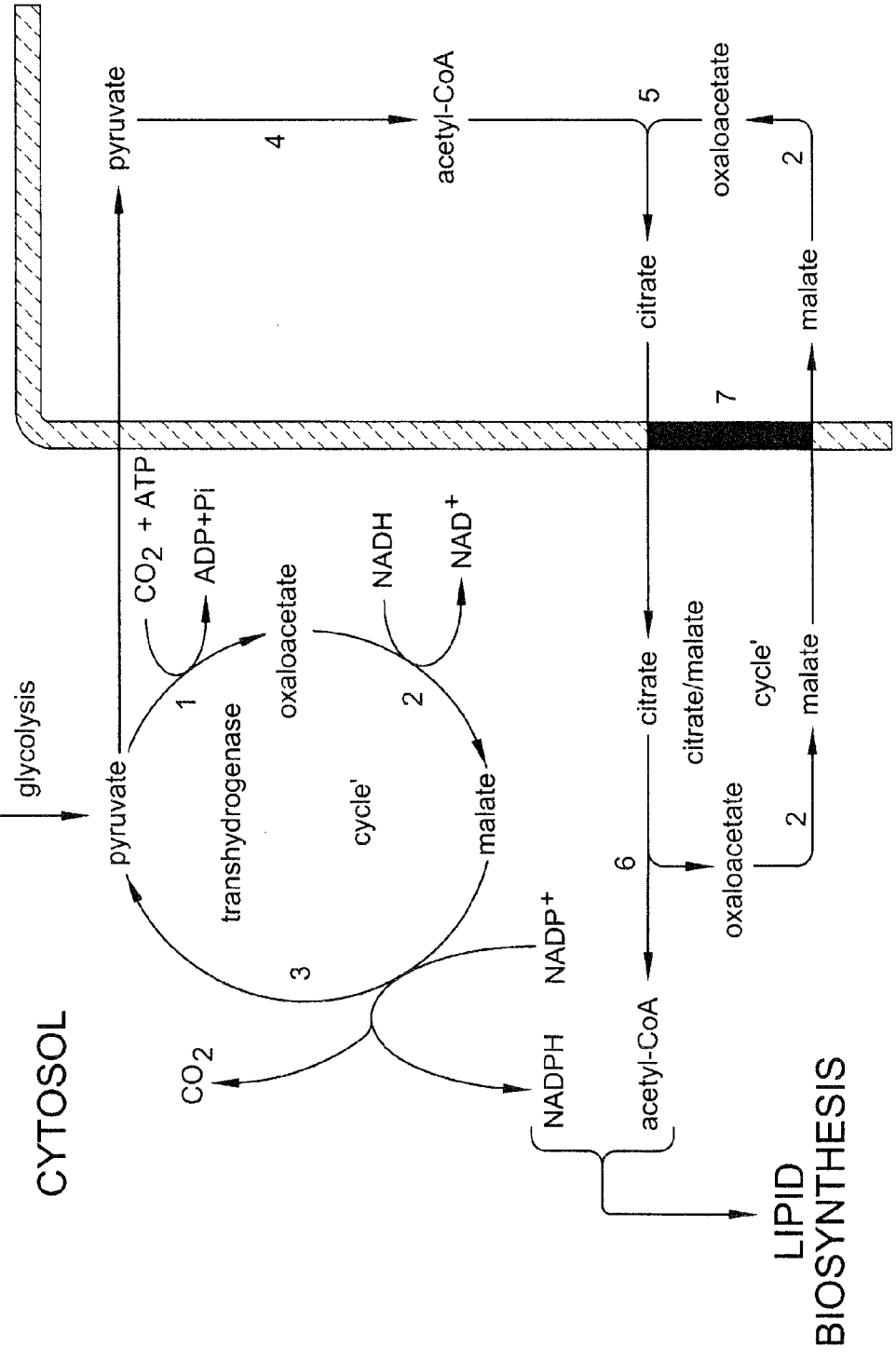
FIG. 2 depicts how sufficient levels of acetyl-CoA and NADPH may be accumulated in the cytosol of oleaginous organisms to allow for production of significant levels of cytosolic lipids. Enzymes: 1, pyruvate decarboxylase; 2, malate dehydrogenase; 3, malic enzyme; 4, pyruvate dehydrogenase; 5, citrate synthase; 6, ATP-citrate lyase; 7, citrate/malate translocase.

AMP depletion, which in oleaginous organisms is believed to initiate the cascade leading to accumulation of citrate (and therefore acetyl-CoA) in the cytoplasm, occurs as a result of the nutrient depletion mentioned above. When oleaginous cells are grown in the presence of excess carbon source but the absence of nitrogen or other nutrient (e.g., phosphate or magnesium), the activity of AMP deaminase, which catalyzes the reaction:

AMP→inosine 5'-monophosphate+NH$_3$ (2)

is strongly induced. The increased activity of this enzyme depletes cellular AMP in both the cytosol and the mitochondria. Depletion of AMP from the mitochondria is thought to inactivate the AMP-dependent isocitrate dehydrogenase, resulting in accumulation of citrate in the mitochondria and, therefore, the cytosol. This series of events is depicted diagrammatically in FIG. 2.

As noted above, oleaginy requires both cytosolic acetyl-CoA and cytosolic NADPH. It is believed that, in many oleaginous organisms, appropriate levels of cytosolic NADPH are provided through the action of malic enzyme (Enzyme 3 in FIG. 2). Some oleaginous organisms (e.g., *Lipomyces* and some *Candida*) do not appear to have malic enzymes, however, so apparently other enzymes can provide comparable activity, although it is expected that a dedicated source of NADPH is probably required for fatty acid synthesis (see, for example, Wynn et al., *Microbiol* 145:1911, 1999; Ratledge *Adv. Appl. Microbiol.* 51:1, 2002, each of which is incorporated herein by reference in its entirety).

Other activities which can be involved in regenerating NADPH include, for example, 6-phosphogluconate dehydrogenase (gnd); Fructose 1,6 bisphosphatase (fbp); Glucose 6 phosphate dehydrogenase (g6pd); NADH kinase (EC 2.7.1.86); and/or transhydrogenase (EC 1.6.1.1 and 1.6.1.2).

Gnd is part of the pentose phosphate pathway and catalyses the reaction:

6-phospho-D-gluconate+NADP+→D-ribulose 5-phosphate+CO$_2$+NADPH

Fbp is a hydrolase that catalyses the gluconeogenic reaction:

D-fructose 1,6-bisphosphate+H$_2$O→
D-fructose 6-phosphate+phosphate

Fbp redirects carbon flow from glycolysis towards the pentose phosphate pathway. The oxidative portion of the pentose phosphate pathway, which includes glucose 6 phosphate dehydrogenase and 6-phosphogluconate dehydrogenase, enables the regeneration of NADPH.

G6pd is part of the pentose phosphate pathway and catalyses the reaction:

D-glucose 6-phosphate+NADP$^+$→
D-glucono-1,5-lactone 6-phosphate+NADPH+H$^+$

NADH kinase catalyzes the reaction:

ATP+NADH→ADP+NADPH

Transhydrogenase catalyzes the reaction:

NADPH+NAD$^+$ ↔ NADP$^+$+NADH

Thus, enhancing the expression and/or activity of any of these enzymes can increase NADPH levels and promote anabolic pathways requiring NADPH.

Alternative or additional strategies to promote oleaginy may include one or more of the following: (1) increased or heterologous expression of one or more of acyl-CoA:diacylglycerol acyltransferase (e.g., DGA1; YALI0E32769g); phospholipid:diacylglycerol acyltransferase (e.g., LRO1; YALI0E16797g); and acyl-CoA:cholesterol acyltransferase (e.g., ARE genes such as ARE1, ARE2, YALI0F06578g), which are involved in triglyceride synthesis (Kalscheuer et al. *Appl Environ Microbiol* p. 7119-7125, 2004; Oelkers et al. *J Biol Chem* 277:8877-8881, 2002; and Sorger et al. *J Biol Chem* 279:31190-31196, 2004), (2) decreased expression of triglyceride lipases (e.g., TGL3 and/or TGL4; YALI0D17534g and/or YALI0F10010g (Kurat et al. *J Biol Chem* 281:491-500, 2006); and (3) decreased expression of one or more acyl-coenzyme A oxidase activities, for example encoded by POX genes (e.g. POX1, POX2, POX3, POX4, POX5; YALI0C23859g, YALI0D24750g, YALI0E06567g, YALI0E27654g, YALI0E32835g, YALI0F10857g; see for example Mlickova et al. *Appl Environ Microbiol* 70: 3918-3924, 2004; Binns et al. *J Cell Biol* 173:719, 2006).

Thus, according to the present invention, the oleaginy of a host organism may be enhanced by modifying the expression or activity of one or more polypeptides involved in generating cytosolic acetyl-CoA and/or NADPH and/or altering lipid levels through other mechanisms. For example, modification of the expression or activity of one or more of acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1, 6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, acyl-coenzyme A oxidase can enhance oleaginy in accordance with the present invention. Exemplary polypeptides which can be utilized or derived so as to enhance oleaginy in accordance with the present invention include, but are not limited to those acetyl-CoA carboxylase, pyruvate decarboxylase, isocitrate dehydrogenase, ATP-citrate lyase, malic enzyme, AMP-deaminase, glucose-6-phosphate dehydrogenase, 6-phosphogluconate dehydrogenase, fructose 1, 6 bisphosphatase, NADH kinase, transhydrogenase, acyl-CoA:diacylglycerol acyltransferase, phospholipid:diacylglycerol acyltransferase, acyl-CoA:cholesterol acyltransferase, triglyceride lipase, acyl-coenzyme A oxidase polypeptides provided in Tables 1-6 and 65-81 respectively.

In some embodiments of the invention, where an oleaginous host cell is employed, enzymes and regulatory components relevant to oleaginy are already in place but could be modified, if desired, by for example altering expression or activity of one or more oleaginic polypeptides and/or by introducing one or more heterologous oleaginic polypeptides. In those embodiments of the invention where a non-oleaginous host cell is employed, it is generally expected that at least one or more heterologous oleaginic polypeptides will be introduced.

The present invention contemplates not only introduction of heterologous oleaginous polypeptides, but also adjustment of expression or activity levels of heterologous or endogenous oleaginic polypeptides, including, for example, alteration of constitutive or inducible expression patterns. In some embodiments of the invention, expression patterns are adjusted such that growth in nutrient-limiting conditions is not required to induce oleaginy. For example, genetic modifications comprising alteration and/or addition of regulatory sequences (e.g., promoter elements, terminator elements) and/or regulatory factors (e.g., polypeptides that modulate transcription, splicing, translation, modification, etc.) may be utilized to confer particular regulation of expression patterns. Such genetic modifications may be utilized in conjunction with endogenous genes (e.g., for regulation of endogenous oleagenic polypeptide(s)); alternatively, such genetic modifications may be included so as to confer regulation of expression of at least one heterologous polypeptide (e.g., oleagenic polypeptide(s)).

In some embodiments, at least one oleaginic polypeptide is introduced into a host cell. In some embodiments of the invention, a plurality (e.g., two or more) of different oleaginic polypeptides is introduced into the same host cell. In some embodiments, the plurality of oleaginic polypeptides contains polypeptides from the same source organism; in other embodiments, the plurality includes polypeptides independently selected from different source organisms.

Representative examples of a variety of oleaginic polypeptides that may be introduced into or modified within host cells according to the present invention, include, but are not limited to, those provided in Tables 1-6, and Tables 65-81. As noted above, it is expected that at least some of these polypeptides (e.g., malic enzyme and ATP-citrate lyase) should desirably act in concert, and possibly together with one or more components of fatty acid synthase, such that, in some embodiments of the invention, it will be desirable to utilize two or more oleaginic polypeptides from the same source organism.

In certain embodiments, the oleaginy of a host organism is enhanced by growing the organism on a carbon source comprising one or more oils. For example, an organism may be grown on a carbon source comprising one or more oils selected from the group consisting of, for example, olive, canola, corn, sunflower, soybean, cottonseed, rapeseed, etc., and combinations thereof. In certain embodiments, the oleaginy of a host organism is enhanced by growing the organism on a carbon source comprising one or more oils in combination with modifying the expression or activity of one or more polypeptides such as any of those described above (e.g., oleaginic polypeptides such as polypeptides involved in generating cytosolic acetyl-CoA and/or NADPH) and/or altering lipid levels through other mechanisms.

In general, source organisms for oleaginic polypeptides to be used in accordance with the present invention include, but are not limited to, *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium* (*Gibberella*), *Kluyveromyces, Neurospora, Penicillium, Pichia* (*Hansenula*), *Puccinia, Saccharomyces, Sclerotium, Trichoderma,* and *Xanthophyllomyces* (*Phaffia*). In some embodiments, the source species for acetyl CoA carboxylase, ATP-citrate lyase, malic enzyme and/or AMP deaminase polypeptides include, but are not limited to, *Aspergillus nidulans, Cryptococcus neoformans, Fusarium fujikuroi, Kluyveromyces lactis, Neurospora crassa, Saccharomyces cerevisiae, Schizosaccharomyces pombe, Ustilago maydis,* and *Yarrowia lipolytica*; in some embodiments, source species for pyruvate decarboxylase or isocitrate dehydrogenase polypeptides include, but are not limited to *Neurospora crassa, Xanthophyllomyces dendrorhous* (*Phaffia rhodozyma*), *Aspergillus niger, Saccharomyces cerevisiae, Mucor circinelloides, Rhodotorula glutinis, Candida utilis, Mortierella alpina,* and *Yarrowia lipolytica*.

*Aspergillus niger* accumulates large amounts of citric acid, whereas *Mortierella alpina* and *Thraustochytrium* sp. accumulate large amounts of fatty acid, respectively; *Mortierella alpina* and *Thraustochytrium* are also oleaginous.

To give but one particular example of a host cell engineered to be oleaginous (or at least to accumulate increased levels of lipid) in accordance with the present invention, *S. cerevisiae* can be engineered to express one or more oleaginic polypeptides, e.g., from heterologous source organisms. In some embodiments, a plurality of different oleaginic polypeptides are expressed, optionally from different source organisms. For instance, in some embodiments, *S. cerevisiae* cells are engineered to express (and/or to increase expression of) ATP-citrate lyase (e.g., from *N. crassa*), AMP deaminase (e.g., from *S. cerevisiae*), and/or malic enzyme (e.g., from *M. cir-*

*cinelloides*). In other embodiments, *Candida utilis* and *Phaffia rhodozyma* can be similarly modified. Modified *S. cerevisiae, C. utilis,* and *P. rhodozyma* strains can be further modified as described herein to increase production of one or more sterol compounds.

In certain embodiments, host cells are engineered to be olegaginous by introducing one or more oleaginic polypeptides. In general, any oleaginic polypeptide can be introduced into any host cell of the present invention. In certain embodiments, such oleaginic polypeptides are codon-optimized to accommodate the codon preferences of the host cell. In certain embodiments, an oleaginic polypeptide introduced into a host cell is from the same organism as the host cell and/or a related organism. For example, without limitation, the present invention encompasses the recognition that it may be desirable to introduce a fungal oleaginic polypeptide into a fungal host cell (e.g., from the same and/or a related fungal species). In certain embodiments, the host cell is a *Y. lipolytica* host cell. In certain aspects of such embodiments, a *Y. lipolytica* olegainic polypeptide is introduced into the *Y. lipolytica* host cell. In certain aspects, a *S. cerevisiae* olegainic polypeptide is introduced into the *Y. lipolytica* host cell. In certain aspects, any of a variety of fungal olegainic polypeptides is introduced into the *Y. lipolytica* host cell.

Engineering Sterol Compound Biosynthesis

The present invention encompasses the recognition that lipid-accumulating systems are useful for the production and/or isolation of certain sterol compounds, and particularly of squalene, lanosterol, zymosterol, ergosterol and/or one or more vitamin D compounds (e.g., 7-dehydrocholesterol and/or calcitriol). Without wishing to be bound by theory, the present inventors propose that the higher intracellular membrane content may facilitate increased sterol compound production and/or accumulation. The present invention therefore encompasses the discovery that certain sterol compounds can desirably be produced in oleaginous yeast and fungi. According to the present invention, strains that both (i) accumulate lipid, often in the form of cytoplasmic lipid bodies and typically to at least about 20% of their dry cell weight, and (ii) produce one or more sterol compounds at a level at least about 1%, and in some embodiments at least about 3-20%, of their dry cell weight, are generated through manipulation of generally available strains (e.g., naturally-occurring strains and strains which have been previously genetically modified, whether via recombinant DNA techniques or mutagenesis directed modification). These manipulated strains are then used to produce one or more sterol compounds, so that compound(s) that partitions into the lipid bodies can readily be isolated.

In certain embodiments of the invention, host cells are *Yarrowia lipolytica* cells. Advantages of *Y. lipolytica* include, for example, tractable genetics and molecular biology, availability of genomic sequence, suitability to various cost-effective growth conditions, and ability to grow to high cell density. In addition, *Y. lipolytica* is naturally oleaginous, such that fewer manipulations may be required to generate an oleaginous, sterol-producing *Y. lipolytica* strain than might be required for other organisms. Furthermore, there is already extensive commercial experience with *Y. lipolytica*. In other embodiments, the host cells are *C. utilis, S. cerevisiae* or *P. rhodozyma* cells.

Figure 3:
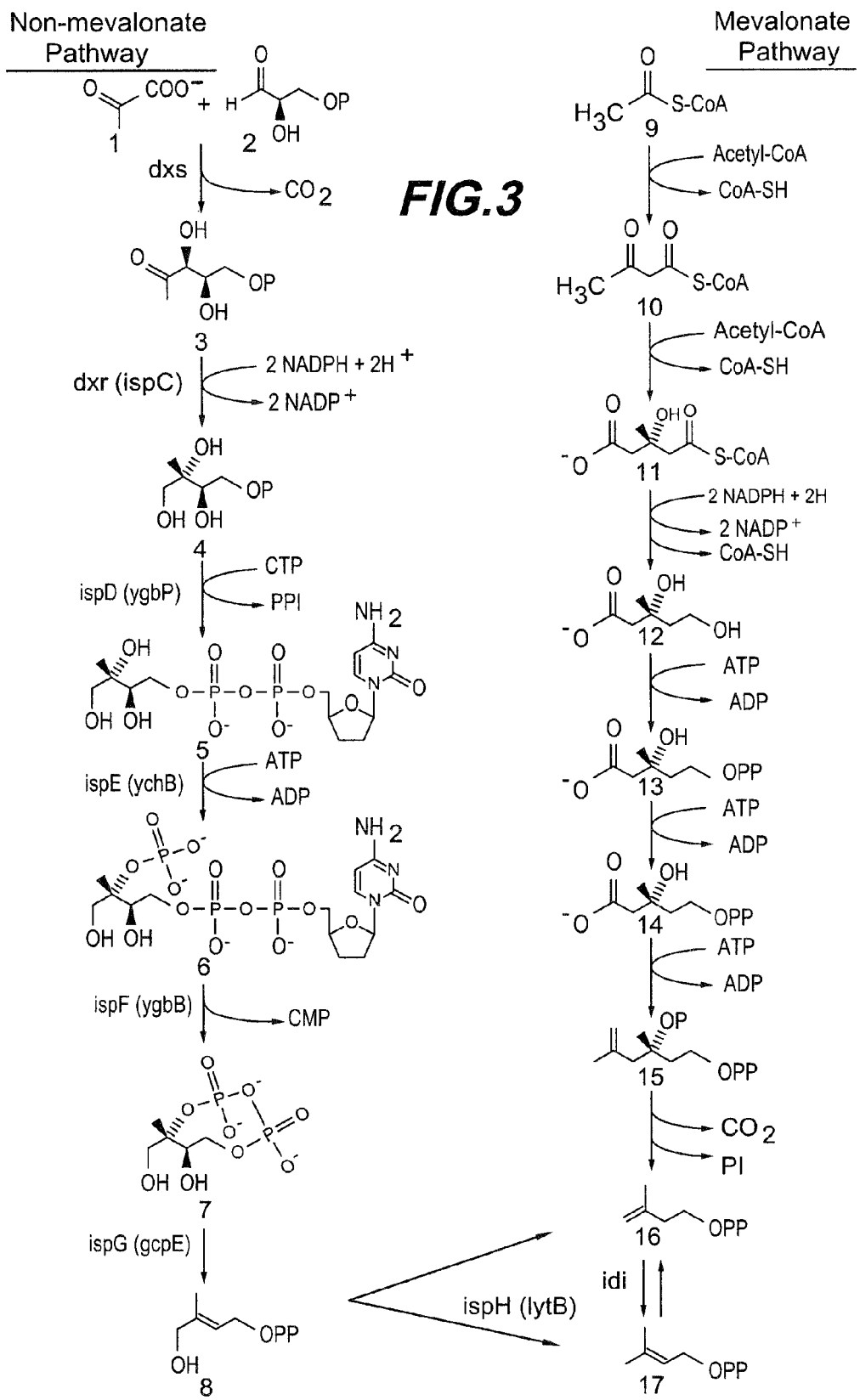
FIG. 3 depicts the mevalonate isoprenoid biosynthesis pathway, which typically operates in eukaryotes, including fungi; as well as the mevalonate-independent isoprenoid biosynthesis pathway, also known as the DXP pathway, which typically operates in bacteria and in the plastids of plants and production of isoprenoid precursors.

As mentioned, sterol compounds are produced from the isoprenoid compound isopentyl pyrophosphate (IPP). IPP can be generated through one of two different isoprenoid biosynthesis pathways. The most common isoprenoid biosynthesis pathway, sometimes referred to as the "mevalonate pathway", is generally depicted in FIG. 3. As shown, acetyl- CoA is converted, via hydroxymethylglutaryl-CoA (HMG-CoA), into mevalonate. Mevalonate is then phosphorylated and converted into the five-carbon compound isopentenyl pyrophosphate (IPP).

Figure 12:
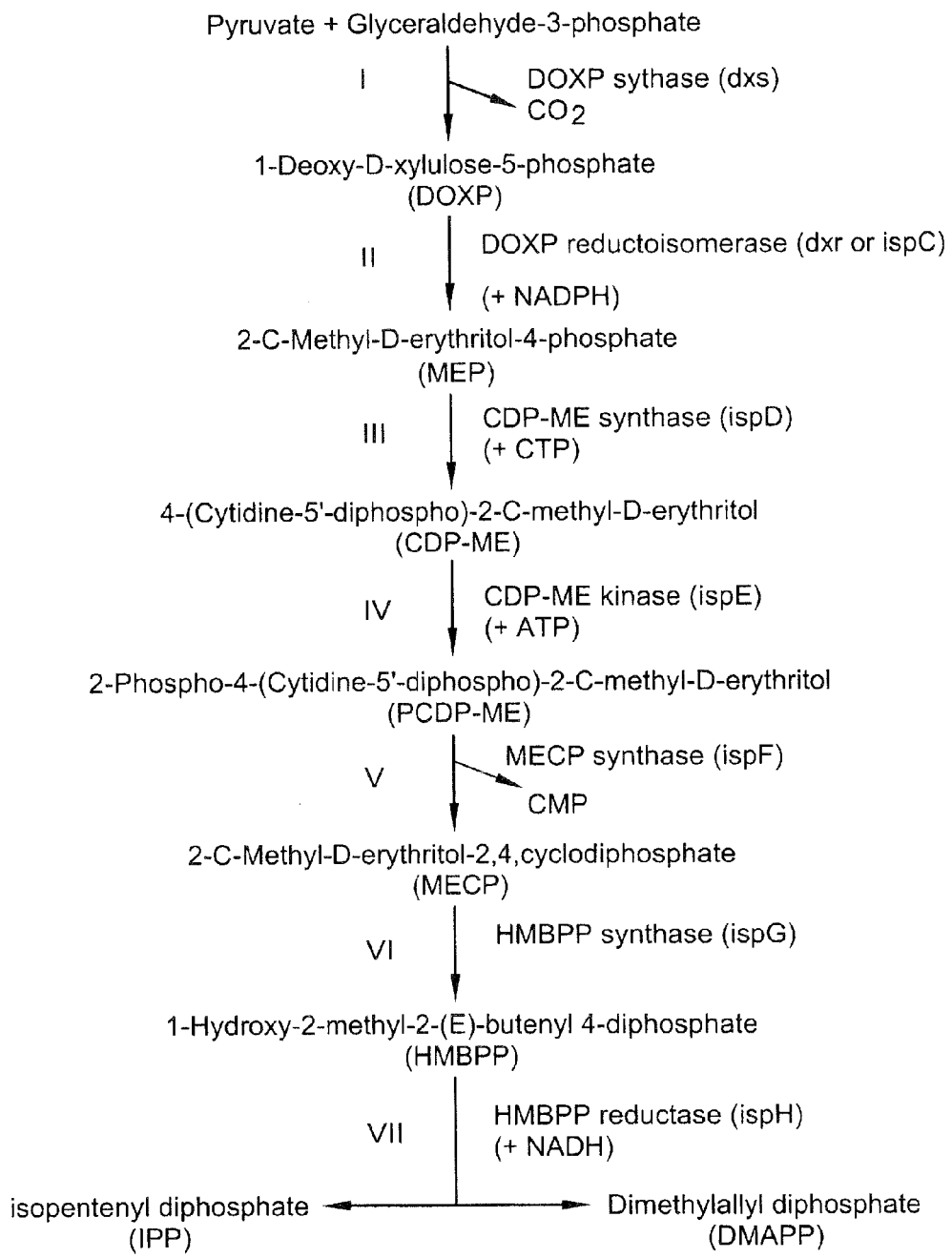
FIG. 12 depicts the mevalonate-independent isoprenoid biosynthesis pathway, also known as the DXP pathway, which typically operates in bacteria and in the plastids of plants.

An alternative isoprenoid biosynthesis pathway, that is utilized by some organisms (particularly bacteria) and is sometimes called the "mevalonate-independent pathway", is also depicted in FIG. 3. This pathway is initiated by the synthesis of 1-deoxy-D-xyloglucose-5-phosphate (DOXP) from pyruvate and glyceraldehyde-3-phosphate. DOXP is then converted, via a series of reactions shown in FIG. 12, into IPP.

Figure 5:
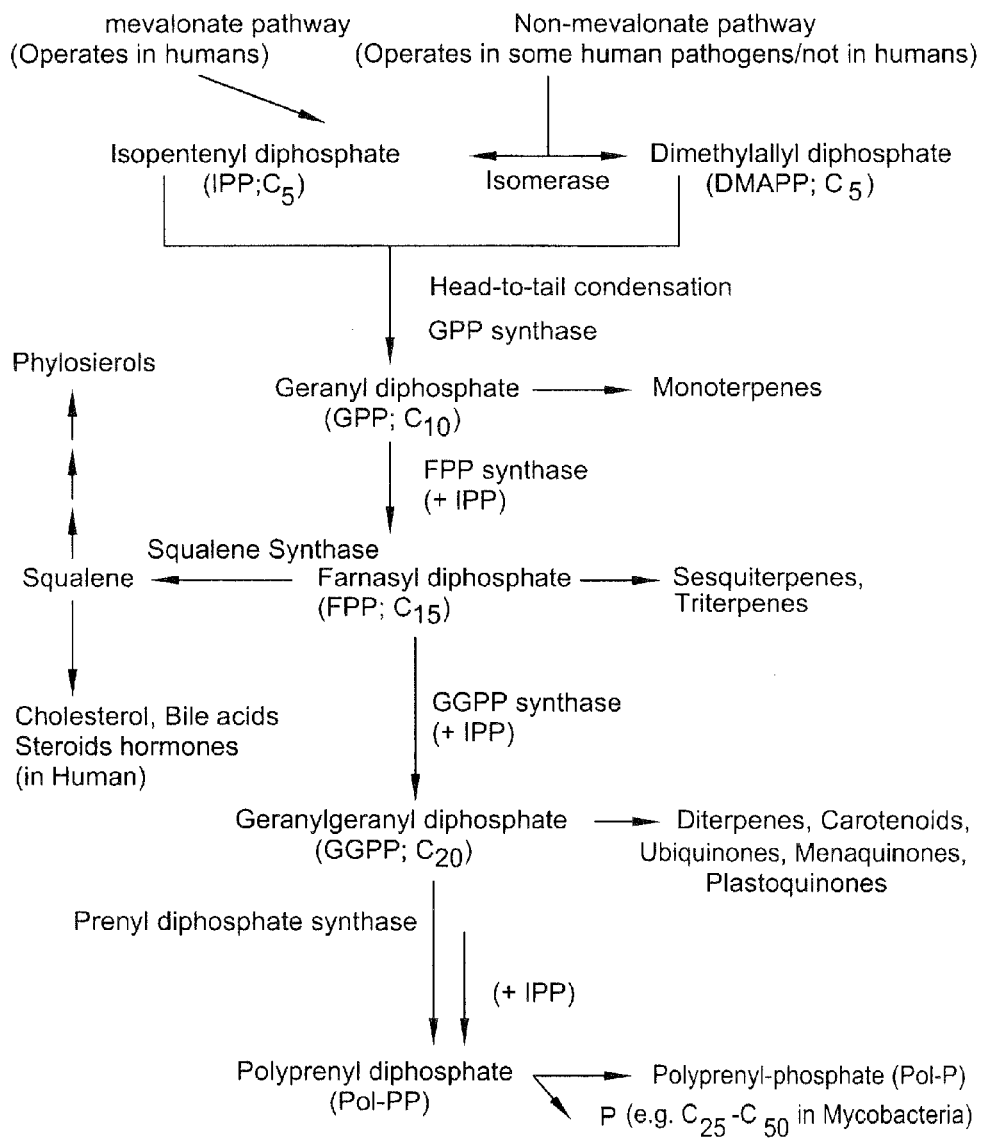
FIG. 5 illustrates how intermediates in the isoprenoid biosynthesis pathway can be processed into biomolecules, including ubiquinones, carotenoids, sterols, etc.
Figure 6:
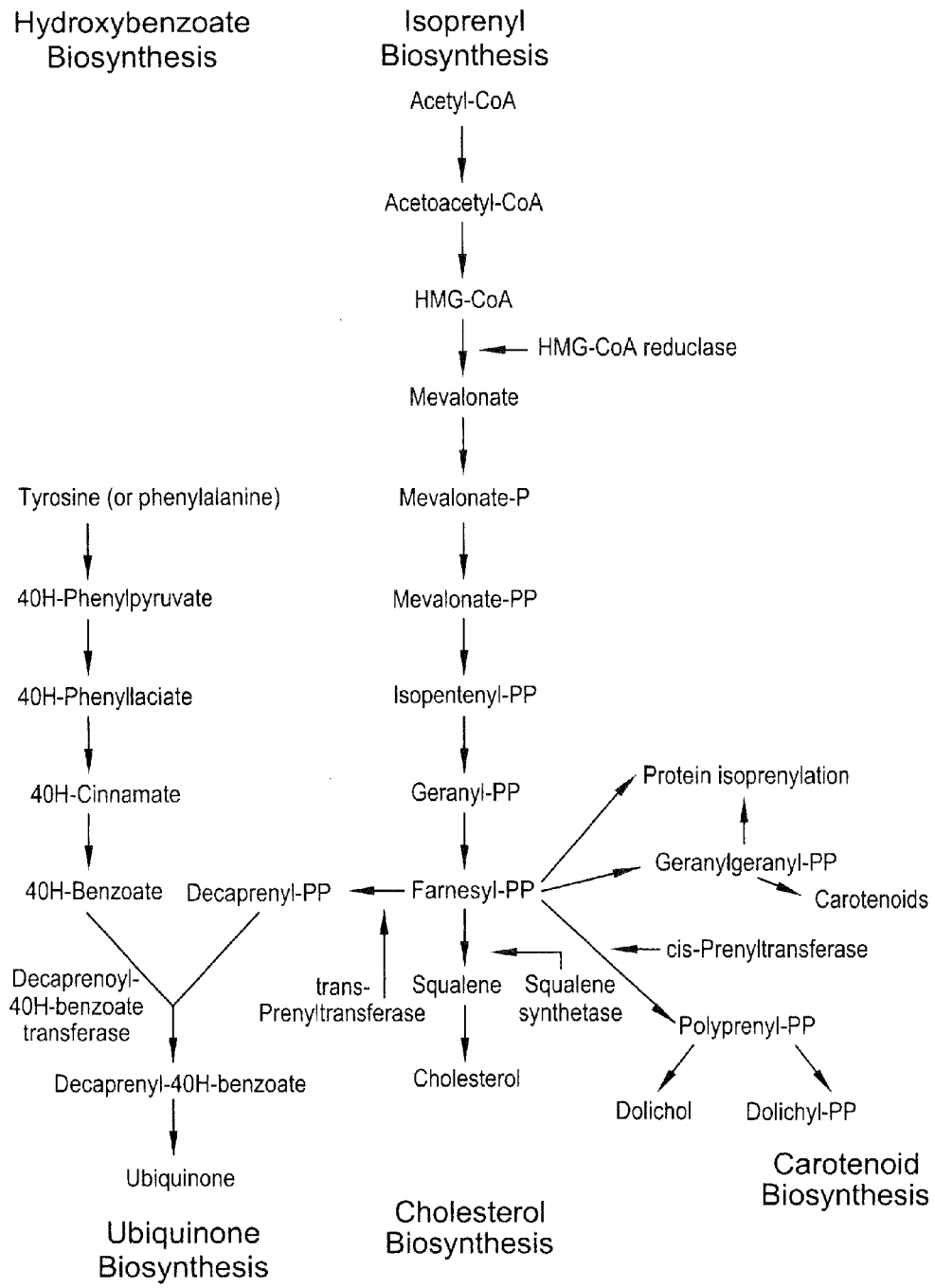
FIG. 6 illustrates how intermediates in isoprenoid biosynthesis feed into the biosynthetic pathway, and how some intermediates can be processed into other molecules.
Figure 9D:
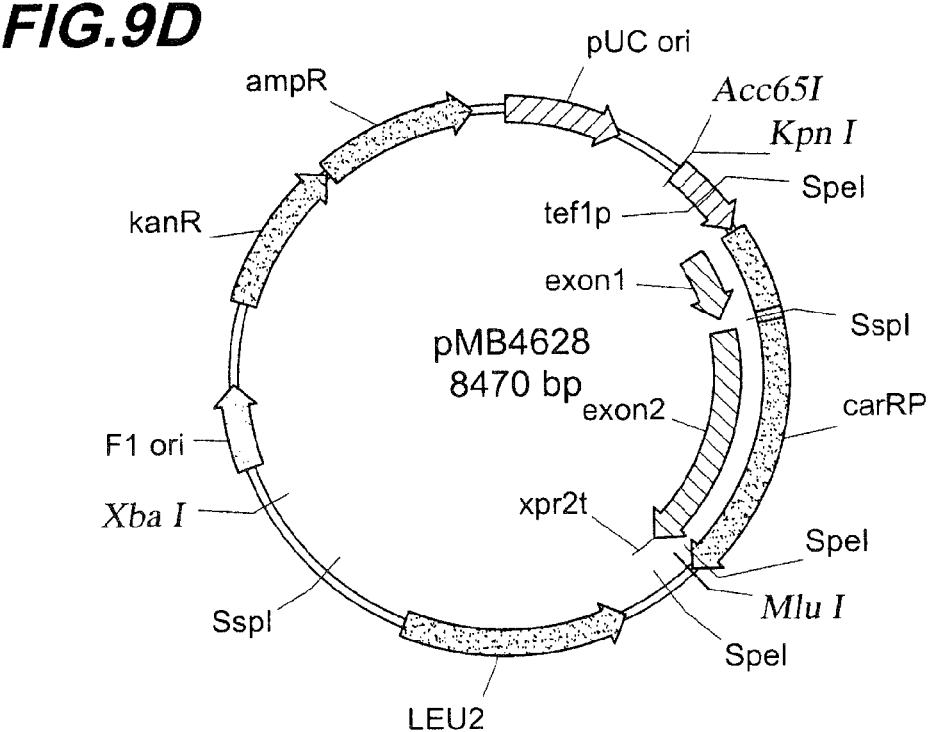
Figure 9E:
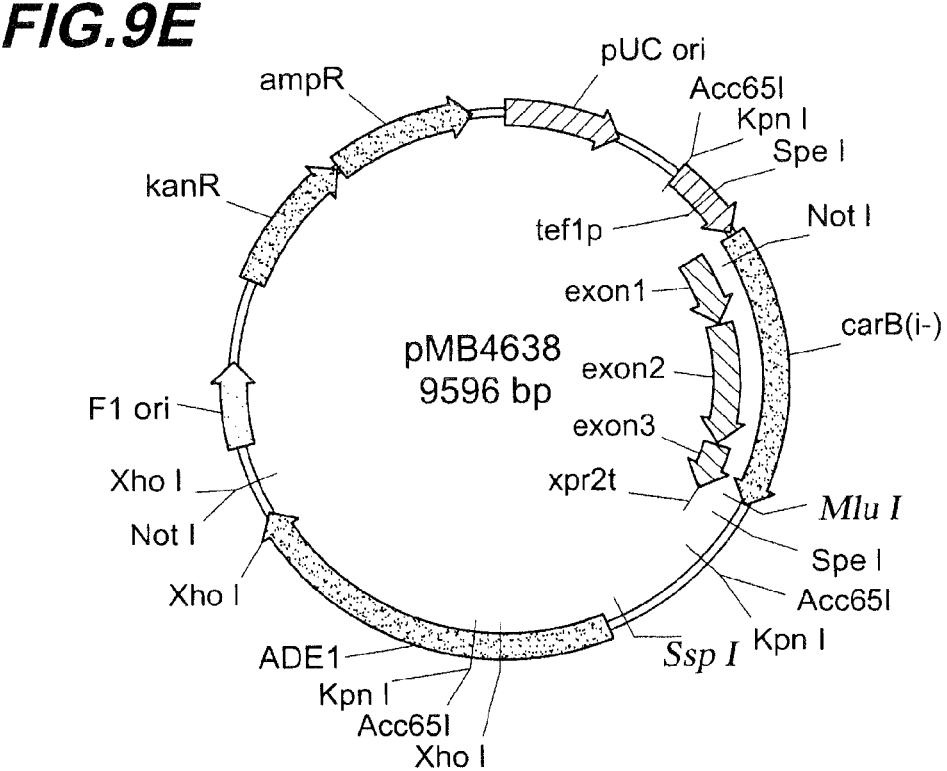
Figure 9F:
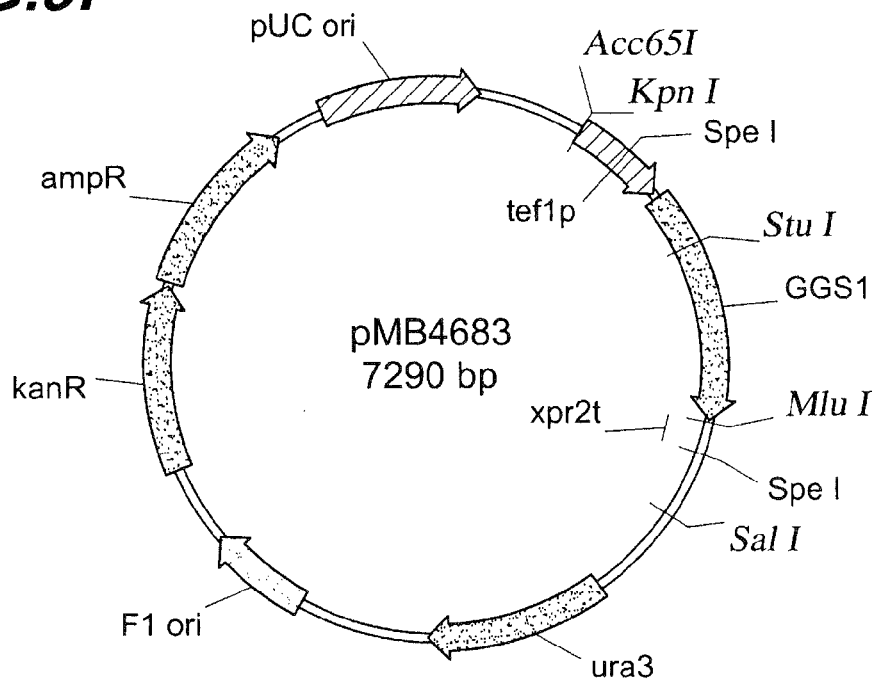
Figure 9G:
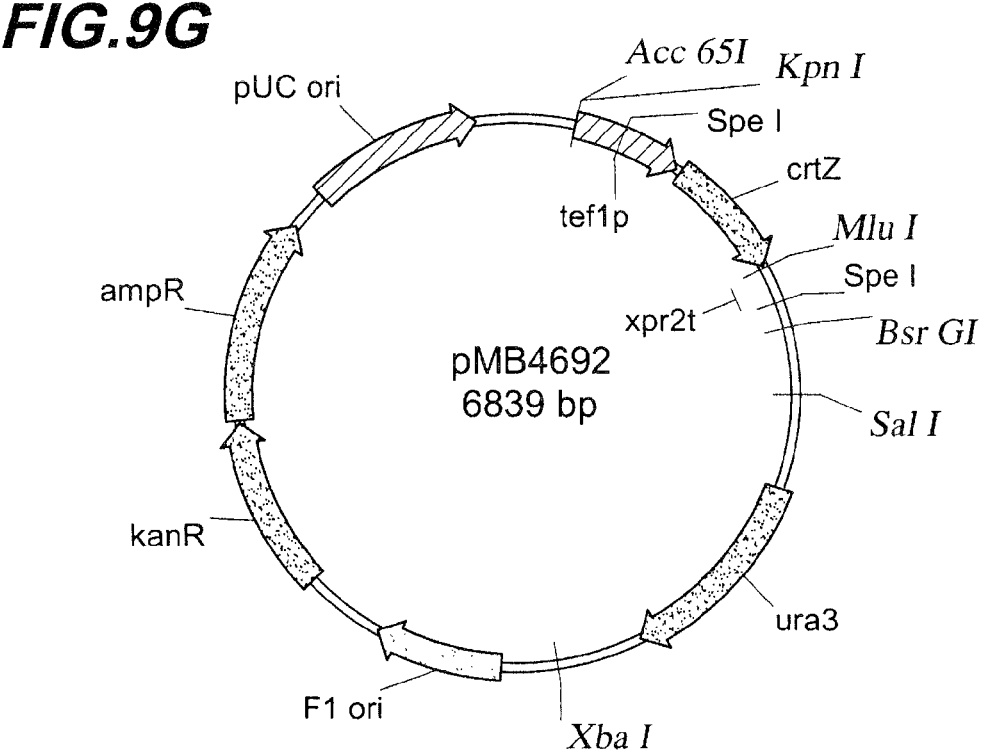
Figure 9H:
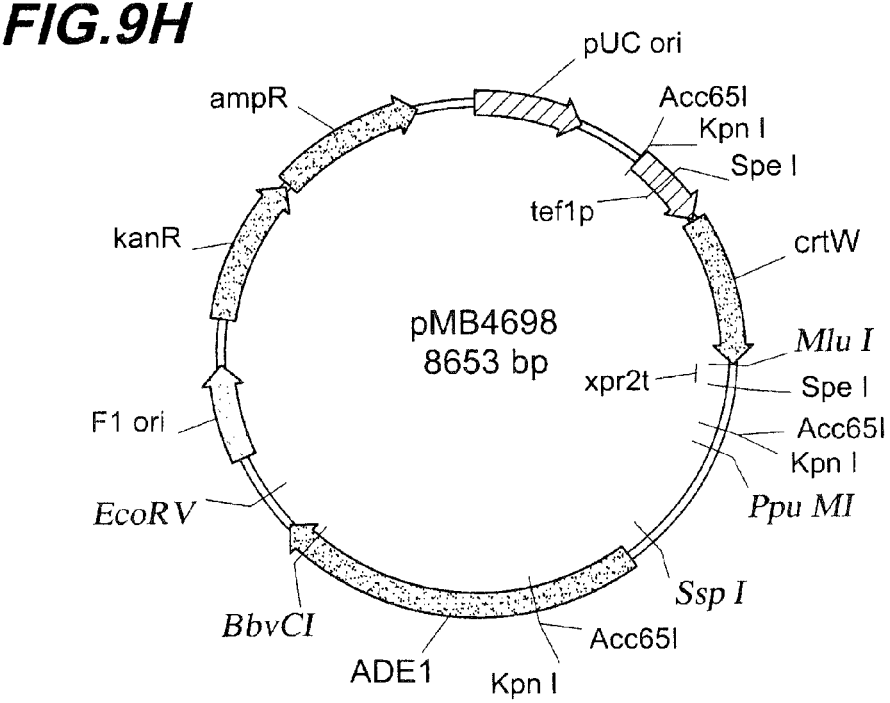
Figure 9I:
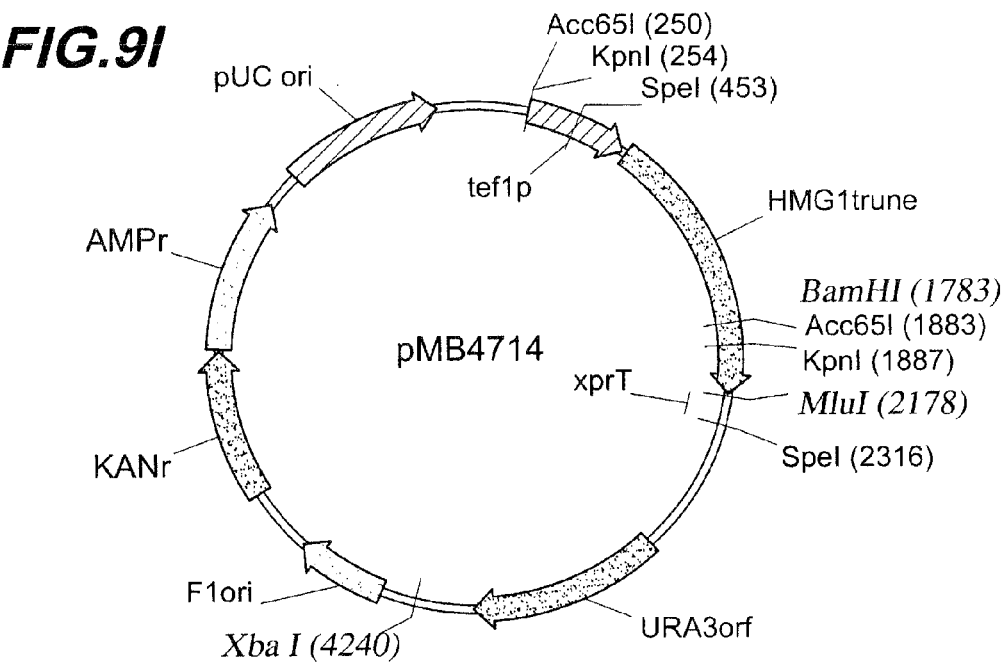
Figure 9J:
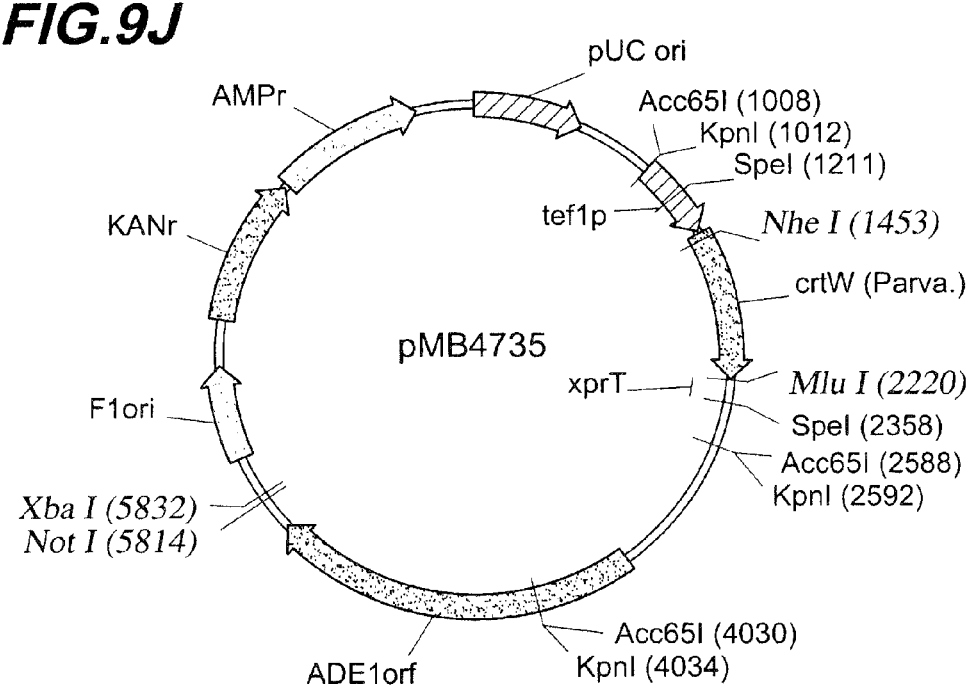
Figure 9K:
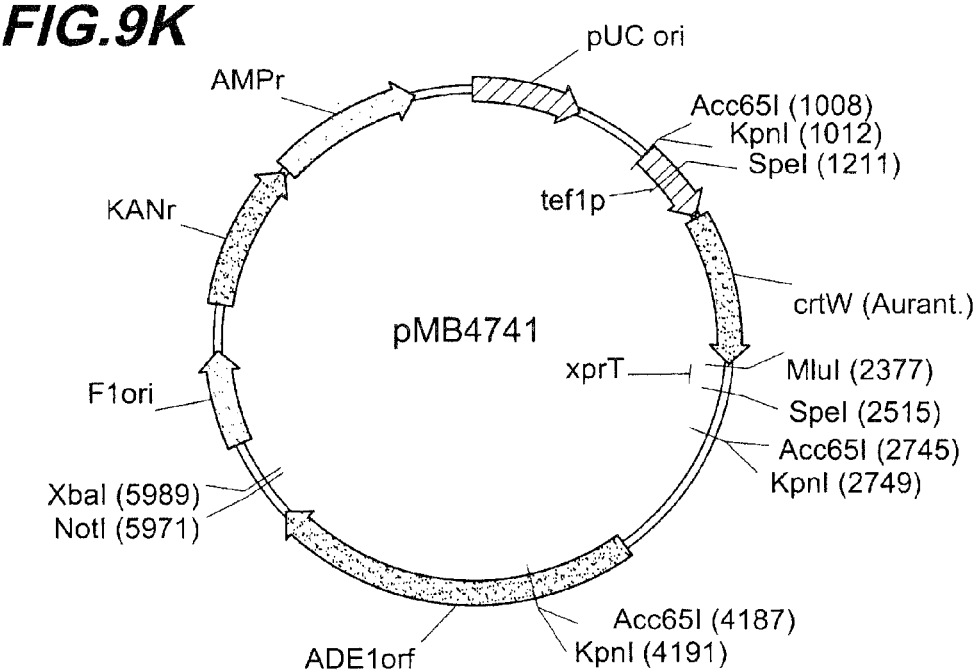
Figure 9L:
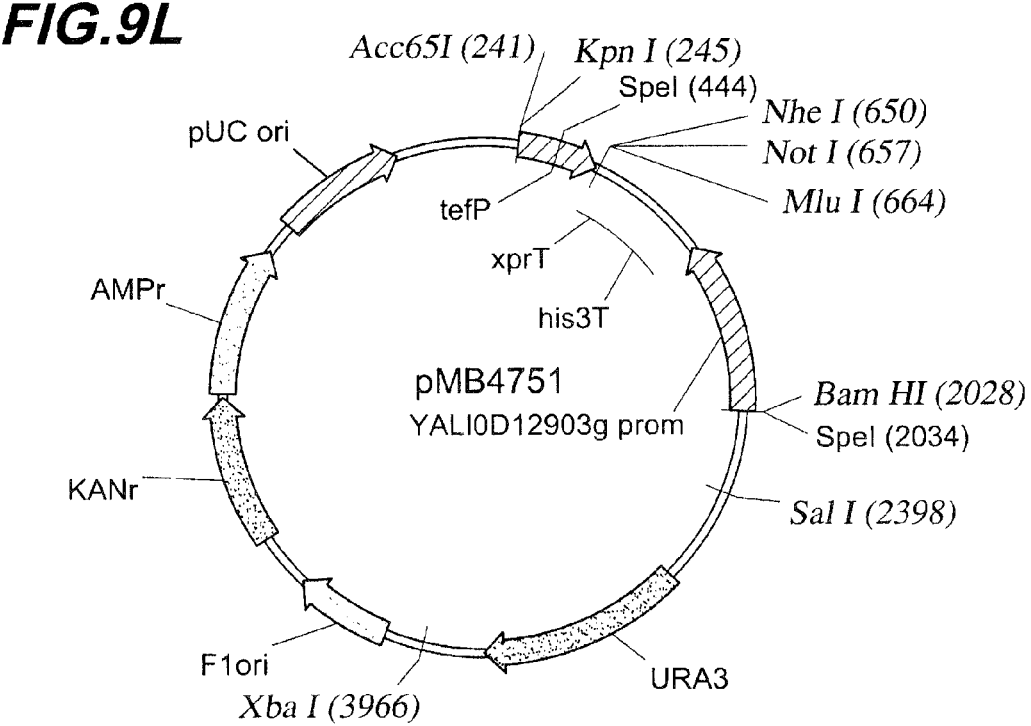
Figure 9M:
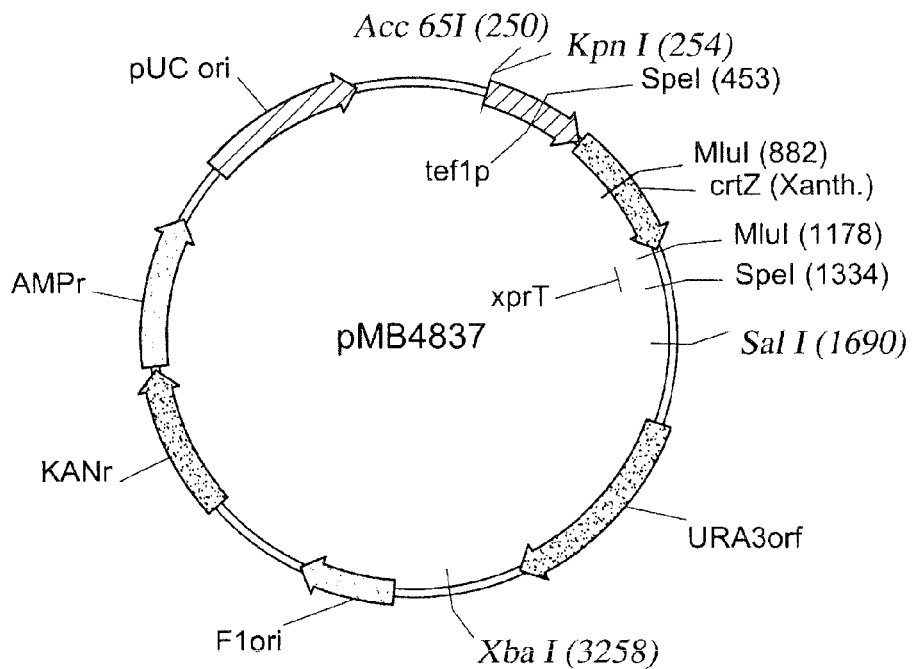

Various proteins involved in isoprenoid biosynthesis have been identified and characterized in a number of organisms. Moreover, isoprenoids are synthesized in many, if not most, organisms. Thus, various aspects of the isoprenoid biosynthesis pathway are conserved throughout the fungal, bacterial, plant and animal kingdoms. For example, polypeptides corresponding to the acetoacetyl-CoA thiolase, HMG-CoA synthase, HMG-CoA reductase, mevalonate kinase, phosphomevalonate kinase, mevalonate pyrophosphate decarboxylase, IPP isomerase, shown in FIGS. 3, 5, and 6, have been identified in and isolated from a wide variety of organisms and cells; representative examples of a wide variety of such polypeptides are provided in Tables 7-13. One or more of the polypeptides selected from those provided in any one of Tables 7-13 may be utilized or derived for use in the methods and compositions in accordance with the present invention.

Alternatively or additionally, modified mevalonate kinase polypeptides that exhibit decreased feedback inhibition properties (e.g., to farnesyl pyrophosphate (FPP)) may be utilized in accordance with the present invention. Such modified mevalonate kinase polypeptides may be of eukaryotic or prokaryotic origin. For example, modified versions of mevalonate kinase polypeptides from animals (including humans), plants, algae, fungi (including yeast), and/or bacteria may be employed; for instance, modified versions of mevalonate kinase polypeptides disclosed in Table 10 herein may be utilized.

Particular examples of modified mevalonate kinase polypeptides include "feedback-resistant mevalonate kinases" disclosed in PCT Application WO 06/063,752. Thus, for example, a modified mevalonate kinase polypeptide may include one or more mutation(s) at one or more amino acid position(s) selected from the group consisting of amino acid positions corresponding to positions 17, 47, 93, 94, 132, 167, 169, 204, and 266 of the amino acid sequence of *Paracoccus zeaxanthinifaciens* mevalonate kinase as shown in SEQ ID NO:1 of PCT Application WO 04/111,214. For example, the modified mevalonate kinase polypeptide may contain one or more substitutions at positions corresponding to one or more of I17T, G47D, K93E, V94I, R204H and C266S.

To give but a few specific examples, when a modified mevalonate kinase polypeptide comprises 2 amino acid changes as compared with a parent mevalonate kinase polypeptide, it may comprise changes at positions corresponding to the following positions 132/375,167/169, 17/47 and/or 17/93 of SEQ ID NO:1 of WO 04/111,214 (e.g. P132A/P375R, R167W/K169Q, I17T/G47D or I17T/K93E); when a modified mevalonate kinase polypeptide comprises 3 amino acid changes as compared with a parent mevalonate kinase, it may comprise changes at positions corresponding to the following positions 17/167/169, 17/132/375, 93/132/375, and/or 17/47/93 of SEQ ID NO: 1 of WO/2004/111214 (e.g., I717R167W/K169Q, I17T/P132A/P375R, K93E/P132A/P375R, I17T/R167W/K169H, I17T/R167T/K169M, I17T/R167T/K169Y, I17T/R167F/K169Q, I17T/R167I/K169N, I17T/R167H/K169Y, I17T/G47D/K93E or I17T/G47D/K93Q).

Thus, for example, a modified mevalonate kinase polypeptide may include one or more mutation(s) (particularly substitutions), as compared with a parent mevalonate kinase polypeptide, at one or more amino acid position (s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO:1 of PCT application WO 06/063,752. For example, such corresponding substitutions may comprise one or more of P55L, F59S, N66K, C117S, or I152M. A modified mevalonate kinase may comprise a substitution corresponding to F59S substitution. A modified mevalonate kinase polypeptide comprising 2 amino acid changes as compared with its parent mevalonate kinase polypeptide may, for example, comprise changes at positions corresponding to the following positions 55/117,66/152, 83/249, 111/375 or 106/218 of to SEQ ID NO: 1 of WO 06/063,752 (e.g. P55L/C117S, N66K/I152M, K83E/S249P, H111N/K375N or L106P/S218P). A modified mevalonate kinase may comprise a substitution corresponding to N66K/I152M. A modified mevalonate kinase polypeptide comprising 4 amino acid changes as compared with its parent mevalonate kinase polypeptide may have changes at positions corresponding to one or more of the following positions 42/158/231/367 of SEQ ID NO:1 of WO 06/063,752 (e.g., I1421-111,158S/L2311/T367S).

According to the present invention, sterol compound production in a host organism may be adjusted by modifying the expression or activity of one or more proteins involved in isoprenoid biosynthesis. In some embodiments, such modification involves introduction of one or more heterologous isoprenoid biosynthesis polypeptides into the host cell; alternatively or additionally, modifications may be made to the expression or activity of one or more endogenous or heterologous isoprenoid biosynthesis polypeptides. Given the considerable conservation of components of the isoprenoid biosynthesis polypeptides, it is expected that heterologous isoprenoid biosynthesis polypeptides will often function well even in significantly divergent organisms. Furthermore, should it be desirable to introduce more than one heterologous isoprenoid biosynthesis polypeptide (e.g., more than one version of the same polypeptide and/or more than one different polypeptides), in many cases polypeptides from different source organisms may function well together. In some embodiments of the invention, a plurality of different heterologous isoprenoid biosynthesis polypeptides is introduced into the same host cell. In some embodiments, this plurality contains only polypeptides from the same source organism; in other embodiments the plurality includes polypeptides from different source organisms.

In certain embodiments of the present invention that utilize heterologous isoprenoid biosynthesis polypeptides, the source organisms include, but are not limited to, fungi of the genera *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium (Gibberella), Kluyveromyces, Neurospora, Penicillium, Pichia (Hansenula), Puccinia, Saccharomyces, Schizosaccharomyces, Sclerotium, Trichoderms Ustilago*, and *Xanthophyllomyces (Phaffia)*. In certain embodiments, the source organisms are of a species including, but not limited to, *Cryptococcus neoformans, Fusarium fujikuroi, Kluyverimyces lactis, Neu-*

*rospora crassa, Saccharomyces cerevisiae, Schizosaccharomyces pombe, Ustilago maydis*, and *Yarrowia lipolytica*.

The commitment step in sterol biosynthesis is the conversion of farnesyl pyrophosphate into presqualene pyrophosphate. Farnesyl pyrophosphate (FPP) is produced from isopentenyl pyrophosphate (IPP), for example in a process that involves isomerization of IPP into dimethylallyl pyrophosphate (DMAPP), followed by three sequential condensation reactions with additional molecules of IPP generate the ten-carbon molecule geranyl pyrophosphate (GPP), followed by the fifteen-carbon molecule farnesyl pyrophosphate (FPP). FPP can either enter the sterol biosynthesis pathway by conversion into presqualene puyrophosphate, or alternatively can be diverted toward biosynthesis of carotenoids and other compounds (e.g., ubiquinone, vitamin E, vitamin K, etc.) by conversion into the twenty-carbon compound geranylgeranyl pyrophosphate (GGPP). In many instances, FPP appears to be the predominant substrate used by polyprenyldiphosphate synthases (e.g. Coq1 polypeptides) during ubiquinone biosynthesis.

Once the sterol biosynthesis pathway has been entered, presqualene pyrophosphate is then converted to squalene by the same enzyme that performed the farnesyl pyrophosphate→presqualene pyrophosphate conversion. Squalene is then converted into a variety of different sterol compounds, including, but not limited to, lanosterol, zymosterol, ergosterol, 7-dehydrocholesterol (provitamin D3), and vitamin D compounds. The vitamin $D_2$ biosynthetic pathway and the vitamin $D_3$ biosynthetic pathway share some common reactions, and there can be multiple points at which a vitamin $D_2$ intermediate can be converted into a vitamin $D_3$ intermediate (see, for example, FIG. 1).

As noted herein, the isoprenoid biosynthesis pathway is also involved in the production of non-sterol compounds, such as carotenoids, ubiquinone, steroids, and vitamins, such as vitamin K or vitamin E. Polypeptides that act on isoprenoid biosynthesis pathway intermediates, and divert them into biosynthesis of non-sterol compounds are therefore indirect inhibitors of sterol biosynthesis (see, for example, FIG. 1, which illustrates certain points at which isoprenoid intermediates are channeled into other biosynthesis pathways). Such polypeptides are therefore considered sterol biosynthesis competitor polypeptides. Reductions of the level or activity of such sterol biosynthesis competitor polypeptides are expected to increase sterol compound production in host cells according to the present invention.

In some embodiments of the present invention, production or activity of endogenous sterol biosynthesis competitor polypeptides may be reduced or eliminated in host cells. In some embodiments, this reduction or elimination of the activity of a sterol biosynthesis competitor polypeptide can be achieved by treatment of the host organism with appropriate small molecule inhibitors.

Thus, in general, according to the present invention, production of one or more sterol compounds in a particular host cell is increased by exposing the cell to a sterologenic modification. In some embodiments of the present invention, the sterologenic modification comprises introducing or increasing expression or activity of one or more sterologenic polypeptides (e.g., isoprenoid biosythesis polypeptides, sterol biosynthesis polypeptides) and/or removing or inhibiting expression or activity of one or more sterol biosynthesis competitor polypeptides (e.g., GGGP synthase).

The present invention contemplates not only introduction of heterologous sterologenic polypeptides, but also adjustment of expression or activity levels of heterologous or endogenous sterologenic and/or sterol biosynthesis inhibitor polypeptides, including, for example, alteration of constitutive or inducible expression patterns so as to increase level and/or activity of one or more sterologenic polypeptides and/or to decrease levels and/or activity of one or more sterol biosynthesis competitor polypeptides. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous sterologenic polypeptide(s) and/or sterol biosynthesis competitor polypeptides); alternatively, such genetic modifications may be included so as to confer regulation of expression of heterologous polypeptides (e.g., sterologenic polypeptide(s)).

In certain embodiments, host cells are engineered to produce sterol compounds by introducing one or more sterol biosynthesis polypeptides. In general, any sterol biosynthesis polypeptide can be introduced into any host cell of the present invention. In certain embodiments, such sterol biosynthesis polypeptides are codon-optimized to accommodate the codon preferences of the host cell. In certain embodiments, a sterol biosynthesis polypeptide introduced into a host cell is from the same organism as the host cell and/or a related organism. For example, without limitation, the present invention encompasses the recognition that it may be desirable to introduce a fungal sterol biosynthesis polypeptide into a fungal host cell (e.g., from the same and/or a related fungal species). In certain embodiments, the host cell is a *Y. lipolytica* host cell. In certain aspects of such embodiments, a *Y. lipolytica* sterol biosynthesis polypeptide is introduced into the *Y. lipolytica* host cell. In certain aspects, a *S. cerevisiae* sterol biosynthesis polypeptide is introduced into the *Y. lipolytica* host cell. In certain aspects, any of a variety of fungal sterol biosynthesis polypeptides is introduced into the *Y. lipolytica* host cell.

Squalene

Squalene is a triterpene hydrocarbon sterol compound that is naturally produced in all higher organisms, including humans. Squalene has found commercial utility as a machine lubricant, and as a component of various nutritional and skin care products.

Squalene has traditionally been isolated from shark livers, but that route of production is expensive and impractical. There is a strong need for improved systems for producing squalene. Produced squalene can be incorporated into any number of a variety of products (for example, see below), and/or may be utilized as a synthetic precursor to any of a variety of other chemical entities. Squalene is the natural biosynthetic precursor to the entire family of steroid compounds (see, for example, FIG. 1).

In some embodiments of the present invention, host cells are engineered to produce squalene and/or to accumulate it in lipid bodies. In some embodiments, squalene production is enhanced in a cell by introduction of one or more sterologenic modifications that increases levels of IPP, FPP and/or squalene itself. In some embodiments, squalene production is enhanced in a cell by increasing the level and/or activity of one or more squalene biosynthesis polypeptides (e.g., one or more isoprenoid biosynthesis polypeptides, an FPP synthase polypeptide, and/or a squalene synthase polypeptide). Alternatively or additionally, in some embodiments, squalene production is enhanced in a cell by decreasing the level and/or activity of one or more sterol biosynthesis competitor polypeptides that diverts one or more intermediates away from squalene production and/or that metabolizes squalene itself.

For example, in some embodiments of the present invention, squalene production in a host cell is increased by introducing or increasing expression and/or activity of one or more squalene synthase polypeptides in the cell. Representative examples of squalene synthase polypeptide sequences are included in Table 16. In some embodiments of the invention that utilize squalene synthase (or modifications of squalene synthase) source organisms include, but are not limited to, *Neurospora crassa, Aspergillus niger, Saccharomyces cerevisiae, Mucor circinelloides, Candida utilis, Mortierella alpina, Phaffia rhodozyma*, and *Yarrowia lipolytica*.

In some embodiments of the invention, squalene production in a host cell is increased by reducing the level or activity of one or more vitamin D biosynthesis polypeptides (e.g., which act to metabolize squalene). For instance, in some embodiments, the level or activity of one or more polypeptides active in the ergosterol biosynthetic pathway (see, for example, FIG. 4) is reduced or eliminated.

Enzymes of the ergosterol biosynthetic pathway include, for example, squalene synthase (Erg9), squalene epoxidase (Erg1), 2,3-oxidosqualene-lanosterol cyclase (Erg7), cytochrome P450 lanosterol 14α-demethylase (Erg11), C-14 sterol reductase (Erg24), C-4 sterol methyl oxidase (Erg25), SAM:C-24 sterol methyltransferase (Erg6), C-8 sterol isomerase (Erg2), C-5 sterol desaturase (Erg3), C-22 sterol desaturase (Erg5), and C-24 sterol reductase (Erg4) polypeptides. Each of these enzymes, other than squalene synthase, is considered a squalene biosynthesis competitor polypeptide. Regulators of these enzymes may also be considered to be squalene biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms.

Known small molecule inhibitors of some squalene biosynthesis competitor enzymes include, but are not limited to terbinafine (e.g., LAMISIL®), naftifine (NAFTIN®), S-allylcysteine, garlic, resveratrol, NB-598 (e.g., from Banyu Pharmaceutical Co), and/or green tea phenols that inhibit squalene epoxidase (see, for example, *J. Biol Chem* 265: 18075, 1990; Biochem. Biophys. Res. Commun. 268:767, 2000); various azoles that inhibit cytochrome P450 lanosterol 14α-demethylase; and fenpropimorph that inhibits the C-14 sterol reductase and the C-8 sterol isomerase. In other embodiments, heterologous squalene biosynthesis competitor polypeptides may be utilized (whether functional or non-functional; in some embodiments, dominant-negative mutants are employed).

Alternatively or additionally, in some embodiments of the present invention, squalene production is enhanced by decreasing the level and/or activity of one or more squalene biosynthesis competitor polypeptides that diverts one or more intermediates away from the isoprenoid biosynthesis pathway, thereby reducing levels of IPP. For instance, in some particular embodiments of the invention, the level and/or activity of acetyl CoA carboxylase, which diverts acetyl CoA from the isoprenoid synthesis pathway into the fatty acid synthesis pathway, is inhibited. Such inhibition may be accomplished, for example, through one or more genetic modifications and/or through use of one or more small molecule inhibitors. In some embodiments, an inhibitor selected from the group consisting of aryloxyphenoxyproprionate, cyclohexanedione (CHD), and combinations thereof (see also other inhibitors described, for example, in Shukla et al., *J Agric Food Chem*. 52:5144, 2004; Webb et al., *J AOAC Int* 0.84:143, 2001; Webb et al., *J Agric Food Chem*. 48:1219, 2000; and Webb et al., *J Agric Food Chem*. 48:1210, 2000).

To give but one particular example of a sterologenic modification that can be employed in accordance with the present invention to reduce or inhibit expression or activity of a squalene biosynthesis competitor polypeptide and thereby to increase production of squalene, we note that it is known that fungal strains (e.g., *S. cerevisiae*) that lack any Erg5 or Erg6 activity are viable. In some embodiments of the invention, host cells are utilized that lack, or that are engineered to lack (or to have reduced levels of), Erg5 and/or Erg6 polypeptide activity. Absence or inhibition of Erg5 and/or Erg6 polypeptide activity reduces diversion of carbon into vitamin $D_2$ production, and thereby allows increase in levels of squalene, lanosterol, zymosterol, ergosterol, 7-dehydrocholesterol (provitamin D3) and/or other vitamin $D_3$ compounds. In some embodiments of the invention, in which increased production of squalene is particularly desired, one or more additional sterologenic modifications may be combined with a reduction or inactivation of Erg5 and/or Erg6 activity in order to reduce metabolism of squalene into vitamin $D_3$ compounds.

Lanosterol

Lanosterol is a tetracyclic triterpenoid that serves as a synthetic intermediate for saponins and steroid hormones. Lanosterol also functions as an emulsifier and active ingredient in a variety of skin creams.

In some embodiments of the present invention, host cells are engineered to produce lanosterol and/or to accumulate it in lipid bodies. In some embodiments, lanosterol production is enhanced in a cell by introduction of one or more sterologenic modifications that increases levels of IPP, FPP and/or lanosterol itself. In some embodiments, lanosterol production is enhanced in a cell by increasing the level and/or activity of one or more lanosterol biosynthesis polypeptides (e.g., one or more isoprenoid biosynthesis polypeptides, an FPP synthase polypeptide, squalene synthase polypeptide, squalene epoxidase polypeptide, or 2,3-oxidosqualene-lanosterol cyclase polypeptide). Alternatively or additionally, in some embodiments, lanosterol production is enhanced in a cell by decreasing the level and/or activity of one or more sterol biosynthesis competitor polypeptides that diverts one or more intermediates away from lanosterol production and/or that metabolizes lanosterol itself.

For example, in some embodiments of the present invention, lanosterol production in a host cell is increased by introducing or increasing expression and/or activity of one or more squalene synthase polypeptide, squalene epoxidase polypeptide, or 2,3-oxidosqualene-lanosterol cyclase polypeptide in the cell. Representative examples of squalene synthase polypeptide, squalene epoxidase polypeptide, and 2,3-oxidosqualene-lanosterol cyclase polypeptide sequences are included in Table 16, 83, and 85. In some embodiments of the invention that utilize squalene synthase polypeptide, squalene epoxidase polypeptide, or 2,3-oxidosqualene-lanosterol cyclase polypeptide (or modifications of these polypeptides) source organisms include, but are not limited to, *Neurospora crassa, Aspergillus niger, Saccharomyces cerevisiae, Phaffia rhodozyma, Mucor circinelloides, Candida utilis, Mortierella alpina*, and *Yarrowia lipolytica*.

In some embodiments of the invention, lanosterol production in a host cell is increased by reducing the level or activity of one or more vitamin D biosynthesis polypeptides (e.g., which act to metabolize squalene). For instance, in some embodiments, the level or activity of one or more polypeptides active in the ergosterol biosynthetic pathway (see, for example, FIG. 4) is reduced or eliminated.

Enzymes of the ergosterol biosynthetic pathway include, for example, squalene synthase (Erg9), squalene epoxidase (Erg1), 2,3-oxidosqualene-lanosterol cyclase (Erg7), cytochrome P450 lanosterol 14α-demethylase (Erg11), C-14 sterol reductase (Erg24), C-4 sterol methyl oxidase (Erg25), SAM:C-24 sterol methyltransferase (Erg6), C-8 sterol isomerase (Erg2), C-5 sterol desaturase (Erg3), C-22 sterol desaturase (Erg5), and C-24 sterol reductase (Erg4) polypeptides. Each of these enzymes, other than squalene synthase, squalene epoxidase, and 2,3-oxidosqualene-lanosterol cyclase, is considered a lanosterol biosynthesis competitor polypeptide. Regulators of these enzymes may also be considered to be squalene biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms.

Known small molecule inhibitors of some lanosterol biosynthesis competitor enzymes include, but are not limited to various azoles that inhibit cytochrome P450 lanosterol 14α-demethylase; and fenpropimorph that inhibits the C-14 sterol reductase and the C-8 sterol isomerase. In other embodiments, heterologous lanosterol biosynthesis competitor polypeptides may be utilized (whether functional or non-functional; in some embodiments, dominant negative mutants are employed).

Alternatively or additionally, in some embodiments of the present invention, lanosterol production is enhanced by decreasing the level and/or activity of one or more lanosterol biosynthesis competitor polypeptides that diverts one or more intermediates away from the isoprenoid biosynthesis pathway, thereby reducing levels of IPP. For instance, in some particular embodiments of the invention, the level and/or activity of acetyl CoA carboxylase, which diverts acetyl CoA from the isoprenoid synthesis pathway into the fatty acid synthesis pathway, is inhibited. Such inhibition may be accomplished, for example, through one or more genetic modifications and/or through use of one or more small molecule inhibitors. In some embodiments, an inhibitor selected from the group consisting of aryloxyphenoxyproprionate, cyclohexanedione (CHD), and combinations thereof (see also other inhibitors described, for example, in Shukla et al., *J Agric Food Chem.* 52:5144, 2004; Webb et al., *J AOAC Int* 0.84:143, 2001; Webb et al., *J Agric Food Chem.* 48:1219, 2000; Webb et al., *J Agric Food Chem.* 48:1210, 2000).

To give but one particular example of a sterologenic modification that can be employed in accordance with the present invention to reduce or inhibit expression or activity of a lanosterol biosynthesis competitor polypeptide and thereby to increase production of lanosterol, we note that it is known that fungal strains (e.g., *S. cerevisiae*) that lack any Erg5 or Erg6 activity are viable. In some embodiments of the invention, host cells are utilized that lack, or that are engineered to lack (or to have reduced levels of), Erg5 and/or Erg6 polypeptide activity. Absence or inhibition of Erg5 and/or Erg6 polypeptide activity reduces diversion of carbon into vitamin $D_2$ production, and thereby allows increase in levels of squalene, lanosterol, zymosterol, ergosterol, 7-dehydrocholesterol (provitamin D3) and/or other vitamin $D_3$ compounds. In some embodiments of the invention, in which increased production of lanosterol is particularly desired, one or more additional sterologenic modifications may be combined with a reduction or inactivation of Erg5 and/or Erg6 activity in order to reduce metabolism of lanosterol into vitamin $D_3$ compounds.

Zymosterol

Zymosterol also functions as a key synthetic intermediate for saponins and steroid hormones.

In some embodiments of the present invention, host cells are engineered to produce zymosterol and/or to accumulate it in lipid bodies. In some embodiments, zymosterol production is enhanced in a cell by introduction of one or more sterologenic modifications that increases levels of IPP, FPP and/or zymosterol itself. In some embodiments, zymosterol production is enhanced in a cell by increasing the level and/or activity of one or more zymosterol biosynthesis polypeptides (e.g., one or more isoprenoid biosynthesis polypeptides, an FPP synthase polypeptide, squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, or C-4 sterol methyl oxidase polypeptide). Alternatively or additionally, in some embodiments, zymosterol production is enhanced in a cell by decreasing the level and/or activity of one or more sterol biosynthesis competitor polypeptides that diverts one or more intermediates away from lanosterol production and/or that metabolizes lanosterol itself.

For example, in some embodiments of the present invention, zymosterol production in a host cell is increased by introducing or increasing expression and/or activity of one or more squalene synthase polypeptides, squalene epoxidase polypeptides, 2,3-oxidosqualene-lanosterol cyclase polypeptides, cytochrome P450 lanosterol 14α-demethylase polypeptides, C-14 sterol reductase polypeptides, or C-4 sterol methyl oxidase polypeptides in the cell. Representative examples of squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, or C-4 sterol methyl oxidase polypeptide sequences are included in Tables 16, 83-85, and 93-95. In some embodiments of the invention that utilize squalene synthase polypeptides, squalene epoxidase polypeptides, 2,3-oxidosqualene-lanosterol cyclase polypeptides, cytochrome P450 lanosterol 14α-demethylase polypeptides, C-14 sterol reductase polypeptides, or C-4 sterol methyl oxidase polypeptides (or modifications of these polypeptides) source organisms include, but are not limited to, *Neurospora crassa, Aspergillus niger, Saccharomyces cerevisiae, Phaffia rhodozyma, Mucor circinelloides, Candida utilis, Mortierella alpina*, and *Yarrowia lipolytica*.

In some embodiments of the invention, zymosterol production in a host cell is increased by reducing the level or activity of one or more vitamin D biosynthesis polypeptides (e.g., which act to metabolize squalene). For instance, in some embodiments, the level or activity of one or more polypeptides active in the ergosterol biosynthetic pathway (see, for example, FIG. 4) is reduced or eliminated.

Enzymes of the ergosterol biosynthetic pathway include, for example, squalene synthase (Erg9), squalene epoxidase (Erg1), 2,3-oxidosqualene-lanosterol cyclase (Erg7), cytochrome P450 lanosterol 14α-demethylase (Erg11), C-14 sterol reductase (Erg24), C-4 sterol methyl oxidase (Erg25), SAM:C-24 sterol methyltransferase (Erg6), C-8 sterol isomerase (Erg2), C-5 sterol desaturase (Erg3), C-22 sterol desaturase (Erg5), and C-24 sterol reductase (Erg4) polypeptides. SAM:C-24 sterol methyltransferase (Erg6), C-8 sterol isomerase (Erg2), C-5 sterol desaturase (Erg3), C-22 sterol desaturase (Erg5), and C-24 sterol reductase (Erg4) polypeptides are considered zymosterol biosynthesis competitor polypeptides. Regulators of these enzymes may also be considered to be squalene biosynthesis competitor polypeptides (e.g., the yeast proteins Sut1 (Genbank Accession JC4374 GI:2133159) and Mot3 (Genbank Accession NP_013786 GI:6323715), which may or may not have homologs in other organisms. In some embodiments, heterologous zymosterol biosynthesis competitor polypeptides may be utilized (whether functional or non-functional; in some embodiments, dominant negative mutants are employed).

Alternatively or additionally, in some embodiments of the present invention, zymosterol production is enhanced by decreasing the level and/or activity of one or more zymosterol biosynthesis competitor polypeptides that diverts one or more intermediates away from the isoprenoid biosynthesis pathway, thereby reducing levels of IPP. For instance, in some particular embodiments of the invention, the level and/or activity of acetyl CoA carboxylase, which diverts acetyl CoA from the isoprenoid synthesis pathway into the fatty acid synthesis pathway, is inhibited. Such inhibition may be accomplished, for example, through one or more genetic modifications and/or through use of one or more small molecule inhibitors. In some embodiments, an inhibitor selected from the group consisting of aryloxyphenoxyproprionate, cyclohexanedione (CHD), and combinations thereof (see also other inhibitors described, for example, in Shukla et al., *J Agric Food Chem.* 52:5144, 2004; Webb et al., *J AOAC Int* 0.84:143, 2001; Webb et al., *J Agric Food Chem.* 48:1219, 2000; Webb et al., *J Agric Food Chem.* 48:1210, 2000).

To give but one particular example of a sterologenic modification that can be employed in accordance with the present invention to reduce or inhibit expression or activity of a zymosterol biosynthesis competitor polypeptide and thereby to increase production of zymosterol, we note that it is known that fungal strains (e.g., *S. cerevisiae*) that lack any Erg5 or Erg6 activity are viable. In some embodiments of the invention, host cells are utilized that lack, or that are engineered to lack (or to have reduced levels of), Erg5 and/or Erg6 polypeptide activity. Absence or inhibition of Erg5 and/or Erg6 polypeptide activity reduces diversion of carbon into vitamin $D_2$ production, and thereby allows increase in levels of squalene, lanosterol, zymosterol, ergosterol, 7-dehydrocholesterol (provitamin D3) and/or other vitamin $D_3$ compounds. In some embodiments of the invention, in which increased production of zymosterol is particularly desired, one or more additional sterologenic modifications may be combined with a reduction or inactivation of Erg5 and/or Erg6 activity in order to reduce metabolism of zymosterol into vitamin $D_3$ compounds.

Ergosterol

Ergosterol is of commercial importance because it is a precursor for the production of steroid hormones and ultraviolet irradiation of ergosterol can result in the production of vitamin $D_2$.

In some embodiments of the present invention, host cells are engineered to produce ergosterol and/or to accumulate it in lipid bodies. In some embodiments, ergosterol production is enhanced in a cell by introduction of one or more sterologenic modifications that increases levels of IPP, FPP and/or ergosterol itself. In some embodiments, ergosterol production is enhanced in a cell by increasing the level and/or activity of one or more ergosterol biosynthesis polypeptides (e.g., one or more isoprenoid biosynthesis polypeptides, an FPP synthase polypeptide, squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C-4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide). Alternatively or additionally, in some embodiments, ergosterol production is enhanced in a cell by decreasing the level and/or activity of one or more sterol biosynthesis competitor polypeptides that diverts one or more intermediates away from ergosterol production and/or that metabolizes ergosterol itself.

For example, in some embodiments of the present invention, ergosterol production in a host cell is increased by introducing or increasing expression and/or activity of one or more squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C-4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide in the cell. Representative examples of squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C-4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide sequences are included in Table 16, 83-90, and 93-96. In some embodiments of the invention that utilize squalene synthase polypeptide, squalene epoxidase polypeptide, 2,3-oxidosqualene-lanosterol cyclase polypeptide, cytochrome P450 lanosterol 14α-demethylase polypeptide, C-14 sterol reductase polypeptide, C-4 sterol methyl oxidase polypeptide, SAM:C-24 sterol methyltransferase polypeptide, C-8 sterol isomerase polypeptide, C-5 sterol desaturase polypeptide, C-22 sterol desaturase polypeptide, or C-24 sterol reductase polypeptide (or modifications of these polypeptides) source organisms include, but are not limited to, *Neurospora crassa, Aspergillus niger, Saccharomyces cerevisiae, Mucor circinelloides, Candida utilis, Mortierella alpina*, and *Yarrowia lipolytica*.

In some embodiments of the invention, ergosterol production in a host cell is increased by reducing the level or activity of one or more vitamin D biosynthesis polypeptides (e.g., which act to metabolize squalene). For instance, in some embodiments, the level or activity of one or more polypeptides (see, for example, FIG. 4) is reduced or eliminated. Alternatively or additionally, in some embodiments of the present invention, ergosterol production is enhanced by decreasing the level and/or activity of one or more ergosterol biosynthesis competitor polypeptides that diverts one or more intermediates away from the isoprenoid biosynthesis pathway, thereby reducing levels of IPP. For instance, in some particular embodiments of the invention, the level and/or activity of acetyl CoA carboxylase, which diverts acetyl CoA from the isoprenoid synthesis pathway into the fatty acid synthesis pathway, is inhibited. Such inhibition may be accomplished, for example, through one or more genetic modifications and/or through use of one or more small molecule inhibitors. In some embodiments, an inhibitor selected from the group consisting of aryloxyphenoxyproprionate, cyclohexanedione (MD), and combinations thereof (see also other inhibitors described, for example, in Shukla et al., *J Agric Food Chem.* 52:5144, 2004; Webb et al., *J AOAC Int* 0.84:143, 2001; Webb et al., *J Agric Food Chem.* 48:1219, 2000; Webb et al., *J Agric Food Chem.* 48:1210, 2000).

Vitamin D

As noted above, vitamin D compounds are a group of steroid compounds including vitamin $D_3$ (cholecalciferol), vitamin $D_2$ (ergocalciferol), their provitamins, and certain metabolites (see, for example, FIG. 10A-B). Vitamins $D_3$ and $D_2$ can be produced from their respective provitamins (e.g., 7-dehydrocholesterol and ergosterol) by ultraviolet irradiation (e.g., by the action of sunlight). The most biologically active form of vitamin D is 1,25-dihydroxy vitamin $D_3$, which is also known as calcitriol. Calcitriol is produced by hydroxylation of vitamin $D_3$ at the 25 position, followed by hydroxylation to generate calcitriol.

Vitamin D acts in the body as a hormone involved in mineral metabolism and bone growth. Vitamin D binds to intracellular receptors; such binding activates the receptors' activity as a transcriptional regulator, for example activating transcription of various proteins involved in intestinal absorption of calcium (and, to some degree, phosphate and magnesium) and of various bone matrix proteins.

Vitamin D deficiency causes rickets in children and osteomalacia in adults. Both of these disorders result from defective mineralization of newly synthesized bone matrix. Although a Recommended Dietary Allowance has not been established for Vitamin D, the recommended Adequate Intake is 5 µg/day for individuals under 50 years of age; 10 µg/day for individuals 51-70 years of age, and 15 µg/day for individuals over 71 year old.

In some embodiments of the present invention, host cells are engineered to produce one or more vitamin D compounds and/or to accumulate it/them in lipid bodies. In some embodiments, vitamin D production is enhanced in a cell by introduction of one or more sterologenic modifications that increases levels of IPP, FPP and/or squalene. In some embodiments, vitamin D production is enhanced in a cell by increasing the level and/or activity of one or more vitamin D biosynthesis polypeptides (e.g., one or more isoprenoid biosynthesis polypeptides, an FPP synthase polypeptide, a squalene synthase polypeptide, and/or one or more polypeptides involved in converting squalene into a particular vitamin D compound of interest [e.g., 7-dehydrocholesterol and/or calcitriol]). Alternatively or additionally, in some embodiments, vitamin D production is enhanced in a cell by decreasing the level and/or activity of one or more sterol biosynthesis competitor polypeptides that diverts one or more intermediates away from vitamin D production. In some embodiments of the invention, production of a particular vitamin D compound (e.g., 7-dehydrocholesterol and/or calcitriol) is enhanced by decreasing the level and/or activity of one or more polypeptides that diverts a relevant intermediate toward an alternative vitamin D compound (e.g., ergosterol, vitamin $D_2$).

To give but one particular example of a sterologenic modification that can be employed in accordance with the present invention to increase production of one or more vitamin $D_3$ compounds (e.g., 7-dehydrocholesterol and/or calcitriol), in accordance with some embodiments of the present invention, the level and/or activity of one or more polypeptides that diverts a relevant intermediate toward a vitamin $D_2$ compound (e.g., ergosterol, vitamin $D_2$), and away from vitamin $D_3$ compounds, can be inhibited or destroyed.

For example, fungal strains (e.g., *S. cerevisiae*) that lack any Erg5 or Erg6 activity are viable. In some embodiments of the invention, host cells are utilized that lack, or that are engineered to lack (or to have reduced levels of), Erg5 and/or Erg6 polypeptide activity. Absence or inhibition of Erg5 and/or Erg6 polypeptide activity reduces diversion of carbon into vitamin $D_2$ production, and thereby allows increase in levels of squalene, lanosterol, zymosterol, and/or vitamin $D_3$ compounds (e.g., 7-dehydrocholesterol and/or calcitriol). In some embodiments, heterologous vitamin D biosynthesis competitor polypeptides may be utilized (whether functional or non-functional; in some embodiments, dominant-negative mutants are employed).

Alternatively or additionally, one or more small molecule inhibitors that reduce the level and/or activity of one or more vitamin $D_2$ biosynthesis polypeptides that diverts a relevant intermediate away from vitamin $D_3$ production may be employed. Representative such inhibitors include, for example, various azoles that inhibit cytochrome P450 lanosterol 14α-demethylase; and fenpropimorph that inhibits the C-14 sterol reductase and the C-8 sterol isomerase.

Production and Isolation of Sterol Compounds

As discussed above, accumulation of lipid bodies in oleaginous organisms is generally induced by growing the relevant organism in the presence of excess carbon and limiting nitrogen and/or other nutrients (e.g., phosphate and magnesium). Specific conditions for inducing such accumulation have previously been established for a NUMBER of different oleaginous organisms (see, for example, Wolf (ed)) *Nonconventional yeasts in Biotechnology* Vol. 1, Springer-Verlag, Berlin, Germany, pp. 313-338; *Lipids* 18(9):623, 1983; *Indian J. Exp. Biol.* 35(3):313, 1997; *J. Ind. Microbiol. Biotechnol.* 30(1):75, 2003; *Bioresour Technol.* 95(3):287, 2004; each of which is incorporated herein by reference in its entirety).

In general, it will be desirable to cultivate inventive modified host cells under conditions that allow accumulation of at least about 20% of their dry cell weight as lipid. In other embodiments, the inventive modified host cells are grown under conditions that permit accumulation of at least about 15%, 16%, 17%, 18%, 19%, 20%, 21%, 22%, 23%, 24%, 25%, 30%, 35%, 40%, 45%, 50%, 55%, 60%, 65%, 70%, 75%, or even 80% or more of their dry cell weight as lipid. In certain embodiments, the host cells utilized are cells which are naturally oleaginous and induced to produce lipid to the desired levels. In other embodiments, the host cells are cells which naturally produce lipid, but have been engineered to increase production of lipid such that desired levels of lipid production and accumulation are achieved.

In certain embodiments, the host cells of the invention are not naturally oleaginous, but have been engineered to produce lipid such that desired levels of lipid production are obtained. Those of ordinary skill in the art will appreciate that, in general, growth conditions that are effective for inducing lipid accumulation in a source organism, may well also be useful for inducing lipid accumulation in a host cell into which the source organism's oleaginic polypeptides have been introduced. Of course, modifications may be required in light of characteristics of the host cell, which modifications are within the skill of those of ordinary skill in the art.

It will also be appreciated by those of ordinary skill in the art that it will often be desirable to ensure that production of the desired sterol compound by the inventive modified host cell occurs at an appropriate time in relation to the induction of oleaginy such that the sterol compound(s) accumulate(s) in the lipid bodies. In some embodiments, it will be desirable to induce production of one or more sterol compounds (e.g., squalene, lanosterol, zymosterol, ergosterol, 7-dehydrocholesterol (provitamin D3), vitamin D compounds, etc.) in a host cell which does not naturally produce the compound such that detectable levels of the compound are produced. In certain aspects the host cells which do not naturally produce a particular sterol compound of interest (e.g., squalene, lanosterol, zymosterol, ergosterol, 7-dehydrocholesterol (provitamin D3), vitamin D compounds, etc.) are capable of producing other sterol compounds. In other embodiments, it will be desirable to increase production levels of a particular sterol compound (e.g., squalene, lanosterol, zymosterol, ergosterol, 7-dehydrocholesterol (provitamin D3), vitamin D compounds, etc.) in a host cell which does naturally produce low levels of the compound, such that increased detectable levels of the compound are produced. In certain aspects, the host cells which do naturally produce the particular sterol compound of interest (e.g., squalene, lanosterol, zymosterol, ergosterol, 7-dehydrocholesterol (provitamin D3), vitamin D compounds, etc.) also produce additional sterol compounds;

in other embodiments, the cells which naturally produce a particular sterol compound of interest (e.g., squalene, lanosterol, zymosterol, ergosterol, 7-dehydrocholesterol (provitamin D3), vitamin D compounds, etc.) do not produce additional sterol compound(s).

In certain embodiments of the invention, it will be desirable to accumulate one or more sterol compounds (i.e., considering the total amount of all produced sterol compounds together or considering a particular sterol compound [e.g., squalene, lanosterol, zymosterol, ergosterol, 7-dehydrocholesterol (provitamin D3), vitamin D compounds, etc.]) to levels that are greater than at least about 1% of the dry weight of the cells. In some embodiments, the total sterol compound accumulation will be to a level at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells.

In some particular embodiments of the present invention, squalene is accumulated to a level above 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some particular embodiments of the present invention, squalene is accumulated to a level above 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some particular embodiments of the present invention, squalene is accumulated in $S.\ cerevisiae$ to a level above 17%, at least about 17.5%, at least about 18%, at least about 18.5%, at least about 19%, at least about 19.5%, at least about 20%, at least about 20.5%, at least about 21%, at least about 21.5%, at least about 22%, at least about 22.5%, at least about 23%, at least about 23.5%, at least about 24%, at least about 24.5%, at least about 25%, at least about 25.5%, at least about 26%, at least about 26.5%, at least about 27%, at least about 27.5%, at least about 28%, at least about 28.5%, at least about 29%, at least about 29.5%, at least about 30%, at least about 35%, at least about 40%, at least about 45% or more of the total dry weight of the cells and in some cases to a level above about 50% the total dry weight of the cells.

In some particular embodiments of the present invention, squalene is accumulated in $Y.\ lipolytica$ cells to a level above 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some particular embodiments of the present invention, lanosterol is accumulated to a level above 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some particular embodiments of the present invention, zymosterol is accumulated to a level above 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some particular embodiments of the present invention, ergosterol is accumulated to a level above 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some particular embodiments of the present invention, ergosterol is accumulated to a level above 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, at least about 10%, at least about 10.5%, at least about 11%, at least about 11.5%, at least about 12%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20% or more of the total dry weight of the cells and in some cases to a level above about 25% the total dry weight of the cells.

In some embodiments of the invention, a particular sterol compound (e.g. a vitamin D compound) may not accumulate to a level as high as 1% of the total dry weight of the cells; appropriately engineered cells according to the present invention, and any lipid bodies and/or sterol compound(s) they produce, remain within the scope of the present invention. Thus, in some embodiments, the cells accumulate a given sterol compound to a level below about 1% of the dry weight of the cells. In some embodiments, the sterol compound accumulates to a level below about 0.9%, 0.8%, 0.7%, 0.6%, 0.5%, 0.4%, 0.3%, 0.2%, 0.1%, 0.05%, or lower, of the dry cell weight of the cells.

In some embodiments of the invention, one or more sterol compound(s) accumulate both within lipid bodies and elsewhere in the cells. In some embodiments, one or more sterol compound(s) accumulate primarily within lipid bodies. In some embodiments, one or more sterol compound(s) accumulate substantially exclusively within lipid bodies. In some embodiments, at least about 10%, 15%, 20%, 25%, 30%, 35%, 40%, 45%, 50%, 55%, 60%, 65%, 70%, 75%, 80%, 85%, 90%, 95% or more of desired produced sterol compound(s) accumulates in lipid bodies.

In some embodiments of the invention, modified host cells are engineered to produce one or more sterol compound(s) characterized by negligible solubility in water (whether hot or cold) and detectable solubility in one or more oils. In some embodiments, such compounds have a solubility in oil below about 0.2%. In some embodiments, such compounds have a solubility in oil within the range of about <0.001%-0.2%.

The present invention therefore provides engineered host cells (and methods of making and using them) that contain lipid bodies and that further contain one or more sterol compounds accumulated in the lipid bodies, where the compounds are characterized by a negligible solubility in water and a solubility in oil within the range of about <0.001%-0.2%; 0.004%-0.15%; 0.005-0.1%; or 0.005-0.5%. For example, in some embodiments, such compounds have a solubility in oil below about 0.15%, 0.14%, 0.13%, 0.12%, 0.11%, 0.10%. 0.09, 0.08%, 0.07%, 0.06%, 0.05%, 0.04%, 0.03%, 0.02%, 0.01%, 0.05%, or less. In some embodiments, the compounds show such solubility in an oil selected from the group consisting of sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and mixtures thereof.

Also, it should be noted that, the absolute and/or relative amounts of particular sterol compounds produced in accordance with the present invention, and/or the absolute and/or relative amounts of other compounds derived from isoprenoids can sometimes be altered by adjustment of growth conditions. For example, it has been reported that controlling the concentration of dissolved oxygen in a culture during cultivation can regulate relative production levels of certain sterol compounds (see, for example, J. Cell. Comp. Physiol. Vol. 41, p 23, 1953). Such condition alterations can therefore be utilized in accordance with the present invention to favor partition of carbons into pathways that produce one or more sterol compounds of interest, and/or to disfavor partition of carbon into pathways that compete with such sterol biosynthesis pathways.

In certain embodiments, fungal or yeast sterologenic genes (when fungi make the sterol of interest) may be transferred from one organism to another, and are therefore useful in accordance with the present invention Similarly, bacterial sterologenic genes may be transferred from one organism to another. In other embodiments, it may be desirable to utilize genes from other source organisms such as plant, alga, or microalgae. Still additional useful source organisms include insect, protozoal, and mammalian sources of polypeptides.

In some embodiments of the present invention, isoprenoid production is increased in host cells (e.g., in *Y. lipolytica* cells) through expression of a truncated variant of a hydroxymethylglutaryl-CoA (HMG CoA) reductase polypeptide. In some embodiments, the truncated variant is a truncated variant of a *Y. lipolytica* HMG CoA reductase polypeptide. According to the present invention, expression of such a truncated HMG CoA reductase polypeptide can result in increased isoprenoid and/or sterol compound production in host cells (e.g., *Y. lipolytica* cells).

Alternatively or additionally, in some embodiments of the present invention, isoprenoid production is increased in host cells (e.g., in *Y. lipolytica, S. cerevisiae* cells, or *C. utilis* cells) through application of one or more sterologenic modification(s) that increase(s) level and/or activity of a polypeptide selected from the group consisting of squalene synthase, squalene epoxidase, and combinations thereof. In some embodiments, the source organism for the selected polypeptide is *Y. lipolytica*. In some specific embodiments of the present invention, *Y. lipolytica* cells are engineered to express elevated amounts of endogenous or exogenous squalene synthase and/or squalene oxidase polypeptides. In some embodiments, such cells further express a truncated HMG CoA reductase polypeptide (e.g., a truncated *Y. lipolytica* HMG CoA reductase polypeptide.

Inventive modified cells, that have been engineered to produce sterol compounds and/or to accumulate lipid (including to be oleaginous), can be cultured under conditions that achieve sterol production and/or oleaginy. In some embodiments, it will be desirable to control growth conditions in order to maximize production of a particular sterol compound or set of sterol compounds (including all sterol compounds) and/or to optimize accumulation of the particular sterol compound(s) in lipid bodies. In some embodiments it will be desirable to control growth conditions to adjust the relative amounts of different sterol compound products produced.

In some embodiments, it will be desirable to limit accumulation of a particular intermediate, for example ensuring that substantially all of a particular intermediate compound is converted so that accumulation is limited. For example, particularly in situations where a downstream enzyme may be less efficient than an upstream enzyme and it is desirable to limit accumulation of the product of the upstream enzyme (e.g., to avoid its being metabolized via a competitive pathway and/or converted into an undesirable product), it may be desirable to grow cells under conditions that control (e.g., slow) activity of the upstream enzyme so that the downstream enzyme can keep pace.

Those of ordinary skill in the art will appreciate that any of a variety of growth parameters, including for example amount of a particular nutrient, pH, temperature, pressure, oxygen concentration, timing of feeds, content of feeds, etc can be adjusted as is known in the art to control growth conditions as desired.

To give but a few examples, in some embodiments, growth and/or metabolism is/are limited by limiting the amount of biomass accumulation. For example, growth and/or metabolism can be limited by growing cells under conditions that are limiting for a selected nutrient. The selected limiting nutrient can then be added in a regulated fashion, as desired. In some embodiments, the limiting nutrient is carbon, nitrogen (e.g., via limiting ammonium or protein), phosphate, magnesium, one or more trace metals, or combinations thereof. In some embodiments, the limiting nutrient is carbon. In some embodiments, the limiting nutrient is one or more trace metals.

In some embodiments, use of a limiting nutrient can by utilized to control metabolism of a particular intermediate and/or to adjust relative production of particular sterol compounds. In some embodiments, this result can be achieved by controlling metabolism of a particular intermediate as discussed above; in some embodiments, it can be achieved, for example, by limiting progress through the sterol biosynthesis pathway so that a desired sterol compound product (e.g., squalene, lanosterol, zymosterol, ergosterol, 7-dehydrocholesterol (provitamin D3) and/or vitamin D compounds, etc.) is not converted to a downstream compound.

In some embodiments, cells are grown in the presence of excess carbon source and limiting nitrogen, phosphate, and/or magnesium to induce oleaginy. In some embodiments cells are grown in the presence of excess carbon source and limiting nitrogen. In some embodiments, the carbon:nitrogen ratio is within the range of about 200:1, 150:1, 125:1, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, or less. Those of ordinary skill in the art are aware of a wide variety of carbon sources, including, for example, glycerol, glucose, galactose, dextrose, any of a variety of oils (e.g., olive, canola, corn, sunflower, soybean, cottonseed, rapeseed, etc., and combinations thereof) that may be utilized in accordance with the present invention. Combinations of such may also be utilized. For example, common carbon source compositions contain oil: glucose in a ratio within the range of about 5:95 to 50:50 (e.g. about 5:95, about 10:90, about 15:85, about 20:80, about 25:75, about 30:70, about 35:65, about 40:60, about 45:55, about 50:50).

Those of ordinary skill in the art are also aware of a variety of different nitrogen sources (e.g., ammonium sulfate, proline, sodium glutamate, soy acid hydrolysate, yeast extract-peptone, yeast nitrogen base, corn steep liquor, etc, and combinations thereof) that can be utilized in accordance with the present invention.

In some embodiments, cultures are grown at a selected oxygen concentration (e.g., within a selected range of oxygen concentrations). In some embodiments, oxygen concentration may be varied during culture. In some embodiments, oxygen concentration may be controlled during some periods of culture and not controlled, or controlled at a different point, during others. In some embodiments, oxygen concentration is not controlled. In some embodiments, cultures are grown at an oxygen concentration within the range of about 5-30%, 5-20%, 10-25%, 10-30%, 15-25%, 15-30%, including at about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or more. In some embodiments, oxygen concentration is maintained above about 20%, at least for some period of the culture.

In some embodiments, cells are grown via fed-batch fermentation. In some embodiments, feed is continued until feed exhaustion and/or the feed is controlled to initiate or increase once a certain level of dissolved oxygen is detected in the culture medium (e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more dissolved oxygen). The feed rate can be modulated to maintain the dissolved oxygen at a specific level (e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or more dissolved oxygen).

In some embodiments, inventive modified cells are grown in a two-phase feeding protocol in which the first phase is designed to maintain conditions of excess carbon and limiting oxygen, and the second phase results in conditions of excess oxygen and limiting carbon. The carbon sources in each phase can be the same (e.g., both glucose) or different (e.g., glucose then glucose-oil mixture, oil then glucose, or glucose-oil mixture then glucose).

In some embodiments, inventive modified cells are cultivated at constant temperature (e.g., between about 20-40, or 20-30 degrees, including for example at about 20, 20.5, 21, 21.5, 22, 22.5, 23, 23.5, 24, 24.5, 25, 25.5, 26, 26.5, 27, 27.5, 28, 28.5, 29, 29.5, 30° C. or above) and/or pH (e.g., within a range of about 4-7.5, or 4-6.5, 3.5-7, 3.5-4, 4-4.5, 4.5-5, 5-5.5, 5.5-6, 6-6.5, 6.5-7, 7-7.5, 7-8, etc., including at about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5 or above); in other embodiments, temperature and/or pH may be varied during the culture period, either gradually or in a stepwise fashion.

For example, in some embodiments, the pH at inoculation is lower than the pH during the course of the fermentation. For example, the pH may be 7.0 at inoculation and increased to pH 8.0 during the course of the fermentation. The pH may be increased either continuously or in discrete steps. In certain embodiments, the pH in increased continuously by increasing the pH at a rate of 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050 or more units/hour.

In certain embodiments, the pH in increased in discrete steps by increasing the pH by 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050 or more at each step.

In certain embodiments, the pH is increased employing a combination of continuous increase and discrete steps.

In certain embodiments, increasing the pH during the course of fermentation results in one or more beneficial effects such as, without limitation, an increase in total biomass accumulation and/or an increase in the percentage of biomass representing sterol accumulation. Those of ordinary skill in the art will be able to select without undue experimentation an appropriate rate of increase, an appropriate type of increase (e.g. continuous, discrete steps or a combination of the two), and/or an optimum pH within the selected range to maximize these and/or other beneficial effects.

In some embodiments, the temperature at which inventive cells are cultivated is selected so that production of one or more particular sterol compound(s) is adjusted (e.g., so that production of one or more particular compound(s) is increased and/or production of one or more other compound(s) is decreased). In some embodiments, the temperature at which inventive cells are cultivated is selected so that the ratio of one sterol compound to another, is adjusted. To give but one example, in some embodiments, a temperature is selected to be sufficiently low that levels of one sterol compound levels are reduced and the level of at least one sterol compound is increased.

In some embodiments, cultures are grown at about pH 5.5, at about pH 7.0, and or at a temperature between about 28-30° C. In some embodiments, it may be desirable to grow inventive modified cells under low pH conditions, in order to minimize growth of other cells. In some embodiments, it will be desirable to grow inventive modified cells under relatively higher temperature conditions in order to slow growth rate and/or increase the ultimate dry cell weight output of sterols. In some embodiments, it will be desirable to grow inventive modified cells under conditions in which the pH in increased (e.g. continuously, in discrete steps, or both) during the course of fermentation (e.g. increased from pH 7.0 to pH 8.0). In some embodiments, it will be desirable to grow inventive modified cells under two or more of these conditions. For example, inventive modified cells can be grown under relatively higher temperature conditions while simultaneously increasing the pH over the course of the fermentation. Those of ordinary skill in the art will be able to select appropriate growth conditions to achieve their experimental, production and/or other cell culture goals.

One advantage provided by the present invention is that, in addition to allowing the production of high levels of one or more sterol compound(s), certain embodiments of the present invention allow produced compounds to be readily isolated because they accumulate in the lipid bodies within oleaginous organisms. Methods and systems for isolating lipid bodies have been established for a wide variety of oleaginous organisms (see, for example, U.S. Pat. Nos. 5,164,308; 5,374,657; 5,422,247; 5,550,156; 5,583,019; 6,166,231; 6,541,049; 6,727,373; 6,750,048; and 6,812,001, each of which is incorporated herein by reference in its entirety). In brief, cells are typically recovered from culture, often by spray drying, filtering or centrifugation.

Of course, it is not essential that lipid bodies be specifically isolated in order to collect sterol compounds produced according to the present invention. Any of a variety of approaches can be utilized to isolate and/or purify sterol compounds. Many useful extraction and/or purification procedures for particular sterol compounds, and/or for sterols generally, are known in the art (see, for example, EP670306, EP719866, U.S. Pat. No. 4,439,629, U.S. Pat. No. 4,680,314, U.S. Pat. No. 5,310,554, U.S. Pat. No. 5,328,845, U.S. Pat. No. 5,356,810, U.S. Pat. No. 5,422,247, U.S. Pat. No. 5,591, 343, U.S. Pat. No. 6,166,231, U.S. Pat. No. 6,750,048, U.S. Pat. No. 6,812,001, U.S. Pat. No. 6,818,239, U.S. Pat. No. 7,015,014, US2003/0054070, US2005/0266132, each of which is incorporated herein by reference).

In many typical isolation procedures, cells are disrupted (e.g., mechanically (for example using a bead mill, mashing), enzymatically (e.g. using zymolyase or a β-1,3 glucanase such as Glucanex 200G (Novozyme), chemically (e.g., by exposure to a mild caustic agent such as a detergent or 0.1 N NaOH, for example at room temperature or at elevated temperature), using a reducing agent (e.g. dithiothreitol, β-mercaptoethanol), using high pressure homogenization/shearing, by changing pH, etc. and combinations thereof) to allow access of intracellular sterol compound(s) to an extraction solvent, and are then extracted one or more times. In certain embodiments, cells are disrupted mechanically using a bead mill/mashing at high pressure (e.g. at 25K, 10K-30K, 15K-25K, or 20-25K, pound-force per square inch (psi)). Cells may optionally be concentrated (e.g., to at least about 100 g/L or more, including to at least about 120 g/l, 150 g/l, 175 g/L, 200 g/L or more) and/or dried (e.g., with a spray dryer, double drum dryer (e.g. Blaw Knox double drum dryer), single drum vacuum dryer, etc.), prior to exposure to extraction solvent (and/or prior to disruption or homogenization). Disruption can, of course, be performed prior to and/or during exposure to extraction solvent. After extraction, solvent is typically removed (e.g., by evaporation, for example by application of vacuum, change of temperature, etc.).

In some instances, cells are disrupted and then subjected to supercritical liquid extraction or solvent extraction. Typical liquids or solvents utilized in such extractions include, for example, organic or non-organic liquids or solvents. To give but a few specific examples, such liquids or solvents may include acetone, supercritical fluids (e.g. carbon dioxide, propane, xenon, ethane, propylene, methane, ethylene, ethanol), carbon dioxide, chloroform, ethanol, ethyl acetate, heptane, hexane, isopropanol, methanol, methylene chloride, octane, tetrahydrofuran (THF), cyclohexane, isobutyl acetate, methyl ketone, ethyl ketone, toluene, cyclohexanone, benzene, propylene glycol, vegetable oils (e.g. soybeen soybean oil, rapeseed oil, corn oil, cottonseed oil, canola oil, etc.) and combinations thereof (e.g. hexane:ethyl acetate, combination of a polar and non-polar solvent, combination of an alcohol with either hexane or ethyl acetate). Particular solvents may be selected, for example, based on their ability to solubilize particular sterol compounds, or sets of sterol compounds (e.g., all sterols), and/or based on regulatory or other considerations (e.g., toxicity, cost, ease of handling, ease of removal, ease of disposal, etc.).

In some embodiments, combinations of solvents may be utilized In some embodiments, combinations of a relatively polar solvent (e.g., alcohols, acetone, chloroform, methylene chloride, ethyl acetate, etc.) and a relatively non-polar solvent (e.g., hexane, cyclohexane, oils, etc.) are utilized for extraction. Those of ordinary skill in the art will readily appreciate that different ratios of polar to non-polar solvent may be employed as appropriate in a particular situation. Just to give a few examples, common ratios include 1:1, 2:1, 3:1, 3:2, 95:5, 90:10, 85:15, 80:20, 75:25, 70:30, 65:45, 60:40, 55:45, and 50:50. It will be appreciated that solvents or solvent mixtures of different polarities may be more effective at extracting particular sterols (e.g., based on their polarities and/or as a function of other attributes of the host cell material from which they are being extracted). Those of ordinary skill in the art are well able to adjust the overall polarity of the extracting solvent, for instance by adjusting the relative amounts of polar and non-polar solvents in a solvent blend, in order to achieve more efficient extraction.

Extraction may be performed under any of a variety of environmental conditions, including any of a variety of temperatures. For example, extraction may be performed on ice (for example at 4° C., 0° C., less than 0° C.), at room temperature, or at any of a variety of other temperatures. For example, a solvent may be maintained at a selected temperature (e.g., about less than 0, 0, 4, 25, 28, 30, 37, 68, 70, 75, 80, 85, 90, 95, or 100° C.) in order to improve or adjust extraction of a particular desired sterol compound.

Extraction typically yields a crude oil suspension. In some embodiments, the crude oil suspension contains some intact host cells but is at least about 95% free of intact host cells. In some embodiments, the crude oil suspension is at least about 96%, 97%, 98%, or 99% or more free of intact host cells. In some embodiments, the suspension is substantially free of water-soluble cell components (e.g., nucleic acids, cell wall or storage carbohydrates, etc.). In some embodiments, the suspension contains less than about 5%, 4%, 3%, 2%, or 1% or less water-soluble cell components.

Extraction conditions that yield a crude oil suspension will enrich for lipophilic components that accumulate in the lipid bodies within oleaginous organisms. In general, the major components of the lipid bodies consist of triacylglycerols, ergosteryl esters, other steryl esters, free ergosterol, phospholipids, and some proteins, which often function in the synthesis or regulation of the levels of other lipid body components. C16 and C18 (e.g. C16:0, C16:1, C18:0, C18:1, and C18:2) are generally the major fatty acids present in lipid bodies, mainly as components of triacylglycerol and steryl esters.

In some embodiments of the invention, the crude oil suspension contains at least about 2.5% by weight sterol compound(s); in some embodiments, the crude oil suspension contains at least about 5% by weight sterol compound(s), at least about 10% by weight sterolog compound(s), at least about 20% by weight sterol compound(s), at least about 30% by weight sterol compound(s), at least about 40% by weight sterol compound(s), or at least about 50% by weight sterol compound(s).

The crude oil suspension may optionally be refined as known in the art. Refined oils may be used directly as feed or food additives. Alternatively or additionally, sterols can be isolated from the oil using conventional techniques.

Given the sensitivity of sterols generally to oxidation, many embodiments of the invention employ oxidative stabilizers (e.g., ascorbyl palmitate, tocopherols, vitamin C (e.g., sodium ascorbate), ethoxyquin, vitamin E, BHT, BHA, TBHQ, etc., or combinations thereof) during and/or after sterol isolation. Alternatively or additionally, nitrogen or an inert gas can be utilized to purge oxygen from the process lines of any tanks or equipment. Alternatively or additionally, microencapsulation, for example with a microencapsulation ingredients such as proteins, carbohydrates (e.g. maltodextrin, gum acacia, xanthan gum, starches/sugars like sucrose), or gelatins, or any other substance which creates a physical barrier to air and/or light), may be employed to add a physical barrier to oxidation and/or to improve handling (see, for example, U.S. Patent Applications 2004/0191365 and 2005/0169999). For example, sterol compounds produced according to the present invention may be microencapsulated after isolation during the formulation of commercial products (e.g. pharmaceuticals, food supplements, electro-optic applications, animal feed additives, cosmetics, etc.) to minimize or eliminate oxidation during production, storage, transport, etc.

Extracted sterols may be further isolated and/or purified, for example, by crystallization, washing, recrystallization, and/or other purification strategies. In some embodiments, sterol crystals are collected by filtration and/or centrifugation. Isolated or purified sterols may be dried and/or formulated for storage, transport, sale, and/or ultimate use. To give but a few specific examples, sterols may be prepared as a water (e.g. cold-water) dispersible powder (e.g., 1%-20% sterol:microencapsulation ingredient), as a suspension of crystals in oil (e.g., vegetable oil, e.g., about 1%-30%, 5%-30%, 10%-30% w/w), etc.

Uses

Sterol compounds of interest (e.g., squalene, lanosterol, zymosterol, ergosterol, 7-dehydrocholesterol (provitamin D3), vitamin D compounds [e.g., 7-dehydrocholesterol, calcitriol]) produced according to the present invention can be utilized in any of a variety of applications, for example exploiting biological or nutritional (e.g., metabolic, anti-oxidant, anti-proliferative, etc.) properties.

For example, according to the present invention, one or more vitamin D compounds (and particularly 7-dehydrocholesterol, and/or calcitriol) may be used in pharmaceutical and/or nutraceutical applications for treatment and/or prevention of disorders associated with vitamin D deficiency. Alternatively or additionally, one or more vitamin D compounds (and/or optionally one or more other sterol compounds, such as squalene, lanosterol, zymosterol, ergosterol, 7-dehydrocholesterol (provitamin D3)) may be incorporated into a nutritional supplement or a cosmetic product (e.g., a skin cream, etc.). Sterol compound(s) produced herein can also be co-administered with an HMG CoA reductase inhibitor (e.g. a statin such as atorvastatin, simvastatin, rosuvastatin, etc.).

It will be appreciated that, in some embodiments of the invention, one or more sterol compound(s) (e.g., squalene, lanosterol, zymosterol, ergosterol, 7-dehydrocholesterol (provitamin D3), produced by manipulated host cells as described herein are incorporated into a final product (e.g., food or feed supplement, pharmaceutical, cosmetic, etc.) in the context of the host cell. For example, host cells may be lyophilized, freeze dried, frozen or otherwise inactivated, and then whole cells may be incorporated into or used as the final product. The host cells may also be processed prior to incorporation in the product to, e.g., increase bioavailability (e.g., via lysis). Alternatively or additionally, a final product may incorporate only a portion of a host cell (e.g., fractionated by size, solubility), separated from the whole. For example, in some embodiments of the invention, lipid bodies are isolated from host cells and are incorporated into or used as the final product. For instance, inventive sterol compound-containing lipid bodies (e.g., from engineered cells, and particularly from engineered fungal cells) may be substitutes for the plant oil bodies described in U.S. Pat. No. 6,599,513 (the entire contents of which are hereby incorporated by reference) and incorporated into emulsions or emulsion formulations, as described thereon. In other embodiments, ubiquinone itself is isolated and reformulated into a final product.

It will further be understood that, in some embodiments of the present invention, host cells are engineered to produce and/or accumulate a compound that is an intermediate to a commercial product. For instance, in some embodiments, squalene, lanosterol, zymosterol, or ergosterol can be utilized as an intermediate to production of various steroids. Also, in some embodiments, a vitamin D compound is produced (e.g., 7-dehydrocholestrol) that is a precursor to an ultimate active compound (e.g., calcitriol). In other embodiments, the inventive system is utilized to prepare commercial end products.

Preparations of sterol compound(s) produced according to the present invention, including formulations, dosing, supplements, have been described and are known in the art. For example, see citations relating to pharmaceutical preparations, nutritional supplement, and food additives described above. Additionally, see, for example, International Patent Publication No. WO 06/072175, U.S. Patent Publication No. US 2006/0067960, U.S. Patent Publication No. US 2006/0134095, International Patent Publication No. WO 91/016914, and International Patent Publication No. WO 02/055060.

The amount of sterol compound(s) produced according to the present invention that is incorporated into a given product may vary dramatically depending on the product, and the particular compound(s) involved. Amounts may range, for example, from less than 0.01% by weight of the product, to more than 1%, 10%, 20%, 30% or more; in some cases the sterol compound may comprise 100% of the product. Thus, the amount of sterol compound incorporated into a given product may be, for example, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%. In some embodiments of the invention, one or more produced sterol compound(s) (e.g., squalene, lanosterol, zymosterol, ergosterol, 7-dehydrocholesterol (provitamin D3), is incorporated into a component of food or feed (e.g., a food supplement, food additive). Types of food products into which ssch compound(s) can be incorporated according to the present invention are not particularly limited, and include beverages such as milk, water, sports drinks, energy drinks, teas, juices, and liquors; confections such as jellies and biscuits; fat-containing foods and beverages such as dairy products; processed food products such as rice and soft rice (or porridge); infant formulas; breakfast cereals or the like. In some embodiments, one or more produced sterol compounds is incorporated into a dietary supplements, such as for example a multi-vitamin. In certain embodiments, squalene, lanosterol, zymosterol, ergosterol, 7-dehydrocholesterol (provitamin D3) and/or one or more vitamin D compounds produced according to the present invention are included in a dietary supplement. In some embodiments of this aspect of the invention, it may be useful to one or more sterol compounds within bodies of edible lipids as it may facilitate incorporation into certain fat-containing food products. Thus, for example, when the edible fungus, *Candida utilis* is used as a host, its sterol compound containing lipids may be directly incorporated into a component of food or feed (e.g., a food supplement).

Examples of feedstuffs into which sterol compound(s) produced in accordance with the present invention may be incorporated include, for instance, pet foods such as cat foods, dog foods and the like, feeds for aquarium fish or cultured fish, etc., feed for farm-raised animals (including livestock and further including fish raised in aquaculture). Food or feed material into which such compound(s) is/are incorporated is preferably palatable to the organism which is the intended recipient. Such food or feed material may have any physical properties currently known for a food material (e.g., solid, liquid, soft).

In some embodiments, feedstuffs containing sterol compounds produced in accordance with the present invention are substantially free of intact host cells. For example, feedstuffs of the present invention may be at least about 95% free of intact host cells. In some embodiments, feedstuffs of the present invention are at least about 96%, 97%, 98%, or 99% or more free of intact host cells. Such embodiments are typical when the sterol compounds are highly purified away from the host cell in which they were produced (see section entitled "Production and Isolation of Sterol Compounds").

In some embodiments, feedstuffs containing sterol compounds produced in accordance with the present invention are not substantially free of intact host cells. For example, feedstuffs of the present invention may comprise greater than about 95% intact host cells. In certain embodiments, feedstuffs of the present invention comprise greater than about 70%, 75%, 85%, or 90% intact host cells. In certain embodiments, feedstuffs of the present invention comprise nearly intact host cells. For example, feedstuffs of the present invention may comprise greater than about 70%, 75%, 85%, 90%, or 95% nearly intact host cells. As will be appreciated by those of ordinary skill in the art, sterol compound-containing feedstuffs of the present invention that contain intact cells and/or nearly intact cells will have great utility in providing the sterol compounds of interest present in such host cells to an animal. Such embodiments are advantageous when host cells that produce the sterol compounds of interest contain additional vitamins, nutrients, etc. that benefit the animal.

In some embodiments of the invention, produced sterol compound(s) is/are incorporated into a cosmetic product. Examples of such cosmetics include, for instance, skin cosmetics (e.g., lotions, emulsions, liquids, creams and the like), lipsticks, anti-sunburn cosmetics, makeup cosmetics, fragrances, products for daily use (e.g., toothpastes, mouthwashes, bad breath preventive agents, solid soaps, liquid soaps, shampoos, conditioners), etc.

In some embodiments, produced sterol compound(s) is/are incorporated into a pharmaceutical. Examples of such pharmaceuticals include, for instance, various types of tablets, capsules, drinkable agents, troches, gargles, etc. In some embodiments, the pharmaceutical is suitable for topical application. Dosage forms are not particularly limited, and include capsulae, oils, granula, granula subtilae, pulveres, tabellae, pilulae, trochisci, or the like. Oils and oil-filled capsules may provide additional advantages both because of their lack of ingredient decomposition during manufacturing, and because inventive sterol-compound-containing lipid droplets may be readily incorporated into oil-based formulations.

Pharmaceuticals according to the present invention may be prepared according to techniques established in the art including, for example, the common procedure as described in the United States Pharmacopoeia, for example.

In still other embodiments, produced sterol compound(s) is/are incorporated into a nutritional supplement or nutraceutical. Examples of such nutraceuticals, include, for instance, various types of tablets, capsules, drinkable agents, troches, gargles, etc. In some embodiments, the nutraceutical is suitable for topical application. Dosage forms are, as in pharmaceutical products, not particularly limited and include any of the same types of dosages as pharmaceuticals.

Sterol compound(s) produced according to the present invention (whether isolated or in the context of lipid droplets or of cells, e.g., fungal cells) may be incorporated into products as described herein by combination with any of a variety of agents. For instance, such compound(s) may be combined with one or more binders or fillers. In some embodiments, inventive products will include one or more chelating agents, pigments, salts, surfactants, moisturizers, viscosity modifiers, thickeners, emollients, fragrances, preservatives, etc., and combinations thereof.

Useful surfactants include, for example, anionic surfactants such as branched and unbranched alkyl and acyl hydrocarbon compounds, sodium dodecyl sulfate (SDS); sodium lauryl sulfate (SLS); sodium lauryl ether sulfate (SLES); sarconisate; fatty alcohol sulfates, including sodium, potassium, ammonium or triethanolamine salts of $C_{10}$ to $C_{18}$ saturated or unsaturated forms thereof; ethoxylated fatty alcohol sulfates, including alkyl ether sulfates; alkyl glyceryl ether sulfonate, alpha sulpho fatty acids and esters; fatty acid esters of isethionic acid, including Igepon A; acyl (fatty) N-methyltaurides, including Igepon T; dialkylsulfo succinate esters, including $C_8$, $C_{10}$ and $C_{12}$ forms thereof; Miranot BT also referred to as lauroamphocarboxyglycinate and sodium tridecath sulfate; N-acylated amino acids, such as sodium N-lauroyl sarconisate or gluconate; sodium coconut monoglyceride sulfonate; and fatty acid soaps, including sodium, potassium, DEA or TEA soaps.

Among the cationic surfactants that are useful are monoalkyl trimethyl quartenary salts; dialkyl dimethyl quartenary salts; ethoxylated or propoxylated alkyl quaternary ammonium salts, also referred to in the art as ethoquats and propoquats; cetyl benzylmethylalkyl ammonium chloride; quaternized imidazolines, which are generally prepared by reacting a fat or fatty acid with diethylenetriamine followed by quaternization, and non-fat derived cationic polymers such as the cellulosic polymer, Polymer JR (Union Carbide).

Further useful cationic surfactants include lauryl trimethyl ammonium chloride; cetyl pyridinium chloride; and alkyltrimethylammonium bromide. Cationic surfactants are particularly useful in the formulation of hair care products, such as shampoos, rinses and conditioners.

Useful nonionic surfactants include polyethoxylated compounds and polypropoxylated products. Examples of ethoxylated and propoxylated non-ionic surfactants include ethoxylated anhydrohexitol fatty esters, for example Tween-20; mono- and di-ethanolamides; Steareth-20, also known as Volpo20; polyethylene glycol fatty esters (PEGs), such as PEG-8-stearate, PEG-8 distearate; block co-polymers, which are essentially combinations of hydrophilic polyethoxy chains and lipophilic polypropoxy chains and generically known as Poloaxamers.

Still other useful non-ionic surfactants include fatty esters of polyglycols or polyhydric alcohols, such as mono and diglyceride esters; mono- and di-ethylene glycol esters; diethylene glycol esters; sorbitol esters also referred to as Spans; sucrose esters; glucose esters; sorbitan monooleate, also referred to as Span80; glyceryl monostearate; and sorbitan monolaurate, Span20 or Arlacel 20.

Yet other useful nonionic surfactants include polyethylene oxide condensates of alkyl phenols and polyhydroxy fatty acid amide surfactants which may be prepared as for example disclosed in U.S. Pat. No. 2,965,576.

Examples of amphoteric surfactants which can be used in accordance with the present invention include betaines, which can be prepared by reacting an alkyldimethyl tertiary amine, for example lauryl dimethylamine with chloroacetic acid. Betaines and betaine derivatives include higher alkyl betaine derivatives including coco dimethyl carboxymethyl betaine; sulfopropyl betaine; alkyl amido betaines; and cocoamido propyl betaine. Sulfosultaines which may be used include for example, cocoamidopropyl hydroxy sultaine. Still other amphoteric surfactants include imidazoline derivatives and include the products sold under the trade name "Miranol" described in U.S. Pat. No. 2,528,378 which is incorporated herein by reference in its entirety. Still other amphoterics include phosphates for example, cocamidopropyl PG-dimonium chloride phosphate and alkyldimethyl amine oxides.

Suitable moisturizers include, for example, polyhydroxy alcohols, including butylene glycol, hexylene glycol, propylene glycol, sorbitol and the like; lactic acid and lactate salts, such as sodium or ammonium salts; $C_3$ and $C_6$ diols and triols including hexylene glycol, 1,4 dihydroxyhexane, 1,2,6-hexane triol; aloe vera in any of its forms, for example aloe vera gel; sugars and starches; sugar and starch derivatives, for example alkoxylated glucose; hyaluronic acid; lactamide monoethanolamine; acetamide monoethanolamine; glycolic acid; alpha and beta hydroxy acids (e.g. lactic, glycolic salicylic acid); glycerine; pantheol; urea; vaseline; natural oils; oils and waxes (see: the emollients section herein) and mixtures thereof.)

Viscosity modifiers that may be used in accordance with the present invention include, for example, cetyl alcohol; glycerol, polyethylene glycol (PEG); PEG-stearate; and/or Keltrol.

Appropriate thickeners for use in inventive products include, for example, gelling agents such as cellulose and derivatives; Carbopol and derivatives; carob; carregeenans and derivatives; xanthane gum; sclerane gum; long chain alkanolamides; bentone and derivatives; Kaolin USP; Veegum Ultra; Green Clay; Bentonite NFBC; etc.

Suitable emollients include, for example, natural oils, esters, silicone oils, polyunsaturated fatty acids (PUFAs), lanoline and its derivatives and petrochemicals.

Natural oils which may be used in accordance with the present invention may be obtained from sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and mixtures thereof.

Esters which may be used include, for example, $C_8$-$C_{30}$ alkyl esters of $C_8$-$C_{30}$ carboxylic acids; $C_1$-$C_6$ diol monoesters and diesters of $C_8$-$C_{30}$ carboxylic acids; $C_{10}$-$C_{20}$ alcohol monosorbitan esters, $C_{10}$-$C_{20}$ alcohol sorbitan di- and tri-esters; $C_{10}$-$C_{20}$ alcohol sucrose mono-, di-, and tri-esters and $C_{10}$-$C_{20}$ fatty alcohol esters of $C_2$-$C_6$ 2-hydroxy acids and mixtures thereof. Examples of these materials include isopropyl palmitate; isopropyl myristate; isopropyl isononate; $C_{12}$/$C_{14}$ benzoate ester (also known as Finesolve); sorbitan palmitate, sorbitan oleate; sucrose palmitate; sucrose oleate; isostearyl lactate; sorbitan laurate; lauryl pyrrolidone carboxylic acid; panthenyl triacetate; and mixtures thereof.

Further useful emollients include silicone oils, including non-volatile and volatile silicones. Examples of silicone oils that may be used in the compositions of the present invention are dimethicone; cyclomethycone; dimethycone-copolyol; aminofunctional silicones; phenyl modified silicones; alkyl modified silicones; dimethyl and diethyl polysiloxane; mixed $C_1$-$C_{30}$ alkyl polysiloxane; and mixtures thereof. Additionally useful silicones are described in U.S. Pat. No. 5,011,681 to Ciotti et al., incorporated by reference herein.

A yet further useful group of emollients includes lanoline and lanoline derivatives, for example lanoline esters.

Petrochemicals which may be used as emollients in the compositions of the present invention include mineral oil; petrolatum; isohexadecane; permethyl 101; isododecanol; $C_{11}$-$C_{12}$ Isoparrafin, also known as Isopar H.

Among the waxes which may be included in inventive products are animal waxes such as beeswax; plant waxes such as carnauba wax, candelilla wax, ouricurry wax, Japan wax or waxes from cork fibres or sugar cane. Mineral waxes, for example paraffin wax, lignite wax, microcrystalline waxes or ozokerites and synthetic waxes may also be included.

Exemplary fragrances for use in inventive products include, for instance, linear and cyclic alkenes (i.e., terpenes);

primary, secondary and tertiary alcohols; ethers; esters; ketones; nitrites; and saturated and unsaturated aldehydes; etc.

Examples of synthetic fragrances that may be used in accordance with the present invention include without limitation acetanisole; acetophenone; acetyl cedrene; methyl nonyl acetaldehyde; musk anbrette; heliotropin; citronellol; sandella; methoxycitranellal; hydroxycitranellal; phenyl ethyl acetate; phenylethylisobutarate; gamma methyl ionone; geraniol; anethole; benzaldehyde; benzyl acetate; benzyl salicate; linalool; cinnamic alcohol; phenyl acetaldehyde; amyl cinnamic aldehyde; caphore; p-tertiairy butyl cyclohexyl acetate; citral; cinnamyl acetate; citral diethyl acetal; coumarin; ethylene brasslate; eugenol; 1-menthol; vanillin; etc.

Examples of natural fragrances of use herein include without limitation lavandin; heliotropin; sandlewood oil; oak moss; pathouly; ambergris tincture; ambrette seed absolute; angelic root oil; bergamont oil; benzoin Siam resin; buchu leaf oil; *cassia* oil; cedarwood oil; *cassia* oil; castoreum; civet absolute; chamomile oil; geranium oil; lemon oil; lavender oil; Ylang Ylang oil; etc.

A list of generally used fragrance materials can be found in various reference sources, for example, "Perfume and Flavor Chemicals", Vols. I and II; Steffen Arctander Allured Pub. Co. (1994) and "Perfumes: Art, Science and Technology"; Muller, P. M. and Lamparsky, D., Blackie Academic and Professional (1994) both incorporated herein by reference.

Suitable preservatives include, among others, (e.g., sodium metabisulfite; Glydant Plus; Phenonip; methylparaben; Germall 115; Germaben II; phytic acid; sodium lauryl sulfate (SLS); sodium lauryl ether sulfate (SLES); Neolone; Kathon; Euxyl and combinations thereof), anti-oxidants (e.g., butylated hydroxytoluened (BHT); butylated hydroxyanisol (BHA); ascorbic acid (vitamin C); tocopherol; tocopherol acetate; phytic acid; citric acid; pro-vitamin A.

In some embodiments, inventive products will comprise an emulsion (e.g., containing inventive lipid bodies), and may include one or more emulsifying agents (e.g., Arlacel, such as Alacel 165; Glucamate; and combinations thereof) and/or emulsion stabilizing agents.

In some embodiments, inventive products will include one or more biologically active agents other than the sterols(s). To give but a few examples, inventive cosmetic or pharmaceutical products may include one or more biologically active agents such as, for example, sunscreen actives, anti-wrinkle actives, anti-aging actives, whitening actives, bleaching actives, sunless tanning actives, anti-microbial actives, anti-acne actives, anti-psoriasis actives, anti-eczema actives, anti-oxidants, anesthetics, vitamins, protein actives, etc.

Engineering Production of Multiple Isoprenoid Compounds

In certain embodiments of the invention, it may be desirable to generate engineered organisms that accumulate one or more other compounds in addition to the sterol compound(s), and further to accumulate such other compound, optionally together with the sterol compound(s), in lipid bodies. For example, certain inventive engineered organisms may accumulate sterol compound(s) together with at least one other compound derived from an isoprenoid precursor. In some embodiments, the other compound derived from an isoprenoid precursor will be one or more quinone-derived compounds as discussed in either or both of in U.S. patent application 60/848,064, filed on Sep. 28, 2006 and U.S. patent application 60/784,499 filed on Mar. 20, 2006 (e.g., Vitamin K, Vitamin E, and/or related quinone compounds (e.g., $C_{5-9}$)). Alternatively or additionally, in some embodiments the other compound derived from an isoprenoid precursor will be one or more carotenoids. Production of carotenoids in oleaginous organisms is described in U.S. Provisional Application No. 60/663,621, filed Mar. 18, 2005, and is also described in U.S. patent application Ser. No. 11/385,580, entitled Production of Carotenoids in Oleaginous Yeast and Fungi, filed Mar. 20, 2006. Each of these applications is incorporated herein by reference in its entirety.

In some embodiments of the invention, host cells are engineered to produce at least two sterol compounds, and particularly at least two compounds selected from the group consisting of squalene, lanosterol, zymosterol, ergosterol, 7-dehydrocholesterol, and calcitriol. In some such embodiments, host cells are engineered to produce a least one compound selected from the group consisting of squalene, lanosterol, zymosterol, ergosterol, 7-dehydrocholesterol (provitamin D3), and calcitriol, and at least one other compound. Such host cells are particularly useful for producing mixtures or combination products that contain squalene, lanosterol, zymosterol, ergosterol, 7-dehydrocholesterol (provitamin D3) and/or one or more vitamin D compounds. Such host cells are also useful for producing combination products including one or more ubiquinones, one or more ubiquinone-related compounds (e.g., vitamin E, vitamin K, $C_{5-9}$ quinones, etc) and/or one or more carotenoids.

In some embodiments of the invention, host cells are engineered to produce at least one sterol compound and at least one carotenoid. Carotenoids, which have an isoprene backbone consisting of 40 carbon atoms, have antioxidant effects as well as use in coloring agents. Carotenoids such as β-carotene, astaxanthin, and cryptoxanthin are believed to possess cancer preventing and immunopotentiating activity.

The carotenoid biosynthesis pathway branches off from the isoprenoid biosynthesis pathway at the point where GGPP is formed (see FIG. 1). The commitment step in carotenoid biosynthesis is the formation of phytoene by the head-to-head condensation of two molecules of GGPP, catalyzed by phytoene synthase (often called crtB). A series of dehydrogenation reactions, each of which increases the number of conjugated double bonds by two, converts phytoene into lycopene via neurosporene. The pathway branches at various points, both before and after lycopene production, so that a wide range of carotenoids can be generated. For example, action of a cyclase enzyme on lycopene generates γ-carotene; action of a desaturase instead produces 3,4-didehydrolycopene. γ-carotene is converted to 0-carotene through the action of a cyclase. β-carotene can be processed into any of a number of products, including astaxanthin (via echinenone, hydroxyechinenone, and phoenicoxanthin).

Carotenoid production in a host organism may be adjusted by modifying the expression or activity of one or more polypeptides involved in carotenoid biosynthesis. In some embodiments of the invention, it will be desirable to utilize as host cells organisms that naturally produce one or more carotenoids. In some such cases, the focus will be on increasing production of a naturally-produced carotenoid, for example by increasing the level and/or activity of one or more proteins involved in the synthesis of that carotenoid and/or by decreasing the level or activity of one or more proteins involved in a competing biosynthetic pathway. Alternatively or additionally, in some embodiments it will be desirable to generate production of one or more carotenoids not naturally produced by the host cell.

In some embodiments of the invention, it will be desirable to introduce one or more carotenogenic modifications into a host cell. In certain embodiments the carotenogenic modification may confer expression of one or more heterologous carotenogenic polypeptides into a host cell. As will be apparent to those of ordinary skill in the art, any of a variety of heterologous polypeptides may be employed; selection will consider, for instance, the particular carotenoid whose production is to be enhanced. Still further, selection will consider the complementation and/or ability of the selected polypeptide to function in conjunction with additional oleaginic and/or sterologenic modifications of a cell such that each of oleaginy, sterol biosynthesis and carotenoid biosynthesis are effectuated to the desired extent.

Proteins involved in carotenoid biosynthesis include, but are not limited to, phytoene synthase, phytoene dehydrogenase, lycopene cyclase, carotenoid ketolase, carotenoid hydroxylase, astaxanthin synthase (a single multifunctional enzyme found in some source organisms that typically has both ketolase and hydroxylase activities), carotenoid epsilon hydroxylase, lycopene cyclase (beta and epsilon subunits), carotenoid glucosyltransferase, and acyl CoA:diacyglycerol acyltransferase. Representative example sequences for carotenoid biosynthesis polypeptides are provided in Tables 17a-21 and Tables 38-41.

Alternatively or additionally, modified carotenoid ketolase polypeptides that exhibit improved carotenoid production activity may be utilized in accordance with the present invention. For example, carotenoid ketolase polypeptides comprising one more mutations to corresponding to those identified *Sphingomonas* sp. DC18 which exhibited improved astaxanthin production (Tao et al., 2006 Metab Eng. 2006 Jun. 27) and *Paracoccus* sp. strain N81106 which exhibited altered carotenoid production (Ye et al., 2006 Appl Environ Microbiol 72:5829-37).

In some embodiments of the invention, potential source organisms for carotenoid biosynthesis polypeptides include, but are not limited to, genera of naturally oleaginous or non-oleaginous fungi that naturally produce carotenoids. These include, but are not limited to, *Botlytis, Cercospora, Fusarium (Gibberella), Mucor, Neurospora, Phycomyces, Puccina, Rhodotorula, Sclerotium, Trichoderma*, and *Xanthophyllomyces*. Exemplary species include, but are not limited to, *Neurospora crassa, Xanthophyllomyces dendrorhous (Phaffia rhodozyma), Mucor circinelloides,* and *Rhodotorula glutinis*. Of course, carotenoids are produced by a wide range of diverse organisms such as plants, algae, yeast, fungi, bacteria, cyanobacteria, etc. Any such organisms may be source organisms for carotenoid biosynthesis polypeptides according to the present invention.

It will be appreciated that the particular carotenogenic modification to be applied to a host cell in accordance with the present invention will be influenced by which carotenoid(s) is desired to be produced. For example, isoprenoid biosynthesis polypeptides are relevant to the production of most carotenoids. Carotenoid biosynthesis polypeptides are also broadly relevant. Carotenoid ketolase activity is particularly relevant for production of canthaxanthin, as carotenoid hydroxylase activity is for production of lutein and zeaxanthin, among others. Both carotenoid hydroxylase and ketolase activities (and/or astaxanthin synthase) are particularly useful for production of astaxanthin.

Bacterial carotenogenic genes have already been demonstrated to be transferable to other organisms, and are therefore particularly useful in accordance with the present invention (see, for example, Miura et al., *Appl. Environ. Microbiol.* 64:1226, 1998). In other embodiments, it may be desirable to utilize genes from other source organisms such as plant, alga, or microalgae; these organisms provide a variety of potential sources for ketolase and hydroxylase polypeptides. Still additional useful source organisms include fungal, yeast, insect, protozoal, and mammalian sources of polypeptides.

In some embodiments of the invention, host cells are engineered to produce at least one sterol compound and at least one quinone derived compound. Quinone derived compounds are produced from the isoprenoid compound isopentyl pyrophosphate (IPP), via geranylgeranyl pyrophosphate (see, for example, FIG. 5. IPP can be generated through one of two different isoprenoid biosynthesis pathways. The most common isoprenoid biosynthesis pathway, sometimes referred to as the "mevalonate pathway", is generally depicted in FIG. 3. As shown, acetyl-CoA is converted, via hydroxymethylglutaryl-CoA (HMG-CoA), into mevalonate. Mevalonate is then phosphorylated and converted into the five-carbon compound isopentenyl pyrophosphate (IPP).

An alternative isoprenoid biosynthesis pathway, that is utilized by some organisms (particularly bacteria) and is sometimes called the "mevalonate-independent pathway", is also depicted in FIG. 3. This pathway is initiated by the synthesis of 1-deoxy-D-xyloglucose-5-phosphate (DOXP) from pyruvate and glyceraldehyde-3-phosphate. DOXP is then converted, via a series of reactions shown in FIG. 3, into IPP.

Various proteins involved in isoprenoid biosynthesis have been identified and characterized in a number of organisms. Moreover, isoprenoids are synthesized in many, if not most, organisms. Thus, various aspects of the isoprenoid biosynthesis pathway are conserved throughout the fungal, bacterial, plant and animal kingdoms. For example, polypeptides corresponding to the acetoacetyl-CoA thiolase, synthase, HMG-CoA reductase, mevalonate kinase, phosphomevalonate kinase, mevalonate pyrophosphate decarboxylase, IPP isomerase, FPP synthase, and GGPP synthase, some of which are shown for example in FIGS. 5-6 have been identified in and isolated from a wide variety of organisms and cells; representative examples of a wide variety of such polypeptides are provided in Tables 7-15. One or more of the polypeptides selected from those provided in any one of Tables 7-15 may be utilized or derived for use in the methods and compositions in accordance with the present invention.

Alternatively or additionally, modified mevalonate kinase polypeptides that exhibit decreased feedback inhibition properties (e.g., to farnesyl pyrophosphate (FPP)) may be utilized in accordance with the present invention. Such modified mevalonate kinase polypeptides may be of eukaryotic or prokaryotic origin. For example, modified versions of mevalonate kinase polypeptides from animals (including humans), plants, algae, fungi (including yeast), and/or bacteria may be employed; for instance, modified versions of mevalonate kinase polypeptides disclosed in Table 10 herein may be utilized.

Particular examples of modified mevalonate kinase polypeptides include "feedback-resistant mevalonate kinases" disclosed in PCT Application WO 06/063,752. Thus, for example, a modified mevalonate kinase polypeptide may include one or more mutation(s) at one or more amino acid position(s) selected from the group consisting of amino acid positions corresponding to positions 17, 47, 93, 94, 132, 167, 169, 204, and 266 of the amino acid sequence of *Paracoccus zeaxanthinifaciens* mevalonate kinase as shown in SEQ ID NO:1 of PCT Application WO 04/111,214. For example, the modified mevalonate kinase polypeptide may contain one or more substitutions at positions corresponding to one or more of I17T, G47D, K93E, V94I, R204H and C266S.

To give but a few specific examples, when a modified mevalonate kinase polypeptide comprises 2 amino acid changes as compared with a parent mevalonate kinase polypeptide, it may comprise changes at positions corresponding to the following positions 132/375,167/169, 17/47 and/or 17/93 of SEQ ID NO:1 of WO 04/111,214 (e.g. P132A/P375R, R167W/K169Q, I17T/G47D or I17T/K93E); when a modified mevalonate kinase polypeptide comprises 3 amino acid changes as compared with a parent mevalonate kinase, it may comprise changes at positions corresponding to the following positions 17/167/169, 17/132/375, 93/132/375, and/or 17/47/93 of SEQ ID NO: 1 of WO/2004/111214 (e.g., I17T/R167W/K169Q, I17T/P132A/P375R, K93E/P132A/P375R, I17T/R167W/K169H, I17T/R167T/K169M, I17T/R167T/K169Y, I17T/R167F/K169Q, I17T/R1671/K169N, I17T/R167H/K169Y, I17T/G47D/K93E or I17T/G47D/K93Q).

Thus, for example, a modified mevalonate kinase polypeptide may include one or more mutation(s) (particularly substitutions), as compared with a parent mevalonate kinase polypeptide, at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO:1 of PCT application WO 06/063,752. For example, such corresponding substitutions may comprise one or more of P55L, F59S, N66K, C117S, or I152M. A modified mevalonate kinase may comprise a substitution corresponding to F59S substitution. A modified mevalonate kinase polypeptide comprising 2 amino acid changes as compared with its parent mevalonate kinase polypeptide may, for example, comprise changes at positions corresponding to the following positions 55/117, 66/152, 83/249, 111/375 or 106/218 of to SEQ ID NO: 1 of WO 06/063,752 (e.g. P55L/C117S, N66K/I152M, K83E/S249P, H111N/K375N or L106P/S218P). A modified mevalonate kinase may comprise a substitution corresponding to N66K/I152M. A modified mevalonate kinase polypeptide comprising 4 amino acid changes as compared with its parent mevalonate kinase polypeptide may have changes at positions corresponding to one or more of the following positions 42/158/231/367 of SEQ ID NO:1 of WO 06/063,752 (e.g., I142N/L158S/L2311/T367S).

According to the present invention, quinone derived compound production in a host organism may be adjusted by modifying the expression or activity of one or more proteins involved in isoprenoid biosynthesis. In some embodiments, such modification involves introduction of one or more heterologous isoprenoid biosynthesis polypeptides into the host cell; alternatively or additionally, modifications may be made to the expression or activity of one or more endogenous or heterologous isoprenoid biosynthesis polypeptides. Given the considerable conservation of components of the isoprenoid biosynthesis polypeptides, it is expected that heterologous isoprenoid biosynthesis polypeptides will often function well even in significantly divergent organisms. Furthermore, should it be desirable to introduce more than one heterologous isoprenoid biosynthesis polypeptide (e.g., more than one version of the same polypeptide and/or more than one different polypeptides), in many cases polypeptides from different source organisms may function well together. In some embodiments of the invention, a plurality of different heterologous isoprenoid biosynthesis polypeptides is introduced into the same host cell. In some embodiments, this plurality contains only polypeptides from the same source organism; in other embodiments the plurality includes polypeptides from different source organisms.

In certain embodiments of the present invention that utilize heterologous isoprenoid biosynthesis polypeptides, the source organisms include, but are not limited to, fungi of the genera *Blakeslea, Candida, Cryptococcus, Cunninghamella, Lipomyces, Mortierella, Mucor, Phycomyces, Pythium, Rhodosporidium, Rhodotorula, Trichosporon, Yarrowia, Aspergillus, Botrytis, Cercospora, Fusarium* (*Gibberella*), *Kluyveromyces, Neurospora, Penicillium, Pichia* (*Hansenula*), *Puccinia, Saccharomyces, Schizosaccharomyces, Sclerotium, Trichoderms Ustilago*, and *Xanthophyllomyces* (*Phaffia*). In certain embodiments, the source organisms are of a species including, but not limited to, *Cryptococcus neoformans, Fusarium fujikuroi, Kluyverimyces lactis, Neurospora crassa, Saccharomyces cerevisiae, Schizosaccharomyces pombe, Ustilago maydis*, and *Yarrowia lipolytica*.

Figure 13:
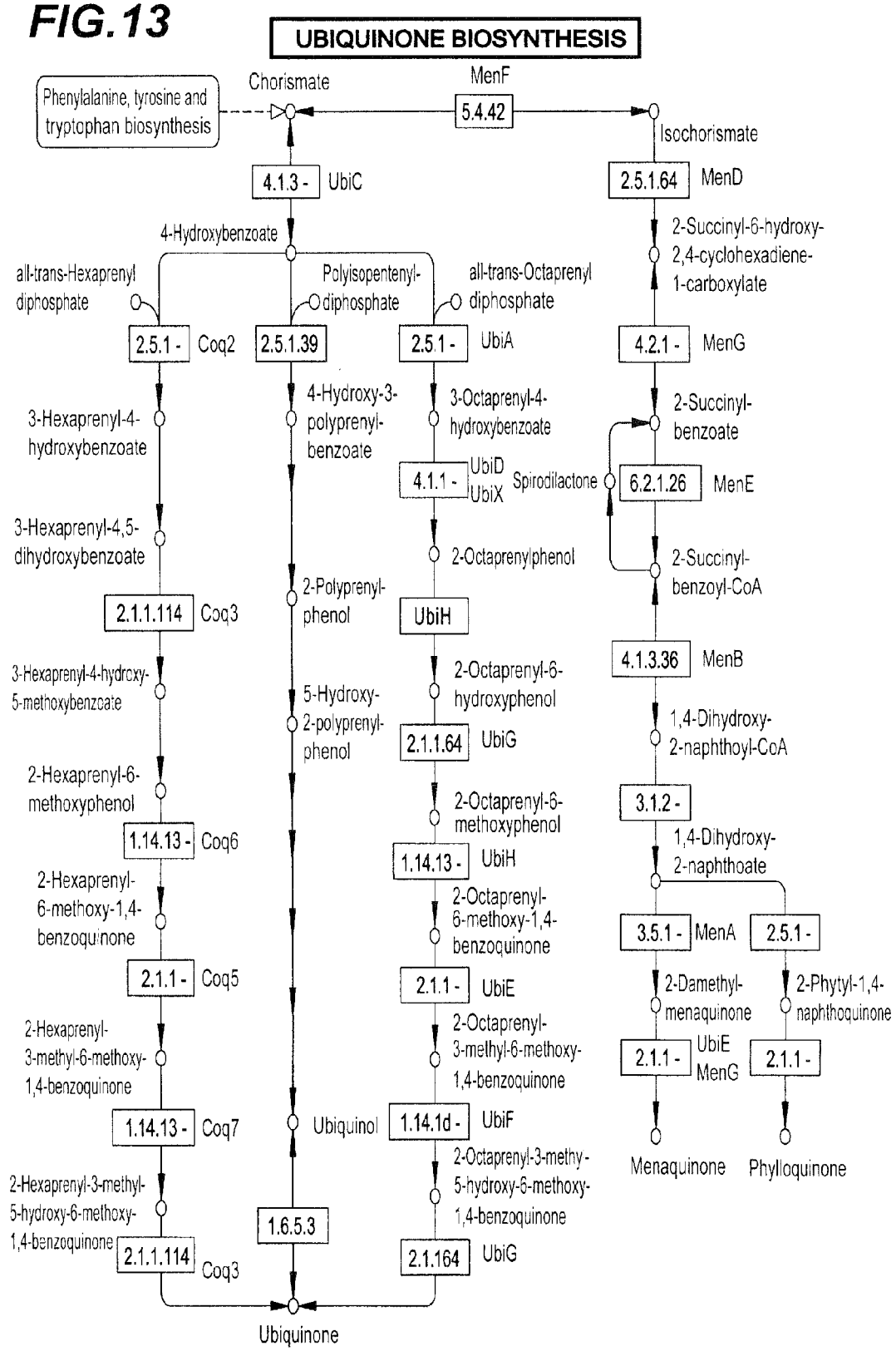
FIG. 13 depicts the ubiquinone and vitamin K biosynthesis pathways.

In some embodiments of the invention, the quinone derived compound whose production is engineered is ubiquinone. The commitment step in ubiquinone biosynthesis is the formation of para-hydroxybenzoate (PHB) from tyrosine or phenylalanine in mammals or chorismate in bacteria, followed by condensation of PHB and isoprene precursor, resulting in addition of the prenyl group (see FIG. 13). Lower eukaryotes, such as yeast, can synthesize PHB from either tyrosine or chorismate. The 3-decaprenyl-4-hydroxybenzoic acid resulting from the condensation reaction undergoes further modifications, which include hydroxylation, methylation and decarboxylation, in order to form ubiquinone. Ubiquinone biosynthetic enzymes and genes encoding these proteins have been characterized in several organisms. The most extensive analysis has been performed in bacterial systems such as *Escherichia coli* and *Rhodobacter sphaeroides* as well as the yeast, *Saccharomyces cerevisiae*. At least 8 enzymes are required for the synthesis of CoQ10 from PHB and the isoprene precursors.

As mentioned, ubiquinone is formed by the combination of para-hydroxybenzoate and isoprenoid chains produced, for example, via the isoprenoid biosynthesis pathways discussed above. Once IPP is formed according to that pathway, it ismoerizes into dimethylallyl pyrophophate (DMAPP). Three sequential condensation reactions with additional molecules of IPP generate the ten-carbon molecule geranyl pyrophosphate (GPP), followed by the fifteen-carbon molecule farnesyl pyrophosphate (FPP), which can be used to form the twenty-carbon compound geranylgeranyl pyrophosphate (GGPP). In many instances, FPP appears to be the predominant substrate used by polyprenyldiphosphate synthases (e.g., Coq1 polypeptides) during ubiquinone biosynthesis. According to the present invention, ubiquinone production in a host organism may be adjusted by modifying the expression or activity of one or more proteins involved in isoprenoid biosynthesis as discussed above.

Figure 14:
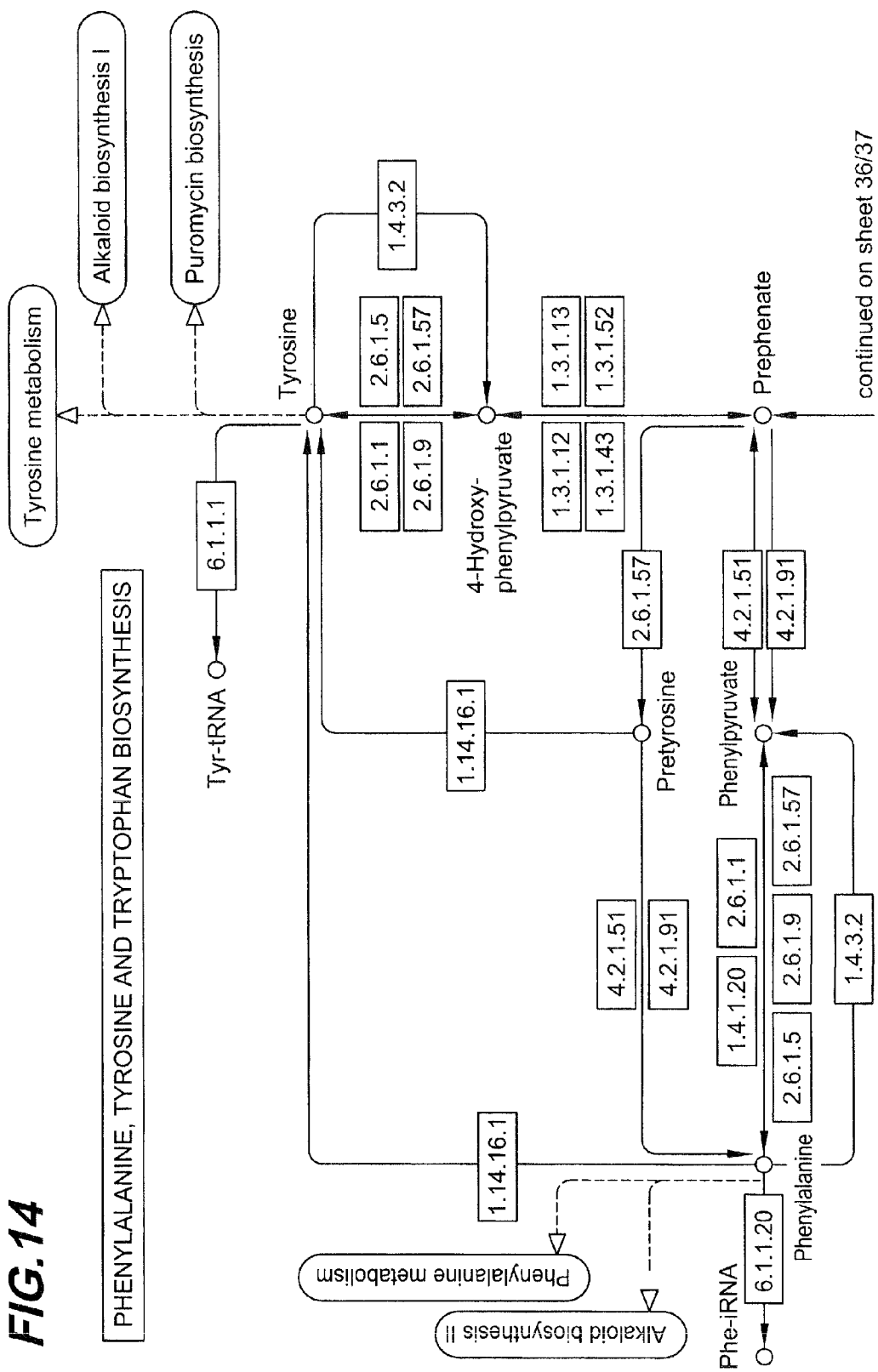
FIG. 14 illustrates biosynthetic pathways of aromatic amino acids, and the shikimate pathway for production of chorismate. A depiction of how these pathways feed into ubiquinone biosynthesis is depicted. Boxed numerical references are IUBMB Enzyme Nomenclature EC numbers for enzymes catalyzing the relevant reaction.
Figure 14:
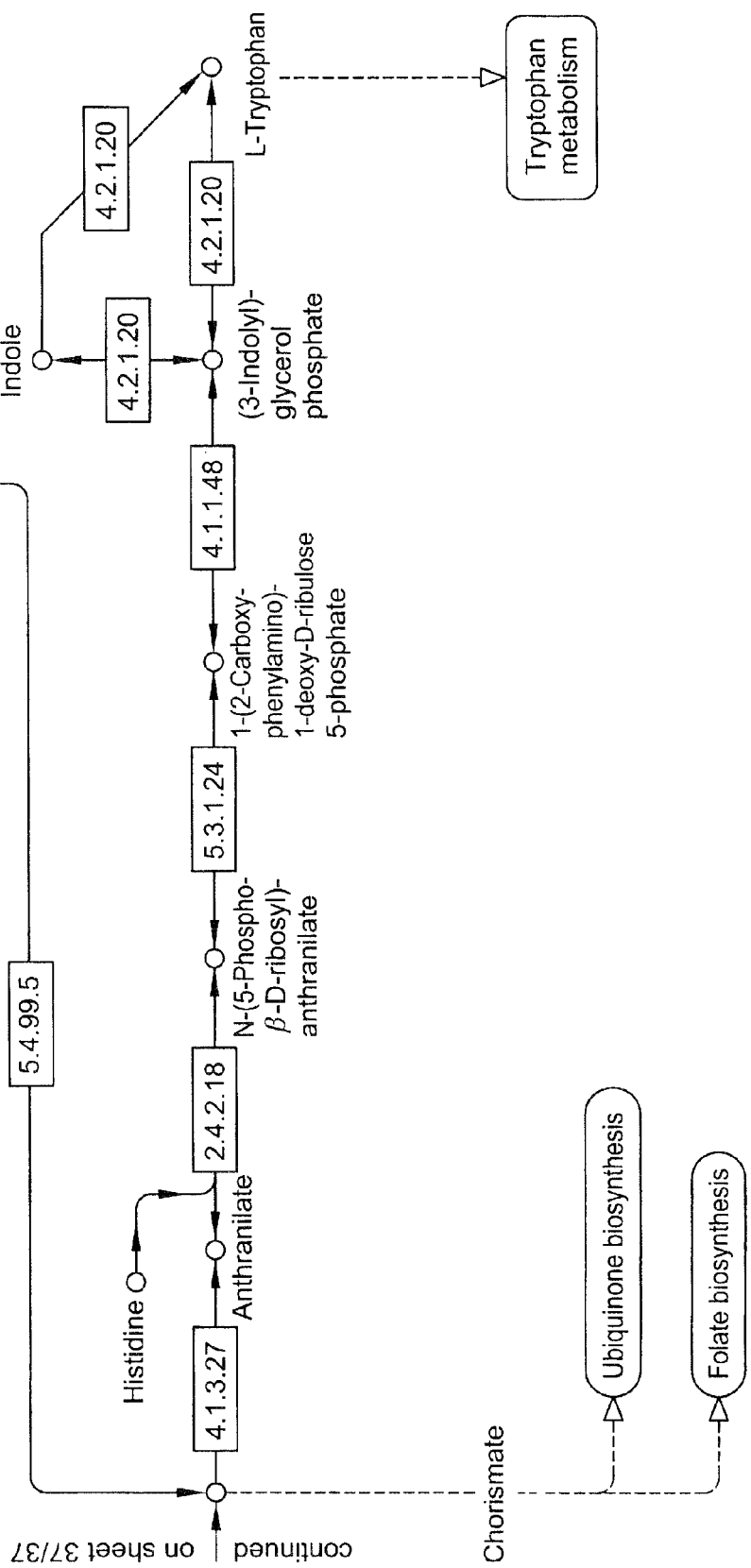
Figure 14:
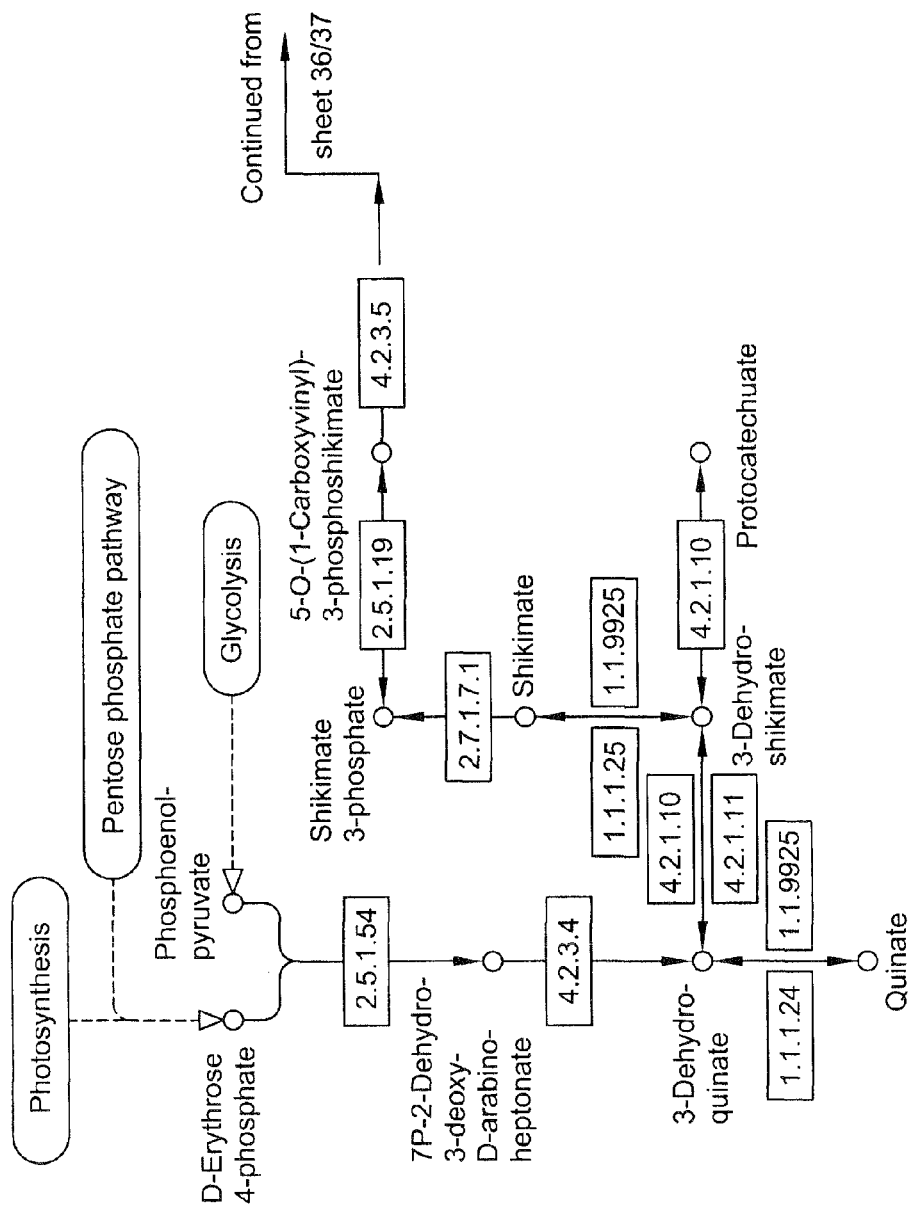

As discussed herein, two different pathways can produce the ubiquinoid precursor para-hydroxybenzoate—the first, the "shikimate pathway" is utilized in prokaryotes and yeast, involves synthesis of para-hydroxybenzoate (PHB) through chorismate. Biosynthesis of para-hydroxybenzoate from chorismate occurs by the action of chorismate pyruvate lyase. For example, as discussed herein, enzymes of the shikimate pathway, chorismate synthase, DAHP synthase, and transketolase are involved in this process. Representative examples of these enzymes are provided in Table 33 and Tables 35 through 37. In the second possible pathway, para-hydroxybenzoate is produced by derivation of tyrosine or phenylalanine. Biosynthesis of para-hydroxybenzoate from tyrosine or phenylalanine occurs through a five step process in mammalian cells (see, for example FIG. 14).

Accordingly, ubiquinone production in a host organism may be adjusted by modifying the expression or activity of one or more proteins involved in PHB biosynthesis. In some embodiments, such modification involves introduction of one or more heterologous PHB polypeptides into the host cell;

alternatively or additionally, modifications may be made to the expression or activity of one or more endogenous or heterologous additional PHB polypeptide, and/or isoprenoid biosynthesis polypeptides. Given the considerable conservation of components of the PHB biosynthesis polypeptides, it is expected that heterologous PHB biosynthesis polypeptides will often function well even in significantly divergent organisms. Further, given the conservation of the pathways among organism, it is anticipated that heterologous polypeptides throughout the ubiquinone biosynthetic pathway will function together effectively. Furthermore, should it be desirable to introduce more than one heterologous PHB polypeptide and/or isoprenoid biosynthesis polypeptide, in many cases polypeptides from different source organisms will function well together. In some embodiments of the invention, a plurality of different heterologous PHB and/or isoprenoid biosynthesis polypeptides is introduced into the same host cell. In some embodiments, this plurality contains only polypeptides from the same source organism; in other embodiments the plurality includes polypeptides from different source organisms. In still other embodiments, modification of endogenous PHB and/or isoprenoid biosynthesis polypeptides are also utilized, either alone or in combination with heterologous polypeptides as discussed herein.

Particularly for embodiments of the present invention directed toward production of CoQ10, it will often be desirable to utilize one or more genes from a natural CoQ10-producing organism. In general, where multiple heterologous polypeptides are to be expressed, it may be desirable to utilize the same source organism for all, or to utilize closely related source organisms.

Bacterial ubiquinogenic genes have already been demonstrated to be transferrable to other organisms, and are therefore useful in accordance with the present invention (see, for example, Okada et al., *FEMS Lett.* 431:241-244 (1998)). In some embodiments of this invention, it may be desirable to fused sequences encoding specific targeting signals to bacterial ubiquinogenic genes. For example, in certain embodiments mitochondrial signal sequences are useful in conjunction with, e.g., bacterial ubiquinogenic polypeptides for effective targeting of polypeptides for proper functioning. Mitochondrial signal sequences are known in the art, and include, but are not limited to example, mitochondrial signal sequences provided in Table 22. In other embodiments, it may be desirable to utilize genes from other source organisms such as animals, plants, alga, or microalgae, fungi, yeast, insect, protozoa, and mammals.

The present invention contemplates not only introduction of heterologous ubiquinogenic polypeptides, but also adjustment of expression or activity levels of heterologous or endogenous ubiquinogenic polypeptides, including, for example, alteration of constitutive or inducible expression patterns so as to increase activity of ubiquinogenic polypeptides. For example, genetic modifications comprising alteration and/or addition of regulatory sequences (e.g., promoter elements, terminator elements) may be utilized to confer particular regulation of expression patterns. Such genetic modifications may be utilized in conjunction with endogenous genes (e.g., for regulation of endogenous ubiquinogenic polypeptide(s)); alternatively, such genetic modifications may be included so as to confer regulation of expression of heterologous polypeptides (e.g., ubiquinogenic polypeptide(s)).

In some embodiments of the present invention, the quinone derived compound that host cells are engineered to produce along with one or more sterol compound(s) is Vitamin K. Vitamin K is a generic term that refers to derivatives of 2-methyl-1,4-naphthoquinone that have coagulation activity. The two natural forms of vitamin K differ in the identity of their side chains at position 3. Vitamin $K_1$, also known as phylloquinone (based on its presence in plants), has a phytyl side chain in position 3; vitamin $K_2$, also known as menaquinone, has an isoprenyl side chain at position 3. Different forms of menaquinone, having side chains with different numbers of isoprene units (typically 4-13) are found in different types of cells. The present invention provides engineered host cells, e.g., fungal cells, that produce vitamin K as a result of the engineering. That is, the present invention provides engineered host cells containing a Vitamin K production modification. Such a modification may comprise, for instance, introduction or activation of one or more Vitamin K biosynthetic polypeptides within a host cell. Exemplary such polypeptides include, for example, MenF, MenD, MenC, MenE, MenB, MenA, UbiE, and/or MenG polypeptides.

In some embodiments of the present invention, the quinone derived compound that host cells are engineered to produce along with at least one sterol compound is Vitamin E. Vitamin E is a generic term for a family of structurally related compounds that have a 6-chromanol ring, an isoprenoid side chain, and the biologic activity of α-tocopherol. The term encompasses the eight known naturally occurring vitamin E compounds, the four tocopherols (α, β, γ, δ) and four tocotrienols (α, β, γ, δ), which all contain a hydrophilic chromanol ring and a hydrophobic side chain. The α, β, γ, and δ forms differ from one another in the number of methyl groups on the chromanol ring. Several synthetic vitamin E compounds have also been prepared, and still others are possible (see, for example, Bramley et al., *J. Sci Food Agric* 80:913, 2000). α-tocopherol is a potent antioxidant, and is generally considered to be the most active vitamin E compound in humans.

Vitamin E compounds are synthesized by higher plants and cyanobacteria by two pathways: the isoprenoid pathway and the homogentisic acid formation pathway. The first step is formation of the homogentisic head group (HGA), which is produced from p-hydroxyphenylpyruvic acid (HPP) by the enzyme p-hydroxyphenylpyruvic acid dioxygenase (HPP-Dase). This is a complex reaction involving the addition of two oxygen atoms as well as the decarboxylation and rearrangement of the HPP side chain.

In the next step, HGS is prenylated and decarboxylated to form 2-methyl-6-phytylplastoquinol. This step also represents the commitment step for production of tocopherols and/or tocotrienols, as 2-methyl-6-phytylplastoquinol represents the common intermediate in the synthesis of all tocopherols. The present invention provides host cells that have been engineered to accumulate 2-methyl-6-phytylplastoquinol. In some embodiments, the host cells are (or have been engineered to be) oleaginous or lipid-accumulating. In some embodiments, produced 2-methyl-6-phytylplastoquinol accumulates in lipid bodies within the engineered host cells.

In the final steps of tocopherol synthesis, methylation and ring cyclization reactions convert the 2-methyl-6-phytylplastoquinol into various tocopherols.

It is expected in accordance with the present invention that availability of tocopherol precursors and/or intermediates may well affect the rate and/or extent of tocopherol (or other vitamin E compound) production and/or accumulation by and/or within cells. The present invention therefore encompasses engineering host cells to adjust the rate or amount of one or more tocopherol precursors and/or intermediates.

The present invention provides engineered host cells, e.g., fungal cells, that produce vitamin E as a result of the engineering. The present invention specifically provides engineered host cells, e.g., fungal cells, that produce larger amounts of vitamin E that an otherwise identical non-engineered host cell. That is, the present invention provides engineered host cells containing a Vitamin E production modification. Such a modification may comprise, for instance, introduction or activation of one or more Vitamin E biosynthetic polypeptides within a host cell. Exemplary such polypeptides include, for example, tyrA, pds1(hppd), VTE1, HPT1(VTE2), VTE3, VTE4, and/or GGH polypeptides. Specific examples of each of these can be found, for example, in Tables 50-56.

It will be appreciated by those of ordinary skill in the art that, in some embodiments of the invention, where multiple heterologous polypeptides are to be expressed (e.g., because one or more activities of interest require two or more polypeptide chains and/or because multiple activities of interest are being engineered), it may be desirable to utilize the same source organism for all, or to utilize closely related source organisms; in other embodiments, heterologous polypeptides may be from different source organisms. In some embodiments, two or more versions of a particular heterologous polypeptide, optionally from different source organisms, may be introduced into and/or engineered within, a single host cell.

Having now generally described the invention, the same will be more readily understood through reference to the following exemplification which is provided by way of illustration, and is not intended to be limiting of the present invention.

EXEMPLIFICATION

All basic molecular biology and DNA manipulation procedures described herein are generally performed according to Sambrook et al., or Ausubel et al., (Sambrook J, Fritsch E F, Maniatis T (ed.) 1989, *Molecular Cloning: A Laboratory Manual*, Cold Spring Harbor Laboratory Press: New York; Ausubel F M, Brent R, Kingston R E, Moore D D, Seidman J G, Smith J A, Struhl K (ed.) 1998 *Current Protocols in Molecular Biology*, Wiley: New York). The TEF1 promoter is from *Y. lipolytica* as is the XPR2 terminator.

Plasmids are generated for construction of sterol-derived metabolite producing strains, including strains to produce metabolic precursors of vitamin $D_3$. The following subparts describe production of plasmids used for construction of said strains. All PCR amplifications use NRRL Y-1095 genomic DNA as template. The URA5 gene described below is allelic with the ura2-21 auxotrophy below in Table 82.

Example 1

Production of Plasmids for Sterol Strain Construction

1A. Production of pMB4637 (ADE1 tef-*Y. lipolytica* Hmg1$^{trunc}$), Encoding a Truncated *Y. lipolytica* HMG-CoA Reductase.

The native HMG1 gene from *Y. lipolytica* was modified using primers M04658 (described above) and M04657, to create pMB4637:

M04657  5'-CACACTCTAGACACAAAAATGACCCAGTCTGTGAAGGTGG

M04658  5'-CACACACGCGTACACCTATGACCGTATGCAAAT

Primers M04657, which encodes a start methionine, and M04658 were used to amplify a 1.5 kb fragment encoding the C-terminal 499 residues of the Hmg1 protein of *Y. lipolytica*, using genomic DNA as template. The resulting fragment was blunt-end cloned into pBluescript SKII-, which had been EcoRV digested and treated with calf intestinal phosphatase. Following sequence verification, the resulting plasmid pMB4623 was digested with XbaI and MluI, and the 1.5 kb fragment was ligated to NheI/MluI digested pMB4629. pMB4629 is a *Yarrowia* expression vector containing the ADE1 auxotrophic marker, the native TEF1 promoter, and the native XPR2 terminator.

The resulting nucleic acid coding sequence in pMB4637 encoded Hmg1$^{trunc}$ protein, which was comprised of a start methionine followed by the carboxy-terminal 499 amino acids of the *Y. lipolytica* HMG-CoA reductase protein are as follows:

DNA:

```
atgacccagtctgtgaaggtggttgagaagcacgttcctatcgtcatt gagaagcccagcgagaaggaggaggacacctcttctgaagactccatt gagctgactgtcggaaagcagcccaagcccgtgaccgagacccgttct ctggacgacctagaggctatcatgaaggcaggtaagaccaagcttctg gaggaccacgaggttgtcaagctctctctcgagggcaagcttcctttg tatgctcttgagaagcagcttggtgacaacacccgagctgttggcatc cgacgatctatcatctcccagcagtctaataccaagactttagagacc tcaaagcttccttacctgcactacgactacgaccgtgttttggagcc tgttgcgagaacgttattggttacatgcctctccccgttggtgttgct ggccccatgaacattgatggcaagaactaccacattcctatggccacc actgagggttgtcttgttgcctcaaccatgcgaggttgcaaggccatc
```

TABLE 82

| Yarrowia lipolytica strains. | | |
|---|---|---|
| NRRL Y-1095 | Wild type diploid | |
| ATCC76861 | MATB ura2-21 lyc1-5 LYS1-5B | |
| ATCC76982 | MATB ade1 leu2-35 lyc1-5 xpr2 | |
| ATCC201249 | MATA ura3-302 leu2-270 lys8-11 PEX17-HA | |
| MF346 | MATA ura2-21 | ATCC76861 × ATCC201249 |
| MF350 | MATB ura2-21 leu2-35 ade1 | ATCC76982 × MF346 |

-continued

```
aacgccggtggcggtgttaccactgtgcttactcaggacggtatgaca
cgaggtccttgtgtttccttccctctctcaagcgggctggagccgct
aagatctggcttgattccgaggagggtctcaagtccatgcgaaaggcc
ttcaactccacctctcgatttgctcgtctccagtctcttcactctacc
cttgctggtaacctgctgtttattcgattccgaaccaccactggtgat
gccatgggcatgaacatgatctccaagggcgtcgaacactctctggcc
gtcatggtcaaggagtacggcttccctgatatggacattgtgtctgtc
tcgggtaactactgcactgacaagaagcccgcagcgatcaactggatc
gaaggccgaggcaagagtgttgttgccgaagccaccatccctgctcac
attgtcaagtctgttctcaaaagtgaggttgacgctcttgttgagctc
aacatcagcaagaatctgatcggtagtgccatggctggctctgtggga
ggtttcaatgcacacgccgcaaacctggtgaccgccatctaccttgcc
actggccaggatcctgctcagaatgtcgagtcttccaactgcatcacg
ctgatgagcaacgtcgacggtaacctgctcatctccgtttccatgcct
tctatcgaggtcggtaccattggtggaggtactattttggagccccag
ggggctatgctggagatgcttggcgtgcgaggtcctcacatcgagacc
cccggtgccaacgcccaacagcttgctcgcatcattgcttctggagtt
cttgcagcggagctttcgctgtgttctgctcttgctgccggccatctt
gtgcaaagtcatatgacccacaaccggtcccaggctcctactccggcc
aagcagtctcaggccgatctgcagcgtctacaaaacggttcgaatatt
tgcatacggtcatag
```

Protein:

```
mtqsvkvvekhvpiviekpsekeedtssedsieltvgkqpkpvtetrs
lddleaimkagktklledhevvklslegklplyalekqlgdntravgi
rrsiisqqsntktletsklpylhydydrvfgaccenvigymplpvgva
gpmnidgknyhipmattegclvastmrgckainaggputtvltqdgmtr
gpcvsfpslkragaakiwldseeglksmrkafnstsrfarlqslhstl
agnllfirfrttgdamgmnmiskgvehslavmvkeygfpdmdivsys
gnyctdkkpaainwiegrgksvvaeatipahivksvlksevdalveln
isknligsamagsvggfnahaanlvtaiylatgqdpaqnvessncitl
msnvdgnllisysmpsievgtigggtilepqgamlemlgvrgphietp
ganaqqlariiasgvlaaelslcsalaaghlvqshmthnrsqaptpak
qsqadlqrlqngsnicirs
```

1B. Production of pMBERG9 (URA5 tef-*Y. lipolytica* ERG9), Encoding a *Y. lipolytica* Squalene Synthase.

The native ERG9/SQS1 gene from *Y. lipolytica* may be modified using primers MOSQSNHE and SQSMLU, to create a plasmid for expression of ERG9 in fungi (e.g. *Y. lipolytica*):

```
MOSQSNHE  5'-CACAGCTAGCACACAAAAATGG-
          GAAAACTCATCGAACTG

MOSQSMLU  5'-CACACACGCGTACACCTAATCTCTCAGAGGAAA
```

Primers MOSQSNHE and MOSQSMLU are used to amplify a 1.34 kb fragment encoding the Erg9/Sqs1 protein of *Y. lipolytica*, using genomic DNA or cDNA as template. Following T4 polynucleotide kinase treatment, the resulting fragment is blunt-end cloned into pBluescript SKII-, which is EcoRV digested and treated with calf intestinal phosphatase. Following sequence verification, the resulting plasmid is digested with NheI and MluI, and the 1.34 kb fragment is ligated to NheI/MluI digested pMB4590. pMB4590 is a *Yarrowia* expression vector containing the URA5 auxotrophic marker, the native TEF1 promoter, and the native XPR2 terminator.

The resulting nucleic acid coding sequence in pMBERG9 encodes Erg9/Sqs1 protein, a protein of 445 amino acids. The DNA and corresponding protein are as follows:

DNA:

```
atgggaaaactcatcgaactgctcttgcaccctagcgaactgtctgct
gctatccactacaagctgtggcgtcagcctctgcatccccgcgatctt
tccaaggagtccactgagctgcgacgatgctatgagcttctagacgtg
tgctcacgatcatttgcagccgttattcgagaactgcatcctgaggtg
cgagacgctgtaatgctgttctatctgattcttcgtgctctcgacacg
attgaagacgatatgactctgtcgcgtgacatcaagatcccaattctt
cgagacttcacgaagtgcatgaagacacctggctggaagttcaccgac
tctgatcccaacgagcgagatcgtgtggtgctacaggagtttcctgtg
gttatgactgagttcaacaagctcaagcccaagtaccaggaagtaatc
tacgacattaccgacagaatgggaaacggaatggccgattacgtcatt
gatgacgacttcaacaacaacggcgtggacaccattgccgcttatgat
ctgtactgtcatcatgttgccggcatcgtgggtgagggccttacccga
attacgattctcgctggttttggaaccgacgtgttgcacgaaaacccc
cgacttcaggagtctatgggcttgttcttgcaaaaggtcaacatcatc
cgagactacagagaagacattgacgtgaacagagctttctggcctcga
gaaatctggcacaagtacgccgaagaaatgcgagatttcaaggacccg
aagtattccaagaaggccttgcattgcacctccgatctggttgcaaat
gccctcggacatgccacagactgcctcgattacctcgacaacgtcacc
gatccttcaaccttcactttctgcgccattccccaggtcatggccatt
gctaccctggacttggtctaccgaaacccgacgttttccagaagaac
gtcaagttgcgcaagggaactactgtcagcctgattcttgaggccagc
aacgtttctggagtatgtgacattttcactcgatacgccggaaggtg
tacaagaagtccgaccccaatgaccccaactacttccgagtgtctgtg
ctctgcggtaagatcgagcagcatgcggctctgatcaagagacagcga
ggaccccccgctaaaaccattgcacaactggaaggtgaacgaaaagag
atggccctgtcgctaattgtctgtttagcagttatcttctcgatgtct
ggactgatggcttatatcgcctacgtgtctggattcagatggtcaccc
cgagagattttcgactctaagatgtttcctctgagagattag
```

Protein:

mgklielllhpselsaaihyklwrqplhprdlskestelrrcyelldvcs rsfaavirelhpevrdavmlfylilraldtieddmtlsrdikipilrdft kcmktpgwkftdsdpnerdrvvlqefpvvmtefnklkpkyqeviyditdr mgngmadyvidddfnnngvdtiaaydlychhvagivgegltritilagfg tdvlhenprlqesmglflqkvniirdyredidynrafwpreiwhkyaeem rdfkdpkyskkalhctsdlvanalghatdcldyldnvtdpstftfcaipq vmaiatldlyrnpdvfqknvklrkgttvslileasnvsgvcdiftryark vykksdpndpnyfrysvlcgkieqhaalikrqrgppaktiaqlegerkem alslivclavifsmsglmayiayvsgfrwspreifdskmfplrd 1C. Production of pMBERGI (LEU2 tef-*Y. lipolytica* ERG1), Encoding a *Y. lipolytica* Squalene Epoxidase.

The native ERG1 gene from *Y. lipolytica* may be modified using primers MOERG1XBA and MOERG1MLU, to create a plasmid for expression of ERG1 in Y

| | |
|---|---|
| MOERG1XBA | 5'-CACACTCTAGACACAAAAATGGTCACCCAA CAGTCTGCA |
| MOERG1MLU | 5'-CACACACGCGTACACCTAAGTCAGCTCGCT CCA |

Primers MOERG1XBA and MOERG1MLU are used to amplify a 1.47 kb fragment encoding the Erg1 protein of *Y. lipolytica*, using genomic DNA or cDNA as template. Following T4 polynucleotide kinase treatment, the resulting fragment is blunt-end cloned into pBluescript SKII-, which is EcoRV digested and treated with calf intestinal phosphatase. Following sequence verification, the resulting plasmid is digested with XbaI and MluI, and the 1.47 kb fragment is ligated to NheI/MluI digested pMB4603. pMB4603 is a *Yarrowia* expression vector containing the LEU2 auxotrophic marker, the native TEF1 promoter, and the native XPR2 terminator.

The resulting nucleic acid coding sequence in pMBERG1 encodes Erg1 protein, a protein of 489 amino acids. The DNA and corresponding protein are as follows:

DNA:

atggtcacccaacagtctgcagcagagaccagcgccacccagaccaac
gagtacgacgtggtcattgtcggagctggtattgccgggcccgctctg
gccgtggctcttggaaatcagggcagaaaggttcttgttgtggaacga
gatctctccgaaccggaccgaatcgtgggagagctgcttcagcccgga
ggagtcgctgctctcaagactctgggtctcggctcttgtatcgaggat
atcgacgcgatccctgccagggatacaacgtgatctactctggagaa
gagtgcgttctcaaataccccaaggtcccccgagacatccagcaggac
tacaacgagctgtacagaagcggaaagtctgccgacatctccaacgag
gctccccgaggagtatccttccaccacggccgatttgtcatgaacttg
cgaagggccgcacgagacacacccaatgtgactctgctggaggccaca
gtcaccgaggtggtcaagaaccttacaccggccacattggagtc
aagacct tctctaaaactggaggcgccaaaatctacaagcacttcttt
gctcctctcaccgtcgtctgtgatggaactttttccaagttccgaaag
gactttagcaccaacaagacgtctgtgcgttcgcatttcgccggtctg
attctcaaggacgctgttctgccctcccccagcatggccacgtgatt
ctgtcgcccaactcgtgtcccgttcttgtctaccaggttggagctcga
gagacccgaattctgtgtgacattcagggaccgctcccctaatgca
accggagccctcaaggaacacatggagaagaacgtcatgccccacctg
cctaagtccatccagccgtctttccaagccgctctcaaggagcagacc
attcgagtcatgccaacctctttcctgtcggcctccaagaaacgatcac
cacggtttgattctgctgggtgacgcactcaacatgcgacatccactt
accggaggaggaatgaccgttgctctcaatgatgccctt ctactcagc
agacttctcaccggcgttaacctggaagacacctatgccgtgtcctcc
gtcatgagctcgcagttccactggcagcgaaaacacctcgactccatc -continued gtcaacattctctccatggccctctactcgctcttcgccgccgactcg
gactacctgcgaatcctgcagctcggatgcttcaactacttcaagctg
ggaggcatctgtgtggaccacccgtcatgctgttggctggagttctc
cccccgacccatgtacctgtttacgcatttcttcgtagtggccatctac
ggcggaatctgcaacatgcaggccaacggcattgccaagctgcccgcg
tcgctactgcaatttgtcgcctctctggtcaccgcttgcatcgtcatc
ttcccttacatttggagcgagctgacttag Protein:

mvtqqsaaetsatqtneydvvivgagiagpalavalgnqgrkvlvverdl sepdrivgellqpggvaalktlglgsciedidaipcqgynviysgeecvl kypkvprdiqqdynelyrsgksadisneaprgvsfhhgrfvmnlrraard tpnvtlleatvtevvknpytghiigvktfsktggakiykhffapltvvcd gtfskfrkdfstnktsvrshfaglilkdavlpspqhghvilspnscpvlv yqvgaretrilcdiqgpvpsnatgalkehmeknvmphlpksiqpsfqaal keqtirvmpnsflsaskndhhglillgdalnmrhpltgggmtvalndall lsrlltgvnledtyavssvmssqfhwqrkhldsivnilsmalyslfaads dylrilqlgcfnyklggicvdhpvmllagylprpmylfthffvvaiyggi cnmqangiaklpasllqfvaslvtacivifpyiwselt Example 2

Engineering *Yarrowia lipolytica* for Increased Sterol Production

2A. Production of *Y. lipolytica* Expressing a Truncated *Y. lipolytica* HMG-CoA Reductase.

MF350 (MATB ura2-21 leu2-35 ade1) is transformed with pMB4637 (ADE1 tef-*Y. lipolytica* Hmg1$^{trunc}$) that has been cleaved with SnaBI, and Ade$^+$ colonies are selected. One such colony, MFHMG, produces elevated (for example, in the range of 2-fold or more) 5,7-diene-containing sterols than MF350 after 2 days of growth in YPD at 30° C.

2B. Production of *Y. lipolytica* Expressing a *Y. lipolytica* Squalene Synthase MF350 (MATB ura2-21 leu2-35 ade1) is transformed with pMBERG9 (URA5 tef-*Y. lipolytica* ERG9), that has been cleaved upstream of URA5 with SspI; a Ura transformant carrying the plasmid at the ura2 locus is identified and named MFERG9. One such colony, MFERG9, produces elevated (for example, in the range of about 1.5-fold or more) 5,7-diene-containing sterols than MF350 after 2 days of growth in YPD at 30° C.

2C. Production of *Y. lipolytica* Expressing a *Y. lipolytica* Squalene Epoxidase.

MF350 (MATB ura2-21 leu2-35 ade1) is transformed with SspI-cleaved pMBERG1 (LEU2 tef-*Y. lipolytica* ERG 1), and Leu$^+$ transformants are identified. One such colony is named MFERG9. MFERG1 produces elevated (for example, in the range of about 1.3-fold or more) 5,7-diene-containing sterols than MF350 after 2 days of growth in YPD at 30° C.

2D. Production of *Y. lipolytica* Expressing a Truncated *Y. lipolytica* HMG-CoA Reductase, Squalene Synthase, and Squalene Epoxidase.

MFHMG is transformed with pMBERG9 (URA5 tef-*Y. lipolytica* ERG9), that has been cleaved upstream of URA5 with SspI; a Ura$^+$ transformant carrying the plasmid at the ura2 locus is identified and named MFHMGERG9. MFHMGERG9 can be subsequently transformed with SspI-cleaved pMBERG1 (LEU2 tef-*Y. lipolytica* ERG1), and Leu$^+$ transformants can be identified. One such colony is named MFHMGERG1ERG9. MFERG9 produces elevated (for example, in the range of about 3.5-fold or more) 5,7-diene-containing sterols than MF350 after 2 days of growth in YPD at 30° C. Alternatively, *Y. lipolytica* strains expressing *Y. lipolytica* HMG-CoA reductase and squalene synthase, or squalene epoxidase and HMG-CoA reductase, or squalene synthase and squalene epoxidase can be made and tested.

Example 3

Extraction of Sterols from *Yarrowia lipolytica* Cells 50 ml cultures of *Y. lipolytica* strains are grown for 2 days in YPD liquid medium at 30° C. prior to harvesting for sterol analysis. Analysis is performed upon the non-saponifiable fractions. Saponification and extraction are performed essentially as described (Methods in Molecular Biology, Vol. 53, Yeast Protocols, pp 123-131, 1996; J. Bacteriol. Vol. 108, No. 1, pp 69-73, 1971). In brief, cells are harvested by centrifugation, and then saponified in a screw cap bottle using a mixture of methanol (3 ml), 0.5% pyrogallol (2 ml), and 60% potassium hydroxide (2 ml). The tubes are then incubated at 90° C. for 2 hours prior to extraction with n-heptane (3 extractions using 5 ml of n-heptane). Each extraction is centrifuged at 500 g for 5 minutes to enable phase separation. If GC-MS analysis is to be performed, then the heptane-containing fractions are evaporated under nitrogen at 55° C.

Example 4

Quantification of Sterol Production

UV spectrophotometry scanning between 220-300 nm can be used to estimate the relative content of 5,7-diene-containing sterols in the heptane fractions described above. 5,7-diene-containing sterols such as ergosta-5,7,24(28)-treinol, ergosta-5,7,22,24(28)-tetraenol, and ergosterol give a characteristic triple peak at 293, 281.5, and 271 nm, whereas many of the other yeast sterols display a peak at 250 nm. By using an authentic ergosterol standard and extinction values provided by Shaw and Jefferies (Analyst 28: 509-528, 1953), it is possible to estimate the sterol content in crude heptane extracts.

More detailed analysis of *Y. lipolytica* sterol content can be attained by subjecting the same extracts to either gas-liquid chromatography or, more preferably, gas chromatography coupled to mass spectrometry, as described (e.g. *Proc. Natl. Acad. Sci. USA*, Vol. 94, pp. 11173-11178, 1997). Specific metabolites to examine include squalene, 2,3-epoxysqualene, lanosterol, 4,4-dimethylcholesta-8,14,24-trienol, 4,4-dimethylzymysterol, 4-methylzymosterol, zymosterol, fecosterol, episterol, ergosta-5,7,24(28)-treinol, ergosta-5,7,22,24(28)-tetraenol, and ergosterol.

Example 5

Constructing an Oleaginous Strain of *Saccharomyces cerevisiae*

Genes encoding the two subunits of ATP-citrate lyase from *N. crassa*, the AMP deaminase from *Saccharomyces cerevisiae*, and the cytosolic malic enzyme from *M. circinelloides* are overexpressed in *S. cereviseae* strains in order to increase the total lipid content. Similar approaches to enhance lipid production could be employed in other host organisms such as *Xanthophyllomyces dendrorhous* (*Phaffia rhodozyma*), using the same, homologous, or functionally similar oleaginic polypeptides.

Qiagen RNAEasy kits (Qiagen, Valencia, Calif.) are used to prepare messenger RNA from lyophilized biomass prepared from cultures of *N. crassa*. Subsequently, RT-PCR is performed in two reactions containing the mRNA template and either of the following primer pairs.

```
acl1:
1fwd:  5' CACACGGATCCTATAatgccttccgcaacgaccg

1rev:  5' CACACACTAGttaaatttggacctcaacacgaccc acl2:
2fwd:  5' CACACGGATCCAATATAAatgtctgcgaagagcatcctcg 2rev:  5' CACACGCATGCttaagcttggaactccaccgcac
```

The resulting fragment from the acl1 reaction is cleaved with SpeI and BamHI, and that from the acl2 reaction is cleaved with BamHI and SphI, and both are ligated together into YEp24 that has been digested with NheI and SphI, creating the plasmid "p12". The bi-directional GAL1-10 promoter is amplified from *S. cerevisiae* genomic DNA using the primers.

```
gal10:
5' CACACGGATCCaattttcaaaaattcttactttttttttggatggac gal1:
5' CACACGGATCCttttttctccttgacgttaaagtatagagg,
``` and the resulting 0.67 kb fragment is cleaved with BamHI and ligated in either orientation to BamHI-digested "p12" to create "p1gal2" and "p2gal1", containing GAL1-acl1/GAL10-acl2 and GAL10-acl1/GAL1-acl2, respectively (Genbank accession: adl1: CAB91740.2; acl2: CAB91741.2).

In order to amplify the *S. cereviseae* gene encoding AMP deaminase and a promoter suitable for expressing this gene, *S. cerevisiae* genomic DNA is amplified using two primer pairs in separate reactions:

AMD1 ORF:

```
AMD 1 FWD:
5' CACACGAGCTCAAAAatggacaatcaggctacacagag

AMD 1 rev:
5' CACACCCTAGGtcacttttcttcaatggttctcttgaaattg
```

GAL7p:

```
gal7prox:
5' CACACGAGCTCggaatattcaactgttttttttatcatgttgatg gal7dist:
5' CACACGGAtccttcttgaaaatatgcactctatatcttttag,
```

The resulting fragment from the AMD1 reaction (2.4 kb) is cleaved with SacI and AvrII, and that from the GAL7 reaction (0.7 kb) is cleaved with BamHI and SphI, and both are ligated together into YEp13 that has been digested with NheI and BamHI, creating the plasmid "pAMPD". This plasmid carries the *S. cerevisiae* gene, AMD1, encoding AMP deaminase, under the control of the galactose-inducible GAL7 promoter.

Messenger RNA is prepared from lyophilized biomass of *M. circinelloides*, as described above, and the mRNA template is used in a RT-PCR reaction with two primers:

MAEfwd:
5' CACACGCTAGCTACAAAatgttgtcactcaaacgcatagcaac

MAErev:
5' CACACGTCGACttaatgatctcggtatacgagaggaac, and the resulting fragment is cleaved with NheI and SalI, and ligated to XbaI- and XhoI-digested pRS413TEF (Mumberg, D. et al., (1995) Gene, 156:119-122), creating the plasmid "pTEFMAE", which contains sequences encoding the cytosolic NADP$^+$-dependant malic enzyme from *M. circinelloides* (E.C. 1.1.1.40; mce gene; Genbank accession: AY209191) under the control of the constitutive TEF1 promoter.

The plasmids "p1gal2", "pAMPD", and "pTEFMAE" are sequentially transformed into a strain of *S. cereviseae* to restore prototrophy for uracil ("p1gal2"), leucine ("pAMPD"), and histidine ("pTEFMAE") (Guthrie and Fink *Methods in Enzymology* 194:1-933, 1991). The resulting transformants are tested for total lipid content following shake flask testing (e.g., 20 ml cultures in 125 ml flasks grown at 30° C. for 72-96 hour cultures) in either synthetic complete (SC) medium lacking uracil, leucine and histidine or in a 2-step fermentation process. In the 2-step process, 1.5 ml of cells from an overnight 2 ml roll tube culture containing SC medium lacking uracil, leucine and histidine are centrifuged, washed in distilled water, and resuspended in 20 ml of a nitrogen-limiting medium suitable for lipid accumulation (30 g/L glucose, 1.5 g/L yeast extract, 0.5 g/L NH$_4$Cl, 7 g/L KH$_2$PO$_4$, 5 g/L Na$_2$HPO$_4$-12H$_2$O, 1.5 g/L MgSO$_4$.7H$_2$O, 0.08 g/L FeCl$_3$-6H$_2$O, 0.01 g/L ZnSO$_4$-7H$_2$O, 0.1 g/L CaCl$_2$-2H$_2$O, 0.1 mg/L MnSO$_4$.5H$_2$O, 0.1 mg/L CuSO$_4$.5H$_2$O, 0.1 mg/L Co(NO$_3$)$_2$-6H$_2$O; pH 5.5 (J Am Oil Chem Soc 70:891-894 (1993)).

Intracellular lipid content of the modified and control *S. cerevisiae* strains is analyzed using the fluorescent probe, Nile Red (J Microbiol Meth (2004) 56:331-338). In brief, cells diluted in buffer are stained with Nile Red, excited at 488 nm, and the fluorescent emission spectra in the wavelength region of 400-700 nm are acquired and compared to the corresponding spectra from cells not stained with Nile Red. To confirm results from the rapid estimation method, the total lipid content is determined by gas chromatographic analysis of the total fatty acids directly transmethylesterified from dried cells, as described (Appl Microbiol Biotechnol. 2002 November; 60(3):275-80). Yeast strains expressing the multiple oleaginic polypeptides produce elevated total lipid (for example, in the range of 17% and 25% dry cell weight basis) following growth in YPD and lipid accumulation medium when compared to non-transformed *S. cerevisiae* strains which may, for example, produce in the range of 6% and 10% total lipid after growth in YPD and lipid accumulation medium.

Example 6

*Y. lipolytica* Oleaginic and Isoprenoid Biosynthesis Genes

FIG. 8 is a list of *Y. lipolytica* genes representing various polypeptides (e.g. oleaginic and isoprenoid biosynthesis peptides) useful in the fungal strains and methods described herein. The Genbank accession number and GI number is given for each polypeptide in addition to oligo pairs which can be used to amplify the coding region for each gene from *Y. lipolytica* genomic DNA or cDNA. Resulting PCR fragments can be cleaved with restriction enzyme pairs (e.g. depending on what site is present within the oligo sequence, XbaI/MluI or NheI/MluI or XbaI/AscI or NheI/AscI) and inserted into expression vectors (e.g. fungal expression vectors including *Y. lipolytica* expression vectors disclosed herein such as MB4629).

The DNA and proteins they encode of the *Y. lipolytica* genes represented in FIG. 8 are as follows (intron sequence is underlined):

YALI0F30481g
DNA:

atgtcgcaaccccagaacgttggaatcaaagccctcgagatctacgtgcc ttctcgaattgtcaaccaggctgagctcgagaagcacgacggtgtcgctg ctggcaagtacaccattggtcttggtcagaccaacatggcctttgtcgac gacagagaggacatctattcctttgccctgaccgccgtctctcgactgct caagaacaacaacatcgaccctgcatctattggtcgaatcgaggttggta ctgaaaccatctggacaagtccaagtccgtcaagtctgtgctcatgcagc tcttggcgagaacagcaacattgagggtgtggacaacgtcaacgcctgc tacggaggaaccaacgccctgttcaacgctatcaactgggttgagggtcg atcttgggacggccgaaacgccatcgtcgttgccggtgacattgccctct acgcaaagggcgctgcccgacccaccggaggtgccggctgtgttgccatg ctcattggccccgacgctccectggttcttgacaacgtccacggatctta cttcgagcatgcctacgatttctacaagcctgatctgacctccgagtacc cctatgttgatggccactactccctgacctgttacacaaaggccctcgac aaggcctacgctgcctacaacgcccgagccgagaaggtcggtctgttcaa ggactccgacaagaagggtgctgaccgatttgactactctgccttccacg tgcccacctgcaagcttgtcaccaagtcttacgctcgacttctctacaac gactacctcaacgacaagagcctgtacgagggccaggtccccgaggaggt tgctgccgtctcctacgatgcctctctcaccgacaagaccgtcgagaaga ccttccttggtattgccaaggctcagtccgccgagcgaatggctccttct ctccagggacccaccaacaccggtaacatgtacaccgcctctgtgtacgc ttctctcatctctctgctgacttttgtccccgctgagcagctgcagggca agcgaatctctctcttctcttacggatctggtcttgcttccactcttttc tctctgaccgtcaagggagacatttctcccatcgtcaaggcctgcgactt caaggctaagctcgatgaccgatccaccgagactcccgtcgactacgagg ctgccaccgatctccgagagaaggcccacctcaagaagaactttgagccc cagggagacatcaagcacatcaagtctggcgtctactacctcaccaacat cgatgacatgttccgacgaaagtacgagatcaagcagtag Protein:

Msqpqnvgikaleiyvpsrivnqaelekhdgvaagkytiglgqtnmafvd drediysfaltavsrllknnnidpasigrievgtetlldksksvksvlmq lfgensniegvdnvnacyggtnalfnainwvegrswdgrnaivvagdial -continued yakgaarptggagcvamligpdaplvldnvhgsyfehaydfykpdltsey
pyvdghysltcytkaldkayaaynaraekvglfkdsdkkgadrfdysafh
vptcklvtksyarllyndylndkslyegqvpeevaavsydasltdktvek
tflgiakaqsaermapslqgptntgnmytasvyaslisllltfvpaeqlqg
krislfsygsglastlfsltvkgdispivkacdfkaklddrstetpvdye
aatdlrekahlkknfepqgdikhiksgvyyltniddmfrrkyeikq YALI0B16038g
DNA:

atggactacatcatttcggcgccaggcaaagtgattctatttggtgaaca
tgccgctgtgtttggtaagcctgcgattgcagcagccatcgacttgcgaa
catacctgcttgtcgaaaccacaacatccgacaccccgacagtcacgttg
gagtttccagacatccacttgaacttcaaggtccaggtggacaagctggc
atctctcacagcccagaccaaggccgaccatctcaattggtcgactccca
aaactctggataagcacattttcgacagcttgtctagcttggcgcttctg
gaagaacctgggctcactaaggtccagcaggccgctgttgtgtcgttctt
gtacctctacatccacctatgtccccttctgtgtgcgaagattcatcaa
actgggtagttcgatcaacgctgcctatcggcgcgggcctgggctcttcc
gcatccatttgtgtctgtttggctgcaggtcttctggttctcaacggcca
gctgagcattgaccaggcaagagatttcaagtccctgaccgagaagcagc
tgtctctggtggacgactggtccttcgtcggtgaaatgtgcattcacggc
aacccgtcgggcatcgacaatgctgtggctactcagggaggtgctctgtt
gttccagcgacctaacaaccgagtccctcttgttgacattcccgagatga
agctgctgcttaccaatacgaagcatcctcgatctaccgcagacctggtt
ggtgagtcggagttctcactaaagagtttggctccatcatggatcccat
catgacttcagtaggcgagatttccaaccaggccatggagatcatttcta
gaggcaagaagatggtggaccagtctaaccttgagattgagcagggtatc
ttgcctcaaccacctctgaggatgcctgcaacgtgatggaagatggagc
tactcttcaaaagttgagagatatcggttcggaaatgcagcatctagtga
gaatcaatcacggcctgcttatcgctatgggtgtttccacccgaagctc
gaaatcattcgaactgcctccattgtccacaacctgggtgagaccaagct
cactggtgctggaggaggaggttgcgccactactctagtcacttctaaag
acaagactgcgacccagctggaggaaaatgtcattgattcacagaggaga
tggctacccatggcttcgaggtgcacgagactactattggtgccagagga
gttggtatgtgcattgaccatccctctctcaagactgttgaagccttcaa
gaaggtggagcgggcggatctcaaaaacatcggtccctggacccattag Protein:

mdyiisapgkvilfgehaavfgkpaiaaaidlrtyllvetttsdtptvtl
efpdihlnfkvqvdklasltaqtkadhlnwstpktldkhifdslsslall
eepgltkvqqaavvsflylyihlcppsvcedssnwvvrstlpigaglgss -continued asicvclaagllvlngqlsidgardfksltekqlslvddwsfvgemcihg
npsgidnavatqggallfqrpnnrvplvdipemklllltntkhprstadlv
ggvgvltkefgsimdpimtsvgeisnqameiisrgkkmvdqsnleieqgi
lpqptsedacnvmedgatlqklrdigsemqhlvrinhglliamgvshpkl
eiirtasivhnlgetkltgaggggcaitlvtskdktatqleenviaftee
mathgfevhettigargvgmcidhpslktveafkkveradlknigpwth YALI0E06193g
DNA:

atgaccacctattcggctccgggaaaggccctcctttgcggcggttattt
ggttattgatccggcgtattcagcatacgtcgtgggcctctcggcgcgta
tttacgcgacagtttcggcttccgaggcctccaccacctctgtccatgtc
gtctctccgcagtttgacaagggtgaatggacctacaactacacgaacgg
ccagctgacggccatcggacacaacccatttgctcacgcggccgtcaaca
ccgttctgcattacgttcctcctcgaaacctccacatcaacatcagcatc
aaaagtgacaacgcgtaccactcgcaaattgacagcacgcagagaggcca
gtttgcataccacaaaaaggcgatccacgaggtgcctaaaacgggcctcg
gtagctccgctgctcttaccaccgttcttgtggcagctttgctcaagtca
tacggcattgatcccttgcataacacccacctcgttcacaacctgtccca
ggttgcacactgctcggcacagaagaagattgggtctggatttgacgtgg
cttcggccgtttgtggctctctagtctatagacgtttccggcggagtcc
gtgaacatggtcattgcagctgaagggaccctcgaatacggggctctgtt
gagaactaccgttaatcaaaagtggaaggtgactctggaaccatccttct
tgccgccgggaatcagcctgcttatgggagacgtccaggaggatctgag
actccaggtatggtggccaaggtgatggcatggcgaaaagcaaagcccg
agaagccgagatggtgtggagagatctcaacgctgccaacatgctcatgg
tcaagttgttcaacgacctgcgcaagctctctctcactaacaacgaggcc
tacgaacaacttttggccgaggctgctcctctcaacgctctaaagatgat
aatgttgcagaaccctctcggagaactagcacgatgcattatcactattc
gaaagcatctcaagaagatgacacgggagactggtgctgctattgagccg
gatgagcagtctgcattgctcaacaagtgcaacacttatagtggagtcat
tggaggtgttgtgcctggagcaggaggctacgatgctatttctcttctgg
tgatcagctctacggtgaacaatgtcaagcgagagagccagggagtccaa
tggatggagctcaaggaggagaacgagggtctgcggctcgagaaggggtt
caagtag Protein:

mttysapgkallcggylvidpaysayvvglsariyatvsaseasttsvhv
vspqfdkgewtynytngqltaighnpfahaavntvlhyvpprnlhinisi
ksdnayhsqidstqrgqfayhkkaihevpktglgssaalttylvaallks
ygidplhnthlvhnlsqvahcsaqkkigsgfdvasavcgslvyrrfpaes -continued
vnmviaaegtseygallrttvnqkwkvtlepsflppgisllmgdvqggse
tpgmvakvmawrkakpreaemvwrdlnaanmlmvklfndlrklsltnnea
yeqllaeaaplnalkmimlqnplgelarciitirkhlkkmtretgaaiep
deqsallnkcntysgviggvvpgaggydaisllvisstvnnvkresqgvq
wmelkeeneglrlekgfk YALI0F05632g
DNA:

atgatccaccaggcctccaccaccgctccggtgaacattgcgacactcaa
gtactggggcaagcgagaccctgctctcaatctgcccactaacaactcca
tctccgtgactttgtcgcaggatgatctgcggaccctcaccacagcctcg
tgttcccctgatttcacccaggacgagctgtggctcaatggcaagcagga
ggacgtgagcggcaaacgtctggttgcgtgtttccgagagctgcgggctc
tgcgacacaaaatggaggactccgactcttctctgcctaagctggccgat
cagaagctcaagatcgtgtccgagaacaacttccccaccgccgctggtct
cgcctcatcggctgctggctttgccgccctgatccgagccgttgcaaatc
tctacgagctccaggagaccccgagcagctgtccattgtggctcgacag
ggctctggatccgctgtcgatctctctacggaggctacgtggcatggga
aatgggcaccgagtctgacggaagcgactcgcgagcggtccagatcgcca
ccgccgaccactggcccgagatgcgagccgccatcctcgttgtctctgcc
gacaagaaggacacgtcgtccactaccggtatgcaggtgactgtgcacac
ttctcccctcttcaaggagcgagtcaccactgtggttcccgagcggtttg
cccagatgaagaagtcgattctggaccgagacttccccacctttgccgag
ctcaccatgcgagactcaaaccagttccacgccacctgtctggactcgta
tcctcccattttctacctcaacgacgtgtcgcgagcctccattcgggtag
ttgaggccatcaacaaggctgccggagccaccattgccgcctacaccttt
gatgctggacccaactgtgtcatctactacgaggacaagaacgaggagct
ggttctgggtgctctcaaggccattctgggccgtgtggagggatgggaga
agcaccagtctgtggacgccaagaagattgatgttgacgagcggtgggag
tccgagctggccaacggaattcagcgggtgatccttaccaaggttggagg
agatcccgtgaagaccgctgagtcgcttatcaacgaggatggttctctga
agaacagcaagtag Protein:

mihqasttapvniatlkywgkrdpalnlptnnsisvtlsqddlrtlttas
cspdftqdelwlngkqedvsgkrlvacfrelralrhkmedsdsslpklad
qklkivsennfptaaglassaagfaaliravanlyelqetpeqlsivarq
gsgsacrslyggyvawemgtesdgsdsravqiatadhwpemraailvvsa
dkkdtssttgmqvtvhtsplfkercttvvperfaqmkksildrdfptfae
ltmrdsnqfhatcldsyppifylndvsrasirvveainkaagatiaaytf
dagpncviyyedkneelvlgalkailgrvegwekhqsvdakkidvderwe
selangiqrviltkvggdpvktaeslinedgslknsk YALI0F04015g
DNA:

Atgacgacgtatacagcgacaaaatcaagagtatcagcgtgagctctgtg
gctcagcagtttcctgaggtggcgccgattgcggacgtgtccaaggctag
ccggcccagcacggagtcgtcggactcgtcggccaagctatttgatggcc
acgacgaggagcagatcaagctgatggacgagatctgtgtggtgctggac
tgggacgacaagccgattggcggcgcgtccaaaaagtgctgtcatctgat
ggacaacatcaacgacggactggtgcatcgggccttttccgtgttcatgt
tcaacgaccgcggtgagctgcttctgcagcagcgggcggcggaaaaaatc
acctttgccaacatgtggaccaacacgtgctgctcgcatcctctggcggt
gcccagcgagatgggcgggctggatctggagtcccggatccaggcgcca
aaaacgccgcggtccggaagcttgagcacgagctgggaatcgaccccaag
gccgttccggcagacaagttccatttcctcacccggatccactacgccgc
gccctcctcgggccctgggcgagcacgagattgactacattctgtttg
tccggggcgaccccgagctcaaggtggtggccaacgaggtccgcgatacc
gtgtgggtgtcgcagcagggactcaaggacatgatggccgatcccaagct
ggattcaccccttggttccggctcatttgtgagcaggcgctgtttccctg
gtgggaccagttggacaatctgcccgcgggcgatgacgagattcggcggt
ggatcaagtag Protein:

mttsysdkiksisvssvaqqfpevapiadvskasrpstessdssaklfdg
hdeeqiklmdeicvvldwddkpiggaskkcchlmdninglvhrafsvfm
fndrgelllqqraaekitfanmwtntccshplavpsemggldlesriqga
knaavrklehelgidpkavpadkfhfltrihyaapssgpwgeheidyilf
vrgdpelkvvanevrdtvwvsqqglkdmmadpklvftpwfrliceqalfp
wwdqldnlpagddeirrwik

YALI0E05753
DNA:

atgtccaaggcgaaattcgaaagcgtgttcccccgaatctccgaggagct
ggtgcagctgctgcgagacgagggtctgcccaggatgccgtgcagtggt
tttccgactcacttcagtacaactgtgtgggtggaaagctcaaccgaggc
ctgtctgtggtcgacacctaccagctactgaccggcaagaaggagctcga
tgacgaggagtactaccgactcgcgctgctcggctggctgattgagctgc
tgcaggcgttttcctcgtgtcggacgacattatggatgagtccaagacc
cgacgaggccagccctgctggtacctcaagcccaaggtcggcatgattgc
catcaacgatgctttcatgctagagagtggcatctacattctgcttaaga
agcatttccgacaggagaagtactacattgaccttgtcgagctgttccac

```
gacatttcgttcaagaccgagctgggccagctggtggatcttctgactgc
ccccgaggatgaggttgatctcaaccggttctctctggacaagcactcct
ttattgtgcgatacaagactgcttactactccttctacctgcccgttgtt
ctagccatgtacgtggccggcattaccaaccccaaggacctgcagcaggc
catggatgtgctgatccctctcggagagtacttccaggtccaggacgact
accttgacaactttggagaccccgagttcattggtaagatcggcaccgac
atccaggacaacaagtgctcctggctcgttaacaaagcccttcagaaggc
cacccccgagcagcgacagatcctcgaggacaactacggcgtcaaggaca
gtccaaggagctcgtcatcaagaaactgtatgatgacatgaagattgag
caggactaccttgactacgaggaggaggttgttggcgacatcaagaagaa
gatcgagcaggttgacgagagccgaggcttcaagaaggaggtgctcaacg
cttttcctcgccaagatttacaagcgacagaagtag
```

Protein:

```
mskakfesvfpriseelvqllrdeglpqdavqwfsdslqyncvggklnrg
lsvvdtyqlltgkkelddeeyyrlallgwliellqafflvsddimdeskt
rrgqpcwylkpkvgmiaindafmlesgiyillkkhfrqekyyidlvelfh
disfktelgqlvdlltapedevdlnrfsldkhsfivryktayysfylpvv
lamyvagitnpkdlqqamdvliplgeyfqvqddyldnfgdpefigkigtd
iqdnkcswlvnkalqkatpeqrqilednygvkdkskelvikklyddmkie
qdyldyeeevvgdikkkieqvdesrgfkkevlnaflakiykrqk
```

YALI0E18634g
DNA:

```
atgttacgactacgaaccatgcgacccacacagaccagcgtcagggcggc
gcttgggcccaccgccgcggcccgaaacatgtcctcctccagcccctcca
gatcgaatactcgtcctacgtcaagggcacgcgggaaatcggccaccgaa
aggcgcccacaaccgtctgtcggttgagggccccatctacgtgggcttc
gacggcattcgtcttctcaacctgccgcatctcaacaagggctcgggatt
cccccctcaacgagcgacgggaattcagactcagtggtcttctgccctctg
ccgaagccaccctggaggaacaggtcgaccgagcataccaacaattcaaa
aagtgtggcactccatagccaaaaacgggttctgcacctcgctcaagttc
caaaacgaggtgctctactacgccctgctgctcaagcacgttaaggaggt
cttccccatcatctatacaccgactcagggagaagccattgaacagtact
cgcggctgttccggcggcccgaaggctgcttcctcgacatcaccagtccc
tacgacgtggaggagcgtctgggagcgtttggagaccatgacgacattga
ctacattgtcgtgactgactccgagggtattctcggaattggagaccaag
gagtgggcggtattggtatttccatcgccaagctggctctcatgactcta
tgtgctggagtcaaccctcacgagtcattcctgtggttctggatacggg
aaccaacaaccaggagctgctgcacgaccccctgtatctcggccgacgaa
tgccccgagtgcgaggaaagcagtacgacgacttcatcgacaactttgtg
```

```
cagtctgcccgaaggctgtatcccaaggcggtgatccatttcgaggactt
tgggctcgctaacgcacacaagatcctcgacaagtatcgaccggagatcc
cctgcttcaacgacgacatccagggcactggagccgtcactttggcctcc
atcacggccgctctcaaggtgctgggcaaaaatatcacagatactcgaat
tctcgtgtacggagctggttcggccggcatgggtattgctgaacaggtct
atgataacctggttgcccagggtctcgacgacaagactgcgcgacaaaac
atctttctcatggaccgaccgggtctactgaccaccgcacttaccgacga
gcagatgagcgacgtgcagaagccgtttgccaaggacaaggccaattacg
agggagtggacaccaagactctggagcacgtggttgctgccgtcaagccc
catattctcattggatgttccactcagcccggcgccttaacgagaaggt
cgtcaaggagatgctcaaacacaccctcgacccatcattctccctcttt
ccaaccccacacgtcttcatgaggctgtccctgcagatctgtacaagtgg
accgacggcaaggctctggttgccaccggctcgccattgacccagtcaac
ggcaaggagacgtctgagaacaataactgattgttttccccggaatcggg
ctgggagccattctgtctcgatcaaagctcatcaccaacaccatgattgc
tgctgccatcgagtgcctcgccgaacaggcccccattctcaagaaccacg
acgaggagtacttcccgactagctctcatccagatctttcggcccgg
gtggccactgccgtggttcttcaggccaaggctgagggcctagccactgt
cgaggaagagctcaagcccggcaccaaggaacatgtgcagattcccgaca
actttgacgagtgtctcgcctgggtcgagactcagatgtggcggcccgtc
taccggcctctcatccatgtgcgggattacgactag
```

Protein:

```
mlrlrtmrptqtsvraalgptaaarnmssspssfeyssyvkgtreighr
kapttrlsvegpiyvgfdgirllnlphlnkgsgfplnerrefrlsgllps
aeatleeqvdrayqqfkkcgtplakngfctslkfqnevlyyalllkhvke
vfpiiytptqgeaieqysrlfrrpegcflditspydveerlgafgdhddi
dyivvtdsegilgigdqgvggigisiaklalmtlcagvnpsrvipvvldt
gtnnqellhdplylgrrmprvrgkqyddfidnfvqsarrlypkavihfed
fglanahkildkyrpeipcfnddiqgtgavtlasitaalkvlgknitdtr
ilvygagsagmgiaeqvydnlvaqglddktarqniflmdrpgllttaltd
eqmsdvqkpfakdkanyegvdtktlehvvaavkphiligcstqpgafnek
vvkemlkhtprpiilplsnptrlheavpadlykwtdgkalvatgspfdpv
ngketsennncfvfpgiglgailsrsklitntmiaaaieclaeqapilkn
hdegvlpdvaliqiisarvatavvlqakaeglatveeelkpgtkehvqip
dnfdeclawvetqmwrpvyrplihvrdyd
```

YALI0E11495g
DNA:

```
atgccgcagcaagcaatggatatcaagggcaaggccaagtctgtgcccat
gcccgaagaagacgacctggactcgcattttgtgggtcccatctctcccc
```

-continued

```
gacctcacggagcagacgagattgctggctacgtgggctgcgaagacgac
gaagacgagcttgaagaactgggaatgctgggccgatctgcgtccaccca
cttctcttacgcggaagaacgccacctcatcgaggttgatgccaagtaca
gagctatcatggccatctgcctcatcagcactctcagagtcccgtgtcca
gatcttcgtcatttgtgcgggccgaaatgaaccacccccctcccccaccc
tccagccacacccaccaacagccagaggacgatgacgcatcttccactcg
atctcgatcgtcgtctcgagatctggacgcaagttcaacagaaacagaac
caagtctggatcttcgctgagcaagggtctccagcagctcaacatgaccg
gatcgctcgaagaagagccctacgagagcgatgacgatgcccgactatct
gcggaagacgacattgtctatgatgctacccagaaagacacctgcaagcc
catatctcctactctcaaacgcacccgcaccaaggacgacatgaagaaca
tgtccatcaacgacgtcaaaatcaccaccaccacagaagatcctcttgtg
gcccaggagctgtccatgatgttcgaaaaggtgcagtactgccgagacct
ccgagacaagtaccaaaccgtgtcgctacagaaggacggagacaacccca
aggatgacaagacacactggaaaatttaccccgagcctccaccaccctcc
tggcacgagaccgaaaagcgattccgaggctcgtccaaaaaggagcacca
aaagaaagaccgacaatggatgaattcaaattcgaggactgcgaaatcc
ccggacccaacgacatggtcttcaagcgagatcctacctgtgtctatcag
gtctatgaggatgaaagctctctcaacgaaaataagccgtttgttgccat
cccctcaatccgagattactacatggatctggaggatctcattgtggctt
cgtctgacggacctgccaagtcttttgattccgacgactgcaatatctag
aagccaagtggaacctctactacctgctcaacgagtacacggagacaacc
gagtccaagaccaacccccatcgagacttttacaacgtacgaaaggtcga
cacccacgttcaccactctgcctgcatgaaccagaagcatctgctgcgat
tcatcaaatacaagatgaagaactgccctgatgaagttgtcatccaccga
gacggtcgggagctgacactctcccaggtgtttgagtcacttaacttgac
tgcctacgacctgtctatcgataccctttgatatgcatgctcacaaggact
cgttccatcgatttgacaagttcaacctcaagtacaaccctgtcggtgag
tctcgactgcgagaaatcttcctaaagaccgacaactacatccagggtcg
ataccctagctgagatcacaaaggaggtgttccaggatctcgagaactga
agtaccagatggcggagtaccgtatttccatctacggtcggtccaaggac
gagtgggacaagctggctgcctgggtgctggacaacaaactgttttcgcc
caatgttcggtggtgatccaggtgcctcgactgtacgacatttacaaga
aggctggtctggttaacacctttgccgacattgtgcagaacgtctttgag
cctcttttcgaggtcaccaaggatcccagtacccatcccaagctgcacgt
gttcctgcagcgagttgtgggctttgactctgtcgatgacgagtcgaagc
tggaccgacgtttccaccgaaagttcccaactgcagcatactgggacagc
gcacagaaccctccctactcgtactggcagtactatctatacgccaacat
ggcctccatcaacacctggagacagctttgggctataatacttttgagt
tgcgaccccatgctggagaggctggtgacccagagcatcttctgtgcact
tatctggttgctcagggtatcaaccacggtattctgttgcgaaaggtgcc
```

-continued

```
cttcattcagtacctttactacctggaccagatccccattgccatgtctc
ctgtgtccaacaatgcgctgttcctcacgttcgacaagaaccccttctac
tcatacttcaagcggggtctcaacgtgtccttgtcatcggatgatcctct
gcagtttgcttacactaaggaggctctgattgaggagtactctgtggctg
cgctcatttacaagcttccaacgtggatatgtgtgagcttgctcgaaac
tcggtactgcaatctggctttgagcgaatcatcaaggagcattggatcgg
cgaaaactacgagatccatggccccgagggcaacaccatccagaagacaa
acgtgcccaatgtgcgtctggccttccgagacgagactttgacccacgag
cttgctctggtggacaagtacaccaatcttgaggagtttgagcggctgca
tggttaa
```

Protein:

```
mpqqamdikgkaksvpmpeeddldshfvgpisprphgadeiagyvgcedd
edeleelgmlgrsasthfsyaeerhlievdakyralhghlphqhsqspvs
rsssfvraemnhppppsshthqqpedddasstrsrsssrasgrkfnrnr
tksgsslskglqqlnmtgsleeepyesdddarlsaeddivydatqkdtck
pisplkrtrtkddmknmsindvkittttedplvaqelsmmfekvqycrdl
rdkyqtyslqkdgdnpkddkthwkiypeppppswhetekrfrgsskkehq
kkdptmdefkfedceipgpndmvfkrdptcvyqvyedesslnenkpfvai
psirdyymdledlivassdgpaksfafrrlqyleakwnlyyllneytett
esktnphrdfynvrkvdthvhhsacmnqkhllrfikykmkncpdevvihr
dgreltlsqvfeslnltaydlsidtldmhahkdsfhrfdkfnlkynpvge
srlreiflktdnyiqgrylaeitkevfqdlenskyqmaeyrisiygrskd
ewdklaawvldnklfspnvrwliqvprlydiykkaglvntfadivqnvfe
plfevtkdpsthpklhvflqrvvgfdsvddeskldrrfhrkfptaaywds
aqnppysywqyylyanmasintwrqrlgyntfelrphageagdpehllct
ylvaqginhgillrkvpfiqylyyldqipiamspvsnnalfltfdknpfy
syfkrglnvslsssddplqfaytkealieeysvaaliyklsnvdmcelarn
svlqsgferiikehwigenyeihgpegntiqktnvpnvrlafrdetlthe
lalvdkytnleeferlhg
```

YALI0D16753g
DNA:

```
atgttccgaacccgagttaccggctccaccctgcgatccttctccacctc
cgctgcccgacagcacaaggttgtcgtccttggcgccaacggaggcattg
gccagcccgtctctgctgctcaagctcaacaagaacgtgaccgacctc
ggtctgtacgatctgcgaggcgcccccggcgttgctgccgatgtctccca
catccccaccaactccaccgtggccggctactctcccgacaacaacggca
ttgccgaggccctcaagggcgccaagctggtgctgatccccgccggtgtc
ccccgaaagcccgcatgacccgagacgatctgttcaacaccaacgcctc
cattgtgcgagacctggccaaggccgtcggtgagcacgcccccgacgcct
```

```
ttgtcggagtcattgctaacccccgtcaactccaccgtccccattgtcgcc
gaggtgctcaagtccaagggcaagtacgaccccaagaagctcttcggtgt
caccaccctcgacgtcatccgagccgagcgattcgtctcccagctcgagc
acaccaaccccaccaaggagtacttccccgttgttggcggccactccggt
gtcaccattgtccccctcgtgtcccagtccgaccaccccgacattgccgg
tgaggctcgagacaagcttgtccaccgaatccagtttggcggtgacgagg
ttgtcaaggccaaggacggtgccggatccgccacccttccatggcccag
gctgccgccgattcgccgactactcctccgaggtgtcaacggcgagaag
gacgttgttgagcccactttcgtcgactctcctagttcaagggtgagggc
atcgacttcttctccaccaaggtcactcttggccctaacggtgttgagga
gatccacccccatcggaaaggtcaacgagtacgaggagaagctcatcgagg
ctgccaaggccgatctcaagaagaacattgagaagggtgtcaactttgtc
aagcagaaccccttaa
```

Protein:

```
mfrtrvtgstlrsfstsaarqhkvvvlganggigqplslllklnknvtdl
glydlrgapgvaadvshiptnstvagyspdnngiaealkgaklvlipagv
prkpgmtrddlfntnasivrdlakavgehapdafvgvianpvnstvpiva
evlkskgkydpkklfgvttldviraerfvsqlehtnptkeyfpvvgghsg
vtivplvsgsdhpdiageardklvhriqfggdevvkakdgagsatlsmaq
aaaarfadsllrgvngekdvveptfvdsplfkgegidffstkvtlgpngve
eihpigkvneyeeklieaakadlkkniekgvnfvkqnp
```

YALI0D16247g
DNA:

```
atgacacaaacgcacaatctgttttcgccaatcaaagtgggctcttcgga
gctccagaaccggatcgttctcgcacccttgactcgaaccagagctctgc
ccggaaacgtgccctcggatcttgccacagagtactacgcacaaagagca
gcatctccaggcactctcctcatcaccgaggccacatacatctcccccgg
atctgctggagtgcccattccaggagacggaatcgttccgggcatctgga
gtgacgagcagctcgaagcatggaaaaaggtgttcaaggccgtgcacgac
cgaggatccaaaatctacgtccagctgtgggacattggacgtgtcgcatg
gtaccacaagctgcaggaactgggcaactacttccctacaggcccctcag
ctatccccatgaagggagaggagagcgagcatctcaaggctctgactcac
tgggagatcaagggcaaggtggccctctacgtcaacgctgccaagaacgc
cattgccgcaggcgctgatggcgtcgagatccactcggccaacggctacc
ttccccgacacatttctgagaagcgcctccaaccaacgaacagacgaatat
ggaggaagcatcgagaacccgggcccgattctcgctggagattgtcgacgc
tatcaccgaggccattggagcagacaaaaccgccatccgtctgtctccct
ggtccacttttccaggacattgaggtgaatgacaccgagaccccgcacag
ttcacataccctgtttgagcagctgcagaagcgagccgacgagggaaagca
```

```
gctggcctacgtgcatgtagttgagccccgactgtttggtcccccgagc
cctgggccaccaatgagccttcagaaaaatttggaagggtaacttcatt
agagcaggtggatacgatagagagactgctatgaggatgcagacaagtca
gacaacaccctgattgcctttggtcgagacttcattgccaatcctgatct
cgtccaacgcctcaagaataacgagcctttggccaagtacgacagaacaa
ccttctacgttccaggtgccaagggctacactgattaccctgcgtacaag
atgtaa
```

Protein:

```
mtqthnlfspikvgsselqnrivlapltrtralpgnvpsdlateyyaq
raaspgtllliteatyispgsagvpipgdgivpgiwsdeqleawkkvfk
avhdrgskiyvqlwdigrvawyhklqelgnyfptgpsaipmkgeeseh
lkalthweikgkvalyvnaaknaiaagadgveihsangylpdtflrsa
snqrtdeyggsienrarfsleivdaiteaigadktairlspwstfqdi
evndtetpaqftylfeqlqkradegkqlayvhvveprlfgppepwatn
epfrkiwkgnfiraggydretaledadksdntliafgrdfianpdlvq
rlknnenplakydrttfyvpgakgytdypaykm
```

YALI0A15972g
DNA:

```
atggaagccaaccccgaagtccagaccgatatcatcacgctgacccggtt
cattctgcaggaacagaacaaggtgggcgcgtcgtccgcaatccccaccg
gagacttcactctgctgctcaactcgctgcagtttgccttcaagttcatt
gcccacaacatccgacgatcgaccctggtcaacctgattggcctgtcggg
aaccgccaactccaccggc gacgaccagaagaagctggacgtgatcgga
gacgagatcttcatcaacgccatgaaggcctccggtaaggtcaagctggt
ggtgtccgaggagcaggaggacctcattgtgtttgagggcgacggccgat
acgccgtggtctgcgaccccatcgacggatcctccaacctcgacgccggc
gtctccgtcggcacctttccggcgtctacaagctccccgagggctcct
ccggatccatcaaggacgtgctccgacccggaaaggagatggttgccgcc
ggctacaccatgtacggtgcctccgccaacctggtgctgtccaccggaaa
cggctgcaacggcttcactctcgatgaccctctgggagagttcatcctga
cccacccccgatctcaagctccccgatctgcgatccatctactccgtcaac
gagggtaactcctccctgtggtccgacaacgtcaaggactacttcaaggc
cctcaagttccccgaggacggctccaagccctactcggcccgatacattg
gctccatggtcgccgacgtgcaccgaaccattctctacggaggtatgttt
gcctaccccgccgactccaagtccaagaagggcaagctccgactttgta
cgagggtttccccatggcctacatcattgagcaggccggcggtcttgcca
tcaacgacaacggcgagcgaatcctcgatctggtccccaccgagatccac
gagcgatccggcgtctggctgggctccaagggcgagattgagaaggccaa
gaagtaccttctgaaatga
```

Protein:

meanpevqtdiitltrfilqeqnkvgassaiptgdftlllnslqfafkfi
ahnirrstlvnliglsgtanstgddqkkldvigdeifinamkasgkvklv
vseeqedlivfegdgryavvcdpidgssnldagvsvgtifgvyklpegss
gsikdvlrpgkemvaagytmygasanlvlstgngcngftlddplgefilt
hpdlklpdlrsiysvnegnsslwsdnvkdyfkalkfpedgskpysaryig
smvadvhrtilyggmfaypadskskkgklrllyegfpmayiieqagglai
ndngerildlvpteihersgvwlgskgeiekakkyllk YALI0E11099g
DNA:

atgcgactcactctgccccgacttaacgccgcctacattgtaggagccgc
ccgaactcctgtcgcaagttcaacggagccctcaagtccgtgtctgcca
ttgacctcggtatcaccgctgccaaggccgctgtccagcgatccaaggtc
cccgccgaccagattgacgagtttctgtttggccaggtgctgaccgccaa
ctccggccaggcccccgcccgacaggtggttatcaagggtggtttccccg
agtccgtcgaggccaccaccatcaacaaggtgtgctcttccggcctcaag
accgtggctctggctgcccaggccatcaaggccggcgaccgaaacgttat
cgtggccggtggaatggagtccatgtccaacaccccctactactccggtc
gaggtcttgttttcggcaaccagaagctcgaggactccatcgtcaaggac
ggtctctgggacccctacaacaacatccacatgggcaactgctgcgagaa
caccaacaagcgagacggcatcaccccgagagcagcaggacgagtacgca
tcgagtcctaccgacgggcaacgagtccatcaagaacggcgccttcaag
gatgagattgtccccgttgagatcaagacccgaaagggcaccgtgactgt
ctccgaggacgaggagcccaagggagccaacgccgagaagctcaagggcc
tcaagcctgtctttgacaagcagggctccgtcactgccggtaacgcctcc
cccatcaacgatggtgcttctgccgttgtcgttgcctctggcaccaaggc
caaggagctcggtaccccgtgctcgccaagattgtctcttacgcagacg
ccgccaccgccccattgactttaccattgctccctctctggccattccc
gccgccctcaagaaggctggccttaccaaggacgacattgccctctggga
gatcaacgaggccttctccggtgtcgctctcgccaacctcatgcgactcg
gaattgacaagtccaaggtcaacgtcaaggtggagctgttgctctcggc
cacccccattggtgcctccggtaaccgaatctttgtgactttggtcaacgc
cctcaaggagggcgagtacggagttgccgccatctgcaacggtggaggag
cttccaccgccatcgtcatcaagaaggtctcttctgtcgagtag Protein mrltlprlnaayivgaartpvgkfngalksvsaidlgitaakaavqrskv
padqidefflfgqvltansgqaparqvvikggfpesveattinkvcssglk
tvalaaqaikagdrnvivaggmesmsntpyysgrglvfgnqkledsivkd
glwdpynnihmgnccentnkrdgitreqqdeyaiesyrranesikngafk deivpveiktrkgtvtvsedeepkganaeklkglkpvfdkqgsvtagnas
pindgasavvvasgtkakelgtpvlakivsyadaatapidftiapslaip
aalkkagltkddialwieneafsgvalanlmrlgidkskvnvkggavalg
hpigasgnrifvtlvnalkegeygvaaicnggastaivikkvssve YALI0E34793g
DNA:

atgtctgccaacgagaacatctcccgattcgacgcccctgtgggcaagga
gcaccccgcctacgagctcttccataaccacacgatctttcgtctatg
gtctccagcctcgagcctgccagggtatgctggacttcgacttcatctgt
aagcgagagaaccccccgtggccggtgtcatctatcccttcggcggcca
gttcgtcaccaagatgtactgggcaccaaggagactcttctcccctgtct
accagcaggtcgagaaggccgctgccaagcaccccgaggtcgatgtcgtg
gtcaactttgcctcctctcgatccgtctactcctctaccatggagctgct
cgagtaccccagttccgaaccatcgccattattgccgagggtgtcccg
agcgacgagcccgagagatcctccacaaggcccagaagaagggtgtgacc
atcattggtcccgctaccgtcggaggtatcaagcccggttgcttcaaggt
tggaaacaccggaggtatgatggacaacattgtcgcctccaagctctacc
gaccccggctccgttgcctacgtctccaagtccggaggaatgtccaacgag
ctgaacaacattatctctcacaccaccgacggtgtctacgagggtattgc
tattggtggtgaccgatacccctggtactaccttcattgaccatatcctgc
gatacgaggccgaccccaagtgtaagatcatcgtcctccttggtgaggtt
ggtggtgttgaggagtaccgagtcatcgaggctgttaagaacggccagat
caagaagcccatcgtcgcttgggccattggtacttgtgcctccatgttca
agactgaggttcagttcggccacgccggctccatggccaactccgacctg
gagactgccaaggctaagaacgccgccatgaagtctgctggcttctacgt
ccccgataccttcgaggacatgcccgaggtccttgccgagctctacgaga
gatggtcgccaagggcgagctgtctcgaatctctgagcctgaggtcccc
aagatccccattgactactcttgggcccaggagcttggtcttatccgaaa
gcccgctgctttcatctccactatttccgatgaccgaggccaggagcttc
tgtacgctggcatgcccatttccgaggttttcaaggaggacattggtatc
ggcggtgtcatgtctctgctgtggttccgacgacgactccccgactacgc
ctccaagtttcttgagatggttctcatgcttactgctgaccacggtcccg
ccgtatccggtgccatgaacaccattatcaccacccgagctggtaaggat
ctcatttcttccctggttgctggtctcctgaccattggtacccgattcgg
aggtgctcttgacggtgctgccaccgagttcaccactgcctacgacaagg
gtctgtccccccgacagttcgttgataccatgcgaaagcagaacaagctg
attcctggtattggccatcgagtcaagtctgaaacaaccccgatttccg
agtcgagcttgtcaaggactttgttaagaagaacttccctccaccccagc
tgctcgactacgcccttgctgtcgaggaggtcaccacctccaagaaggac
aacctgattctgaacgttgacggtgctattgctgtttcttttgtcgatct

```
catgcgatcttgcggtgcctttactgtggaggagactgaggactacctca agaacggtgttctcaacggtctgttcgttctcggtcgatccattggtctc attgccaccatctcgatcagaagcgactcaagaccggtctgtaccgaca tccttgggacgatatcacctacctggttggccaggaggctatccagaaga agcgagtcgagatcagcgccggcgactttccaaggccaagactcgatca tag
```

Protein:

```
msanenisrfdapvgkehpayelfhnhtrsfvyglqpracqgmldfdfic
krenpsvagviypfggqfvtkmywgtketllpvyqqvekaaakhpevdvv
vnfassrsvyssstmelleypqfrtiaiiaegvperrareilhkaqkkgvt
iigpatvggikpgcfkvgntggmmdnivasklyrpgsvayvsksggmsne
lnniishttdgvyegiaiggdrypgttfidhilryeadpckciivllgev
ggveeyrvieavkngqikkpivawaigtcasmfktevqfghagsmansdl
etakaknaamksagfyvpdtfedmpevlaelyekmvakgelsrisepevp
kipidyswaqelglirkpaafistisddrgqellyagmpisevfkedigi
ggvmsllwfrrrlpdyaskflemvlmltadhgpavsgamntiittragkd
lissslvaglltigtrfggaldgaateftttaydkglsprqfvdtmrkqnkl
ipgighrvksrnnpdfrvelvkdfvkknfpstqlldyalaveevttskkd
nlilnvdgaiavsfvdlmrscgaftveetedylkngvlnglfvlgrsigl
iahhldqkrlktglyrhpwdditylvgqeaiqkkrveisagdvskaktrs
```

YALI0D24431g
DNA:

```
atgtcagcgaaatccattcacgaggccgacggcaaggccctgctcgcaca
ctttctgtccaaggcgcccgtgtgggccgagcagcagcccatcaacacgt
ttgaaatgggcacacccaagctggcgtctctgacgttcgaggacggcgtg
gcccccgagcagatcttcgccgccgctgaaaagacctaccctggctgct
ggagtccggcgccaagtttgtggccaagcccgaccagctcatcaagcgac
gaggcaaggccggcctgctggtactcaacaagtcgtgggaggagtgcaag
ccctggatcgccgagcgggccgccaagcccatcaacgtggagggcattga
cggagtgctgcgaacgttcctggtcgagccctttgtgccccacgaccaga
agcacgagtactacatcaacatccactccgtgcgagagggcgactggatc
ctcttctaccacgagggaggagtcgacgtcggcgacgtggacgccaaggc
cgccaagatcctcatccccgttgacattgagaacgagtaccccctccaacg
ccacgctcaccaaggagctgctggcacacgtgcccgaggaccagcaccag
accctgctcgacttcatcaaccggctctacgccgtctacgtcgatctgca
gtttacgtatctggagatcaaccccctggtcgtgatccccaccgccagg
gcgtcgaggtccactacctggatcttgccggcaagctcgaccagaccgca
gagtttgagtgcggccccaagtgggctgctgcgcggtccccgccgctct
gggccaggtcgtcaccattgacgccggctccaccaaggtgtccatcgacg
```

```
ccggccccgccatggtcttccccgctcctttcggtcgagagctgtccaag
gaggaggcgtacattgcggagctcgattccaagaccggagcttctctgaa
gctgactgttctcaatgccaagggccgaatctggaccttgtggctggtg
gaggagcctccgtcgtctacgccgacgccattgcgtctgccggctttgct
gacgagctcgccaactacggcgagtactctggcgctcccaacgagaccca
gacctacgagtacgccaaaaccgtactggatctcatgacccggggcgacg
ctcaccccgagggcaaggtactgttcattggcggaggaatcgccaacttc
acccaggttggatccaccttcaagggcatcatccgggccttccgggacta
ccagtcttctctgcacaaccacaaggtgaagatttacgtgcgacgaggcg
gtcccaactggcaggagggtctgcggttgatcaagtcggctggcgacgag
ctgaatctgcccatggagatttacggccccgacatgcacgtgtcgggtat
tgttcctttggctctgcttggaaagcggcccaagaatgtcaagccttttg
caccggaccttctactgaggcttccactcctctcggagtttaa
```

Protein:

```
Msaksiheadgkallahflskapvwaeqqpintfemgtpklasltfedgv
apeqifaaaektypwllesgakfvakpdqlikrrgkaglllvnlnksweeck
pwiaeraakpinvegidgvlrtflvepfvphdqkheyyinihsvregdwi
lfyheggvdvgdvdakaakilipvdieneypsnatltkellahypedqhq
tlldfinrlyavyvdlqftyleinplvviptaqgvevhyldlagkldqta
efecgpkwaaarspaalgqvvtidagstkvsidagpamvfpapfgrelsk
eeayiaeldsktgaslkltvlnakgriwtlvagggasvvyadaiasagfa
delanygeysgapnetqtyeyaktvldlmtrgdahpegkvlfigggianf
tqvgstfkgiirafrdyqsslhnhkvkiyvrrggpnwqeglrliksagde
lnlpmeiygpdmhvsgivplallgkrpknvkpfgtgpsteastplgv
```

YALI0E14190g
DNA:

```
atggttattatgtgtgtgggacctcagcacacgcatcatcccaacacagg
gtgcagtatatatagacagacgtgttccttcgcaccgttcttcacatatc
aaaacactaacaaattcaaaagtgagtatcatggtaggagtcaattgatt
gctcggggagttgaacaggcaacaatggcatgcacagggccagtgaaggc
agactgcagtcgctgcacatggatcgtggttctgaggcgttgctatcaaa
agggtcaattacctcacgaaacacagctggatgttgtgcaatcgtcaatt
gaaaaacccgacacaatgcaagatctctttgcgcgcattgccatcgctgt
tgccatcgctgtcgccatcgccaatgccgctgcggattattatccctacc
ttgttccccgcttccgcacaaccggcgatgtctttgtatcatgaactctc
gaaactaactcagtggttaaagctgtcgttgccggagccgctggtggtat
tggccagccctttctcttctcctcaaactctctccttacgtgaccgagc
ttgctctctacgatgtcgtcaactcccccggtgttgccgctgacctctcc
cacatctccaccaaggctaaggtcactggctacctccccaaggatgacgg
```

```
tctcaagaacgctctgaccggcgccaacattgtcgttatccccgccggta
tcccccgaaagcccggtatgacccgagacgatctgttcaagatcaacgct
ggtatcgtccgagatctcgtcaccggtgtcgcccagtacgcccctgacgc
ctttgtgctcatcatctccaacccgtcaactctaccgtccctattgctg
ccgaggtcctcaagaagcacaacgtcttcaaccctaagaagctcttcggt
gtcaccacccttgacgttgtccgagcccagaccttcaccgccgctgttgt
tggcgagtctgaccccaccaagctcaacatcccgtcgttggtggccact
ccggagacaccattgtccctctcctgtctctgaccaagcctaaggtcgag
atccccgccgacaagctcgacgacctcgtcaagcgaatccagtttggtgg
tgacgaggttgtccaggctaaggacggtcttggatccgctaccctctcca
tggcccaggctggtttccgatttgccgaggctgtcctcaagggtgccgct
ggtgagaagggcatcatcgagcccgcctacatctaccttgacggtattga
tggcacctccgacatcaagcgagaggtcggtgtcgccttcttctctgtcc
ctgtcgagttcggccctgagggtgccgctaaggcttacaacatccttccc
gaggccaacgactacgagaagaagcttctcaaggtctccatcgacggtct
ttacggcaacattgccaagggcgaggagttcattgttaaccctcctcctg
ccaagtaa
```

Protein:

```
vvkavvagaaggigqplsllllklspyvtelalydvvnspgvaadlshist
kakvtgylpkddglknaltganivvipagiprkpgmtrddlfkinagivr
dlvtgvaqyapdafvliisnpvnstvpiaaevlkkhnvfnpkklfgvttl
dvvraqtftaavvgesdptklnipvvgghsgdtivpllsltkpkveipad
klddlvkriqfggdevvqakdglgsatlsmaqagfrfaeavlkgaagekg
iiepayiyldgidgtsdikrevgvaffsvpvefgpegaakaynilpeand
yekkllkvsidglygniakgeefivnpppak
```

Glucose 6 Phosphate Dehydrogenase YALI0E22649g
DNA:

```
atgactggcaccttacccaagttcggcgacggaaccaccattgtggttct
tggagcctccggcgacctcgctaagaagaagaccgtgagtattgaaccag
actgaggtcaattgaagagtaggagagtctgagaacattcgacggacctg
attgtgctctggaccactcaattgactcgttgagagcccaatgggtctt
ggctagccgagtcgttgacttgttgacttgttgagcccagaaccccaac
ttttgccaccatacaccgccatcaccatgacacccagatgtgcgtgcgta
tgtgagagtcaattgttccgtggcaaggcacagcttattccaccgtgttc
cttgcacaggtggtctttacgctctcccactctatccgagcaataaaagc
ggaaaaacagcagcaagtcccaacagacttctgctccgaataaggcgtct
agcaagtgtgcccaaaactcaattcaaaaatgtcagaaacctgatatcaa
cccgtcttcaaaagctaaccccagttccccgccctcttcggcctttaccg
aaacggcctgctgcccaaaaatgttgaaatcatcggctacgcacggtcga
aaatgactcaggaggagtaccacgagcgaatcagccactacttcaagacc
cccgacgaccagtccaaggagcaggccaagaagttccttgagaacacctg
ctacgtccaggcccttacgacggtgccgagggctaccagcgactgaatg
aaaagattgaggagtttgagaagaagaagcccgagccccactaccgtctt
ttctacctggctctgcccccagcgtcttccttgaggctgccaacggtct
gaagaagtatgtctaccccggcgagggcaaggcccgaatcatcatcgaga
agccctttggccacgacctggcctcgtcacgagagctccaggacggcctt
gctcctctctggaaggagtctgagatcttccgaatcgaccactacctcgg
aaaggagatggtcaagaacctcaacattctgcgatttggcaaccagttcc
tgtccgccgtgtgggacaagaacaccatttccaacgtccagatctccttc
aaggagccctttggcactgagggccgaggtggatacttcaacgacattgg
aatcatccgagacgttattcagaaccatctgttgcaggttctgtccattc
tagccatggagcgaccccgtcactttcggcgccgaggacattcgagatgag
aaggtcaaggtgctccgatgtgtcgacattctcaacattgacgacgtcat
tctcggccagtacggcccctctgaagacggaaagaagcccggatacaccg
atgacgatggcgttcccgatgactcccgagctgtgacctttgctgctctc
catctccagatccacaacgacagatgggagggtgttcctttcatcctccg
agccggtaaggctctggacgagggcaaggtcgagatccgagtgcagttcc
gagacgtgaccaagggcgttgtggaccatctgcctcgaaatgagctcgtc
atccgaatccagcccctccgagtccatctacatgaagatgaactccaagct
gcctggcctactgccaagaacattgtcaccgacctggatctgacctaca
accgacgatactcggacgtgcgaatccctgaggcttacgagtctctcatt
ctggactgcctcaaggtgaccacaccaactttgtgcgaaacgacgagct
ggacatttcctggaagattttcaccgatctgctgcacaagattgacgagg
acaagagcattgtgcccgagaagtacgcctacggctctcgtggccccgag
cgactcaagcagtggctccgagaccgaggctacgtgcgaaacggcaccga
gctgtaccaatggcctgtcaccaagggctcctcgtga
```

Protein:

```
mtgtlpkfgdgttivvlgasgdlakkktfpalfglyrngllpknveiigy
arskmtqeeyherishyfktpddqskeqakkflentcyvqgpydgaegyg
rlnekieefekkkpephyrlfylalppsvfleaanglkkyvypgegkari
iiekpfghdlassrelqdglaplwkeseifridhylgkemvknlnilrfg
nqflsavwdkntisnvqisfkepfgtegrggyfndigiirdviqnhllqv
lsilamerpvtfgaedirdekvkvlrcvdilniddvilgqygpsedgkkp
gytdddgvpddsravtfaalhlqihndrwegvpfilragkaldegkveir
vqfrdvtkgvvdhlprnelviriqpsesiymkmnsklpgltaknivtdld
ltynrrysdvripeayeslildclkgdhtnfvrndeldiswkiftdllhk
idedksivpekyaygsrgperlkqwlrdrgyvrngtelyqwpvtkgss
```

YALI0B15598g
DNA:

atgactgacacttcaaacatcaagtgagtattgccgcacacaattgcaat
caccgccgggctctacctcctcagctctcgacgtcaatgggccagcagcc
gccatttgaccccaattacactggttgtgtaaaaccctcaaccacaatcg
cttatgctcaccacagactacgacttaaccaagtcatgtcacaggtcaaa
gtaaagtcagcgcaacacccctcaatctcaacacacttttgctaactca
ggcctgtcgctgacattgccctcatcggtctcgccgtcatgggccagaac
ctgatcctcaacatggccgaccacggtaagtatcaattgactcaagacgc
accagcaagatacagagcatacccagcaatcgctcctctgataatcgcca
ttgtaacactacgttggttagattgatctaaggtcgttgctggttccatg
cacttccacttgctcatatgaagggagtcaaactctattttgatagtgtc
ctctcccatccccgaaatgtcgcattgttgctaacaataggctacgaggt
tgttgcctacaaccgaaccacctccaaggtcgaccacttcctcgagaacg
aggccaagggtgagtatccgtccagctatgctgtttacagccattgaccc
caccttcccccacaattgctacgtcaccattaaaaaacaaaattaccggt
atcggcaagctagactttcatgcaacctacgcaggtaacaagttgagtt
tcagccgtgcaccttacaggaaaaccagtcatacgccgaggcagtgtgaa
agcgaaagcacacagcctacggtgattgattgcattttttgacatagga
gggaaacacgtgacatggcaagtgcccaacacgaatactaacaaacagga
aagtccattattggtgctcactctatcaaggagctgtgtgctctgctgaa
gcgaccccgacgaatcattctgctcgttaaggccggtgctgctgtcgatt
cttccatcgaacagctcctgccctatctcgataagggtgatatcatcatt
gacggtggtaactcccacttccccgactccaaccgacgatacgaggagct
taacgagaagggaatcctcttcgttggttccggtgtttccggcggtgagg
agggtgcccgatacggtcccctccatcatgcccggtggaaacaaggaggcc
tggccccacattaagaagatttttccaggacatctctgctaaggctgatgg
tgagccctgctgtgactgggtcggtgacgctggtgccggccactttgtca
agatggttcacaacggtattgagtatggtgacatgcagcttatctgcgag
gcttacgacctcatgaagcgaggtgctggtttcaccaatgaggagattgg
agacgttttcgccaagtggaacaacggtatcctcgactccttcctcattg
agatcacccgagacatcttcaagtacgacgacggctctggaactcctctc
gttgagaagatctccgacactgctggccagaagggtactggaaagtggac
cgctatcaacgctcttgaccttggtatgcccgtcaccctgatcggtgagg
ccgtcttcgctcgatgcctttctgccctcaagcaggagcgtgtccgagct
tccaaggttcttgatggccccgagcccgtcaagttcactggtgacaagaa
ggagtttgtcgaccagctcgagcaggcccttacgcctccaagatcatct
cttacgcccagggtttcatgcttatccgagaggccgccaagacctacggc
tgggagctcaacaacgccggtattgccctcatgtggcgaggtggttgcat
catccgatccgtcttccttgctgacatcaccaaggcttaccgacaggacc
ccaacctcgagaacctgctgttcaacgacttcttcaagaacgccatctcc aaggccaacccctcttggcgagctaccgtggccaaggctgtcacctgggg
tgttcccactcccgcctttgcctcggctctggctttctacgacggttacc
gatctgccaagctccccgctaacctgctccaggcccagcgagactacttc
ggcgcccacacctaccagctcctcgatggtgatggaaagtggatccacac
caactggaccggccgaggtggtgaggtttcttcttccacttacgatgctt
aa Protein:

mtdtsnikpvadialiglavmgqnlilnmadhgyevvaynrttskvdhfl
eneakgksiigahsikelcallkrprriillvkagaavdsfieqllpyld
kgdiiidggnshfpdsnrryeelnekgilfvgsgvsggeegarygpsimp
ggnkeawphikkifqdisakadgepccdwvgdagaghfvkmvhngieygd
mqliceaydlmkrgagftneeigdvfakwnngildsflieitrdifkydd
gsgtplvekisdtagqkgtgkwtainaldlgmpvtligeavfarclsalk
qervraskvldgpepvkftgdkkefvdqleqalyaskiisyaqgfmlire
aaktygwelnnagialmwrggciirsvfladitkayrqdpnlenllfndf
fknaiskanpswratvakavtwgvptpafasalafydgyrsaklpanllq
aqrdyfgahtyqlldgdgkwihtnwtgrggevsssstyda YALI0D06303g
DNA:

atgctcaaccttagaaccgcccttcgagctgtgcgacccgtcactctggt
gagtatctcggagcccgggacggctaccaacacacaagcaagatgcaaca
gaaaccggacttttaaatgcggattgcggaaaatttgcatggcggcaac
gactcggagaaggagcgggacaattgcaatggcaggatgccattgacgaa
ctgagggtgatgagagaccgggcctccgatgacgtggtggtgacgacagc
ccggctggtgttgccgggactgtctctgaaaagcaatttctctatctccg
gtctcaacagactccccttctctagctcaattggcattgtcttcagaagg
tgtcttagtggtatccccattgttatcttcttttccccaatgtcaatgtc
aatgtcaatggctccgacctctttcacattaacacgcgcaaacacagat
accacggaaccgactcaaacaaatccaaagagacgcagcggaataattgg
catcaacgaacgatttgggatactctggcgagaatgccgaaatatttcgc
ttgtcttgttgtttctcttgagtgagttgtttgtgaagtcgtttggaaga
aggtttcccaatgtcacaaaccataccaactcgttacagccagcttgtaat
ccccccacctcttcaatacatactaacgcagaccgatcctacgccacttc
cgtggcctctttcaccggccagaagaactccaacggcaagtacactgtgt
ctctgattgagggagacggtatcggaaccgagatctccaaggctgtcaag
gacatctaccatgccgccaaggtccccatcgactgggaggttgtcgacgt
cacccccactctggtcaacgcaagaccaccatccccgacagcgccattg
agtccatcaaccgaaacaaggttgccctcaagggtcccctcgccacccc
atcggtaagggccacgtttccatgaacctgactctgcgacgaaccttcaa -continued cctgttcgccaacgtccgaccttgcaagtccgtcgtgggctacaagaccc cttacgagaacgtcgacaccctgctcatccgagagaacactgagggtgag tactccggtatcgagcacaccgtcgtccccggtgtcgttcagtccatcaa gctgatcacccgagaggcttccgagcgagtcatccggtacgcttacgagt acgccctgtcccgaggcatgaagaaggtccttgttgtccacaaggcctct attatgaaggtctccgatggtcttttccttgaggttgctcgagagctcgc caaggagtacccctccattgaccttccgtcgagctgatcgacaacacct gtctgcgaatggtccaggacccgctctctaccgagatgtcgtcatggtc atgcccaaccttacggtgacattctgtccgatcttgcctccggtcttat cggtggtcttggtctgaccccctccggtaacatgggtgacgaggtctcca tcttcgaggccgtccacggatccgctcccgacattgctggcaagggtctt gctaaccccactgctctgctgctctcctccgtgatgatgctgcgacacat gggtctcaacgacaacgccaccaacatcgagcaggccgtcttggcacca ttgcttccggccccgagaaccgaaccaaggatcttaaggggtaccgccacc acttctcactttgctgagcagattatcaagcgactcaagtag Protein:

mlnlrtalravrpvtltrsyatsvasftgqknsngkytvsliegdgigte
iskavkdiyhaakvpidwevvdvtptlvngkttipdsaiesinrnkvalk
gplatpigkghvsmnltlrrtfnlfanvrpcksvvgykthpyenvdtllir
entegeysgiehtvvpgvvqsiklitreaservityayeyalsrgmkkvl
vvhkasimkvsdglflevarelakeypsidlsvelidntclrmvqdpaly
rdvvmvmpnlygdilsdlasgligglgltpsgnmgdevsifeavhgsapd
iagkglanptalllssvmmlrhmglndnatnieqavfgtiasgpenrtkd
lkgtattshfaeqiikrlk

Example 7

Regulatory Sequences

Sequences which consist of, consist essentially of, or comprise the following regulatory sequences (e.g. promoters and terminator sequences, including functional fragments thereof) may be useful to control expression of endogenous and heterologous genes in recombinant fungi described herein.

Met2 Promoter

5'cctctcactttgtgaatcgtgaaacatgaatcttcaagccaagaatgt taggcaggggaagctttctttcagactttttggaattggtcctcttttgg acattattgacgatattattattttttccccgtccaatgttgacccttgt aagccattccggttctggagcgcatctcgtctgaaggagtcttcgtgtgg ctataactacaagcgttgtatggtggatcctatgaccgtctatataggggc aactttttgctcttgttcttcccctccttgagggacgtatggcaatggct atgacaactatcgtagtgagcctctataacccattgaagtacaagtcctc caccttgctgccaaactcgcgagaaaaaaagtccaccaactccgccggga aatactggagaacacctctaagacgtgggcttctgcacctgtgtggcttg ggtctgggttttgcgagctctgagccacaacctaaggacggtgtgattgg gagataagtagtcgttggttttctaatcgcacgtgatatgcaagccacac ttataacacaatgaagacaggccgatgaactgcatgtcattgtacaggtg cggagagcaagaaactctggggcggaggtgaaagatgagacaaaaagcct caggtgcaaggtagggagttgatcaacgtcaaacacaaataatctaggtt gttaggcagctaaacatgtatataactgggctgccaccgagtgttacttg tcattaacgtcgcattttcgcctacacaaaatttgggttactcgccacta cactgctcaaatctttcagctgtgcaacaagcttcaggtcacacataga ctcgcataaggacccgggtcatctgttattctccactggtaaaccaatag tcctagctgattgggtacagaagctcactttcacatcttttcatcttct tctacaaccatc Met3 Promoter 5'atctgtgaggagcccctggcgtcactgtcgactgtgccggcatttctg atggtatttccagcccccgcagttctcgagaccccccgaacaaatgtgccac acccttgccaaaatgacgaatacacggcgtcgcggccgggaatcgaactc ttggcaccgccacaggagtgaaatttgaaatttgaaatttgaaaaataat tcacattttgagtttcaataatatatcgatgaccctcccaaaagacccaa gtcgagacgcaaaaaaacacccagacgacatggatgcggtcacgtgaccg caaaaaccgccccggaaatccgtttgtgacgtgttcaattccatctctat gtttttctgcggtttctacgatgccgcaatggtggccaatgtgcgtttca ctgccgtagtggctggaacaagccacaggggggtcgtcgggccaatcagac ggtccctgacatggttctgcgccctaacccgggaactctaaccccccgtgg tggcgcaatcgctgtcttcatgtgctttatctcacgtgacggctggaatc tggcagaagacggagtatgtacattttgtcgttggtcacgttatccctaa aacgtggtgtttaaactggtcgaatgcttggcccagaacacaagaagaaa aaaacgagacaacttgatcagtttcaacgccacagcaagcttgtcttcac tgtggttggtcttctccacgccacaagcaacacgtacatgtcaattacgt cagggtcttttaagttctgtggcttttgaaccagttataaagaaccaacc acccttttttcaaagctaatcaagacggggaaattttttttttgatattt ttcgaca Met6 Promoter 5'gatactgcagacggtgcattacttacccgtgtcgactgagagtctact tggtacttggccctgtggctaagcagtatttgagcaacaatgcaatgcag ttgctgactcggttccagatcccctttgccccgatgtgtggaagcgttgtt tttggggcaagggcatgtggggctgcatcatactgtggctggggccgtt ggaagagccgtcggcagcgagcctgagtcgcttctcggggccttattccc cccgcctctaggtcagcggcggccgaagtgtcgtactcagctcgcctgta -continued cagtatgacgtgaccgaatagcctctggaaggttggagaagtacagtgca
aaaaaaagttgcaaaatttcattttagcgttcgatccgacgtggcagttg
gacaatgaatcgatggagacatgatcatgggcagaaatagaaggtctcca
tgttcaatggcagtaccaattgagcaacagacgggtcgacaggcggcggg
cacaccatccgccctccacatggcgcaatcgtcagtgcagcgattcgtac
tcggattgcatcatgttgcaccgaaagttggggcccgcacgttggagagg
cgaggagccagggttagctttggtggggtcctttgttgtcacgtggcatc
agcgaatggcgtcctccaatcagggccgtcagcgaagtcggcgtgtgata
gtgcgtggggagcgaatagagtttctggggggggcggcccaaaacgtga
aatccgagtacgcatgtagagtgtaaattgggtgtatagtgacattgttt
gactctgaccctgagagtaatatataatgtgtacgtgtccccctccgttg
gtcttctttttttctcctttctcctaaccaacacccaaactaatcaatc Met25 Promoter 5'aagtcgtattaacataactttccttacattttttttaaagcacgtcact
atccacgtgacctagccacgcgataccaagtattcatccataatgacaca
ctcatgacgtccggaggacgtcatcatcgtccagtcacgtgccaaggcac
atgactaatcataacaccttatgactagcttctgaatcgctacacagttc
caattcgcaaataaactcgaaatgacgaaatgccataataaaaatgacga
aactcgagattgagagcagcacatgcactgaagtggtggacaaccagcgt
atccggagacacgacggatccagcaccatggaagctggccgaaaaagaga
tccccagcacattgagcaaccaagtcagctcaattgagtaacatcacaca
ctcagatcgagtctgatggtggtccccttttgttccttcacttgaaaaat
aattgaaaataacaataacaataaaaataaaaacaaaataaaaatAAAAA
taaaaataaaaataaaaaaataaaaaaaaccttgccgcatttagcgtcagc
caccccccgcattgacctgagtacgttggattgacccgatcctgcacgt
cgagcgtggtcggccaaaaagcgcccgtggctggtgagtcagaaatagca
gggttgcaagagagagctgcgcaacgagcaataaacggtgtttttttcgc
ttctgtgctgcttagagtggagagccgaccctcgccatgctcacgtgacc
attcacgtggttgcaaactccaccttagtatagccgtgtccctctcgcta
cccattatcgcatcgtactccagccacatttttttgttccccgctaaatc
cggaaccttatctgggtcacgtgaaattgcaatctcgacaggaggttata
cttatagagtgagacactccacgcaaggtgttgcaagtcaattgacacca
cctcacctcagactaacatccaca Pox2 Promoter 5'gaatctgccccacattttatctccgcttttgactgttttttctccccc
ctttcacactctgcttttggctacataaaccccgcaccgtttggaactct
gttggtccggggaagccgccgttaggtgtgtcagatggagagcgccagac
gagcagaaccgagggacagcggatcggggagggctgtcacgtgacgaag
ggcactgttgacgtggtgaatgtcgcccgttctcacgtgacccgtctcct -continued ctatatgtgtatccgcctctttgtttggtttttttttctgcttcccccccc
ccccccccaccccaatcacatgctcagaaagtagacatctgcatcgtcct
gcatgccatcccacaagacgaacaagtgataggccgagagccgaggacga
ggtggagtgcacaaggggtaggcgaatggtacgattccgccaagtgagac
tggcgatcgggagaagggttggtggtcatgggggatagaatttgtacaag
tggaaaaaccactacgagtagcggatttgataccacaagtagcagagata
tacagcaatggtgggagtgcaagtatcggaatgtactgtacctcctgtac
tcgtactcgtacggcactcgtagaaacggggcaatacggggagaagcga
tcgcccgtctgttcaatcgccacaagtccgagtaatgctcgagtatcgaa
gtcttgtacctccctgtcaatcatggcaccactggtcttgacttgtctat
tcatactggacaagcgccagagttaagcttgtagcgaatttcgccctcgg
acatcaccccatacgacggacacacatgcccgacaaacagcctctcttat
tgtagctgaaagtatattgaatgtgaacgtgtacaatatcaggtaccagc
gggaggttacggccaaggtgataccggaataaccctggcttggagatggt
cggtccattgtactgaagtgtccgtgtcgtttccgtcactgccccaattg
gacatgtttgttttttccgatcttcgggcgccctctccttgtctccttgt
ctgtctcctggactgttgctaccccatttctttggcctccattggttcct
ccccgtcttcacgtcgtctatggttgcatggtttcccttatacttttcc
ccacagtcacatgttatggaggggtctagatggaggcctaattttgacgt
gcaaggggcgaattgggggcgagaaacacgtcgtggacatggtgcaaggcc
cgcagggttgattcgacgcttttccgcgaaaaaacaagtccaaatAcccc
ccgtttattctccctcggctctcggtatttcacatgaaaactataaccta
gactacacgggcaaccttaaccccagagtatacttatataccaagggat
gggtcctcaaaaacacacaagcaacg Yef3 (YALI0E13277g) Promoter 5'cgccattcggttccttccagaccattccagatcaatccacctcttctt
atctcaggtgggtgtgctgacatcagaccccgtagcccttctcccagtgg
cgaacagcaggcataaaacagggccattgagcagagcaaacaaggtcggt
gaaatcgtcgaaaaagtcggaaaacggttgcaagaaattggagcgtcacc
tgccaccctccaggctctatataaagcattgccccaattgctaacgcttc
atatttacacctttggcaccccagtccatccctccaataaaatgtactac
atgggacacaacaagagaggatgcgcgcccaaacccctaacctagcacatg
cacgatgattctctttgtctgtgaaaaaattttttccaccaaaatttcccc
attgggatgaaaccctaaccgcaaccaaaagttttaactatcatcttgt
acgtcacggtttccgattcttctcttctctttcatcatcatcacttgtga
cc 5'aactaccataaagtaccgagaaatataggcaattgtacaaattgtcca
cctccttcacttacattaccgaaccatggccatatcaccaaaataccccg
agtgctaaaacacctccctccaaatgttctcttaccttccaccgaaaacc -continued

```
gatcttattatcccaacgcttgttgtggcttgacgcgccgcacccgctgg
gcttgccatttcgataccaatccaagaggaaaagctcatgagaaacaatc
ggaatatcacgagaacggcctggcgaaccaacaggatattttgaatata
attaccctcgaatctagtcatatctatgtctactgtagacttgggcggc
atcatgatgtacattattttagcgtctggaaccctaaagttcacgtacaa
tcatgtgacaaacgaggctaaaaaatgtcaatttcgtatattagtgttat
tacgtggctcacatttccgaatcatctaccacccccacctaaaaa
```

YALI0D16467g promoter

```
5'ttttttttaattttcatatttattttcatatttattttcatatttatttt
tcatttatttattcatgtatttatttattacttttttaagtattttaaact
cctcactaaaccgtcgattgcacaatattaaccttcattacacctgcagc
gtggttttgtggtcgttagccgaagtcttccaacgtgggtataagtagg
aacaattgggccgatttttgagccgtctaaatctctcgactcaattgat
ctgctgtcgaaaatccggctctctagctccttttcccgtccgctggagc
tcctcttcattgtgccgttttccaacatttaactttgccacccaccacc
accccactaccatcacccactcgatctctgttcgtgtcaccacgacttt
gtcttctcacacatactctgtttgtgcaccacacattgcgaa
```

Tef4 (YALI0B12562g) promoter

```
5'gctacaatagctttattggccctattgagcacgctacaattcggtcca
gtatgtacaacgtctatgcgcactaacggccatacagtgagttacagcac
acccaaaagtaaccctgcctgacctgtctgcctgagacaggaagattaac
tcttgtagtgaccgagctcgataagactcaagccacacaatttttttata
gccttgcttcaagagtcgccaaaatgacattacacaactccacggaccgt
cggttccatgtccacacccttggatgggtaagcgctccacgcacgtacca
cgtgcattgagtttaaccacaaacataggtctgtgtcccagagttaccct
gctgcatcagccaagtcttgaaagcaaaattcttgcacaatttttcctc
ttcttttcttcactgatcgcagtccaaacacaaaca
```

YALI0D12903g Promoter

```
5'gcgctctgatccacttgtatggctccaagttcagtgtaccaagtagtt
ggtgatgcagggagggatgtctctatccaccaataatgaactcatgggcg
aaattgtttctgttaaacactccaactgtcgttttaaatctcattctctt
tgcatttggactccattcgcttccgttgggccaatataatccatcgtaac
gtactttagatggaaatttagttacctgctacttgtctcaacaccccaac
aggggctgttcgacagaggtaatagagcgtcaatgggttaataaaaacac
actgtcgattttcactcattgtctttatgatattacctgttttccgctgt
tatcaatgccgagcatcgtgttatatcttccaccccaactacttgcattt
acttaactattacctcaactatttacaccccgaattgttacctcccaata
agtaactttatttcaaccaatgggacgagagcatctctgagaacatcgat
```

```
ctatctctgtcaatattgcccagaatcgttcgaaaaaaaacaccaaaagg
tttacagcgccattataaatataaattcgttgtcaattcccccgcaatgt
ctgttgaaatctcattttgagaccttccaacattaccctctctcccgtct
ggtcacatgacgtgactgcttcttcccaaaacgaacactcccaactcttc
cccccgtcagtgaaaagtatacatccgacctccaaatcttttcttcact
caac
```

Tef1 (YALI0009141g) Promoter

```
5'agagacgggttggcggcgtatttgtgtcccaaaaaacagccccaattg
ccccaattgaccccaaattgacccagtagcgggcccaaccccggcgagag
cccccttcaccccacatatcaaacctcccccggttcccacacttgccgtt
aagggcgtagggtactgcagtctggaatctacgcttgttcagactttgta
ctagtttctttgtctggccatccgggtaacccatgccggacgcaaaatag
actactgaaaattttttttgctttgtggttgggactttagccaagggtata
aaagaccaccgtccccgaattaccttcctcttcttttctctctctctt
gtcaactcacacccgaaatcgttaagcatttccttctgagtataagaatc
attc
```

Fba1 (YALI0E26004g Promoter

```
5'gctgcgctgatctggacaccacagaggttccgagcactttaggttgca
ccaaatgtcccaccaggtgcaggcagaaaacgctggaacagcgtgtacag
tttgtcttagcaaaaagtgaaggcgctgaggtcgagcagggtggtgtgac
ttgttatagcctttagagctgcgaaagcgcgtatggatttggctcatcag
gccagattgagggtctgtggacacatgtcatgttagtgtacttcaatcgc
cccctggatatagccccgacaataggccgtggcctcatttttttgccttc
cgcacatttccattgctcggtacccacaccttgcttctcctgcacttgcc
aaccttaatactggtttacattgaccaacatcttacaagcgggggggcttg
tctagggtatatataaacagtggctctcccaatcggttgccagtctcttt
tttcctttctttccccacagattcgaaatctaaactacacatc
```

Pox2 Terminator:

```
5'gatgaggaatagacaagcgggtatttattgtatgaataaagattatgt
attgattgcaaaaagtgcatttgtagatgtggtttattgtagagagtac
ggtatgtactgtacgaacattaggagctacttctacaagtagattttctt
aacaagggtgaaatttactaggaagtacatgcatatttcgttagtagaat
cacaaaagaaatgtacaagcacgtactacttgtactccacaatgtggagt
gggagcaaaaaaattggacgacaccggaatcgaaccggggacctcgcgca
tgctaagcgcatgtgataaccaactacaccagacgcccaagaactttctt
ggtgattatggaatacgtggtctgctatatctcaattttgctgtaatgaa
tcattagaattaaaaaaaaacccccattttttgtgtgattgtcggccaaga
gatggaacaggaagaatacgtgaacaagcgagcacgaatgccatatgctc
```

-continued
```
ttctgaacaaccgagtccgaatccgatttgtgggtatcacatgtctcaag tagctgaaatgtatttcgctagaataaaataaatgagattaagaattaaa aatattggaatatattttcctagaatagaaactttggattttttttcggc tattacagtctgaactggacaaacggctgactatatataaatattattgg gtctgttttcttgtttatgtcgaaattatctgggttttactactgtgtcg tcgagtatagagtggcctgactggagaaaatgcagtagtatggacagtag gtactgccagccagagaagttttggaattgatacttgagtcattttcc attccccattccccattccaacacaatcaactgtttctgaacattttcca aaacgcggagatgtatgtcacttggcactgcaagtctcgattcaaaatgc atctctttcagaccaaagtgtcatcagctttgtttggccccaaattaccg caaatacttgtcgaaattgaagtgcaatacggcctcgtctgccatgaaac ctgcctattctcttcaaattggcgtcaggtttcacgtccagcattcctcg cccagacagagttgctatggttgaatcgtgtactgttaatatatgtatgt attatactcgtactacgatatactgttcaatagagtctcttataatcgta cgacgattctgggca
```

Example 8

Cultures Conditions, Such as Limitation for Nitrogen, Magnesium or Phosphate, can Promote Lipid Accumulation in *Y. lipolytica*

8A. Strains Used to Analyze Lipid Accumulation During Growth Under Various Conditions.

Strains MF760, MF858, and MF921 were grown under an array of culture conditions, and then harvested cells were extracted and analyzed for total lipid content and levels of specific lipophilic metabolites. FIG. 9 depicts schematic representations of plasmids generated and described in this example. Strain MF760 has genotype MATB ura2::URA2/tef-GGS1 ChrA-1635618::tef-carB ura3-302 ade1::?ADE1/tef-HMG1trunc leu2::?LEU2/tef-carRP (questions marks denote presumed loci of chromosomal integration). Strain MF760 harbors four insertion plasmids, pMB4637, pMB4591, pMB4705, and pMB4660, which encode native or heterologous genes required for synthesis of either isoprenoid metabolites in general, or carotenoid metabolites specifically. In all insertion plasmids, except pMB4789, described in this example, the *Y. lipolytica* TEF1 promoter and XPR2 terminator were the regulatory sequences used to control expression of genes of interest. Also, in some instances multiple URA3-containing plasmids can be utilized in the same strain, since 5-fluoroorotic acid can be used to select for Ura⁻ sergeants following transformation with a URA3 plasmid. pMB4637 is an ADE1 plasmid that encodes a truncated variant of the *Y. lipolytica* HMG-CoA reductase. pMB4591 is a URA5 plasmid that encodes the *Y. lipolytica* geranylgeranylpyrophosphate synthase. pMB4705 is a LEU2 plasmid that encodes the phytoene synthase/lycopene cyclase (CarRP) from *Mucor circinelloides*. pMB4660 is a URA3 plasmid that encodes a phytoene dehydrogenase from *M. circinelloides*.

Strain MF858 has genotype MATB ura2::URA2/tef-GGS1 ChrA-1635618::tef-carB ura3-302::?URA3/tef-plasmid ade1::?ADE1/tef-HMG1trunc leu2::?LEU2/tef-carRP. Strain MF858 harbors the same four plasmids as MF760, and an addition control plasmid (pMB4691), which is a URA3 plasmid that contains regulatory sequences but no gene of interest.

Strain MF921 has genotype MATB erg9-3'UTR::URA3 ura2::URA2/tef-GGS1 ChrA-1635618::tef-carB ura3-302 ade1::?ADE1/tef-HMG1trunc leu2::?LEU2/tef-carRP. Strain MF921 harbors the same four plasmids as MF760, and an addition URA3 plasmid, pMB4789, which contains sequences for insertion into the 3' UTR of the native ERG9. Insertion into 3' UTR of ERG9 is presumed to result in a hypomorphic mutation to decrease squalene synthase activity.

8B. Lipid Accumulation in Media Containing Various Carbon:Nitrogen Ratios

Shake flask testing was conducted using carbon to nitrogen (C/N) ratios of 160, 80, 60, 40, 30, 20, and 10 with yeast nitrogen base being the base medium providing vitamins, trace elements and salts. Ammonium sulfate (which contains 21% nitrogen) was used as the nitrogen source and glucose (which contains 40% carbon) was used as the carbon source at a concentration of 30 g/L. The concentrations of ammonium sulfate corresponding to these ratios are: 0.36, 0.71, 0.95, 1.43, 1.91, 2.86, and 4.6 g/L, respectively. Uracil was supplemented at 0.2 mM. As controls, strains were also grown in yeast extract-peptone with 50 g/L of glucose (media in which lipids do not accumulate at high levels) and yeast extract-peptone with 5% olive oil (v/v) (media in which lipids accumulate at high levels). Strain MF760 (10-14 ml of culture) was harvested after 4 days of growth at 30° C., during which time the cultures were shaking at 250 rpm. Following harvesting, cells were washed three times with water, with the exception of the oil-grown cells which were washed three times in 0.5% BSA and one time with water before lipid extractions. Lipids were extracted as described in Folch J, Lees, M, and Stanley, G. H. S. *J. Biol. Chem.* 226: 497-509, 1957. In brief, cell pellets were resuspended in 6 ml of water. A 1 ml aliquot was transferred to a pre-weighed tube with a hole on the lid, spun down and the cell pellet lyophilized overnight to determine the dry cell weight. The remaining 5 ml were placed in a 15 ml Falcon tube and spun down. Cell pellets were frozen at −20° C. until extractions were performed. Two to three volumes of a Zymolyase solution (2 mg/ml Zymolyase 100T in 1M Sorbitol, 50 mM EDTA and 0.01% β-mercaptoethanol) was added to each cell pellet and placed at 37° C. with constant agiatation for 1 hr. Two volumes of cubic zirconia beads were added to each tube and vortexed for 15-20 min. Samples were viewed under a microscope to ensure cell breakage before continuing with extractions. After cell breakage was complete, 6 ml of extraction solvent was added (a 2:1 mix of chloroform and methanol) and mixed. The mixture was spun down for 5 min at 3000 rpm and the organic layer was transferred to a clean tube. NaCl was added to the remaining aqueous layer to make it a 0.29% NaCl solution. 6 ml of extraction solvent was added and mixed, and the mixture was spun down for 5 min. The organic layers were pooled and filtered through a 0.2 μm filter to get rid of any cell debris. The extract was washed with 0.2 volumes of 0.29% NaCl solution and another 6 ml of extraction solvent added and mixed. Mixtures were spun and the organic layer was placed in a pre-weighed glass vial, the solvent was evaporated under a flow on nitrogen and the vial was weighed again to determine the weight of the lipid extracted. The dry cell weight is used to determine the percentage of lipid per dry cell weight. The lipid accumulation results are in the Table 62 below:

TABLE 62

Lipid accumulation under various carbon:nitrogen ratio growth conditions

|  | C/N Ratio | % lipid |
|---|---|---|
| YNB | 160 | 61 |
| 3% Glucose | 80 | 49 |
|  | 60 | 34 |
|  | 40 | 17 |
|  | 30 | 16 |
|  | 20 | 14 |
|  | 10 | 15 |
| YEP | 5% Glucose | 22 |
|  | 5% olive oil | 38 |

Other nitrogen sources tested were proline (12% nitrogen), sodium glutamate (7% nitrogen), soy acid hydrolysate (12% nitrogen), and yeast extract-peptone (26.8% nitrogen). All nitrogen sources tested at C/N ratios of 80 (with glucose as a carbon source), had significantly larger lipid bodies than at C/N ratios of 10 (also with glucose as a carbon source).

Strains MF858 and MF921 were harvested after 4 days of growth at 30° C. (3% glucose was used as the carbon source). Cells were washed three times with water and lipids extracted as described above. Lipid accumulation data for soy hydrolysate, yeast extract-peptone and yeast nitrogen base, used as a control, are listed in Table 63 below.

TABLE 63

Lipid accumulation under different carbon and nitrogen conditions with various nitrogen sources

|  |  | % lipid | |
|---|---|---|---|
|  | C/N Ratio | MF858 | MF921 |
| Soy hydrolysate | 80 | 36 | 36 |
|  | 60 | 36 | 35 |
|  | 10 | 14 | 15 |
| Yeast Extract-Peptone | 80 | 37 | 37 |
|  | 10 | 15 | 14 |
| Yeast Nitrogen Base | 80 | 37 | 38 |
|  | 10 | 13 | 11 |

8C. Determination of Lipid Levels Under High Carbon and Phosphate or Magnesium Limiting Conditions.

To test whether other nutrient limitations, under high carbon conditions, will allow for higher lipid accumulation, phosphate or magnesium limiting conditions were tested. For phosphate limiting conditions, yeast nitrogen base medium without phosphate was prepared. Shake flask testing was performed using carbon to phosphate ratios ranging from 5376 down to 42. This range corresponds to 7.8 mg/L up to 1 g/L, respectively, and the latter concentration corresponds to that are commonly used in yeast nitrogen base medium. Glucose, at 30 g/L, was used at the carbon source. Potassium phosphate monobasic (containing 28.7% phosphate) was used as the phosphate source.

For magnesium limiting conditions, yeast nitrogen base medium without magnesium was prepared. Shake flask testing was conducted using carbon to magnesium ratios ranging from 31360 down to 245. This range corresponds to 0.375 mg/L up to 0.5 g/L, and the latter magnesium concentration corresponds to that commonly used in yeast nitrogen base. Glucose, at 30 g/L, was used as the carbon source. Magnesium sulfate (containing 9.8% magnesium) was used as the magnesium source.

Strains MF858 and MF921 were harvested after 4 days of growth at 30° C., during which time the cultures were shaking at 250 rpm. Cells were washed three times with water before lipid extraction. Lipids were extracted as described above. Lipid accumulation data is listed in the Table 64 below:

TABLE 64

Lipid accumulation in phosphate or magnesium limiting growth conditions

|  |  | % Lipid | |
|---|---|---|---|
|  | g/L | MF858 | MF921 |
| phosphate | 1 | 14 | 14 |
|  | 0.0625 | 18 | 20 |
|  | 0.0313 | 34 | 41 |
|  | 0.0156 | 62 | 63 |
|  | 0.0078 | 83 | 76 |
| magnesium | 0.5 | 12 | 11 |
|  | 0.0313 | NA | 16 |
|  | 0.0156 | NA | 25 |
|  | 0.0078 | NA | 42 |
|  | 0.0039 | 48 | 48 |

The following tables are referenced throughout the description. Each reference and information designated by each of the Genbank Accession and GI numbers are hereby incorporated by reference in their entirety. The order of genes, polypeptides and sequences presented in the tables is not indicative of their relative importance and/or suitability to any of the embodiments disclosed herein.

Lengthy table referenced here

US08367395-20130205-T00001

Please refer to the end of the specification for access instructions.

Lengthy table referenced here

US08367395-20130205-T00002

Please refer to the end of the specification for access instructions.

Lengthy table referenced here

US08367395-20130205-T00003

Please refer to the end of the specification for access instructions.

Lengthy table referenced here

US08367395-20130205-T00004

Please refer to the end of the specification for access instructions.

|     103     |     104     |
|:-----------:|:-----------:|

Lengthy table referenced here

US08367395-20130205-T00005

Please refer to the end of the specification for access instructions.

Lengthy table referenced here

US08367395-20130205-T00012

Please refer to the end of the specification for access instructions.

Lengthy table referenced here

US08367395-20130205-T00006

Please refer to the end of the specification for access instructions.

Lengthy table referenced here

US08367395-20130205-T00013

Please refer to the end of the specification for access instructions.

Lengthy table referenced here

US08367395-20130205-T00007

Please refer to the end of the specification for access instructions.

Lengthy table referenced here

US08367395-20130205-T00014

Please refer to the end of the specification for access instructions.

Lengthy table referenced here

US08367395-20130205-T00008

Please refer to the end of the specification for access instructions.

Lengthy table referenced here

US08367395-20130205-T00015

Please refer to the end of the specification for access instructions.

Lengthy table referenced here

US08367395-20130205-T00009

Please refer to the end of the specification for access instructions.

Lengthy table referenced here

US08367395-20130205-T00016

Please refer to the end of the specification for access instructions.

Lengthy table referenced here

US08367395-20130205-T00010

Please refer to the end of the specification for access instructions.

Lengthy table referenced here

US08367395-20130205-T00017

Please refer to the end of the specification for access instructions.

Lengthy table referenced here

US08367395-20130205-T00011

Please refer to the end of the specification for access instructions.

Lengthy table referenced here

US08367395-20130205-T00018

Please refer to the end of the specification for access instructions.

105

Lengthy table referenced here

US08367395-20130205-T00019

Please refer to the end of the specification for access instructions.

Lengthy table referenced here

US08367395-20130205-T00020

Please refer to the end of the specification for access instructions.

Lengthy table referenced here

US08367395-20130205-T00021

Please refer to the end of the specification for access instructions.

Lengthy table referenced here

US08367395-20130205-T00022

Please refer to the end of the specification for access instructions.

Lengthy table referenced here

US08367395-20130205-T00023

Please refer to the end of the specification for access instructions.

Lengthy table referenced here

US08367395-20130205-T00024

Please refer to the end of the specification for access instructions.

Lengthy table referenced here

US08367395-20130205-T00025

Please refer to the end of the specification for access instructions.

106

Lengthy table referenced here

US08367395-20130205-T00026

Please refer to the end of the specification for access instructions.

Lengthy table referenced here

US08367395-20130205-T00027

Please refer to the end of the specification for access instructions.

Lengthy table referenced here

US08367395-20130205-T00028

Please refer to the end of the specification for access instructions.

Lengthy table referenced here

US08367395-20130205-T00029

Please refer to the end of the specification for access instructions.

Lengthy table referenced here

US08367395-20130205-T00030

Please refer to the end of the specification for access instructions.

Lengthy table referenced here

US08367395-20130205-T00031

Please refer to the end of the specification for access instructions.

Lengthy table referenced here

US08367395-20130205-T00032

Please refer to the end of the specification for access instructions.

| | |
|---|---|
| Lengthy table referenced here | Lengthy table referenced here |
| US08367395-20130205-T00033 | US08367395-20130205-T00040 |
| Please refer to the end of the specification for access instructions. | Please refer to the end of the specification for access instructions. |

| | |
|---|---|
| Lengthy table referenced here | Lengthy table referenced here |
| US08367395-20130205-T00034 | US08367395-20130205-T00041 |
| Please refer to the end of the specification for access instructions. | Please refer to the end of the specification for access instructions. |

| | |
|---|---|
| Lengthy table referenced here | Lengthy table referenced here |
| US08367395-20130205-T00035 | US08367395-20130205-T00042 |
| Please refer to the end of the specification for access instructions. | Please refer to the end of the specification for access instructions. |

| | |
|---|---|
| Lengthy table referenced here | Lengthy table referenced here |
| US08367395-20130205-T00036 | US08367395-20130205-T00043 |
| Please refer to the end of the specification for access instructions. | Please refer to the end of the specification for access instructions. |

| | |
|---|---|
| Lengthy table referenced here | Lengthy table referenced here |
| US08367395-20130205-T00037 | US08367395-20130205-T00044 |
| Please refer to the end of the specification for access instructions. | Please refer to the end of the specification for access instructions. |

| | |
|---|---|
| Lengthy table referenced here | Lengthy table referenced here |
| US08367395-20130205-T00038 | US08367395-20130205-T00045 |
| Please refer to the end of the specification for access instructions. | Please refer to the end of the specification for access instructions. |

| | |
|---|---|
| Lengthy table referenced here | Lengthy table referenced here |
| US08367395-20130205-T00039 | US08367395-20130205-T00046 |
| Please refer to the end of the specification for access instructions. | Please refer to the end of the specification for access instructions. |

Lengthy table referenced here
US08367395-20130205-T00047

Please refer to the end of the specification for access instructions.

Lengthy table referenced here
US08367395-20130205-T00048

Please refer to the end of the specification for access instructions.

Lengthy table referenced here
US08367395-20130205-T00049

Please refer to the end of the specification for access instructions.

Lengthy table referenced here
US08367395-20130205-T00050

Please refer to the end of the specification for access instructions.

Lengthy table referenced here
US08367395-20130205-T00051

Please refer to the end of the specification for access instructions.

Lengthy table referenced here
US08367395-20130205-T00052

Please refer to the end of the specification for access instructions.

Lengthy table referenced here
US08367395-20130205-T00053

Please refer to the end of the specification for access instructions.

Lengthy table referenced here
US08367395-20130205-T00054

Please refer to the end of the specification for access instructions.

Lengthy table referenced here
US08367395-20130205-T00055

Please refer to the end of the specification for access instructions.

Lengthy table referenced here
US08367395-20130205-T00056

Please refer to the end of the specification for access instructions.

Lengthy table referenced here
US08367395-20130205-T00057

Please refer to the end of the specification for access instructions.

Lengthy table referenced here
US08367395-20130205-T00058

Please refer to the end of the specification for access instructions.

Lengthy table referenced here
US08367395-20130205-T00059

Please refer to the end of the specification for access instructions.

Lengthy table referenced here
US08367395-20130205-T00060

Please refer to the end of the specification for access instructions.

111

Lengthy table referenced here

US08367395-20130205-T00061

Please refer to the end of the specification for access instructions.

Lengthy table referenced here

US08367395-20130205-T00062

Please refer to the end of the specification for access instructions.

Lengthy table referenced here

US08367395-20130205-T00063

Please refer to the end of the specification for access instructions.

Lengthy table referenced here

US08367395-20130205-T00064

Please refer to the end of the specification for access instructions.

Lengthy table referenced here

US08367395-20130205-T00065

Please refer to the end of the specification for access instructions.

Lengthy table referenced here

US08367395-20130205-T00066

Please refer to the end of the specification for access instructions.

Lengthy table referenced here

US08367395-20130205-T00067

Please refer to the end of the specification for access instructions.

112

Lengthy table referenced here

US08367395-20130205-T00068

Please refer to the end of the specification for access instructions.

Lengthy table referenced here

US08367395-20130205-T00069

Please refer to the end of the specification for access instructions.

Lengthy table referenced here

US08367395-20130205-T00070

Please refer to the end of the specification for access instructions.

Lengthy table referenced here

US08367395-20130205-T00071

Please refer to the end of the specification for access instructions.

Lengthy table referenced here

US08367395-20130205-T00072

Please refer to the end of the specification for access instructions.

Lengthy table referenced here

US08367395-20130205-T00073

Please refer to the end of the specification for access instructions.

Lengthy table referenced here

US08367395-20130205-T00074

Please refer to the end of the specification for access instructions.

Lengthy table referenced here

US08367395-20130205-T00075

Please refer to the end of the specification for access instructions.

Lengthy table referenced here

US08367395-20130205-T00076

Please refer to the end of the specification for access instructions.

Lengthy table referenced here

US08367395-20130205-T00077

Please refer to the end of the specification for access instructions.

Lengthy table referenced here

US08367395-20130205-T00078

Please refer to the end of the specification for access instructions.

Lengthy table referenced here

US08367395-20130205-T00079

Please refer to the end of the specification for access instructions.

Lengthy table referenced here

US08367395-20130205-T00080

Please refer to the end of the specification for access instructions.

Lengthy table referenced here

US08367395-20130205-T00081

Please refer to the end of the specification for access instructions.

Lengthy table referenced here

US08367395-20130205-T00082

Please refer to the end of the specification for access instructions.

Lengthy table referenced here

US08367395-20130205-T00083

Please refer to the end of the specification for access instructions.

Lengthy table referenced here

US08367395-20130205-T00084

Please refer to the end of the specification for access instructions.

Lengthy table referenced here

US08367395-20130205-T00085

Please refer to the end of the specification for access instructions.

Lengthy table referenced here

US08367395-20130205-T00086

Please refer to the end of the specification for access instructions.

Lengthy table referenced here

US08367395-20130205-T00087

Please refer to the end of the specification for access instructions.

Lengthy table referenced here

US08367395-20130205-T00088

Please refer to the end of the specification for access instructions.

Lengthy table referenced here

US08367395-20130205-T00089

Please refer to the end of the specification for access instructions.

Lengthy table referenced here

US08367395-20130205-T00090

Please refer to the end of the specification for access instructions.

Lengthy table referenced here

US08367395-20130205-T00091

Please refer to the end of the specification for access instructions.

Lengthy table referenced here

US08367395-20130205-T00092

Please refer to the end of the specification for access instructions.

Lengthy table referenced here

US08367395-20130205-T00093

Please refer to the end of the specification for access instructions.

EQUIVALENTS

Those skilled in the art will recognize, or be able to understand that the foregoing description and examples are illustrative of practicing the provided invention. Those skilled in the art will be able to ascertain using no more than routine experimentation, many variations of the detail presented herein may be made to the specific embodiments of the invention described herein without departing from the spirit and scope of the present invention.

LENGTHY TABLES

The patent contains a lengthy table section. A copy of the table is available in electronic form from the USPTO web site (http://seqdata.uspto.gov/?pageRequest=docDetail&DocID=US08367395B2). An electronic copy of the table will also be available from the USPTO upon request and payment of the fee set forth in 37 CFR 1.19(b)(3).

What is claimed is:

1. An engineered *Y. lipolytica* strain that produces at least one sterol compound selected from the group consisting of: squalene, lanosterol, zymosterol, ergosterol or 7-dehydrocholesterol (provitamin D3), the strain containing one or more sterologenic modifications selected from the group consisting of:
 a. decreased expression or activity of a *Y. lipolytica* GGPP synthase polypeptide compared to an otherwise comparable strain lacking the one or more sterologenic modification;
 b. increased expression or activity of a truncated HMG CoA reductase polypeptide compared to an otherwise comparable strain lacking the one or more sterologenic modification;
 c. increased expression or activity of an FPP synthase polypeptide compared to an otherwise comparable strain lacking the one or more sterologenic modification;
 d. increased expression or activity of an IPP isomerase polypeptide compared to an otherwise comparable strain lacking the one or more sterologenic modification;
 e increased expression or activity of an HMG-CoA synthase polypeptide compared to an otherwise comparable strain lacking the one or more sterologenic modification;
 f. increased expression or activity of a mevalonate kinase polypeptide compared to an otherwise comparable strain lacking the one or more sterologenic modification;
 g. increased expression or activity of a phosphomevalonate kinase polypeptide compared to an otherwise comparable strain lacking the one or more sterologenic modification;
 h. increased expression or activity of a mevalonate pyrophosphate decarboxylate polypeptide compared to an otherwise comparable strain lacking the one or more sterologenic modification;
 i. increased expression or activity of a cytosolic malic enzyme polypeptide compared to an otherwise comparable strain lacking the one or more sterologenic modification;
 j. increased expression or activity of a malate dehydrogenase polypeptide compared to an otherwise comparable strain lacking the one or more sterologenic modification;
 k. increased expression or activity of an AMP deaminase polypeptide compared to an otherwise comparable strain lacking the one or more sterologenic modification;
 l. increased expression or activity of a glucose 6 phosphate dehydrogenase polypeptide compared to an otherwise comparable strain lacking the one or more sterologenic modification;
 m. increased expression or activity of a malate dehydrogenase homolog 2 polypeptide compared to an otherwise comparable strain lacking the one or more sterologenic modification;

n. increased expression or activity of a GND1-6-phosphogluconate dehydrogenase polypeptide compared to an otherwise comparable strain lacking the one or more sterologenic modification;
o. increased expression or activity of a isocitrate dehydrogenase polypeptide compared to an otherwise comparable strain lacking the one or more sterologenic modification;
p. increased expression or activity of a IDH2-isocitrate dehydrogenase polypeptide compared to an otherwise comparable strain lacking the one or more sterologenic modification;
q. increased expression or activity of a fructose 1,6 bisphosphatase polypeptide compared to an otherwise comparable strain lacking the one or more sterologenic modification;
r. increased expression or activity of a Erg10-acetoacetyl CoA thiolase polypeptide compared to an otherwise comparable strain lacking the one or more sterologenic modification;
s. increased expression or activity of a squalene synthase polypeptide; and combinations thereof compared to an otherwise comparable strain lacking the one or more sterologenic modification;
  wherein the engineered strain can accumulate lipid to at least about 20% of its dry cell weight; and
  wherein as a result of genetic engineering the engineered strain produces the at least one sterol compound to a level at least about 1% of its dry cell weight.

2. The engineered *Y. lipolytica* strain of claim 1, wherein the one or more sterologenic modifications is selected from the group consisting of:

a. decreased expression or activity of a *Y. lipolytica* GGPP synthase polypeptide compared to an otherwise comparable strain lacking the one or more sterologenic modification;
b. increased expression or activity of a squalene synthase polypeptide compared to an otherwise comparable strain lacking the one or more sterologenic modification;
c. increased expression or activity of a truncated HMG CoA reductase polypeptide compared to an otherwise comparable strain lacking the one or more sterologenic modification; and combinations thereof.

3. The engineered *Y. lipolytica* strain of claim 1, wherein the produced sterol compound accumulates to levels that are greater than at least about 1.0%, greater than at least about 2.5%, or greater than at least about 5% of the dry weight of the cells.

4. The engineered *Y. lipolytica* strain of claim 1, wherein the sterol compound is squalene.

5. The engineered *Y. lipolytica* strain of claim 1, wherein the sterol compound is lanosterol.

6. The engineered *Y. lipolytica* strain of claim 1, wherein the sterol compound is zymosterol.

7. The engineered *Y. lipolytica* strain of claim 1, wherein the sterol compound is ergosterol.

8. The engineered *Y. lipolytica* strain of claim 1, wherein the sterol compound is 7-dehydrocholesterol.

9. The engineered *Y. lipolytica* strain of claim 1, further comprising at least one, oleaginic modification,
  wherein as a result of the at least one oleaginic modification, the strain produces the at least one sterol compound to a level at least about 1% of its dry cell weight.

* * * * *

UNITED STATES PATENT AND TRADEMARK OFFICE
CERTIFICATE OF CORRECTION

PATENT NO. : 8,367,395 B2  
APPLICATION NO. : 12/443350  
DATED : February 5, 2013  
INVENTOR(S) : Richard B. Bailey, Joshua Trueheart and Kevin T. Madden Page 1 of 1

It is certified that error appears in the above-identified patent and that said Letters Patent is hereby corrected as shown below:

On the title page of the patent, in the left-hand column at INID code 60, under the heading "Related U.S. Application Data":

Insert the following text in front of the existing citation:

--This application is a 371 of PCT/US2007/021091, filed September 28, 2007, which claims benefit of--

Signed and Sealed this  
Ninth Day of April, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,367,395 B2  
APPLICATION NO. : 12/443350  
DATED : February 5, 2013  
INVENTOR(S) : Richard B. Bailey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 436 days.

Signed and Sealed this
Twentieth Day of August, 2013

Teresa Stanek Rea
*Acting Director of the United States Patent and Trademark Office*